(12) United States Patent
Barnett et al.

(10) Patent No.: US 7,662,916 B2
(45) Date of Patent: Feb. 16, 2010

(54) MODIFIED HIV ENV POLYPEPTIDES

(75) Inventors: Susan Barnett, San Francisco, CA (US); Karin Hartog, Piedmont, CA (US); Eric Martin, El Cerrito, CA (US)

(73) Assignee: Novartis Vaccines & Diagnostics, Inc, Emeryville, CA (US)

( * ) Notice: Subject to any disclaimer, the term of this patent is extended or adjusted under 35 U.S.C. 154(b) by 128 days.

(21) Appl. No.: 10/452,018

(22) Filed: Jul. 25, 2003

(65) Prior Publication Data

US 2009/0304740 A1    Dec. 10, 2009

Related U.S. Application Data

(63) Continuation of application No. 09/476,242, filed on Dec. 30, 1999, now Pat. No. 6,689,879.

(60) Provisional application No. 60/114,495, filed on Dec. 31, 1998, provisional application No. 60/156,670, filed on Sep. 29, 1999.

(51) Int. Cl.
  *C07K 14/00* (2006.01)
  *A61K 39/00* (2006.01)
(52) U.S. Cl. ..................... 530/350; 424/184.1
(58) Field of Classification Search ............... 530/326, 530/350, 826; 424/185.1, 188.1, 192.1, 208.1
See application file for complete search history.

(56) References Cited

U.S. PATENT DOCUMENTS

| | | | |
|---|---|---|---|
| 4,652,639 A | 3/1987 | Stabinsky | |
| 4,861,707 A | 8/1989 | Ivanoff et al. | |
| RE33,653 E | 7/1991 | Mark et al. | |
| 5,032,510 A | 7/1991 | Kovacevic et al. | |
| 5,082,767 A | 1/1992 | Hatfield et al. | |
| 5,128,319 A | 7/1992 | Arlinghaus | |
| 5,130,247 A | 7/1992 | Kniskern et al. | |
| 5,156,949 A | 10/1992 | Luciw et al. | |
| 5,256,767 A | 10/1993 | Salk et al. | |
| 5,304,472 A | 4/1994 | Bass et al. | |
| 5,364,773 A | 11/1994 | Paoletti et al. | |
| 5,419,900 A | 5/1995 | Lane et al. | |
| 5,503,833 A | 4/1996 | Redmond et al. | |
| 5,550,280 A | 8/1996 | Dao-Cong et al. | |
| 5,637,677 A | 6/1997 | Greene et al. | |
| 5,665,569 A | 9/1997 | Ohno | |
| 5,665,720 A | 9/1997 | Young et al. | |
| 5,670,152 A | 9/1997 | Weiner et al. | |
| 5,683,864 A | 11/1997 | Houghton et al. | |
| 5,686,078 A | 11/1997 | Becker et al. | |
| 5,688,688 A | 11/1997 | Luciw et al. | |
| 5,693,755 A | 12/1997 | Buonagurio et al. | |
| 5,712,088 A | 1/1998 | Houghton et al. | |
| 5,714,596 A | 2/1998 | Houghton et al. | |
| 5,728,520 A | 3/1998 | Weiner et al. | |
| 5,741,492 A | 4/1998 | Hurwitz et al. | |
| 5,750,373 A | 5/1998 | Garrard et al. | |
| 5,766,845 A | 6/1998 | Weiner et al. | |
| 5,786,464 A | 7/1998 | Seed | |
| 5,792,459 A | 8/1998 | Haigwood | |
| 5,795,737 A | 8/1998 | Seed et al. | |
| 5,817,637 A | 10/1998 | Weiner et al. | |
| 5,837,242 A | 11/1998 | Holliger et al. | |
| 5,837,818 A | 11/1998 | Buonagurio et al. | |
| 5,840,313 A | 11/1998 | Vahlne et al. | |
| 5,846,546 A | 12/1998 | Hurwitz et al. | |
| 5,853,736 A | 12/1998 | Becker et al. | |
| 5,858,675 A | 1/1999 | Hillman et al. | |
| 5,859,193 A | 1/1999 | Devare et al. | |
| 5,866,320 A | 2/1999 | Rovinski et al. | |
| 5,871,747 A | 2/1999 | Gengoux-Sedlik et al. | |
| 5,876,724 A | 3/1999 | Girard | |
| 5,876,731 A | 3/1999 | Sia et al. | |
| 5,879,907 A | 3/1999 | Aberg et al. | |
| 5,879,925 A | 3/1999 | Rovinski et al. | |
| 5,889,176 A | 3/1999 | Rovinski et al. | |
| 5,932,445 A | 8/1999 | Lal et al. | |
| 5,951,975 A | 9/1999 | Falo, Jr. et al. | |
| 5,955,342 A | 9/1999 | Rovinski et al. | |
| 5,965,726 A | 10/1999 | Pavlakis et al. | |
| 5,972,596 A | 10/1999 | Pavlakis et al. | |
| 6,001,977 A | 12/1999 | Chang et al. | |
| 6,004,763 A | 12/1999 | Gengoux et al. | |
| 6,025,125 A | 2/2000 | Rovinski et al. | |
| 6,060,273 A | 5/2000 | Dirks et al. | |
| 6,060,587 A | 5/2000 | Weiner et al. | |
| 6,063,384 A | 5/2000 | Morrow et al. | |
| 6,074,636 A | 6/2000 | Nichols | |
| 6,080,408 A | 6/2000 | Rovinski et al. | |
| 6,087,486 A | 7/2000 | Weiner et al. | |
| 6,090,388 A | 7/2000 | Wang | |
| 6,093,800 A | 7/2000 | Reiter et al. | |
| 6,096,505 A | 8/2000 | Selby et al. | |
| 6,099,847 A | 8/2000 | Tobin et al. | |
| 6,114,148 A | 9/2000 | Seed et al. | |
| 6,132,973 A | 10/2000 | Lal et al. | |
| 6,139,833 A | 10/2000 | Burgess et al. | |
| 6,140,059 A | 10/2000 | Schawaller | |
| 6,146,635 A | 11/2000 | Cano et al. | |

(Continued)

FOREIGN PATENT DOCUMENTS

EP    0187041    7/1986

(Continued)

OTHER PUBLICATIONS

Riffkin et al. "A single amino-acid change between the antigenically different extracellular serine proteases V2 and B2 from *Dichelobacter nodosus*", Gene, vol. 167 (1995), pp. 279-283.*

(Continued)

*Primary Examiner*—Gary B Nickol
*Assistant Examiner*—Nicole Kinsey White
(74) *Attorney, Agent, or Firm*—Regina Bautista; Helen Lee

(57) ABSTRACT

Polynucleotide encoding modified HIV Env polypeptides are disclosed. The Env polypeptides are modified so as to expose at least part of the CD4 binding region. Methods of diagnosis, treatment and prevention using the polynucleotides and polypeptides are also provided.

11 Claims, 65 Drawing Sheets

U.S. PATENT DOCUMENTS

| | | |
|---|---|---|
| 6,172,201 B1 | 1/2001 | Weiner et al. |
| 6,174,666 B1 | 1/2001 | Pavlakis et al. |
| 6,214,804 B1 | 4/2001 | Felgner et al. |
| 6,291,157 B1 | 9/2001 | Rovinski et al. |
| 6,291,664 B1 | 9/2001 | Pavlakis et al. |
| 6,316,253 B1 | 11/2001 | Innis et al. |
| 6,331,404 B1 | 12/2001 | Berman et al. |

FOREIGN PATENT DOCUMENTS

| | | |
|---|---|---|
| EP | 0199301 A | 10/1986 |
| EP | 0242216 | 10/1987 |
| EP | 0314317 A1 | 5/1989 |
| EP | 0449116 B1 | 10/1991 |
| EP | 0617132 A2 | 9/1994 |
| WO | WO 86/03224 | 6/1986 |
| WO | WO 87/02775 | 5/1987 |
| WO | WO 88/00471 | 1/1988 |
| WO | WO 88/10300 | 12/1988 |
| WO | WO 89/01940 | 3/1989 |
| WO | WO 89/02277 | 3/1989 |
| WO | WO 89/02922 | 4/1989 |
| WO | WO 89/03222 | 4/1989 |
| WO | WO 90/00556 | 1/1990 |
| WO | WO 90/02568 | 3/1990 |
| WO | WO 90/03984 | 4/1990 |
| WO | WO 90/10438 | 9/1990 |
| WO | WO 90/11092 | 10/1990 |
| WO | WO 90/11359 | 10/1990 |
| WO | WO 90/12094 | 10/1990 |
| WO | WO 90/15141 | 12/1990 |
| WO | WO 91/04273 | 4/1991 |
| WO | WO 91/06319 | 5/1991 |
| WO | WO 91/07425 | 5/1991 |
| WO | WO 91/07510 | 5/1991 |
| WO | WO 91/13360 | 9/1991 |
| WO | WO 91/13906 | 9/1991 |
| WO | WO 91/15238 | 10/1991 |
| WO | WO 91/15512 | 10/1991 |
| WO | WO 91/16926 | 11/1991 |
| WO | WO 91/18928 | 12/1991 |
| WO | WO 91/19803 | 12/1991 |
| WO | WO 92/03475 | 3/1992 |
| WO | WO 92/04046 | 3/1992 |
| WO | WO 92/05799 | 4/1992 |
| WO | WO 93/02102 | 2/1993 |
| WO | WO 93/04090 | 3/1993 |
| WO | WO 93/08836 | 5/1993 |
| WO | WO 93/14789 | 8/1993 |
| WO | WO 93/20212 | 10/1993 |
| WO | WO 93/21346 | 10/1993 |
| WO | WO 93/23569 | 11/1993 |
| WO | WO 94/04574 | 3/1994 |
| WO | WO 94/07922 | 4/1994 |
| WO | WO 94/11523 | 5/1994 |
| WO | WO 94/13804 | 6/1994 |
| WO | WO 94/15621 | 7/1994 |
| WO | WO 94/16060 | 7/1994 |
| WO | WO 94/16737 | 8/1994 |
| WO | WO 94/18221 | 8/1994 |
| WO | WO 94/20141 | 9/1994 |
| WO | WO 94/20640 | 9/1994 |
| WO | WO 94/22477 | 10/1994 |
| WO | WO 94/26293 | 11/1994 |
| WO | WO 94/28929 | * 12/1994 |
| WO | WO 94/29339 | 12/1994 |
| WO | WO 95/03407 | 2/1995 |
| WO | WO 95/04818 | 2/1995 |
| WO | WO 95/11317 | 4/1995 |
| WO | WO 95/11701 | 5/1995 |
| WO | WO 95/24485 | 9/1995 |
| WO | WO 95/25124 | 9/1995 |
| WO | WO 95/27505 | 10/1995 |
| WO | WO 95/29700 | 11/1995 |
| WO | WO 95/33206 | 12/1995 |
| WO | WO 95/33835 | 12/1995 |
| WO | WO 96/02273 | 2/1996 |
| WO | WO 96/02557 | 2/1996 |
| WO | WO 96/04382 | 2/1996 |
| WO | WO 96/09066 | 3/1996 |
| WO | WO 96/09378 | 3/1996 |
| WO | WO 96/16178 | 5/1996 |
| WO | WO 96/20732 | 7/1996 |
| WO | WO 96/23509 | 8/1996 |
| WO | WO 96/25177 | 8/1996 |
| WO | WO 96/30523 | 10/1996 |
| WO | WO 96/40290 | 12/1996 |
| WO | WO 97/03198 | 1/1997 |
| WO | WO 97/11605 | 4/1997 |
| WO | WO 97/26009 | 7/1997 |
| WO | WO 97/31115 | 8/1997 |
| WO | WO 97/48370 | 12/1997 |
| WO | WO 98/08539 | 3/1998 |
| WO | WO 98/12207 | 3/1998 |
| WO | WO 98/34640 | 8/1998 |
| WO | WO 98/41536 | 9/1998 |
| WO | WO 98/41645 | 9/1998 |
| WO | WO 98/43182 | 10/1998 |
| WO | WO 98/48843 | 11/1998 |
| WO | WO 98/59074 | 12/1998 |
| WO | WO 99/02694 | 1/1999 |
| WO | WO 99/06599 | 2/1999 |
| WO | WO 99/09412 | 2/1999 |
| WO | WO 99/12416 | 3/1999 |
| WO | WO 99/13864 | 3/1999 |
| WO | WO 99/16883 | 4/1999 |
| WO | WO 99/33346 | 7/1999 |
| WO | WO 99/41397 | 8/1999 |
| WO | WO 99/41398 | 8/1999 |
| WO | WO 99/52463 | 10/1999 |
| WO | WO 99/53960 | 10/1999 |
| WO | WO 99/67395 | 12/1999 |
| WO | WO 00/08043 | 2/2000 |
| WO | WO 00/15819 | 3/2000 |
| WO | WO 00/18929 | 4/2000 |
| WO | WO 00/21556 | 4/2000 |
| WO | WO 00/29561 | 5/2000 |
| WO | WO 00/39302 | 7/2000 |
| WO | WO 00/39303 | 7/2000 |
| WO | WO 00/39304 | 7/2000 |
| WO | WO 00/44926 | 8/2000 |
| WO | WO 00/65076 | 11/2000 |
| WO | WO 00/66179 | 11/2000 |
| WO | WO 00/67761 | 11/2000 |
| WO | WO 00/67787 | 11/2000 |
| WO | WO 00/71561 | 11/2000 |
| WO | WO 01/02607 | 1/2001 |
| WO | WO 01/12223 | 2/2001 |
| WO | WO 01/16342 | 3/2001 |
| WO | WO 01/19958 | 3/2001 |
| WO | WO 01/21270 | 3/2001 |
| WO | WO 01/26681 | 4/2001 |
| WO | WO 01/29225 | 4/2001 |
| WO | WO 01/36614 | 5/2001 |
| WO | WO 01/42308 | 6/2001 |
| WO | WO 01/43693 | 6/2001 |
| WO | WO 01/45748 | 6/2001 |
| WO | WO 01/46408 | 6/2001 |
| WO | WO 01/47955 | 7/2001 |
| WO | WO 01/54701 | 8/2001 |
| WO | WO 01/54719 | 8/2001 |
| WO | WO 01/60393 | 8/2001 |

WO    WO 01/60838    8/2001

OTHER PUBLICATIONS

Abaza et al. "Effects of amino acid substitutions outside an antigenic site on protein binding to monoclonal antibodies of predetermined specificity obtained by peptide immunization", Journal of Protein Chemistry, vol. 11, No. 5 (1992), pp. 433-444.*
Cruse et al. Illustrated Dictionary of Immunology (Boca Raton, Fl, CRC Press, Inc., 1995), p. 309. QR180.4.C78.*
Paul, Fundamental Immunology, (Philadelphia & New York, Lippincott-Raven Publishers, 1993), pp. 250 and 1311-1312. QR181.F84.*
Cohen et al. "Pronounced acute immunosuppression in vivo mediated by HIV Tat challenge", Proceedings of the National Academy of Sciences of the United States of America, vol. 96, Issue 19(Sep. 14, 1999), pp. 10842 10847.*
Bryant et al., Site-Directed Mutagenesis of the src Gene of Rous Sarcoma Virus: Construction and Characterization of a Deletion Mutant Temperature Sensitive for Transformation, Journal of Virology, 1982, 44(2):683-691.*
Bullerjahn et al., Site-directed Deletion Mutants of a Carboxyl-terminal Region of Human Dihydrofolate Reductase, Journal of Biological Chemistry, 1992, 267(2):864-870.*
GenBank accession no: AF110965.
GenBank accession no: AF110967.
GenBank accession no: AF110968.
GenBank accession no: AF110975.
GenBank accession no: M65024.
Adams et al., "The Expression of Hybrid Hiv:ty Virus-like Particles in Yeast," *Nature* 329:68-70 (1987).
Anderson, et al., "Human Gene Therapy," *Nature* 392(6679 Suppl):25-30 (1998).
Andre et al. *J. Virol.* 72(2)1497-1503 (1998).
Arthur, et al., "Serological Responses in Chimpanzees Inoculated with Human Immunodeficiency Virus Glycoprotein (Gp120) Subunit Vaccine," *Proc Natl Acad Sci USA* 84(23):8583-8587 (1987).
Azevedo et al., "Main Features of DNA-Based Immunization Vectors," *Braz J Med Biol Res.* 32(2):147-153 (1999).
Baker et al., "Structures of Bovine and Human Papillomaviruses. Analysis by Cryoelectron Microscopy and Three-dimensional Image Reconstruction, " *Biophys. J.* 60:1445-1456 (1991).
Barr, et al., "Antigenicity and Immunogenicity of Domains of the Human Immunodeficiency Virus (HIV) Envelope Polypeptide Expressed in the Yeast *Saccharomyces cerevisiae*," *Vaccine* 5(2):90-101 (1987).
Barre-Sinoussi et al., "Isolation of a T-Lymphotropic Retrovirus From a Patient at Risk for Acquired Immune Deficiency Syndrome (AIDS)," *Science* 220:868-871 (1983).
Barrett, et al., "Large-scale production and purification of a vaccinia recombinant-derived HIV-1 gp160 and analysis of its immunogenicity," *AIDS Res Hum Retroviruses* 5(2):159-71 (1989).
Beard, W. A., et al.,"Role of the "Helix Clamp" in HIV-1 Reverse Transcriptase Catalytic Cycling as Revealed by Alanine-Scanning Mutagenesis," *Journal of Biological Chemistry* 271(21):12213-12220 (1996).
Berger, P.B., "New Directions in Research: Report from the 10th International Conference on AIDS," *Canadian Medical Association Journal* 152(12):1991-1995 (1995).
Berman, et al., "Human Immunodeficiency Virus Type 1 Challenge of Chimpanzees Immunized with Recombinant Envelope Glycoprotein gp120," *Proc Natl Acad Sci USA* 85(14):5200-5204 (1988).
Berman, et al., "Expression and Immunogenicity of the Extracellular Domain of the Human Immunodeficiency Virus Type 1 Envelope Glycoprotein, gp160," *J Virol.* 63(8):3489-3498 (1989).
Birx and Redfield, "HIV Vaccine Therapy," *Int J Immunopharmacol.* 13(1):129-132 (1991).
Bolognesi, D.P., "Progress in Vaccines Against AIDS," *Science* 246:1233-1234 (1989).
Bolognesi et al., "HIV Vaccine Development: A Progress Report," *Ann. Int Med.* 8(7):603- 611 (1994).

Borrow, et al., "Virus-Specific CD8+ Cytotoxic T-Lymphocyte Activity Associated with Control of Viremia in Primary Human Immunodeficiency Virus Type 1 Infection," *J Viral.* 68(9):6103-6110 (1994).
Borsetti et al., *J. Virot* 72(11):9313-9317 (1998).
Bourgault, et al., "Cytotoxic T-Cell Response and AIDS-Free Survival in Simian Immunodeficiency Virus-Infected Macaques," *AIDS.* 7 (Suppl 2):S73-S79 (1993).
Brown et al., "Chimeric Parvovirus B19 Capsids for the Presentation of Foreign Epitopes," *Virology* 198:477-488 (1994).
Bujacz, G., et al., "The Catalytic Domain of Human Immunodeficiency Virus lntegrase: Ordered Active Site in the F185H Mutant," *Febs Letters* 398(2-3):175-178 (1996).
Burton and Montefiori, "The Antibody Response in HIV-1 Infection," *AIDS11*(suppl. A):S87-S98 (1997).
Burton et al., "Why Do We Not Have an HIV Vaccine and How Can We Make One?" *Nat Med.* 4(5 Suppl):495-498 (1998).
Cao et al., "Replication and neutralization of HIV-1 lacking the V1 and V2 variable loops of the gp 120 envelope glycoprotein," *J. Virology* 71(12):9808-9812, 1997.
Carmichael et al., "Quantitative Analysis of the Human Immunodeficiency Virus Type 1 (Hiv-1)-specific Cytotoxic T Lymphocyte (Ctl) Response at Different Stages of Hiv-1 Infection: Differential Ctl Responses to Hiv-1 and Epstein-barr Virus in Late Disease," *J Exp Med.* 177(2):249-256 (1993).
Chazal N. et al., "Phenotypic Characterization of Insertion Mutants of the Human Immunodeficiency Virus Type 1 Gag Precursor Expressed in Recombinant Baculovirus-infected Cells," *Virology* 68(1):111-122 (1994).
Cheng-Mayer, *PNAS USA* 86:8575-8579 (1989).
Ciernik et al., "Induction of Cytotoxic T Lymphocytes and Antitumor Immunity with Dna Vaccines Expressing Single T Cell Epitopes," *J. Immunot* 156(7):2369-2375 (1996).
Clavel et al., "Isolation of a New Human Retrovirus from West African Patients with AIDS," *Science* 233:343-346 (1986).
Clavel et al., "Molecular Cloning and Polymorphism of the Human Immune Deficiency Virus Type 2," *Nature* 324:691-695 (1986).
Daar et al., "Transient High Levels of Viremia in Patients with Primary Human Immunodeficiency Virus Type 1 Infection," *N Engl J Med.* 324(14):961-964 (1991).
Davey et al., "Subcutaneous administration of interleukin-2 in human immunodeficiency virus type 1-infected persons," *J Infect Dis.* 175(4):781-789 (1997).
Davies J. F., et al., "Crystal structure of the ribonuclease H domain of HIV-1 reverse transcriptase," *Science* 252(5002):88-95 (1991).
Deminie et al., "Evaluation of Reverse Transcriptase and Protease Inhibitors in Two-drug Combinations Against Human Immunodeficiency Virus Replication," *Antimicrob Agents Chemother.* 40(6):1346-1351 (1996).
Desai et al., "Molecular Cloning and Primary Nucleotide Sequence Analysis of a Distinct Human Immunodeficiency Virus Isolate Reveal Significant Divergence in its Genomic Sequence," *Proc. Natl. Acad. Sci: USA* 83:8380-8384 (1986).
Doe et al., "Induction of HIV-1 Envelope (gp120)-Specific Cytotoxic T Lymphocyte Responses in Mice by Recombinant CHO Cell-Derived gp120 is Enhanced by Enzymatic Removal of N-Linked Glycans," *Eur. J. Immunol.* 24:2369-2376 (1994).
Doe, B. And Walker, C.M. "HIV-1 p24 Gag-Specific Cytotoxic T-Lymphocyte Responses in Mice," *AIDS10*(7):793-794 (1996).
D'Souza et al., "Evaluation of Monoclonal Antibodies to Human Immunodeficiency Virus Type I Primary Isolates by Neutralization Assays: Performance Criteria for Selecting Candidate Antibodies for Clinical Trials," *J. Infect. Dis.* 175:1056-1062 (1997).
Dyda F., et al., "Crystal Structure of the Catalytic Domain of HIV-1 Integrase: Similarity to Other Polynucleotidyl Transferases," *Science* 266(5193):1981-1986 (1994).
Earl et al., "Isolate-and Group-specific Immune Responses to the Envelope Protein of Human Immunodeficiency Virus Induced by a Live Recombinant Vaccinia Virus in Macaques," *AIDS Res Hum Retro viruses* 5(1):23-32 (1989).
Earl et al., *PNAS USA* 87:648-652 (1990).
Earl et al., *J. Virol* 65:31-41 (1991).

Edelman, R., "Vaccine Adjuvants," *Rev Infect Dis.* 2(3):370-383 (1980).

Engelman, A. et al., "Structure-based Mutagenesis of the Catalytic Domain of Human Immunodeficiency Virus Type 1 Integrase," *Journal of Virology* 71(5):3507-3514 (1997).

Esnouf et al., "Mechanism of Inhibition of HIV-1 Reverse Transcriptase by Nonnucleoside Inhibitors," *Structural Biology* 2(4)303-308 (1995).

Evans et al., "An Engineered Poliovirus Chimaera Elicits Broadly Reactive Hiv-1 Neutralizing Antibodies," *Nature* 339(6223):385-388 (1989).

Faust et al., "Outpatient Biopsies of the Palatine Tonsil: Access to Lymphoid Tissue for Assessment of Human Immunodeficiency Virus RNA Titers," *Otolalyngol Head Neck Surg.* 114(4):593-598 (1996).

Fennie et al., "Model for Intracellular Folding of the Human Immunodeficiency Virus Type 1 gp120," *J Virol.* 63(2):639-646 (1989).

Ferre et al., "Combination Therapies Against HIV-1 Infection:Exploring the Concept of Combining Antiretroviral Drug Treatments with HIV-1 Immune-Based Therapies in Asymptomatic Individuals," *AIDS Patient Care STDS* 10(6):357-361 (1996).

Fiore et al., "The Biological Phenotype of HIV-I Usually Retained During and After Sexual Transmission," *Virology* 204:297-303 (1994).

Fisher, et al., "Biologically diverse molecular variants within a single HIV-1 isolate," *Nature* 334:444-447 (1988).

Fox et al., "No. Winners Against AIDS," *Bio/Technology* 12(2):128 (1994).

Freed, E.O., *Virology* 251:1-15 (1998).

Gamier, L. et al., "Particle Size Determinants in the Human Immunodeficiency Virus Type 1 Gag Protein," *J Virol* 72(6):4667-4677 (1998).

Goldgur, Y. et al., "Three New Structures of the Core Domain of HIV-1 lntegrase: an Active Site That Binds Magnesium," *Proceedings Of the National Academy Of Sciences Of the United States Of America* 95(16):9150-9154 (1998).

Goudsmit et al., "Human Immunodeficiency Virus Type 1 Neutralization Epitope with Conserved Architecture Elicits Early Type-specific Antibodies in Experimentally Infected Chimpanzees," *Proc. Natl. Acad. Sci. USA* 85:4478-4482 (1988).

Greene, "AIDS and the Immune System," *Scientific American Sep.*:99-105 (1993).

Griffiths J.C. et al., "Hybrid Human Immunodeficiency Virus Gag Particles as an Antigen Carrier System: Induction of Cytotoxic T-cell and Humoral Responses by a Gag:V3 Fusion," *J. Virol.* 67(6):3191-3198 (1993).

Grinnison B. and Laurence, J., "Immunodominant Epitope Regions of HIV-1 Reverse Transcriptase: Correlations with HIV-1+ Serum IgG Inhibitory to Polymerase Activity and With Disease Progression," *Journal of Acquired Immune Deficiency Syndromes and Human Retrovirology* 9(1):58-68 (1995).

Gurgo et al., "Envelope Sequences of Two New United States HIV-1 Isolates," *Virology* 164:531-536 (1988).

Gurunathan et al., "CD40 Ligand/Trimer DNA Enhances Both Humoral and Cellular Immune Responses and Induces Protective Immunity to Infectious and Tumor Challenge," *J Immunol.* 161(9):4563-4571 (1998).

Guyader et al., "Genome Organization and Transactivation of the Human Immunodeficiency Virus Type 2," *Nature* 326:662-669 (1987).

Haas et al., *Current Biology* 6(3):315-324 (1996).

Hagensee et al., "Three-dimensional Structure of Vaccinia Virus-produced Human Papillomavirus Type 1 Capsids," *J. Virol* 68:4503-4505 (1994).

Hahn et al., "Genetic Variation in HTLV-III/LAV Over Time in Patients with AIDS or at Risk for AIDS," *Science* 232:1548-1553 (1986).

Hammer et al., "Issues in Combination Antiretroviral Therapy: a Review," *J Acguir Immune Defic Syndr.* 7(Suppl 2):S24-S37 (1994).

Haynes et al., "Update on the Issues of Hiv Vaccine Development," *Ann Med.* 28(1):39-41 (1996).

Haynes et al., "Toward an Understanding of the Correlates of Protective Immunity to HIV Infection," *Science* 271:324-328 (1996).

Heeney et al., "Beta-chemokines and Neutralizing Antibody Titers Correlate with Sterilizing Immunity Generated in HIV-1 Vaccinated Macaques," *Proc Natl Acad Sci USA* 95 (18):10803-10808 (1998).

Hickman, A. B., et al., "Biophysical and enzymatic properties of the catalytic domain of HIV-1 integrase," *Journal of Biological Chemistry* 269(46):29279-29287 (1994).

Ho et al., "Human Immunodeficiency Virus Neutralizing Antibodies Recognize Several conserved Domain son the Envelope Glycoproteins," *J Virol.* 61:2024-2028 (1987).

Hu et al., "Protection of Macaques Against SIV Infection by Subunit Vaccines of SIV Envelope Glycoprotein gp 160," *Science* 255:456-459 (1992).

Jacobo-Molina, A. et al., "Crystal Structure of Human Immunodeficiency Virus Type 1 Reverse Transcriptase Complexed with Double-stranded DNA at 3.0 A Resolution Shows Bent DNA," *Proceedings Of the National Academy Of Sciences Of the United States Of America* 90(13):6320-6324 (1993).

Javaherian, et al., "Principal Neutralizing Domain of the Human Immunodeficiency Virus Type 1 Envelope Protein," *Proc. Natl. Acad. Sci.* 86:6768-6772 (1989).

Jeffs et al., "Antigenicity of truncated forms of the human immunodeficiency virus type 1 envelope glycoprotein," *J. General Virology* 77(7):1403-1410, 1996.

Kang et al., "Evidence for Non-V3-Specific Neutralizing Antibodies that Interfere With gp 120/CD4 Binding in Human Immunodeficiency Virus I-Infected Humans," *Proc. Natl. Acad. Sci. USA* 88:6171-6175 (1991).

Katz, R. A. and Skalka, A. M., "The Retroviral Enzymes," *Annual Review of Biochemistry* 63:133-73 (1994).

Keefer, et al., "Safety and Immunogenicity of Env 2-3, a Human Immunodeficiency Virus Type 1 Candidate Vaccine, in Combination with a Novel Adjuvant, MTP-PE/MF59. NIAID AIDS Vaccine Evaluation Group," *AIDS Res Hum Retroviruses.* 12(8):683-693 (1996).

Kirnbauer et al., "Efficient Self-assembly of Human Papillomavirus Type 16 L1 and L1-L2 into Virus-Like Particles," *J. Virol.* 67:6929-6936 (1993).

Klenerman, et al., "Original Antigenic Sin Impairs Cytotoxic T Lymphocyte Responses to Viruses Bearing Variant Epitopes," *Nature* 394(6692):482-485 (1998).

Koff et al., "Development and Testing of AIDS Vaccines," *Science* 241:426-432 (1988).

Koff and Schultz, "Progress and Challenges Toward and AIDS Vaccine: Brother, Can You Spare a Paradigm?" *J. Clinical Immunology* 16(3):127-133 (1996).

Kohl et al., "Active Human Immunodeficiency Virus Protease Is Required for Viral Infectivity," *PNAS USA* 85:4686-4690 (1988).

Kohlstaedt, L. A. et al., "Crystal Structure at 3.5 A Resolution of HIV-1 Reverse Transcriptase Complexed with an Inhibitor," *Science* 256(5065):1783-1790 (1992).

Koup et al., "Temporal Association of Cellular Immune Responses with the Initial Control of Virennia in Primary Human Immunodeficiency Virus Type 1 Syndrome," *J Virol.* 68(7):4650-4655 (1994).

Kovacs et al., "Increases in CD4 T Lymphocytes with Intermittent Courses of Interleukin-2 in Patients with Human Immunodeficiency Virus Infection," *New England J. Med.* 332(9):567-575 (1995).

Kovacs et al., "Controlled Trial of Interleukin-2 Infusions in Patients Infected with the Human Immunodeficiency Virus," *N. Engl J Med.* 335(18):1350-1356 (1996).

Krausslich et al., "Processing of in Vitro-synthesized Gag Precursor Proteins of Human Immunodeficiency Virus (HIV) Type 1 by HIV Proteinase Generated in *Escherichia coli*," *J. Virol.* 62:4393-4397 (1988).

Kreuter J., et al., "Mode of Action of Immunological Adjuvants: Some Physicochemical Factors Influencing the Effectivity of Polyacrylic Adjuvants," *Infect Immun.* 19(2):667-675 (1978).

Krug, M. S. and Berger, S. L., "Reverse Transcriptase from Human Immunodeficiency Virus: a Single Template-primer Binding Site Serves Two Physically Separable Catalytic Functions," *Biochemistry* 30(44):10614-10623 (1991).

Kwong et al., *Nature* 393a:648-659 (1998).

Lalvani A. et al., "Rapid effector Function in CD8+ Memory T Cells," *J. Exp. Med.* 186:859-865 (1997).

Lasky et al., "Delineation of a Region of the Human Immunodeficiency Virus Type 1 gp120 Glycoprotein Critical for Interaction with the CD4 Receptor," *Cell* 50(6):975-985 (1987).

Levy et al., "Isolation of Lymphocytopathic Retroviruses from San Francisco Patients with AIDS," *Science* 225:840-842 (1984).

Littman et al., "Unusual Intron in the Immunoglobulin Domain of the Newly Isolated Murine CD4 (L3T4) Gene," *Nature* 325(6103):453-455 (1987).

Looney et al., "Type-restricted Neutralization of Molecular Clones of Human Immunodeficiency Virus," *Science* 241:357-359 (1988).

Lu et al., "Immunogenicity of DNA Vaccines Expressing Human Immunodeficiency Virus Type I Envelope Glycoprotein With and Without Deletions in the V½ and V3 Regions," *AIDS Res. And Human Retroviruses* 14(2):151-155 (1998).

Maddon et al., "The Isolation and Nucleotide Sequence of a Cdna Encoding the T Cell Surface Protein 14: a New Member of the Immunoglobulin Gene Family," *Cell* 42(1):93-104 (1985).

Maignan, S., et al. "Crystal Structures of the Catalytic Domain of HIV-1 Integrase Free and Complexed with its Metal Cofactor: High Level of Similarity of the Active Site with Other Viral Integrases," *Journal of Molecular Biology* 282(2):359-368 (1998).

Mammano et al., *J. Virol* 68(8):4927-4936 (1994).

Manca et al., "Antigenicity of Hiv-derived T Helper Determinants in the Context of Carrier Recombinant Proteins: Effect on T Helper Cell Repertoire Selection," *EurJ lmmunol.* 26(10):2461-2469 (1996).

Mascola et al., *J. Infect. Dis.* 169:48-54 (1994).

Mathews et al., "Restricted Neutralization of Divergent Human T-Lymphotropic Virus Type III Isolates by Antibodies to the Major Envelope Glycoprotein," *Proc. Natl. Acad. Sci. USA* 83:9709-9713 (1986).

Matsushita, et al., "Characterization of a Human Immunodeficiency Virus Neutralizing Monoclonal Antibody and Mapping of the Neutralizing Epitope," *J. Viol.* 62(6):2107-2144 (1988).

Mazumder, A., et al., "Effects of nucleotide analogues on human immunodeficiency virus type 1 integrase," *Molecular Pharmacology* 49(4):621-628 (1996).

Mazza et al., "Recombinant Interleukin-2 (Rll-2) in Acquired Immune Deficiency Syndrome (Aids): Preliminary Report in Patients with Lymphoma Associated with Hiv Infection," *Eur J Haematol.* 49(1):1-6 (1992).

McCluskie, et al., "Route and method of delivery of DNA vaccine influence immune responses in mice and non-human primates," *Mol Med.* 5(5):287-300 (1999).

McCornack et al., "HIV Protease Substrate Conformation: Modulation by Cyclophilin A," *FEBS Letts* 414:84-88 (1997).

McDougal et al., "Binding of the Human Retrovirus HTLV-III/LAV/ARV/HIV to the CD4 (T4) Molecule: Conformation Dependence, Epitope Mapping, Antibody Inhibition, and Potential for Idiotypic Mimicry," *J. Immunol.* 137(9):2937-2944 (1986).

Mcheyzer-Williams, M.G. et al, "Enumeration and Characterization of Memory Cells in the Th Compartment," *Immunol. Rev.* 150:5-21 (1996).

McMichael, A.J. And O'Callaghan, C.A., "A New Look at T Cells," *J. Exp. Med.* 187(9)1367-1371 (1998).

Modrow et al., "Computer-assisted Analysis of Envelope Protein Sequences of Seven Human Immunodeficiency Virus Isolates: Prediction of Antigenic Epitopes in Conserved and Variable Regions," *J. Virol.* 61(2):570-578 (1987).

Montagnier et al., "Human T-Cell Leukemia Viruses: The Family of Human T-Lymphotropic Retroviruses: Their Role in Malignancies and Association with AIDS," *Gallo, Essex & Gross, eds.*, pp. 363-379 (1984).

Montefiori and Evans, "Toward an HIV Type I Vaccine that Generates Potent, Broadly Cross-Reactive Neutralizing Antibodies," *AIDS Res. Human Retroviruses* 15(8):689-698 (1999).

Myers et al., "Human retroviruses and AIDS, 1991," published by the Los Alamos National Laboratory, Los Alamos, NM, 1991, pp. I-A-48 to I-A-56 and II-77 to ll-80.

Nara, et al., "Purified Envelope Glycoproteins From Human Immunodeficiency Virus Type 1 Variants Induce Individual, Type-Specific Neutralizing Antibodies," *J. Virol.* 62:2622-2628 (1988).

Nathanson et al., "Biological Considerations in the Development of a Human Immunodeficiency Virus Vaccine," *J Infect Dis.* 182(2):579-589 (2000).

Novitsky et al., "Molecular Cloning and Phylogenetic Analysis of Human Immunodeficiency Virus Type 1 Subtype C: a Set of 23 Full-Length Clones from Botswana," *J. Virol.* 73(5):4427-4432 (1999).

Nowak and Bangham, "Population Dynamics of Immune Responses to Persistent Viruses," *Science* 272(5258):74-79 (1996).

Odile et al., "Anti-HIV Active Immunization, Evidence for Persistent Cell Mediated Immunity after a 2 Year Follow Up," Eighth International Conference on AISA/III STD World Congress Amsterdam, the Netherlands 19-24 Jul. 1992, Abstract No. MOB 0024.

Okuda et al., "Induction of Potent Humoral and Cell-mediated Immune Responses Following Direct Injection of DNA Encoding the HIV Type 1 Env and Rev gene Products," *AIDS Res Hum Retroviruses*. 11(8):933-943 (1995).

Palaniappan, C. et al., "Mutations Within the Primer Grip Region of HIV-1 Reverse Transcriptase Result in Loss of RNase H Function," *Journal Of Biological Chemistry* 272(17):11157-11164 (1997).

Palker et al., "Type-Specific Neutralization of the Human Immunodeficiency Virus With Antibodies to Env-Encoded Synthetic Peptides," *Proc. Natl. Acad. Sci. USA* 85:1932-1936 (1988).

Park et al., "Overexpression of the Gag-pol Precursor From Human Immunodeficiency Virus Type 1 Proviral Genomes Results in Efficient Proteolytic Processing in The Absence of Virion Production," *J. Virol.* 65:5111(1991).

Patel et al., "Insights into DNA Polymerization Mechanisms from Structure and Function Analysis of HIV-1 Reverse Transcriptase," *Biochemistry* 34:5351-5363 (1995).

Peng et al., *AIDS*, 11:587-595 (1997).

Perelson, et al., "Decay Characteristics of Hiv-1-infected Compartments During Combination Therapy," *Nature* 387(6629):188-191 (1997).

Popovic et al., "Detection, Isolation, and Continuous Production of Cytopathic Retroviruses (HTLV-III) from Patients with AIDS and Pre-AIDS" *Science* 224:497-500 (1984).

Putney et al., "HTLV-III/LAV-Neutralizing Antibodies to an *E. Coli*-Produced Fragment of the Virus Envelope," *Science* 234:1392-1395 (1986).

Pyle et al., "Immune Response to Immunostimulatory Complexes (ISCOMs) Prepared from Human Immunodeficiency Virus Type 1 (HIV-1) or the HIV-1 External Envelope Glycoprotein (gp120)," *Vaccine* 7(5):465-473 (1989).

Ratner et al., *Nature* 313:277-284 (1985).

Redfield and Birx, "Hiv-specific Vaccine Therapy: Concepts, Status, and Future Directions, "*AIDS Res Hum Retroviruses* 8(6):1051-1058 (1992).

Reicin, A.S. et al., "Linker Insertion Mutations in the Human Immunodeficiency Virus Type 1 Gag Gene: Effects on Virion Particle Assembly, Release, and Infectivity," *J. Virol.* 69(2):642- 650 (1995).

Robert-Guroff et al., "HTLV-III-Neutralizing Antibodies in Patients With AIDS and AIDS-Related Complex," *Nature* (London) 316:72-74 (1985).

Robey, et al., "Prospect for Prevention of Human Immunodeficiency Virus Infection: Purified 120-kDa Envelope Glycoprotein Induces Neutralizing Antibody," *Proc Natl Acad Sci USA* 83(18):7023-7027 (1986).

Rodgers, D. W. et al., "The Structure of Unliganded Reverse Transcriptase from the Human Immunodeficiency Virus Type 1," *Proceedings Of the National Academy Of Sciences Of the United States of America* 92(4):1222-1226 (1995).

Rusche et al., "Antibodies That Inhibit Fusion of Human Immunodeficiency Virus-Infected Cells Bind a 24-Amino Acid Sequence of the Viral Envelope, gp 120," *Proc. Nat. Acad. Sci. USA* 85:3198-3202 (1988).

Saag, et al., "Extensive Variation of Human Immunodeficiency Virus Type-1 *in vivo,*" *Nature* 334:440-444 (1988).

Saag and Kuritzkes, "Strategies for Continuing Antiretroviral Therapy," *Intl AIDS Society USA* 4(2):16-19 (1996).

Salk et al., "Prospects for the Control of Aids by Immunizing Seropositive Individuals," *Nature* 327(6122):473-476 (1987).

Sanchez-Pescador et al., *Science* 227(4686):484-492 (1985).

Schernthaner, et al., "Endosperm-specific Activity of a Zein Gene Promoter in Transgenic Tobacco Plants," *The EMBO J.* 7:1249-1259 (1988).
Schneider et al., *J. Virol.* 71(7):4892-4903 (1997).
Schulhafer et al., "Acquired Immunodeficiency Syndrome: Molecular Biology and its Therapeutic Intervention (review)," *in Vivo* 3(2):61-78 (1989).
Sheng N. And Dennis, D., "Active Site Labeling of HIV-1 Reverse Transcriptase," *Biochemistry* 32(18):4938-4942 (1993).
Smith et al., "Blocking of HIV-1 infectivity by a soluble, secreted form of the CD4 antigen," *Science* 238(4834):1704-1707 (1987).
Spence R. A., et al., "Mechanism of Inhibition of HIV-1 Reverse Transcriptase by Nonnucleoside Inhibitors," *Science* 267(5200):988-993 (1995).
Srinivasan et al., "Molecular Characterization of Human Immunodeficiency Virus from Zaire: Nucleotide Sequence Analysis Identifies Conserved and Variable Domains in the Envelope Gene," *Gene* 52:71-82 (1987).
Stamatatos et al., "Effect of Major Deletions in the V1 and V2 Loops of a Macrophage-Tropic HIV Type 1 Isolate on Viral Envelope Structure, Cell Entry, and Replication," *AIDS Res. Human Retroviruses* 14(13):1129-1139 (1998).
Stamatatos et al., "An envelope modification that renders a primary, neutralization-resistant clade B HIV-1 isolate highly susceptible to neutralisation by sera from other clades," *J. Virology* 72(10):7840-7845, 1998.
Starcich et al., "Identification and Characterization of Conserved and Variable Regions in the Envelope Gene of HTLV-III/LAV, the Retrovirus of AIDS" *Cell* 45:637-648 (1986).
Steimer et al., "Genetically Engineered Human Immunodeficiency Envelope Glycoprotein Gp120 Produced in Yeast Is the Target of Neutralizing Antibodies," *Vaccines* 87:236-241 (1987).
Sternberg et al., "Prediction of Antigenic Determinants and Secondary Structures of the Major Aids Virus Proteins," *FEBS Letters* 218(2):231-237 (1987).
Thali et al., "Characterization of Conserved Human Immunodeficiency Virus Type 1 gp 120 Neutralization Epitopes Exposed Upon gp 120-CD4 Binding," *J. Virol.* 67(7):3978-3988 (1993).
Tindle et al., "Chimeric Hepatitis B Core Antigen Particles Containing B- and Th-epitopes of Human Papillomavirus Type 16 E7 Protein Induce Specific Antibody and T-helper Responses in Immunised Mice," *Virology* 200:547-557 (1994).
Trkola et al., "Cross-Clade Neutralization of Primary Isolates of Human Immunodeficiency Virus Type 1 by Human Monoclonal Antibodies and Tetrameric CD4-IgG," *J. Virol.* 69:6609- 6617 (1995).
Vacca et al., "L-735,524: an Orally Bioavailable Human Immunodeficiency Virus Type 1 Protease Inhibitor," *Proc Natl Acad Sci USA* 91(9):4096-4100 (1994).
Verma et al., "Gene therapy —Promises, Problems and Prospects," *Nature* 389(6648):239-242 (1997).
Vilmer et al., "Isolation of New Lymphotropic Retrovirus from Two Siblings with Haemophilia B, One with AIDS," *The Lancet* 1:753 (1984).
Wagner R., et al., "Studies on Processing, Particle Formation, and Immunogenicity of the HIV-1 gag Gene Product: a Possible Component of a HIV Vaccine," *Arch Virol* 127:117-137.

Wagner et al., "Assembly and Extracellular Release of Chimeric HIv-1 PR55gag Retrovirus-like Particles," *Virology* 200:162-175 (1994).
Wagner et al., "Construction, Expression, and Immunogenicity of Chimeric HIV-1 Virus-like Particles," *Virology* 220:128-140 (1996).
Wakefield, J. K.et al., "*In Vitro* Enzymatic Activity of Human Immunodeficiency Virus Type 1 Reverse Transcriptase Mutants in the Highly Conserved YMDD Amino Acid Motif Correlates with the Infectious Potential of the Proviral Genome," *Journal of Virology* 66(11):6806-6812 (1992).
Wan et al., "Autoprocessing: an Essential Step for the Activation of HIV-1 Protease," *Biochem. J.* 316:569-573 (1996).
Wang et al., *Virology* 200:524-534 (1994).
Wang et al., "Induction of Humoral and Cellular Immune Responses to the Human Immunodeficiency Type 1 Virus in Nonhuman Primates by in Vivo DNA Inoculation," *Virology* 211(1):102-112 (1995).
Wang C. et al., "Analysis of Minimal Human Immunodeficiency Virus Type 1 Gag Coding Sequences Capable of Virus-like Particle Assembly and Release," *J Virol* 72(10): 7950-7959 (1998).
Weis et al., "Neutralization of Human T-Lymphotropic Virus Type Iii by Sera of AIDS and AIDS-Risk Patients," *Nature* (London) 316:69-72 (1985).
Weis et al., "Variable and Conserved Neutralization Antigens of Human Immunodeficiency Virus," *Nature* (London) 324:572-575 (1986).
Wu X., et al., "Targeting foreign proteins to human immunodeficiency virus particles via fusion with Vpr and Vpx," *J. Virol.* 69(6):3389-3398 (1995).
Wyatt et al., "Involvement of the V1/V2 Variable Loop Structure in the Exposure of Human Immunodeficiency Virus Type 1 gp 120 Epitopes Induced by Receptor Binding," *J. Virol.* 69(9):5723-5733 (1995).
Wyatt et al., *Nature* 393:705-711(1998).
Yeni et al., "Antiretroviral and Immune-based Therapies: Update," *AIDS* 7(Suppl 1):S173-S184 (1993).
Yenofsky et al., "A Mutant Neomycin Phosphotransferase II Gene Reduces the Resistance of Transformants to Antibiotic Selection Pressure," *Proc. Natl. Acad. Sci. USA* 87:3435-3439 (1990).
Yourno et al., "Nucleotide Sequence Analysis of the Env Gene of a New Zairian Isolate of HIV-1," *AIDS Res Hum Retroviruses* 4(3):165-73 (1988).
Zagury et al., "Progress Report IV on Aids Vaccine in Human: Phase I Clinical Trial in Hiv Infected Patients," *VII International Conference on AIDS*, Florence Jun. 16-21, 1991, Abstract No. M.A. 67.
Zagury et al., "One-year Follow-up of Vaccine Therapy in Hiv-infected Immune-deficient Individuals: a New Strategy," *J. Acquired Immune Deficiency Syndromes* 5:676-681 (1992).
Zhang Y., et al., "Analysis of the Assembly Function of the Human Immunodeficiency Virus Type 1 Gag Protein Nucleocapsid Domain," *J Virol* 72(3):1782-1789 (1998).
Zhu et al., "Genotypic and Phenotypic Characterization of HIV-1 in Patients with Primary Infection," *Science* 261:1179-1181 (1993).
zur Megede et al., "Increased Expression and Immunogenicity of Sequence-modified Human Immunodeficiency Virus Type 1 Gag Gene," *J Virol.* 74(6):2628-2635 (2000).

\* cited by examiner

```
                1                      •                  50
HXB2      (1)   MRVK---EKYQHLWRWGWRWGTMLLGMLMIC-SATEKLWVTVYYGVPVWK
162       (1)   ---------MDAMKRGLCCVLLLCGAVFVSPSAVEKLWVTVYYGVPVWK
SF2       (1)   MKVKGTRRNYQHLWRWG----TLLLGMLMIC-SATEKLWVTVYYGVPVWK
CM236     (1)   MRVKETQMNWPNLWKWG----TLLLGIVIIC-SASNNLWVTVYYGVPVWR
US4       (1)   --MR---KHCQHLWRGG----ILLLGILMIC-RATTVLWVTVYYGVPVWK
Consensus (1)   MRVK   YQHLWRWG     TLLLGMLMIC SATEKLWVTVYYGVPVWK 51                     •                 100
HXB2      (47)  EATTTLFCASDAKAYDTEVHNVWATHACVPTDPNPQEVVLVNVTENFNMW
162       (41)  EATTTLFCASDAKAYDTEVHNVWATHACVPTDPNPQEIVLENVTENFNMW
SF2       (46)  EATTTLFCASDARAYDTEVHNVWATHACVPTDPNPQEVVLGNVTENFNMW
CM236     (46)  DADTTLFCASDAKAHETEVHNVWATHACVPTDPNPQEIHLENVTENFNMW
US4       (41)  EATTTLFCASDAKAYKAEAHNVWATHACVPTDPNPQEVNLTNVTENFNMW
Consensus (51)  EATTTLFCASDAKAYDTEVHNVWATHACVPTDPNPQEVVL NVTENFNMW 101             •↓      •         •       150
HXB2      (97)  KNDMVEQMHEDIISLWDQSLKPCVKLTPLCVSLKCTDL------------
162       (91)  KNNMVEQMHEDIISLWDQSLKPCVKLTPLCVTLHCTNL------------
SF2       (96)  KNNMVEQMQEDIISLWDQSLKPCVKLTPLCVTLNCTDL------------
CM236     (96)  KNNMVEQMQEDVISLWDQSLKPCVKLTPLCVTLNCTNAK-----------
US4       (91)  KNNMVEQMHEDIISLWDQSLKPCVKLTPLCVTLNCTDKLTGSTNGTNSTS
Consensus (101) KNNMVEQMHEDIISLWDQSLKPCVKLTPLCVTLNCTDL 151                    •                 200
HXB2      (135) -------KNDTNTNSSSGRMIMEKGEIKNCSFNISTSIRGKVQKEYAFFY
162       (129) -------KNATNTKSSNWKEMD-RGEIKNCSFKVTTSIRNKMQKEYALFY
SF2       (134) -------GKATNTNSSNWKEEI-KGEIKNCSFNITTSIRDKIQKENALER
CM236     (135) ------LTNVNNITSVSNTIGNITDEVRNCSFNMTTELRDKKQKVHALFY
US4       (141) GTNSTSGTNSTSTNSTDSWEKMPEGEIKNCSENITTSVRDKVQKFYSLFY
Consensus (151)        NATNTNSS KE M KGEIKNCSFNITTSIRDKVQKEYALFY 201                   •  ↓•        •      250
HXB2      (178) KLDIIPIDNDTTS-----YKLTSCNTSVITQACPKVSFEPIPIHYCAPAG
162       (171) KLDVVPIDNDNTS-----YKLINCNTSVITQACPKVSFEPIPIHYCAPAG
SF2       (176) NLDVVPIDNASTTTNYTNYRLIHCNRSVITQACPKVSFEPIPIHYCTPAG
CM236     (179) KLDIVPIEDNKTS---SEYRLINCNTSVIKQACPKISFDPIPIHYCTPAG
US4       (191) KLDVVPIDNDNAS-----YRLINCNTSVITQACPKVSFEPIPIHYCAPAG
Consensus (201) KLDVVPIDND TS     YRLINCNTSVITQACPKVSFEPIPIHYCAPAG 251     •              •         •       300
HXB2      (223) FAILKCNNKTFNGTGPCTNVSTVQCTHGIRPVVSTQLLLNGSLAEEEVVI
162       (216) FAILKCNDKKFNGSGPCTNVSTVQCTHGIRPVVSTQLLLNGSLAEEGVVI
SF2       (226) FAILKCNNKTFNGKGPCTNVSTVQCTHGIRPIVSTQLLLNGSLAEEEVVI
CM236     (226) YAILKCNDKNFNGTGPCKNVSSVQCTHGIKPVVSTQLLLNGSLAEEEIII
US4       (236) FAILKCKDKKFNGTGPCKNVSTVQCTHGIRPVVSTQLLLNGSLAEEEIVL
Consensus (251) FAILKCNDK FNGTGPCTNVSTVQCTHGIRPVVSTQLLLNGSLAEEEVVI 301           •         •         •      350
HXB2      (273) RSVNFTDNAKTIIVQLNTSVEINCTRPNNNTRKRIRIQRGPGRAFVTIGK
162       (266) RSENFTDNAKTIIVQLKESVEINCTRPNNNTRKSITT--GPGRAFYATGD
SF2       (276) RSDNFTNNAKTIIVQLNESVAINCTRPNNNTRKSIYI--GPGRAFHTTGR
CM236     (276) RSENLTNNAKTIIVHLNKSVEINCTRPSNNTRTSETT--GPGQVEYRTGD
US4       (286) RSENFTDNAKTIIVQLNESVEINCIRPNNNTRKSIHT--GPGRAFYATGD
Consensus (301) RSENFTDNAKTIIVQLNESVEINCTRPNNNTRKSI I  GPGRAFY TGD
```

*FIG. 2A*

```
                   351         •                                            400
HXB2       (323)   I-GNMRQAHCNISRAKWNNTLKQIASKLREQFGNNKTIIFKQSSGGDPEI
162        (314)   IIGDIRQAHCNLSGEKWNNTLKQIVTKLQAQFG-NKTIVFKQSSGGDPEI
SF2        (324)   LIGDIRKAHCNISRAQWNNTLEQIVKKLREQFGNNKTIVFNQSSGGDPEI
CM236      (324)   IIGDIRKAYCEINGTKWNEVLTQVTEKLKEHFN-NKTIIFQPPSGGDLEI
US4        (334)   IIGDIRQAHCNLSKANWTNTLEQIVEKLREQFGNNKTIIFNSSSGGDPEI
Consensus  (351)   IIGDIRQAHCNISRAKWNNTL QIV KLREQFGNNKTIIFNQSSGGDPEI 401    •        •                                      •450
HXB2       (372)   VTHSFNCGGEFFYCNSTQLFNSTWFNSTWSTEGSNNTEGSDTITLPCRIK
162        (363)   VMHSFNCGGEFFYCNSTQLFNSTW-NN---TIGPNNTNG--TITLPCRIK
SF2        (374)   VMHSFNCRGEFFYCNTTQLFNNTWRLN--HTEG---TKGNDTIILPCRIK
CM236      (373)   TMHHFNCRGEFFYCNTTRLFNNTCIEN--GTMG--GCNG--TIILPCKIK
US4        (384)   VFHSFNCGGEFFYCNTSQLFNSTW--N--ITEEVNKTKENDTIILPCRIR
Consensus  (401)   VMHSFNCGGEFFYCNTTQLFNSTW  N    TEG N T G DTIILPCRIK ↓
                   451         ↓             •                             500
HXB2       (422)   QIINMWQKVGKAMYAPPISGQIRCSSNITGLLLTRDGG---NSNNESEIF
162        (407)   QLINRWQEVGKAMYAPPIRGQIRCSSNITGLLLTRDGGK--EISNTTEIF
SF2        (419)   QIINMWQEVGKAMYAPPIGGQISCSSNITGLLLTRDGGT--NVTNDTEVF
CM236      (417)   QIINMWQGAGQAMYAPPISGRINCVSNITGILLTRDGG---AINTTNETF
US4        (430)   QIINMWQEVGKAMYAPPIRGQIKCSSNITGLLLTRDGGTNNNRTNDTETF
Consensus  (451)   QIINMWQEVGKAMYAPPI GQIRCSSNITGLLLTRDGG     NITNDTEIF 501                                       *           550
HXB2       (469)   RPGGGDMRDNWRSELYKYKVVKIEPLGVAPTKAKRRVVQREKRAVGI-GA
162        (455)   RPGGGDMRDNWRSELYKYKVVKIEPLGVAPTKAKRRVVQREKRAVTL-GA
SF2        (467)   RPGGGDMRDNWRSELYKYKVTKIEPLGIAPTKAKRRVVQREKRAVGIVGA
CM236      (464)   RPGGGNIKDNWRSELYKYKVVQIEPLGIAPTRAKRRVVEREKRAVGI-GA
US4        (480)   RPGGGNMKDNWRSELYKYKVVRIEPLGVAPTQAKRRVVQREKRAVGL-GA
Consensus  (501)   RPGGGDMRDNWRSELYKYKVVKIEPLGVAPTKAKRRVVQREKRAVGI GA 551                                                   600
HXB2       (518)   LFLGFLGAAGSTMGAASMTLTVQARQLLSGIVQQQNNLLRAIEAQQHLLQ
162        (504)   MFLGFLGAAGSTMGARSLTLTVQARQLLSGIVQQQNNLLRAIEAQQHLLQ
SF2        (517)   MFLGFLGAAGSTMGAVSLTLTVQARQLLSGIVQQQNNLLRAIEAQQHLLQ
CM236      (513)   MIFGFLGAAGSTMGAASTTLTVQARQLLSGIVQQQSNLLRAIEAQQHLLQ
US4        (529)   LFIGFLGAAGSTMGAASVTLTVQARQLLSGIVQQQNNLLRAIEAQQHLLQ
Consensus  (551)   MFLGFLGAAGSTMGAASLTLTVQARQLLSGIVQQQNNLLRAIEAQQHLLQ 601                                •       •          650
HXB2       (568)   LTVWGIKQLQARILAVERYLKDQQLLGIWGCSGKLICTTAVPWNASWSNK
162        (554)   LTVWGIKQLQARVLAVERYLKDQQLLGIWGCSGKLICTTAVPWNASWSNK
SF2        (567)   LTVWGIKQLQARVLAVERYLRDQQLLGIWGCSGKLICTTAVPWNASWSNK
CM236      (563)   LTVWGIKQLQARVLAVERYLKDQKFLGLWGCSGKLICTTAVPWNSTWSNR
US4        (579)   LTVWGIKQLQARILAVERYLKDQQLLGIWGCSGKLICTTTVPWNSSWSNK
Consensus  (601)   LTVWGIKQLQARVLAVERYLKDQQLLGIWGCSGKLICTTAVPWNASWSNK
```

*FIG. 2B*

```
             651                                              700
HXB2     (618) SLEQIWNHTTWMEWDREINNYTSLIHSLIEESQNQQEKNEQELLELDKWA
 162     (604) SLDQIWNNMTWMEWEREIDNYTNLIYTLIEESQNQQEKNEQELLELDKWA
 SF2     (617) SLEDIWDNMTWMQWEREIDNYTNTIYTLIEESQNQQEKNEQELLELDKWA
CM236    (613) SYEEIWNNMTWIEWEREISNYTNQIYETLTESQNQQDRNEKDLLELDKWA
 US4     (629) SLTEIWDNMTWMEWEREIGNYTGLIYNLIEIAQNQQEKNEQELLELDKWA
Consensus(651) SLEEIWNNMTWMEWEREI NYTNLIYTLIEESQNQQEKNEQELLELDKWA 701                                              750
HXB2     (668) SLWNWFNITNWLWYIKLFIMIVGGLVGLRIVFAVLSIVNRVRQGYSPLSF
 162     (654) SLWNWFDISKWLWYIKIFIMIVGGLVGLRIVFTVLSIVNRVRQGYSPLSF
 SF2     (667) SLWNWFSITNWLWYIKIFIMTVGGLVGLRIVFAVLSIVNRVRQGYSPLSF
CM236    (663) SLWNWFDITKWLWYIKIFIMIIGGLIGLRIIFAVLSIVNRVRQGYSPLSF
 US4     (679) SLWNWFDITNWLWYIRIFIMIVGGLIGLRIVFAVLSIVNRVRQGYSPISL
Consensus(701) SLWNWFDITNWLWYIKIFIMIVGGLVGLRIVFAVLSIVNRVRQGYSPLSF 751                                             •800
HXB2     (718) QTHLPTPRGPDRPEGIEEEGGERDRDRSIRLVNGSLALIWDDLRSLCLFS
 162     (704) QTRFPAPRGPDRPEGIEEEGGERDRDRSSPLVHGLLALIWDDLRSLCLFS
 SF2     (717) QTRLPVPRGPDRPDGIEEEGGERDRDRSVRLVDGFLALIWEDLRSLCLFS
CM236    (713) QTPFHHQREPDRSERIEEGGGEQGRDRSVRLVSGFLALAWDDLRSLCLFS
 US4     (729) QTRLPAQRGPDRPEGIEEEGGERDRDRSNRLVHGLLALIWDDLRSLCLFS
Consensus(751) QTRLP PRGPDRPEGIEEEGGERDRDRSVRLV G LALIWDDLRSLCLFS 801                                              850
HXB2     (768) YHRLRDLLLIVTRIVELLGR-------RGWEALKYWWNLLQYWSQELKNS
 162     (754) YHRLRDLLLIAARIVELLGR-------RGWEALKYWGNLLQYWIQELKNS
 SF2     (767) YRRLRDLLLIAARTVELLGH-------RGWEALKYWWSLLQYWIQELKNS
CM236    (763) YHRLRDFLLIAARTVKLLGRSSLKGLRRGWEGLKYLGNLLLYWGQELKIS
 US4     (779) YHRLRDLLLIVARIVELLGR-------RGWEALKYWWNLLQYWSQELKSS
Consensus(801) YHRLRDLLLIAARIVELLGR       RGWEALKYWWNLLQYW QELKNS 851                                              900
HXB2     (811) AVSLLNATAIAVAEGTDRVIEVVQGACRAIRHIPRRIRQGLERILL----
 162     (797) AVSLFDAIAIAVAEGTDRIIEVAQRIGRAFLHIPRRIRQGFERALL----
 SF2     (810) AVSWLNATAIAVTEGTDRVIEVAQRAIRAILHTHRRIRQGLERLLL----
CM236    (813) AISLLDATAIIVAGWTDRVIEVAQGAWRAILHIPRRIRQGLERTLL----
 US4     (822) AVSLFNATAIAVAEGTDRIIEIVQRIFRAVIHIPRRIRQGLERALL----
Consensus(851) AVSLLNATAIAVAEGTDRVIEVAQRAFRAILHIPRRIRQGLER LL
```

FIG. 2C

|                  |       | 1                                        40 |
|------------------|-------|---------------------------------------------|
| Leu122-Ser199    | (1)   | GAATTCGCCACCATGGATGCAATGAAGAGAGGGCTCTGCT |
| Val127-Asn195    | (1)   | GAATTCGCCACCATGGATGCAATGAAGAGAGGGCTCTGCT |
| Val120-Ile201B   | (1)   | GAATTCGCCACCATGGATGCAATGAAGAGAGGGCTCTGCT |
| Val120-Ala204    | (1)   | GAATTCGCCACCATGGATGCAATGAAGAGAGGGCTCTGCT |
| Val120-Ile201    | (1)   | GAATTCGCCACCATGGATGCAATGAAGAGAGGGCTCTGCT |
| Val120-Thr202    | (1)   | GAATTCGCCACCATGGATGCAATGAAGAGAGGGCTCTGCT |
| Lys121-Val200    | (1)   | GAATTCGCCACCATGGATGCAATGAAGAGAGGGCTCTGCT |
| Consensus        | (1)   | GAATTCGCCACCATGGATGCAATGAAGAGAGGGCTCTGCT |
|                  |       | 41                                       80 |
| Leu122-Ser199    | (41)  | GTGTGCTGCTGCTGTGTGGAGCAGTCTTCGTTTCGCCCAG |
| Val127-Asn195    | (41)  | GTGTGCTGCTGCTGTGTGGAGCAGTCTTCGTTTCGCCCAG |
| Val120-Ile201B   | (41)  | GTGTGCTGCTGCTGTGTGGAGCAGTCTTCGTTTCGCCCAG |
| Val120-Ala204    | (41)  | GTGTGCTGCTGCTGTGTGGAGCAGTCTTCGTTTCGCCCAG |
| Val120-Ile201    | (41)  | GTGTGCTGCTGCTGTGTGGAGCAGTCTTCGTTTCGCCCAG |
| Val120-Thr202    | (41)  | GTGTGCTGCTGCTGTGTGGAGCAGTCTTCGTTTCGCCCAG |
| Lys121-Val200    | (41)  | GTGTGCTGCTGCTGTGTGGAGCAGTCTTCGTTTCGCCCAG |
| Consensus        | (41)  | GTGTGCTGCTGCTGTGTGGAGCAGTCTTCGTTTCGCCCAG |
|                  |       | 81                                      120 |
| Leu122-Ser199    | (81)  | CGCCGTGGAGAAGCTGTGGGTGACCGTGTACTACGGCGTG |
| Val127-Asn195    | (81)  | CGCCGTGGAGAAGCTGTGGGTGACCGTGTACTACGGCGTG |
| Val120-Ile201B   | (81)  | CGCCGTGGAGAAGCTGTGGGTGACCGTGTACTACGGCGTG |
| Val120-Ala204    | (81)  | CGCCGTGGAGAAGCTGTGGGTGACCGTGTACTACGGCGTG |
| Val120-Ile201    | (81)  | CGCCGTGGAGAAGCTGTGGGTGACCGTGTACTACGGCGTG |
| Val120-Thr202    | (81)  | CGCCGTGGAGAAGCTGTGGGTGACCGTGTACTACGGCGTG |
| Lys121-Val200    | (81)  | CGCCGTGGAGAAGCTGTGGGTGACCGTGTACTACGGCGTG |
| Consensus        | (81)  | CGCCGTGGAGAAGCTGTGGGTGACCGTGTACTACGGCGTG |
|                  |       | 121                                     160 |
| Leu122-Ser199    | (121) | CCCGTGTGGAAGGAGGCCACCACCACCCTGTTCTGCGGCA |
| Val127-Asn195    | (121) | CCCGTGTGGAAGGAGGCCACCACCACCCTGTTCTGCGGCA |
| Val120-Ile201B   | (121) | CCCGTGTGGAAGGAGGCCACCACCACCCTGTTCTGCGGCA |
| Val120-Ala204    | (121) | CCCGTGTGGAAGGAGGCCACCACCACCCTGTTCTGCGCCA |
| Val120-Ile201    | (121) | CCCGTGTGGAAGGAGGCCACCACCACCCTGTTCTGCGCCA |
| Val120-Thr202    | (121) | CCCGTGTGGAAGGAGGCCACCACCACCCTGTTCTGCGCCA |
| Lys121-Val200    | (121) | CCCGTGTGGAAGGAGGCCACCACCACCCTGTTCTGCGCCA |
| Consensus        | (121) | CCCGTGTGGAAGGAGGCCACCACCACCCTGTTCTGCGCCA |
|                  |       | 161                                     200 |
| Leu122-Ser199    | (161) | GCGACGCCAAGGCCTACGACACCGAGGTGCACAACGTGTG |
| Val127-Asn195    | (161) | GCGACGCCAAGGCCTACGACACCGAGGTGCACAACGTGTG |
| Val120-Ile201B   | (161) | GCGACGCCAAGGCCTACGACACCGAGGTGCACAACGTGTG |
| Val120-Ala204    | (161) | GCGACGCCAAGGCCTACGACACCGAGGTGCACAACGTGTG |
| Val120-Ile201    | (161) | GCGACGCCAAGGCCTACGACACCGAGGTGCACAACGTGTG |
| Val120-Thr202    | (161) | GCGACGCCAAGGCCTACGACACCGAGGTGCACAACGTGTG |
| Lys121-Val200    | (161) | GCGACGCCAAGGCCTACGACACCGAGGTGCACAACGTGTG |
| Consensus        | (161) | GCGACGCCAAGGCCTACGACACCGAGGTGCACAACGTGTG |
|                  |       | 201                                     240 |
| Leu122-Ser199    | (201) | GGCCACCCACGCGTGCGTGCCCACCGACCCCAACCCCCAG |
| Val127-Asn195    | (201) | GGCCACCCACGCCTGCGTGCCCACCGACCCCAACCCCCAG |
| Val120-Ile201B   | (201) | GGCCACCCACGCCTGCGTGCCCACCGACCCCAACCCCCAG |
| Val120-Ala204    | (201) | GGCCACCCACGCCTGCGTGCCCACCGACCCCAACCCCCAG |
| Val120-Ile201    | (201) | GGCCACCCACGCCTGCGTGCCCACCGACCCCAACCCCCAG |
| Val120-Thr202    | (201) | GGCCACCCACGCCTGCGTGCCCACCGACCCCAACCCCCAG |
| Lys121-Val200    | (201) | GGCCACCCACGCCTGCGTGCCCACCGACCCCAACCCCCAG |
| Consensus        | (201) | GGCCACCCACGCCTGCGTGCCCACCGACCCCAACCCCCAG |
|                  |       | 241                                     280 |
| Leu122-Ser199    | (241) | GAGATCGTGCTGGAGAACGTGACCGAGAACTTCAACATGT |
| Val127-Asn195    | (241) | GAGATCGTGCTGGAGAACGTGACCGAGAACTTCAACATGT |

FIG. 3A

```
Val120-Ile201B  (241) GAGATCGTGCTGGAGAACGTGACCGAGAACTTCAACATGT
Val120-Ala204   (241) GAGATCGTGCTGGAGAACGTGACCGAGAACTTCAACATGT
Val120-Ile201   (241) GAGATCGTGCTGGAGAACGTGACCGAGAACTTCAACATGT
Val120-Thr202   (241) GAGATCGTGCTGGAGAACGTGACCGAGAACTTCAACATGT
Lys121-Val200   (241) GAGATCGTGCTGGAGAACGTGACCGAGAACTTCAACATGT
    Consensus   (241) GAGATCGTGCTGGAGAACGTGACCGAGAACTTCAACATGT
                      281                                          320
Leu122-Ser199   (281) GGAAGAACAACATGGTGGAGCAGATGCACGAGGACATCAT
Val127-Asn195   (281) GGAAGAACAACATGGTGGAGCAGATGCACGAGGACATCAT
Val120-Ile201B  (281) GGAAGAACAACATGGTGGAGCAGATGCACGAGGACATCAT
Val120-Ala204   (281) GGAAGAACAACATGGTGGAGCAGATGCACGAGGACATCAT
Val120-Ile201   (281) GGAAGAACAACATGGTGGAGCAGATGCACGAGGACATCAT
Val120-Thr202   (281) GGAAGAACAACATGGTGGAGCAGATGCACGAGGACATCAT
Lys121-Val200   (281) GGAAGAACAACATGGTGGAGCAGATGCACGAGGACATCAT
    Consensus   (281) GGAAGAACAACATGGTGGAGCAGATGCACGAGGACATCAT
                      321                                          360
Leu122-Ser199   (321) CAGCCTGTGGGACCAGAGCCTGAAGCCCTGCGTGAAGCTG
Val127-Asn195   (321) CAGCCTGTGGGACCAGAGCCTGAAGCCCTGCGTGAAGCTG
Val120-Ile201B  (321) CAGCCTGTGGGACCAGAGCCTGAAGCCCTGCGTGCC----
Val120-Ala204   (321) CAGCCTGTGGGACCAGAGCCTGAAGCCCTGCGTGGG----
Val120-Ile201   (321) CAGCCTGTGGGACCAGAGCCTGAAGCCCTGCGTGGG----
Val120-Thr202   (321) CAGCCTGTGGGACCAGAGCCTGAAGCCCTGCGTGGG----
Lys121-Val200   (321) CAGCCTGTGGGACCAGAGCCTGAAGCCCTGCGTGAAGG--
    Consensus   (321) CAGCCTGTGGGACCAGAGCCTGAAGCCCTGCGTG
                      361                                          400
Leu122-Ser199   (361) ----------------GGCAA--------------CAGCG
Val127-Asn195   (361) ACCCCCCTGTGCGTGGGGGCAGGGAACTGCAACACCAGCG
Val120-Ile201B  (357) --------------------------------------CG
Val120-Ala204   (357) ----------------------------------------
Val120-Ile201   (357) --------------------------------------CG
Val120-Thr202   (357) --------------------------------------CG
Lys121-Val200   (359) -----------------------------C-----CCCCG
    Consensus   (361)                                        CG
                      401                                          440
Leu122-Ser199   (371) TGATCACCCAGGCCTGCCCCAAGGTGAGCTTCGAGCCCAT
Val127-Asn195   (401) TGATCACCCAGGCCTGCCCCAAGGTGAGCTTCGAGCCCAT
Val120-Ile201B  (359) GCATCACCCAGGCCTGCCCCAAGGTGAGCTTCGAGCCCAT
Val120-Ala204   (357) ----CGCCGGCGCCTGCCCCAAGGTGAGCTTCGAGCCCAT
Val120-Ile201   (359) GCATCACCCAGGCCTGCCCCAAGGTGAGCTTCGAGCCCAT
Val120-Thr202   (359) GCGCGACCCAGGCCTGCCCCAAGGTGAGCTTCGAGCCCAT
Lys121-Val200   (365) TGATCACCCAGGCCTGCCCCAAGGTGAGCTTCGAGCCCAT
    Consensus   (401)     ATCACCCAGGCCTGCCCCAAGGTGAGCTTCGAGCCCAT
                      441                                          480
Leu122-Ser199   (411) CCCCATCCACTACTGCGCCCCCGCCGGCTTCGCCATCCTG
Val127-Asn195   (441) CCCCATCCACTACTGCGCCCCCGCCGGCTTCGCCATCCTG
Val120-Ile201B  (399) CCCCATCCACTACTGCGCCCCCGCCGGCTTCGCCATCCTG
Val120-Ala204   (393) CCCCATCCACTACTGCGCCCCCGCCGGCTTCGCCATCCTG
Val120-Ile201   (399) CCCCATCCACTACTGCGCCCCCGCCGGCTTCGCCATCCTG
Val120-Thr202   (399) CCCCATCCACTACTGCGCCCCCGCCGGCTTCGCCATCCTG
Lys121-Val200   (405) CCCCATCCACTACTGCGCCCCCGCCGGCTTCGCCATCCTG
    Consensus   (441) CCCCATCCACTACTGCGCCCCCGCCGGCTTCGCCATCCTG
                      481                                          520
Leu122-Ser199   (451) AAGTGCAACGACAAGAAGTTCAACGGCAGCGGCCCTGCA
Val127-Asn195   (481) AAGTGCAACGACAAGAAGTTCAACGGCAGCGGCCCCTGCA
Val120-Ile201B  (439) AAGTGCAACGACAAGAAGTTCAACGGCAGCGGCCCCTGCA
Val120-Ala204   (433) AAGTGCAACGACAAGAAGTTCAACGGCAGCGGCCCCTGCA
Val120-Ile201   (439) AAGTGCAACGACAAGAAGTTCAACGGCAGCGGCCCCTGCA
```

FIG. 3B

```
Val120-Thr202   (439) AAGTGCAACGACAAGAAGTTCAACGGCAGCGGCCCCTGCA
Lys121-Val200   (445) AAGTGCAACGACAAGAAGTTCAACGGCAGCGGCCCCTGCA
    Consensus   (481) AAGTGCAACGACAAGAAGTTCAACGGCAGCGGCCCCTGCA
                      521                                          560
Leu122-Ser199   (491) CCAACGTGAGCACCGTGCAGTGCACCCACGGCATCCGCCC
Val127-Asn195   (521) CCAACGTGAGCACCGTGCAGTGCACCCACGGCATCCGCCC
Val120-Ile201B  (479) CCAACGTGAGCACCGTGCAGTGCACCCACGGCATCCGCCC
Val120-Ala204   (473) CCAACGTGAGCACCGTGCAGTGCACCCACGGCATCCGCCC
Val120-Ile201   (479) CCAACGTGAGCACCGTGCAGTGCACCCACGGCATCCGCCC
Val120-Thr202   (479) CCAACGTGAGCACCGTGCAGTGCACCCACGGCATCCGCCC
Lys121-Val200   (485) CCAACGTGAGCACCGTGCAGTGCACCCACGGCATCCGCCC
    Consensus   (521) CCAACGTGAGCACCGTGCAGTGCACCCACGGCATCCGCCC
                      561                                          600
Leu122-Ser199   (531) CGTGGTGAGCACCCAGCTGCTGCTGAACGGCAGCCTGGCC
Val127-Asn195   (561) CGTGGTGAGCACCCAGCTGCTGCTGAACGGCAGCCTGGCC
Val120-Ile201B  (519) CGTGGTGAGCACCCAGCTGCTGCTGAACGGCAGCCTGGCC
Val120-Ala204   (513) CGTGGTGAGCACCCAGCTGCTGCTGAACGGCAGCCTGGCC
Val120-Ile201   (519) CGTGGTGAGCACCCAGCTGCTGCTGAACGGCAGCCTGGCC
Val120-Thr202   (519) CGTGGTGAGCACCCAGCTGCTGCTGAACGGCAGCCTGGCC
Lys121-Val200   (525) CGTGGTGAGCACCCAGCTGCTGCTGAACGGCAGCCTGGCC
    Consensus   (561) CGTGGTGAGCACCCAGCTGCTGCTGAACGGCAGCCTGGCC
                      601                                          640
Leu122-Ser199   (571) GAGGAGGGCGTGGTGATCCGCAGCGAGAACTTCACCGACA
Val127-Asn195   (601) GAGGAGGGCGTGGTGATCCGCAGCGAGAACTTCACCGACA
Val120-Ile201B  (559) GAGGAGGGCGTGGTGATCCGCAGCGAGAACTTCACCGACA
Val120-Ala204   (553) GAGGAGGGCGTGGTGATCCGCAGCGAGAACTTCACCGACA
Val120-Ile201   (559) GAGGAGGGCGTGGTGATCCGCAGCGAGAACTTCACCGACA
Val120-Thr202   (559) GAGGAGGGCGTGGTGATCCGCAGCGAGAACTTCACCGACA
Lys121-Val200   (565) GAGGAGGGCGTGGTGATCCGCAGCGAGAACTTCACCGACA
    Consensus   (601) GAGGAGGGCGTGGTGATCCGCAGCGAGAACTTCACCGACA
                      641                                          680
Leu122-Ser199   (611) ACGCCAAGACCATCATCGTGCAGCTGAAGGAGAGCGTGGA
Val127-Asn195   (641) ACGCCAAGACCATCATCGTGCAGCTGAAGGAGAGCGTGGA
Val120-Ile201B  (599) ACGCCAAGACCATCATCGTGCAGCTGAAGGAGAGCGTGGA
Val120-Ala204   (593) ACGCCAAGACCATCATCGTGCAGCTGAAGGAGAGCGTGGA
Val120-Ile201   (599) ACGCCAAGACCATCATCGTGCAGCTGAAGGAGAGCGTGGA
Val120-Thr202   (599) ACGCCAAGACCATCATCGTGCAGCTGAAGGAGAGCGTGGA
Lys121-Val200   (605) ACGCCAAGACCATCATCGTGCAGCTGAAGGAGAGCGTGGA
    Consensus   (641) ACGCCAAGACCATCATCGTGCAGCTGAAGGAGAGCGTGGA
                      681                                          720
Leu122-Ser199   (651) GATCAACTGCACCCGCCCCAACAACAACACCCGCAAGAGC
Val127-Asn195   (681) GATCAACTGCACCCGCCCCAACAACAACACCCGCAAGAGC
Val120-Ile201B  (639) GATCAACTGCACCCGCCCCAACAACAACACCCGCAAGAGC
Val120-Ala204   (633) GATCAACTGCACCCGCCCCAACAACAACACCCGCAAGAGC
Val120-Ile201   (639) GATCAACTGCACCCGCCCCAACAACAACACCCGCAAGAGC
Val120-Thr202   (639) GATCAACTGCACCCGCCCCAACAACAACACCCGCAAGAGC
Lys121-Val200   (645) GATCAACTGCACCCGCCCCAACAACAACACCCGCAAGAGC
    Consensus   (681) GATCAACTGCACCCGCCCCAACAACAACACCCGCAAGAGC
                      721                                          760
Leu122-Ser199   (691) ATCACCATCGGCCCCGGCCGCGCCTTCTACGCCACCGGCG
Val127-Asn195   (721) ATCACCATCGGCCCCGGCCGCGCCTTCTACGCCACCGGCG
Val120-Ile201B  (679) ATCACCATCGGCCCCGGCCGCGCCTTCTACGCCACCGGCG
Val120-Ala204   (673) ATCACCATCGGCCCCGGCCGCGCCTTCTACGCCACCGGCG
Val120-Ile201   (679) ATCACCATCGGCCCCGGCCGCGCCTTCTACGCCACCGGCG
Val120-Thr202   (679) ATCACCATCGGCCCCGGCCGCGCCTTCTACGCCACCGGCG
Lys121-Val200   (685) ATCACCATCGGCCCCGGCCGCGCCTTCTACGCCACCGGCG
    Consensus   (721) ATCACCATCGGCCCCGGCCGCGCCTTCTACGCCACCGGCG
```

*FIG. 3C*

```
                           761                                        800
Leu122-Ser199    (731)  ACATCATCGGCGACATCCGCCAGGCCCACTGCAACATCAG
Val127-Asn195    (761)  ACATCATCGGCGACATCCGCCAGGCCCACTGCAACATCAG
Val120-Ile201B   (719)  ACATCATCGGCGACATCCGCCAGGCCCACTGCAACATCAG
Val120-Ala204    (713)  ACATCATCGGCGACATCCGCCAGGCCCACTGCAACATCAG
Val120-Ile201    (719)  ACATCATCGGCGACATCCGCCAGGCCCACTGCAACATCAG
Val120-Thr202    (719)  ACATCATCGGCGACATCCGCCAGGCCCACTGCAACATCAG
Lys121-Val200    (725)  ACATCATCGGCGACATCCGCCAGGCCCACTGCAACATCAG
     Consensus   (761)  ACATCATCGGCGACATCCGCCAGGCCCACTGCAACATCAG
                           801                                       840
Leu122-Ser199    (771)  CGGCGAGAAGTGGAACAACACCCTGAAGCAGATCGTGACC
Val127-Asn195    (801)  CGGCGAGAAGTGGAACAACACCCTGAAGCAGATCGTGACC
Val120-Ile201B   (759)  CGGCGAGAAGTGGAACAACACCCTGAAGCAGATCGTGACC
Val120-Ala204    (753)  CGGCGAGAAGTGGAACAACACCCTGAAGCAGATCGTGACC
Val120-Ile201    (759)  CGGCGAGAAGTGGAACAACACCCTGAAGCAGATCGTGACC
Val120-Thr202    (759)  CGGCGAGAAGTGGAACAACACCCTGAAGCAGATCGTGACC
Lys121-Val200    (765)  CGGCGAGAAGTGGAACAACACCCTGAAGCAGATCGTGACC
     Consensus   (801)  CGGCGAGAAGTGGAACAACACCCTGAAGCAGATCGTGACC
                           841                                       880
Leu122-Ser199    (811)  AAGCTGCAGGCCCAGTTCGGCAACAAGACCATCGTGTTCA
Val127-Asn195    (841)  AAGCTGCAGGCCCAGTTCGGCAACAAGACCATCGTGTTCA
Val120-Ile201B   (799)  AAGCTGCAGGCCCAGTTCGGCAACAAGACCATCGTGTTCA
Val120-Ala204    (793)  AAGCTGCAGGCCCAGTTCGGCAACAAGACCATCGTGTTCA
Val120-Ile201    (799)  AAGCTGCAGGCCCAGTTCGGCAACAAGACCATCGTGTTCA
Val120-Thr202    (799)  AAGCTGCAGGCCCAGTTCGGCAACAAGACCATCGTGTTCA
Lys121-Val200    (805)  AAGCTGCAGGCCCAGTTCGGCAACAAGACCATCGTGTTCA
     Consensus   (841)  AAGCTGCAGGCCCAGTTCGGCAACAAGACCATCGTGTTCA
                           881                                       920
Leu122-Ser199    (851)  AGCAGAGCAGCGGCGGCGACCCCGAGATCGTGATGCACAG
Val127-Asn195    (881)  AGCAGAGCAGCGGCGGCGACCCCGAGATCGTGATGCACAG
Val120-Ile201B   (839)  AGCAGAGCAGCGGCGGCGACCCCGAGATCGTGATGCACAG
Val120-Ala204    (833)  AGCAGAGCAGCGGCGGCGACCCCGAGATCGTGATGCACAG
Val120-Ile201    (839)  AGCAGAGCAGCGGCGGCGACCCCGAGATCGTGATGCACAG
Val120-Thr202    (839)  AGCAGAGCAGCGGCGGCGACCCCGAGATCGTGATGCACAG
Lys121-Val200    (845)  AGCAGAGCAGCGGCGGCGACCCCGAGATCGTGATGCACAG
     Consensus   (881)  AGCAGAGCAGCGGCGGCGACCCCGAGATCGTGATGCACAG
                           921                                       960
Leu122-Ser199    (891)  CTTCAACTGCGGCGGCGAGTTCTTCTACTGCAACAGCACC
Val127-Asn195    (921)  CTTCAACTGCGGCGGCGAGTTCTTCTACTGCAACAGCACC
Val120-Ile201B   (879)  CTTCAACTGCGGCGGCGAGTTCTTCTACTGCAACAGCACC
Val120-Ala204    (873)  CTTCAACTGCGGCGGCGAGTTCTTCTACTGCAACAGCACC
Val120-Ile201    (879)  CTTCAACTGCGGCGGCGAGTTCTTCTACTGCAACAGCACC
Val120-Thr202    (879)  CTTCAACTGCGGCGGCGAGTTCTTCTACTGCAACAGCACC
Lys121-Val200    (885)  CTTCAACTGCGGCGGCGAGTTCTTCTACTGCAACAGCACC
     Consensus   (921)  CTTCAACTGCGGCGGCGAGTTCTTCTACTGCAACAGCACC
                           961                                       1000
Leu122-Ser199    (931)  CAGCTGTTCAACAGCACCTGGAACAACACCATCGGCCCCA
Val127-Asn195    (961)  CAGCTGTTCAACAGCACCTGGAACAACACCATCGGCCCCA
Val120-Ile201B   (919)  CAGCTGTTCAACAGCACCTGGAACAACACCATCGGCCCCA
Val120-Ala204    (913)  CAGCTGTTCAACAGCACCTGGAACAACACCATCGGCCCCA
Val120-Ile201    (919)  CAGCTGTTCAACAGCACCTGGAACAACACCATCGGCCCCA
Val120-Thr202    (919)  CAGCTGTTCAACAGCACCTGGAACAACACCATCGGCCCCA
Lys121-Val200    (925)  CAGCTGTTCAACAGCACCTGGAACAACACCATCGGCCCCA
     Consensus   (961)  CAGCTGTTCAACAGCACCTGGAACAACACCATCGGCCCCA
                           1001                                      1040
Leu122-Ser199    (971)  ACAACACCAACGGCACCATCACCCTGCCCTGCCGCATCAA
Val127-Asn195   (1001)  ACAACACCAACGGCACCATCACCCTGCCCTGCCGCATCAA
```

*FIG. 3D*

```
Val120-Ile201B    (959)  ACAACACCAACGGCACCATCACCCTGCCCTGCCGCATCAA
Val120-Ala204     (953)  ACAACACCAACGGCACCATCACCCTGCCCTGCCGCATCAA
Val120-Ile201     (959)  ACAACACCAACGGCACCATCACCCTGCCCTGCCGCATCAA
Val120-Thr202     (959)  ACAACACCAACGGCACCATCACCCTGCCCTGCCGCATCAA
Lys121-Val200     (965)  ACAACACCAACGGCACCATCACCCTGCCCTGCCGCATCAA
Consensus        (1001)  ACAACACCAACGGCACCATCACCCTGCCCTGCCGCATCAA
                         1041                                   1080
Leu122-Ser199    (1011)  GCAGATCATCAACCGCTGGCAGGAGGTGGGCAAGGCCATG
Val127-Asn195    (1041)  GCAGATCATCAACCGCTGGCAGGAGGTGGGCAAGGCCATG
Val120-Ile201B    (999)  GCAGATCATCAACCGCTGGCAGGAGGTGGGCAAGGCCATG
Val120-Ala204     (993)  GCAGATCATCAACCGCTGGCAGGAGGTGGGCAAGGCCATG
Val120-Ile201     (999)  GCAGATCATCAACCGCTGGCAGGAGGTGGGCAAGGCCATG
Val120-Thr202     (999)  GCAGATCATCAACCGCTGGCAGGAGGTGGGCAAGGCCATG
Lys121-Val200    (1005)  GCAGATCATCAACCGCTGGCAGGAGGTGGGCAAGGCCATG
Consensus        (1041)  GCAGATCATCAACCGCTGGCAGGAGGTGGGCAAGGCCATG
                         1081                                   1120
Leu122-Ser199    (1051)  TACGCCGCCCCCATCCGCGGCCAGATCCGCTGCAGCAGCA
Val127-Asn195    (1081)  TACGCCGCCCCCATCCGCGGCCAGATCCGCTGCAGCAGCA
Val120-Ile201B   (1039)  TACGCCGCCCCCATCCGCGGCCAGATCCGCTGCAGCAGCA
Val120-Ala204    (1033)  TACGCCGCCCCCATCCGCGGCCAGATCCGCTGCAGCAGCA
Val120-Ile201    (1039)  TACGCCGCCCCCATCCGCGGCCAGATCCGCTGCAGCAGCA
Val120-Thr202    (1039)  TACGCCGCCCCCATCCGCGGCCAGATCCGCTGCAGCAGCA
Lys121-Val200    (1045)  TACGCCGCCCCCATCCGCGGCCAGATCCGCTGCAGCAGCA
Consensus        (1081)  TACGCCCCCCCCATCCGCGGCCAGATCCGCTGCAGCAGCA
                         1121                                   1160
Leu122-Ser199    (1091)  ACATCACCGGCCTGCTGCTGACCCGCGACGGCGGCAAGGA
Val127-Asn195    (1121)  ACATCACCGGCCTGCTGCTGACCCGCGACGGCGGCAAGGA
Val120-Ile201B   (1079)  ACATCACCGGCCTGCTGCTGACCCGCGACGGCGGCAAGGA
Val120-Ala204    (1073)  ACATCACCGGCCTGCTGCTGACCCGCGACGGCGGCAAGGA
Val120-Ile201    (1079)  ACATCACCGGCCTGCTGCTGACCCGCGACGGCGGCAAGGA
Val120-Thr202    (1079)  ACATCACCGGCCTGCTGCTGACCCGCGACGGCGGCAAGGA
Lys121-Val200    (1085)  ACATCACCGGCCTGCTGCTGACCCGCGACGGCGGCAAGGA
Consensus        (1121)  ACATCACCGGCCTGCTGCTGACCCGCGACGGCGGCAAGGA
                         1161                                   1200
Leu122-Ser199    (1131)  GATCAGCAACACCACCGAGATCTTCCGCCCCGGCGGCGGC
Val127-Asn195    (1161)  GATCAGCAACACCACCGAGATCTTCCGCCCCGGCGGCGGC
Val120-Ile201B   (1119)  GATCAGCAACACCACCGAGATCTTCCGCCCCGGCGGCGGC
Val120-Ala204   (1113)   GATCAGCAACACCACCGAGATCTTCCGCCCCGGCGGCGGC
Val120-Ile201    (1119)  GATCAGCAACACCACCGAGATCTTCCGCCCCGGCGGCGGC
Val120-Thr202    (1119)  GATCAGCAACACCACCGAGATCTTCCGCCCCGGCGGCGGC
Lys121-Val200    (1125)  GATCAGCAACACCACCGAGATCTTCCGCCCCGGCGGCGGC
Consensus        (1161)  GATCAGCAACACCACCGAGATCTTCCGCCCCGGCGGCGGC
                         1201                                   1240
Leu122-Ser199    (1171)  GACATGCGCGACAACTGGCGCAGCGAGCTGTACAAGTACA
Val127-Asn195    (1201)  GACATGCGCGACAACTGGCGCAGCGAGCTGTACAAGTACA
Val120-Ile201B   (1159)  GACATGCGCGACAACTGGCGCAGCGAGCTGTACAAGTACA
Val120-Ala204    (1153)  GACATGCGCGACAACTGGCGCAGCGAGCTGTACAAGTACA
Val120-Ile201    (1159)  GACATGCGCGACAACTGGCGCAGCGAGCTGTACAAGTACA
Val120-Thr202    (1159)  GACATGCGCGACAACTGGCGCAGCGAGCTGTACAAGTACA
Lys121-Val200    (1165)  GACATGCGCGACAACTGGCGCAGCGAGCTGTACAAGTACA
Consensus        (1201)  GACATGCGCGACAACTGGCGCAGCGAGCTGTACAAGTACA
                         1241                                   1280
Leu122-Ser199    (1211)  AGGTGGTGAAGATCGAGCCCCTGGGCGTGGCCCCCACCAA
Val127-Asn195    (1241)  AGGTGGTGAAGATCGAGCCCCTGGGCGTGGCCCCCACCAA
Val120-Ile201B   (1199)  AGGTGGTGAAGATCGAGCCCCTGGGCGTGGCCCCCACCAA
Val120-Ala204    (1193)  AGGTGGTGAAGATCGAGCCCCTGGGCGTGGCCCCCACCAA
Val120-Ile201    (1199)  AGGTGGTGAAGATCGAGCCCCTGGGCGTGGCCCCCACCAA
```

*FIG. 3E*

```
Val120-Thr202    (1199) AGGTGGTGAAGATCGAGCCCCTGGGCGTGGCCCCCACCAA
Lys121-Val200    (1205) AGGTGGTGAAGATCGAGCCCCTGGGCGTGGCCCCCACCAA
      Consensus  (1241) AGGTGGTGAAGATCGAGCCCCTGGGCGTGGCCCCCACCAA
                        1281                                 1320
Leu122-Ser199    (1251) GGCCAAGCGCCGCGTGGTGCAGCGCGAGAAGCGCGCCGTG
Val127-Asn195    (1281) GGCCAAGCGCCGCGTGGTGCAGCGCGAGAAGCGCGCCGTG
Val120-Ile201B   (1239) GGCCAAGCGCCGCGTGGTGCAGCGCGAGAAGCGCGCCGTG
Val120-Ala204    (1233) GGCCAAGCGCCGCGTGGTGCAGCGCGAGAAGCGCGCCGTG
Val120-Ile201    (1239) GGCCAAGCGCCGCGTGGTGCAGCGCGAGAAGCGCGCCGTG
Val120-Thr202    (1239) GGCCAAGCGCCGCGTGGTGCAGCGCGAGAAGCGCGCCGTG
Lys121-Val200    (1245) GGCCAAGCGCCGCGTGGTGCAGCGCGAGAAGCGCGCCGTG
      Consensus  (1281) GGCCAAGCGCCGCGTGGTGCAGCGCGAGAAGCGCGCCGTG
                        1321                                 1360
Leu122-Ser199    (1291) ACCCTGGGCGCCATGTTCCTGGGCTTCCTGGGCGCCGCCG
Val127-Asn195    (1321) ACCCTGGGCGCCATGTTCCTGGGCTTCCTGGGCGCCGCCG
Val120-Ile201B   (1279) ACCCTGGGCGCCATGTTCCTGGGCTTCCTGGGCGCCGCCG
Val120-Ala204    (1273) ACCCTGGGCGCCATGTTCCTGGGCTTCCTGGGCGCCGCCG
Val120-Ile201    (1279) ACCCTGGGCGCCATGTTCCTGGGCTTCCTGGGCGCCGCCG
Val120-Thr202    (1279) ACCCTGGGCGCCATGTTCCTGGGCTTCCTGGGCGCCGCCG
Lys121-Val200    (1285) ACCCTGGGCGCCATGTTCCTGGGCTTCCTGGGCGCCGCCG
      Consensus  (1321) ACCCTGGGCGCCATGTTCCTGGGCTTCCTGGGCGCCGCCG
                        1361                                 1400
Leu122-Ser199    (1331) GCAGCACCATGGGCGCCCGCAGCCTGACCCTGACCGTGCA
Val127-Asn195    (1361) GCAGCACCATGGGCGCCCGCAGCCTGACCCTGACCGTGCA
Val120-Ile201B   (1319) GCAGCACCATGGGCGCCCGCAGCCTGACCCTGACCGTGCA
Val120-Ala204    (1313) GCAGCACCATGGGCGCCCGCAGCCTGACCCTGACCGTGCA
Val120-Ile201    (1319) GCAGCACCATGGGCGCCCGCAGCCTGACCCTGACCGTGCA
Val120-Thr202    (1319) GCAGCACCATGGGCGCCCGCAGCCTGACCCTGACCGTGCA
Lys121-Val200    (1325) GCAGCACCATGGGCGCCCGCAGCCTGACCCTGACCGTGCA
      Consensus  (1361) GCAGCACCATGGGCGCCCGCAGCCTGACCCTGACCGTGCA
                        1401                                 1440
Leu122-Ser199    (1371) GGCCCGCCAGCTGCTGAGCGGCATCGTGCAGCAGCAGAAC
Val127-Asn195    (1401) GGCCCGCCAGCTGCTGAGCGGCATCGTGCAGCAGCAGAAC
Val120-Ile201B   (1359) GGCCCGCCAGCTGCTGAGCGGCATCGTGCAGCAGCAGAAC
Val120-Ala204    (1353) GGCCCGCCAGCTGCTGAGCGGCATCGTGCAGCAGCAGAAC
Val120-Ile201    (1359) GGCCCGCCAGCTGCTGAGCGGCATCGTGCAGCAGCAGAAC
Val120-Thr202    (1359) GGCCCGCCAGCTGCTGAGCGGCATCGTGCAGCAGCAGAAC
Lys121-Val200    (1365) GGCCCGCCAGCTGCTGAGCGGCATCGTGCAGCAGCAGAAC
      Consensus  (1401) GGCCCGCCAGCTGCTGAGCGGCATCGTGCAGCAGCAGAAC
                        1441                                 1480
Leu122-Ser199    (1411) AACCTGCTGCGCGCCATCGAGGCCCAGCAGCACCTGCTGC
Val127-Asn195    (1441) AACCTGCTGCGCGCCATCGAGGCCCAGCAGCACCTGCTGC
Val120-Ile201B   (1399) AACCTGCTGCGCGCCATCGAGGCCCAGCAGCACCTGCTGC
Val120-Ala204    (1393) AACCTGCTGCGCGCCATCGAGGCCCAGCAGCACCTGCTGC
Val120-Ile201    (1399) AACCTGCTGCGCGCCATCGAGGCCCAGCAGCACCTGCTGC
Val120-Thr202    (1399) AACCTGCTGCGCGCCATCGAGGCCCAGCAGCACCTGCTGC
Lys121-Val200    (1405) AACCTGCTGCGCGCCATCGAGGCCCAGCAGCACCTGCTGC
      Consensus  (1441) AACCTGCTGCGCGCCATCGAGGCCCAGCAGCACCTGCTGC
                        1481                                 1520
Leu122-Ser199    (1451) AGCTGACCGTGTGGGGCATCAAGCAGCTGCAGGCCCGCGT
Val127-Asn195    (1481) AGCTGACCGTGTGGGGCATCAAGCAGCTGCAGGCCCGCGT
Val120-Ile201B   (1439) AGCTGACCGTGTGGGGCATCAAGCAGCTGCAGGCCCGCGT
Val120-Ala204    (1433) AGCTGACCGTGTGGGGCATCAAGCAGCTGCAGGCCCGCGT
Val120-Ile201    (1439) AGCTGACCGTGTGGGGCATCAAGCAGCTGCAGGCCCGCGT
Val120-Thr202    (1439) AGCTGACCGTGTGGGGCATCAAGCAGCTGCAGGCCCGCGT
Lys121-Val200    (1445) AGCTGACCGTGTGGGGCATCAAGCAGCTGCAGGCCCGCGT
      Consensus  (1481) AGCTGACCGTGTGGGGCATCAAGCAGCTGCAGGCCCGCGT
```

*FIG. 3F*

```
                              1521                                        1560
Leu122-Ser199    (1491)  GCTGGCCGTGGAGCGCTACCTGAAGGACCAGCAGCTGCTG
Val127-Asn195    (1521)  GCTGGCCGTGGAGCGCTACCTGAAGGACCAGCAGCTGCTG
Val120-Ile201B   (1479)  GCTGGCCGTGGAGCGCTACCTGAAGGACCAGCAGCTGCTG
Val120-Ala204    (1473)  GCTGGCCGTGGAGCGCTACCTGAAGGACCAGCAGCTGCTG
Val120-Ile201    (1479)  GCTGGCCGTGGAGCGCTACCTGAAGGACCAGCAGCTGCTG
Val120-Thr202    (1479)  GCTGGCCGTGGAGCGCTACCTGAAGGACCAGCAGCTGCTG
Lys121-Val200    (1485)  GCTGGCCGTGGAGCGCTACCTGAAGGACCAGCAGCTGCTG
     Consensus   (1521)  GCTGGCCGTGGAGCGCTACCTGAAGGACCAGCAGCTGCTG
                              1561                                        1600
Leu122-Ser199    (1531)  GGCATCTGGGGCTGCAGCGGCAAGCTGATCTGCACCACCG
Val127-Asn195    (1561)  GGCATCTGGGGCTGCAGCGGCAAGCTGATCTGCACCACCG
Val120-Ile201B   (1519)  GGCATCTGGGGCTGCAGCGGCAAGCTGATCTGCACCACCG
Val120-Ala204    (1513)  GGCATCTGGGGCTGCAGCGGCAAGCTGATCTGCACCACCG
Val120-Ile201    (1519)  GGCATCTGGGGCTGCAGCGGCAAGCTGATCTGCACCACCG
Val120-Thr202    (1519)  GGCATCTGGGGCTGCAGCGGCAAGCTGATCTGCACCACCG
Lys121-Val200    (1525)  GGCATCTGGGGCTGCAGCGGCAAGCTGATCTGCACCACCG
     Consensus   (1561)  GGCATCTGGGGCTGCAGCGGCAAGCTGATCTGCACCACCG
                              1601                                        1640
Leu122-Ser199    (1571)  CCGTGCCCTGGAACGCCAGCTGGAGCAACAAGAGCCTGGA
Val127-Asn195    (1601)  CCGTGCCCTGGAACGCCAGCTGGAGCAACAAGAGCCTGGA
Val120-Ile201B   (1559)  CCGTGCCCTGGAACGCCAGCTGGAGCAACAAGAGCCTGGA
Val120-Ala204    (1553)  CCGTGCCCTGGAACGCCAGCTGGAGCAACAAGAGCCTGGA
Val120-Ile201    (1559)  CCGTGCCCTGGAACGCCAGCTGGAGCAACAAGAGCCTGGA
Val120-Thr202    (1559)  CCGTGCCCTGGAACGCCAGCTGGAGCAACAAGAGCCTGGA
Lys121-Val200    (1565)  CCGTGCCCTGGAACGCCAGCTGGAGCAACAAGAGCCTGGA
     Consensus   (1601)  CCGTGCCCTGGAACGCCAGCTGGAGCAACAAGAGCCTGGA
                              1641                                        1680
Leu122-Ser199    (1611)  CCAGATCTGGAACAACATGACCTGGATGGAGTGGGAGCGC
Val127-Asn195    (1641)  CCAGATCTGGAACAACATGACCTGGATGGAGTGGGAGCGC
Val120-Ile201B   (1599)  CCAGATCTGGAACAACATGACCTGGATGGAGTGGGAGCGC
Val120-Ala204    (1593)  CCAGATCTGGAACAACATGACCTGGATGGAGTGGGAGCGC
Val120-Ile201    (1599)  CCAGATCTGGAACAACATGACCTGGATGGAGTGGGAGCGC
Val120-Thr202    (1599)  CCAGATCTGGAACAACATGACCTGGATGGAGTGGGAGCGC
Lys121-Val200    (1605)  CCAGATCTGGAACAACATGACCTGGATGGAGTGGGAGCGC
     Consensus   (1641)  CCAGATCTGGAACAACATGACCTGGATGGAGTGGGAGCGC
                              1681                                        1720
Leu122-Ser199    (1651)  GAGATCGACAACTACACCAACCTGATCTACACCCTGATCG
Val127-Asn195    (1681)  GAGATCGACAACTACACCAACCTGATCTACACCCTGATCG
Val120-Ile201B   (1639)  GAGATCGACAACTACACCAACCTGATCTACACCCTGATCG
Val120-Ala204    (1633)  GAGATCGACAACTACACCAACCTGATCTACACCCTGATCG
Val120-Ile201    (1639)  GAGATCGACAACTACACCAACCTGATCTACACCCTGATCG
Val120-Thr202    (1639)  GAGATCGACAACTACACCAACCTGATCTACACCCTGATCG
Lys121-Val200    (1645)  GAGATCGACAACTACACCAACCTGATCTACACCCTGATCG
     Consensus   (1681)  GAGATCGACAACTACACCAACCTGATCTACACCCTGATCG
                              1721                                        1760
Leu122-Ser199    (1691)  AGGAGAGCCAGAACCAGCAGGAGAAGAACGAGCAGGAGCT
Val127-Asn195    (1721)  AGGAGAGCCAGAACCAGCAGGAGAAGAACGAGCAGGAGCT
Val120-Ile201B   (1679)  AGGAGAGCCAGAACCAGCAGGAGAAGAACGAGCAGGAGCT
Val120-Ala204    (1673)  AGGAGAGCCAGAACCAGCAGGAGAAGAACGAGCAGGAGCT
Val120-Ile201    (1679)  AGGAGAGCCAGAACCAGCAGGAGAAGAACGAGCAGGAGCT
Val120-Thr202    (1679)  AGGAGAGCCAGAACCAGCAGGAGAAGAACGAGCAGGAGCT
Lys121-Val200    (1685)  AGGAGAGCCAGAACCAGCAGGAGAAGAACGAGCAGGAGCT
     Consensus   (1721)  AGGAGAGCCAGAACCAGCAGGAGAAGAACGAGCAGGAGCT
                              1761                                        1800
Leu122-Ser199    (1731)  GCTGGAGCTGGACAAGTGGGCCAGCCTGTGGAACTGGTTC
Val127-Asn195    (1761)  GCTGGAGCTGGACAAGTGGGCCAGCCTGTGGAACTGGTTC
```

*FIG. 3G*

```
                            1801                                    1840
Leu122-Ser199   (1771)   GACATCAGCAAGTGGCTGTGGTACATCAAGATCTTCATCA
Val127-Asn195   (1801)   GACATCAGCAAGTGGCTGTGGTACATCAAGATCTTCATCA
Val120-Ile201B  (1759)   GACATCAGCAAGTGGCTGTGGTACATCAAGATCTTCATCA
Val120-Ala204   (1753)   GACATCAGCAAGTGGCTGTGGTACATCAAGATCTTCATCA
Val120-Ile201   (1759)   GACATCAGCAAGTGGCTGTGGTACATCAAGATCTTCATCA
Val120-Thr202   (1759)   GACATCAGCAAGTGGCTGTGGTACATCAAGATCTTCATCA
Lys121-Val200   (1765)   GACATCAGCAAGTGGCTGTGGTACATCAAGATCTTCATCA
     Consensus  (1801)   GACATCAGCAAGTGGCTGTGGTACATCAAGATCTTCATCA
                            1841                                    1880
Leu122-Ser199   (1811)   TGATCGTGGGCGGCCTGGTGGGCCTGCGCATCGTGTTCAC
Val127-Asn195   (1841)   TGATCGTGGGCGGCCTGGTGGGCCTGCGCATCGTGTTCAC
Val120-Ile201B  (1799)   TGATCGTGGGCGGCCTGGTGGGCCTGCGCATCGTGTTCAC
Val120-Ala204   (1793)   TGATCGTGGGCGGCCTGGTGGGCCTGCGCATCGTGTTCAC
Val120-Ile201   (1799)   TGATCGTGGGCGGCCTGGTGGGCCTGCGCATCGTGTTCAC
Val120-Thr202   (1799)   TGATCGTGGGCGGCCTGGTGGGCCTGCGCATCGTGTTCAC
Lys121-Val200   (1805)   TGATCGTGGGCGGCCTGGTGGGCCTGCGCATCGTGTTCAC
     Consensus  (1841)   TGATCGTGGGCGGCCTGGTGGGCCTGCGCATCGTGTTCAC
                            1881                                    1920
Leu122-Ser199   (1851)   CGTGCTGAGCATCGTGAACCGCGTGCGCCAGGGCTACAGC
Val127-Asn195   (1881)   CGTGCTGAGCATCGTGAACCGCGTGCGCCAGGGCTACAGC
Val120-Ile201B  (1839)   CGTGCTGAGCATCGTGAACCGCGTGCGCCAGGGCTACAGC
Val120-Ala204   (1833)   CGTGCTGAGCATCGTGAACCGCGTGCGCCAGGGCTACAGC
Val120-Ile201   (1839)   CGTGCTGAGCATCGTGAACCGCGTGCGCCAGGGCTACAGC
Val120-Thr202   (1839)   CGTGCTGAGCATCGTGAACCGCGTGCGCCAGGGCTACAGC
Lys121-Val200   (1845)   CGTGCTGAGCATCGTGAACCGCGTGCGCCAGGGCTACAGC
     Consensus  (1881)   CGTGCTGAGCATCGTGAACCGCGTGCGCCAGGGCTACAGC
                            1921                                    1960
Leu122-Ser199   (1891)   CCCCTGAGCTTCCAGACCCGCTTCCCCGCCCCCCGCGGCC
Val127-Asn195   (1921)   CCCCTGAGCTTCCAGACCCGCTTCCCCGCCCCCCGCGGCC
Val120-Ile201B  (1879)   CCCCTGAGCTTCCAGACCCGCTTCCCCGCCCCCCGCGGCC
Val120-Ala204   (1873)   CCCCTGAGCTTCCAGACCCGCTTCCCCGCCCCCCGCGGCC
Val120-Ile201   (1879)   CCCCTGAGCTTCCAGACCCGCTTCCCCGCCCCCCGCGGCC
Val120-Thr202   (1879)   CCCCTGAGCTTCCAGACCCGCTTCCCCGCCCCCCGCGGCC
Lys121-Val200   (1885)   CCCCTGAGCTTCCAGACCCGCTTCCCCGCCCCCCGCGGCC
     Consensus  (1921)   CCCCTGAGCTTCCAGACCCGCTTCCCCGCCCCCCGCGGCC
                            1961                                    2000
Leu122-Ser199   (1931)   CCGACCGCCCCGAGGGCATCGAGGAGGAGGGCGGCGAGCG
Val127-Asn195   (1961)   CCGACCGCCCCGAGGGCATCGAGGAGGAGGGCGGCGAGCG
Val120-Ile201B  (1919)   CCGACCGCCCCGAGGGCATCGAGGAGGAGGGCGGCGAGCG
Val120-Ala204   (1913)   CCGACCGCCCCGAGGGCATCGAGGAGGAGGGCGGCGAGCG
Val120-Ile201   (1919)   CCGACCGCCCCGAGGGCATCGAGGAGGAGGGCGGCGAGCG
Val120-Thr202   (1919)   CCGACCGCCCCGAGGGCATCGAGGAGGAGGGCGGCGAGCG
Lys121-Val200   (1925)   CCGACCGCCCCGAGGGCATCGAGGAGGAGGGCGGCGAGCG
     Consensus  (1961)   CCGACCGCCCCGAGGGCATCGAGGAGGAGGGCGGCGAGCG
                            2001                                    2040
Leu122-Ser199   (1971)   CGACCGCGACCGCAGCAGCCCCCTGGTGCACGGCCTGCTG
Val127-Asn195   (2001)   CGACCGCGACCGCAGCAGCCCCCTGGTGCACGGCCTGCTG
Val120-Ile201B  (1959)   CGACCGCGACCGCAGCAGCCCCCTGGTGCACGGCCTGCTG
Val120-Ala204   (1953)   CGACCGCGACCGCAGCAGCCCCCTGGTGCACGGCCTGCTG
Val120-Ile201   (1959)   CGACCGCGACCGCAGCAGCCCCCTGGTGCACGGCCTGCTG
```
Val120-Ile201B (1719) GCTGGAGCTGGACAAGTGGGCCAGCCTGTGGAACTGGTTC
Val120-Ala204 (1713) GCTGGAGCTGGACAAGTGGGCCAGCCTGTGGAACTGGTTC
Val120-Ile201 (1719) GCTGGAGCTGGACAAGTGGGCCAGCCTGTGGAACTGGTTC
Val120-Thr202 (1719) GCTGGAGCTGGACAAGTGGGCCAGCCTGTGGAACTGGTTC
Lys121-Val200 (1725) GCTGGAGCTGGACAAGTGGGCCAGCCTGTGGAACTGGTTC
Consensus (1761) GCTGGAGCTGGACAAGTGGGCCAGCCTGTGGAACTGGTTC

FIG. 3H

```
Val120-Thr202   (1959) CGACCGCGACCGCAGCAGCCCCCTGGTGCACGGCCTGCTG
Lys121-Val200   (1965) CGACCGCGACCGCAGCAGCCCCCTGGTGCACGGCCTGCTG
    Consensus   (2001) CGACCGCGACCGCAGCAGCCCCCTGGTGCACGGCCTGCTG
                       2041                                    2080
Leu122-Ser199   (2011) GCCCTGATCTGGGACGACCTGCGCAGCCTGTGCCTGTTCA
Val127-Asn195   (2041) GCCCTGATCTGGGACGACCTGCGCAGCCTGTGCCTGTTCA
Val120-Ile201B  (1999) GCCCTGATCTGGGACGACCTGCGCAGCCTGTGCCTGTTCA
Val120-Ala204   (1993) GCCCTGATCTGGGACGACCTGCGCAGCCTGTGCCTGTTCA
Val120-Ile201   (1999) GCCCTGATCTGGGACGACCTGCGCAGCCTGTGCCTGTTCA
Val120-Thr202   (1999) GCCCTGATCTGGGACGACCTGCGCAGCCTGTGCCTGTTCA
Lys121-Val200   (2005) GCCCTGATCTGGGACGACCTGCGCAGCCTGTGCCTGTTCA
    Consensus   (2041) GCCCTGATCTGGGACGACCTGCGCAGCCTGTGCCTGTTCA
                       2081                                    2120
Leu122-Ser199   (2051) GCTACCACCGCCTGCGCGACCTGATCCTGATCGCCGCCCG
Val127-Asn195   (2081) GCTACCACCGCCTGCGCGACCTGATCCTGATCGCCGCCCG
Val120-Ile201B  (2039) GCTACCACCGCCTGCGCGACCTGATCCTGATCGCCGCCCG
Val120-Ala204   (2033) GCTACCACCGCCTGCGCGACCTGATCCTGATCGCCGCCCG
Val120-Ile201   (2039) GCTACCACCGCCTGCGCGACCTGATCCTGATCGCCGCCCG
Val120-Thr202   (2039) GCTACCACCGCCTGCGCGACCTGATCCTGATCGCCGCCCG
Lys121-Val200   (2045) GCTACCACCGCCTGCGCGACCTGATCCTGATCGCCGCCCG
    Consensus   (2081) GCTACCACCGCCTGCGCGACCTGATCCTGATCGCCGCCCG
                       2121                                    2160
Leu122-Ser199   (2091) CATCGTGGAGCTGCTGGGCCGCCGCGGCTGGGAGGCCCTG
Val127-Asn195   (2121) CATCGTGGAGCTGCTGGGCCGCCGCGGCTGGGAGGCCCTG
Val120-Ile201B  (2079) CATCGTGGAGCTGCTGGGCCGCCGCGGCTGGGAGGCCCTG
Val120-Ala204   (2073) CATCGTGGAGCTGCTGGGCCGCCGCGGCTGGGAGGCCCTG
Val120-Ile201   (2079) CATCGTGGAGCTGCTGGGCCGCCGCGGCTGGGAGGCCCTG
Val120-Thr202   (2079) CATCGTGGAGCTGCTGGGCCGCCGCGGCTGGGAGGCCCTG
Lys121-Val200   (2085) CATCGTGGAGCTGCTGGGCCGCCGCGGCTGGGAGGCCCTG
    Consensus   (2121) CATCGTGGAGCTGCTGGGCCGCCGCGGCTGGGAGGCCCTG
                       2161                                    2200
Leu122-Ser199   (2131) AAGTACTGGGGCAACCTGCTGCAGTACTGGATCCAGGAGC
Val127-Asn195   (2161) AAGTACTGGGGCAACCTGCTGCAGTACTGGATCCAGGAGC
Val120-Ile201B  (2119) AAGTACTGGGGCAACCTGCTGCAGTACTGGATCCAGGAGC
Val120-Ala204   (2113) AAGTACTGGGGCAACCTGCTGCAGTACTGGATCCAGGAGC
Val120-Ile201   (2119) AAGTACTGGGGCAACCTGCTGCAGTACTGGATCCAGGAGC
Val120-Thr202   (2119) AAGTACTGGGGCAACCTGCTGCAGTACTGGATCCAGGAGC
Lys121-Val200   (2125) AAGTACTGGGGCAACCTGCTGCAGTACTGGATCCAGGAGC
    Consensus   (2161) AAGTACTGGGGCAACCTGCTGCAGTACTGGATCCAGGAGC
                       2201                                    2240
Leu122-Ser199   (2171) TGAAGAACAGCGCCGTGAGCCTGTTCGACGCCATCGCCAT
Val127-Asn195   (2201) TGAAGAACAGCGCCGTGAGCCTGTTCGACGCCATCGCCAT
Val120-Ile201B  (2159) TGAAGAACAGCGCCGTGAGCCTGTTCGACGCCATCGCCAT
Val120-Ala204   (2153) TGAAGAACAGCGCCGTGAGCCTGTTCGACGCCATCGCCAT
Val120-Ile201   (2159) TGAAGAACAGCGCCGTGAGCCTGTTCGACGCCATCGCCAT
Val120-Thr202   (2159) TGAAGAACAGCGCCGTGAGCCTGTTCGACGCCATCGCCAT
Lys121-Val200   (2165) TGAAGAACAGCGCCGTGAGCCTGTTCGACGCCATCGCCAT
    Consensus   (2201) TGAAGAACAGCGCCGTGAGCCTGTTCGACGCCATCGCCAT
                       2241                                    2280
Leu122-Ser199   (2211) CGCCGTGGCCGAGGGCACCGACCGCATCATCGAGGTGGCC
Val127-Asn195   (2241) CGCCGTGGCCGAGGGCACCGACCGCATCATCGAGGTGGCC
Val120-Ile201B  (2199) CGCCGTGGCCGAGGGCACCGACCGCATCATCGAGGTGGCC
Val120-Ala204   (2193) CGCCGTGGCCGAGGGCACCGACCGCATCATCGAGGTGGCC
Val120-Ile201   (2199) CGCCGTGGCCGAGGGCACCGACCGCATCATCGAGGTGGCC
Val120-Thr202   (2199) CGCCGTGGCCGAGGGCACCGACCGCATCATCGAGGTGGCC
Lys121-Val200   (2205) CGCCGTGGCCGAGGGCACCGACCGCATCATCGAGGTGGCC
    Consensus   (2241) CGCCGTGGCCGAGGGCACCGACCGCATCATCGAGGTGGCC
```

FIG. 3I

```
                              2281                                    2320
Leu122-Ser199    (2251)   CAGCGCATCGGCCGCGCCTTCCTGCACATCCCCCGCCGCA
Val127-Asn195    (2281)   CAGCGCATCGGCCGCGCCTTCCTGCACATCCCCCGCCGCA
Val120-Ile201B   (2239)   CAGCGCATCGGCCGCGCCTTCCTGCACATCCCCCGCCGCA
Val120-Ala204    (2233)   CAGCGCATCGGCCGCGCCTTCCTGCACATCCCCCGCCGCA
Val120-Ile201    (2239)   CAGCGCATCGGCCGCGCCTTCCTGCACATCCCCCGCCGCA
Val120-Thr202    (2239)   CAGCGCATCGGCCGCGCCTTCCTGCACATCCCCCGCCGCA
Lys121-Val200    (2245)   CAGCGCATCGGCCGCGCCTTCCTGCACATCCCCCGCCGCA
    Consensus    (2281)   CAGCGCATCGGCCGCGCCTTCCTGCACATCCCCCGCCGCA
                              2321                                    2360
Leu122-Ser199    (2291)   TCCGCCAGGGCTTCGAGCGCGCCCTGCTGTAACTCGAGCG
Val127-Asn195    (2321)   TCCGCCAGGGCTTCGAGCGCGCCCTGCTGTAACTCGAG--
Val120-Ile201B   (2279)   TCCGCCAGGGCTTCGAGCGCGCCCTGCTGTAACTCGAGCG
Val120-Ala204    (2273)   TCCGCCAGGGCTTCGAGCGCGCCCTGCTGTAACTCGAG--
Val120-Ile201    (2279)   TCCGCCAGGGCTTCGAGCGCGCCCTGCTGTAACTCGAG--
Val120-Thr202    (2279)   TCCGCCAGGGCTTCGAGCGCGCCCTGCTGTAACTCGAG--
Lys121-Val200    (2285)   TCCGCCAGGGCTTCGAGCGCGCCCTGCTGTAACTCGAGCG
    Consensus    (2321)   TCCGCCAGGGCTTCGAGCGCGCCCTGCTGTAACTCGAG
                              2361
Leu122-Ser199    (2331)   TGCT
Val127-Asn195    (2359)   ----
Val120-Ile201B   (2319)   TGCT
Val120-Ala204    (2311)   ----
Val120-Ile201    (2317)   ----
Val120-Thr202    (2317)   ----
Lys121-Val200    (2325)   TGCT
    Consensus    (2361)
```

FIG. 3J

|  |  | 1 | 40 |
|---|---|---|---|
| Ile424-Ala433 | (1) | GAATTCGCCACCATGGATGCAATGAAGAGAGGGCTCTGCT | |
| Trp427-Gly431 | (1) | GAATTCGCCACCATGGATGCAATGAAGAGAGGGCTCTGCT | |
| Gln422-Tyr435B | (1) | GAATTCGCCACCATGGATGCAATGAAGAGAGGGCTCTGCT | |
| Arg426-Gly431 | (1) | GAATTCGCCACCATGGATGCAATGAAGAGAGGGCTCTGCT | |
| Ile423-Met434 | (1) | GAATTCGCCACCATGGATGCAATGAAGAGAGGGCTCTGCT | |
| Gln422-Tyr435 | (1) | GAATTCGCCACCATGGATGCAATGAAGAGAGGGCTCTGCT | |
| Arg426-Lys432 | (1) | GAATTCGCCACCATGGATGCAATGAAGAGAGGGCTCTGCT | |
| Arg426-Gly431B | (1) | GAATTCGCCACCATGGATGCAATGAAGAGAGGGCTCTGCT | |
| Asn425-Lys432 | (1) | GAATTCGCCACCATGGATGCAATGAAGAGAGGGCTCTGCT | |
| Consensus | (1) | GAATTCGCCACCATGGATGCAATGAAGAGAGGGCTCTGCT | |

|  |  | 41 | 80 |
|---|---|---|---|
| Ile424-Ala433 | (41) | GTGTGCTGCTGCTGTGTGGAGCAGTCTTCGTTTCGCCCAG | |
| Trp427-Gly431 | (41) | GTGTGCTGCTGCTGTGTGGAGCAGTCTTCGTTTCGCCCAG | |
| Gln422-Tyr435B | (41) | GTGTGCTGCTGCTGTGTGGAGCAGTCTTCGTTTCGCCCAG | |
| Arg426-Gly431 | (41) | GTGTGCTGCTGCTGTGTGGAGCAGTCTTCGTTTCGCCCAG | |
| Ile423-Met434 | (41) | GTGTGCTGCTGCTGTGTGGAGCAGTCTTCGTTTCGCCCAG | |
| Gln422-Tyr435 | (41) | GTGTGCTGCTGCTGTGTGGAGCAGTCTTCGTTTCGCCCAG | |
| Arg426-Lys432 | (41) | GTGTGCTGCTGCTGTGTGGAGCAGTCTTCGTTTCGCCCAG | |
| Arg426-Gly431B | (41) | GTGTGCTGCTGCTGTGTGGAGCAGTCTTCGTTTCGCCCAG | |
| Asn425-Lys432 | (41) | GTGTGCTGCTGCTGTGTGGAGCAGTCTTCGTTTCGCCCAG | |
| Consensus | (41) | GTGTGCTGCTGCTGTGTGGAGCAGTCTTCGTTTCGCCCAG | |

|  |  | 81 | 120 |
|---|---|---|---|
| Ile424-Ala433 | (81) | CGCCGTGGAGAAGCTGTGGGTGACCGTGTACTACGGCGTG | |
| Trp427-Gly431 | (81) | CGCCGTGGAGAAGCTGTGGGTGACCGTGTACTACGGCGTG | |
| Gln422-Tyr435B | (81) | CGCCGTGGAGAAGCTGTGGGTGACCGTGTACTACGGCGTG | |
| Arg426-Gly431 | (81) | CGCCGTGGAGAAGCTGTGGGTGACCGTGTACTACGGCGTG | |
| Ile423-Met434 | (81) | CGCCGTGGAGAAGCTGTGGGTGACCGTGTACTACGGCGTG | |
| Gln422-Tyr435 | (81) | CGCCGTGGAGAAGCTGTGGGTGACCGTGTACTACGGCGTG | |
| Arg426-Lys432 | (81) | CGCCGTGGAGAAGCTGTGGGTGACCGTGTACTACGGCGTG | |
| Arg426-Gly431B | (81) | CGCCGTGGAGAAGCTGTGGGTGACCGTGTACTACGGCGTG | |
| Asn425-Lys432 | (81) | CGCCGTGGAGAAGCTGTGGGTGACCGTGTACTACGGCGTG | |
| Consensus | (81) | CGCCGTGGAGAAGCTGTGGGTGACCGTGTACTACGGCGTG | |

|  |  | 121 | 160 |
|---|---|---|---|
| Ile424-Ala433 | (121) | CCCGTGTGGAAGGAGGCCACCACCACCCTGTTCTGCGCCA | |
| Trp427-Gly431 | (121) | CCCGTGTGGAAGGAGGCCACCACCACCCTGTTCTGCGCCA | |
| Gln422-Tyr435B | (121) | CCCGTGTGGAAGGAGGCCACCACCACCCTGTTCTGCGCCA | |
| Arg426-Gly431 | (121) | CCCGTGTGGAAGGAGGCCACCACCACCCTGTTCTGCGCCA | |
| Ile423-Met434 | (121) | CCCGTGTGGAAGGAGGCCACCACCACCCTGTTCTGCGCCA | |
| Gln422-Tyr435 | (121) | CCCGTGTGGAAGGAGGCCACCACCACCCTGTTCTGCGCCA | |
| Arg426-Lys432 | (121) | CCCGTGTGGAAGGAGGCCACCACCACCCTGTTCTGCGCCA | |
| Arg426-Gly431B | (121) | CCCGTGTGGAAGGAGGCCACCACCACCCTGTTCTGCGCCA | |
| Asn425-Lys432 | (121) | CCCGTGTGGAAGGAGGCCACCACCACCCTGTTCTGCGCCA | |
| Consensus | (121) | CCCGTGTGGAAGGAGGCCACCACCACCCTGTTCTGCGCCA | |

|  |  | 161 | 200 |
|---|---|---|---|
| Ile424-Ala433 | (161) | GCGACGCCAAGGCCTACGACACCGAGGTGCACAACGTGTG | |
| Trp427-Gly431 | (161) | GCGACGCCAAGGCCTACGACACCGAGGTGCACAACGTGTG | |
| Gln422-Tyr435B | (161) | GCGACGCCAAGGCCTACGACACCGAGGTGCACAACGTGTG | |
| Arg426-Gly431 | (161) | GCGACGCCAAGGCCTACGACACCGAGGTGCACAACGTGTG | |
| Ile423-Met434 | (161) | GCGACGCCAAGGCCTACGACACCGAGGTGCACAACGTGTG | |
| Gln422-Tyr435 | (161) | GCGACGCCAAGGCCTACGACACCGAGGTGCACAACGTGTG | |
| Arg426-Lys432 | (161) | GCGACGCCAAGGCCTACGACACCGAGGTGCACAACGTGTG | |
| Arg426-Gly431B | (161) | GCGACGCCAAGGCCTACGACACCGAGGTGCACAACGTGTG | |
| Asn425-Lys432 | (161) | GCGACGCCAAGGCCTACGACACCGAGGTGCACAACGTGTG | |
| Consensus | (161) | GCGACGCCAAGGCCTACGACACCGAGGTGCACAACGTGTG | |

|  |  | 201 | 240 |
|---|---|---|---|
| Ile424-Ala433 | (201) | GGCCACCCACGGCCTGCGTGCCCACCGACCCGAACCCCAG | |

*FIG. 4A*

| | | 201 240 |
|---|---|---|
| Trp427-Gly431 | (201) | GGCCACCCACGCCTGCGTGCCCACCGAGCCCAACCCCCAG |
| Gln422-Tyr435B | (201) | GGCCACCCACGCCTGCGTGCCCACCGACCCCAACCCCCAG |
| Arg426-Gly431 | (201) | GGCCACCCACGCCTGCGTGCCCACCGACCCCAACCCCCAG |
| Ile423-Met434 | (201) | GGCCACCCACGCCTGCGTGCCCACCGAGCCCAACCCCCAG |
| Gln422-Tyr435 | (201) | GGCCACCCACGCCTGCGTGCCCACCGACCCCAACCCCCAG |
| Arg426-Lys432 | (201) | GGCCACCCACGCCTGCGTGCCCACCGAGCCCAACCCCCAG |
| Arg426-Gly431B | (201) | GGCCACCCACGCCTGCGTGCCCACCGACCCCAACCCCCAG |
| Asn425-Lys432 | (201) | GGCCACCCACGCCTGCGTGCCCACCGACCCCAACCCCCAG |
| Consensus | (201) | GGCCACCCACGCCTGCGTGCCCACCGACCCCAACCCCCAG |

241 280

| Ile424-Ala433 | (241) | GAGATCGTGCTGGAGAACGTGACCGAGAACTTCAACATGT |
|---|---|---|
| Trp427-Gly431 | (241) | GAGATCGTGCTGGAGAACGTGACCGAGAACTTCAACATGT |
| Gln422-Tyr435B | (241) | GAGATCGTGCTGGAGAACGTGACCGAGAACTTCAACATGT |
| Arg426-Gly431 | (241) | GAGATCGTGCTGGAGAACGTGACCGAGAACTTCAACATGT |
| Ile423-Met434 | (241) | GAGATCGTGCTGGAGAACGTGACCGAGAACTTCAACATGT |
| Gln422-Tyr435 | (241) | GAGATCGTGCTGGAGAACGTGACCGAGAACTTCAACATGT |
| Arg426-Lys432 | (241) | GAGATCGTGCTGGAGAACGTGACCGAGAACTTCAACATGT |
| Arg426-Gly431B | (241) | GAGATCGTGCTGGAGAACGTGACCGAGAACTTCAACATGT |
| Asn425-Lys432 | (241) | GAGATCGTGCTGGAGAACGTGACCGAGAACTTCAACATGT |
| Consensus | (241) | GAGATCGTGCTGGAGAACGTGACCGAGAACTTCAACATGT |

281 320

| Ile424-Ala433 | (281) | GGAAGAACAACATGGTGGAGCAGATGCACGAGGACATCAT |
|---|---|---|
| Trp427-Gly431 | (281) | GGAAGAACAACATGGTGGAGCAGATGCACGAGGACATCAT |
| Gln422-Tyr435B | (281) | GGAAGAACAACATGGTGGAGCAGATGCACGAGGACATCAT |
| Arg426-Gly431 | (281) | GGAAGAACAACATGGTGGAGCAGATGCACGAGGACATCAT |
| Ile423-Met434 | (281) | GGAAGAACAACATGGTGGAGCAGATGCACGAGGACATCAT |
| Gln422-Tyr435 | (281) | GGAAGAACAACATGGTGGAGCAGATGCACGAGGACATCAT |
| Arg426-Lys432 | (281) | GGAAGAACAACATGGTGGAGCAGATGCACGAGGACATCAT |
| Arg426-Gly431B | (281) | GGAAGAACAACATGGTGGAGCAGATGCACGAGGACATCAT |
| Asn425-Lys432 | (281) | GGAAGAACAACATGGTGGAGCAGATGCACGAGGACATCAT |
| Consensus | (281) | GGAAGAACAACATGGTGGAGCAGATGCACGAGGACATCAT |

321 360

| Ile424-Ala433 | (321) | CAGCCTGTGGGACCAGAGCCTGAAGCCCTGCGTGAAGCTG |
|---|---|---|
| Trp427-Gly431 | (321) | CAGCCTGTGGGACCAGAGCCTGAAGCCCTGCGTGAAGCTG |
| Gln422-Tyr435B | (321) | CAGCCTGTGGGACCAGAGCCTGAAGCCCTGCGTGAAGCTG |
| Arg426-Gly431 | (321) | CAGCCTGTGGGACCAGAGCCTGAAGCCCTGCGTGAAGCTG |
| Ile423-Met434 | (321) | CAGCCTGTGGGACCAGAGCCTGAAGCCCTGCGTGAAGCTG |
| Gln422-Tyr435 | (321) | CAGCCTGTGGGACCAGAGCCTGAAGCCCTGCGTGAAGCTG |
| Arg426-Lys432 | (321) | CAGCCTGTGGGACCAGAGCCTGAAGCCCTGCGTGAAGCTG |
| Arg426-Gly431B | (321) | CAGCCTGTGGGACCAGAGCCTGAAGCCCTGCGTGAAGCTG |
| Asn425-Lys432 | (321) | CAGCCTGTGGGACCAGAGCCTGAAGCCCTGCGTGAAGCTG |
| Consensus | (321) | CAGCCTGTGGGACCAGAGCCTGAAGCCCTGCGTGAAGCTG |

361 400

| Ile424-Ala433 | (361) | ACCCCCTGTGCGTGACCCTGCACTGCACCAACCTGAAGA |
|---|---|---|
| Trp427-Gly431 | (361) | ACCCCCTGTGCGTGACCCTGCACTGCACCAACCTGAAGA |
| Gln422-Tyr435B | (361) | ACCCCCTGTGCGTGACCCTGCACTGCACCAACCTGAAGA |
| Arg426-Gly431 | (361) | ACCCCCTGTGCGTGACCCTGCACTGCACCAACCTGAAGA |
| Ile423-Met434 | (361) | ACCCCCTGTGCGTGACCCTGCACTGCACCAACCTGAAGA |
| Gln422-Tyr435 | (361) | ACCCCCTGTGCGTGACCCTGCACTGCACCAACCTGAAGA |
| Arg426-Lys432 | (361) | ACCCCCTGTGCGTGACCCTGCACTGCACCAACCTGAAGA |
| Arg426-Gly431B | (361) | ACCCCCTGTGCGTGACCCTGCACTGCACCAACCTGAAGA |
| Asn425-Lys432 | (361) | ACCCCCTGTGCGTGACCCTGCACTGCACCAACCTGAAGA |
| Consensus | (361) | ACCCCCTGTGCGTGACCCTGCACTGCACCAACCTGAAGA |

401 440

| Ile424-Ala433 | (401) | ACGCCACCAACACCAAGAGCAGCAACTGGAAGGAGATGGA |
|---|---|---|
| Trp427-Gly431 | (401) | ACGCCACCAACACCAAGAGCAGCAACTGGAAGGAGATGGA |
| Gln422-Tyr435B | (401) | ACGCCACCAACACCAAGAGCAGCAACTGGAAGGAGATGGA |

*FIG. 4B*

```
Arg426-Gly431    (401) ACGCCACCAACACCAAGAGCAGCAACTGGAAGGAGATGGA
Ile423-Met434    (401) ACGCCACCAACACCAAGAGCAGCAACTGGAAGGAGATGGA
Gln422-Tyr435    (401) ACGCCACCAACACCAAGAGCAGCAACTGGAAGGAGATGGA
Arg426-Lys432    (401) ACGCCACCAACACCAAGAGCAGCAACTGGAAGGAGATGGA
Arg426-Gly431B   (401) ACGCCACCAACACCAAGAGCAGCAACTGGAAGGAGATGGA
Asn425-Lys432    (401) ACGCCACCAACACCAAGAGCAGCAACTGGAAGGAGATGGA
    Consensus    (401) ACGCCACCAACACCAAGAGCAGCAACTGGAAGGAGATGGA
                        441                                          480
Ile424-Ala433    (441) CCGCGGCGAGATCAAGAACTGCAGCTTCAAGGTGACCACC
Trp427-Gly431    (441) CCGCGGCGAGATCAAGAACTGCAGCTTCAAGGTGACCACC
Gln422-Tyr435B   (441) CCGCGGCGAGATCAAGAACTGCAGCTTCAAGGTGACCACC
Arg426-Gly431    (441) CCGCGGCGAGATCAAGAACTGCAGCTTCAAGGTGACCACC
Ile423-Met434    (441) CCGCGGCGAGATCAAGAACTGCAGCTTCAAGGTGACCACC
Gln422-Tyr435    (441) CCGCGGCGAGATCAAGAACTGCAGCTTCAAGGTGACCACC
Arg426-Lys432    (441) CCGCGGCGAGATCAAGAACTGCAGCTTCAAGGTGACCACC
Arg426-Gly431B   (441) CCGCGGCGAGATCAAGAACTGCAGCTTCAAGGTGACCACC
Asn425-Lys432    (441) CCGCGGCGAGATCAAGAACTGCAGCTTCAAGGTGACCACC
    Consensus    (441) CCGCGGCGAGATCAAGAACTGCAGCTTCAAGGTGACCACC
                        481                                          520
Ile424-Ala433    (481) AGCATCCGCAACAAGATGCAGAAGGAGTACGCCCTGTTCT
Trp427-Gly431    (481) AGCATCCGCAACAAGATGCAGAAGGAGTACGCCCTGTTCT
Gln422-Tyr435B   (481) AGCATCCGCAACAAGATGCAGAAGGAGTAGGCCCTGTTCT
Arg426-Gly431    (481) AGCATCCGCAACAAGATGCAGAAGGAGTACGCCCTGTTCT
Ile423-Met434    (481) AGCATCCGCAACAAGATGCAGAAGGAGTACGCCCTGTTCT
Gln422-Tyr435    (481) AGCATCCGCAACAAGATGCAGAAGGAGTAGGCCCTGTTCT
Arg426-Lys432    (481) AGCATCCGCAACAAGATGCAGAAGGAGTACGCCCTGTTCT
Arg426-Gly431B   (481) AGCATCCGCAACAAGATGCAGAAGGAGTACGCCCTGTTCT
Asn425-Lys432    (481) AGCATCCGCAACAAGATGCAGAAGGAGTACGCCCTGTTCT
    Consensus    (481) AGCATCCGCAACAAGATGCAGAAGGAGTACGCCCTGTTCT
                        521                                          560
Ile424-Ala433    (521) ACAAGCTGGACGTGGTGCCCATCGACAACGACAACACCAG
Trp427-Gly431    (521) ACAAGCTGGACGTGGTGCCCATCGACAACGACAACACCAG
Gln422-Tyr435B   (521) ACAAGCTGGACGTGGTGCCCATCGACAACGACAACACCAG
Arg426-Gly431    (521) ACAAGCTGGACGTGGTGCCCATCGACAACGACAACACCAG
Ile423-Met434    (521) ACAAGCTGGACGTGGTGCCCATCGACAACGACAACACCAG
Gln422-Tyr435    (521) ACAAGCTGGACGTGGTGCCCATCGACAACGACAACACCAG
Arg426-Lys432    (521) ACAAGCTGGACGTGGTGCCCATCGACAACGACAACACCAG
Arg426-Gly431B   (521) ACAAGCTGGACGTGGTGCCCATCGACAACGAGAACACCAG
Asn425-Lys432    (521) ACAAGCTGGACGTGGTGCCCATCGACAACGACAACACCAG
    Consensus    (521) ACAAGCTGGACGTGGTGCCCATCGACAACGACAACACCAG
                        561                                          600
Ile424-Ala433    (561) CTACAAGCTGATCAACTGCAACACCAGCGTGATCACCCAG
Trp427-Gly431    (561) CTACAAGCTGATCAACTGCAACACCAGCGTGATCACCCAG
Gln422-Tyr435B   (561) CTACAAGCTGATCAACTGCAACACCAGCGTGATCACCCAG
Arg426-Gly431    (561) CTACAAGCTGATCAACTGCAACACCAGCGTGATCACCCAG
Ile423-Met434    (561) CTACAAGCTGATCAACTGCAACACCAGCGTGATCACCCAG
Gln422-Tyr435    (561) CTACAAGCTGATCAACTGCAACACCAGCGTGATCACCCAG
Arg426-Lys432    (561) CTACAAGCTGATCAACTGCAACACCAGCGTGATCACCCAG
Arg426-Gly431B   (561) CTACAAGCTGATCAACTGCAACACCAGCGTGATCACCCAG
Asn425-Lys432    (561) CTACAAGCTGATCAACTGCAACACCAGCGTGATCACCCAG
    Consensus    (561) CTACAAGCTGATCAACTGCAACACCAGCGTGATCACCCAG
                        601                                          640
Ile424-Ala433    (601) GCCTGCCCCAAGGTGAGCTTCGAGCCCATCCCCATCCACT
Trp427-Gly431    (601) GCCTGCCCCAAGGTGAGCTTCGAGCCCATCCCCATCCACT
Gln422-Tyr435B   (601) GCCTGCCCCAAGGTGAGCTTCGAGCCCATCCCCATCCACT
Arg426-Gly431    (601) GCCTGCCCCAAGGTGAGCTTCGAGCCCATCCCCATCCACT
Ile423-Met434    (601) GCCTGCCCCAAGGTGAGCTTCGAGCCCATCCCCATCCACT
```

*FIG. 4C*

|                  |       |                                          |
|------------------|-------|------------------------------------------|
| Gln422-Tyr435    | (601) | GCCTGCCCCAAGGTGAGCTTCGAGCCCATCCCCATCCACT |
| Arg426-Lys432    | (601) | GCCTGCCCCAAGGTGAGCTTCGAGCCCATCCCCATCCACT |
| Arg426-Gly431B   | (601) | GCCTGCCCCAAGGTGAGCTTCGAGCCCATCCCCATCCACT |
| Asn425-Lys432    | (601) | GCCTGCCCCAAGGTGAGCTTCGAGCCCATCCCCATCCACT |
| Consensus        | (601) | GCCTGCCCCAAGGTGAGCTTCGAGCCCATCCCCATCCACT |
|                  |       | 641                                  680 |
| Ile424-Ala433    | (641) | ACTGCGCCCCGCCGGCTTCGCCATCCTGAAGTGCAACGA  |
| Trp427-Gly431    | (641) | ACTGCGCCCCGCCGGCTTCGCCATCCTGAAGTGCAACGA  |
| Gln422-Tyr435B   | (641) | ACTGCGCCCCGCCGGCTTCGCCATCCTGAAGTGCAACGA  |
| Arg426-Gly431    | (641) | ACTGCGCCCCGCCGGCTTCGCCATCCTGAAGTGCAACGA  |
| Ile423-Met434    | (641) | ACTGCGCCCCGCCGGCTTCGCCATCCTGAAGTGCAACGA  |
| Gln422-Tyr435    | (641) | ACTGCGCCCCGCCGGCTTCGCCATCCTGAAGTGCAACGA  |
| Arg426-Lys432    | (641) | ACTGCGCCCCGCCGGCTTCGCCATCCTGAAGTGCAACGA  |
| Arg426-Gly431B   | (641) | ACTGCGCCCCGCCGGCTTCGCCATCCTGAAGTGCAACGA  |
| Asn425-Lys432    | (641) | ACTGCGCCCCGCCGGCTTCGCCATCCTGAAGTGCAACGA  |
| Consensus        | (641) | ACTGCGCCCCGCCGGCTTCGCCATCCTGAAGTGCAACGA  |
|                  |       | 681                                  720 |
| Ile424-Ala433    | (681) | CAAGAAGTTCAACGGCAGCGGCCCCTGCACCAACGTGAGC |
| Trp427-Gly431    | (681) | CAAGAAGTTCAACGGCAGCGGCCCCTGCACCAACGTGAGC |
| Gln422-Tyr435B   | (681) | CAAGAAGTTCAACGGCAGCGGCCCCTGCACCAACGTGAGC |
| Arg426-Gly431    | (681) | CAAGAAGTTCAACGGCAGCGGCCCCTGCACCAACGTGAGC |
| Ile423-Met434    | (681) | CAAGAAGTTCAACGGCAGCGGCCCCTGCACCAACGTGAGC |
| Gln422-Tyr435    | (681) | CAAGAAGTTCAACGGCAGCGGCCCCTGCACCAACGTGAGC |
| Arg426-Lys432    | (681) | CAAGAAGTTCAACGGCAGCGGCCCCTGCACCAACGTGAGC |
| Arg426-Gly431B   | (681) | CAAGAAGTTCAACGGCAGCGGCCCCTGCACCAACGTGAGC |
| Asn425-Lys432    | (681) | CAAGAAGTTCAACGGCAGCGGCCCCTGCACCAACGTGAGC |
| Consensus        | (681) | CAAGAAGTTCAACGGCAGCGGCCCCTGCACCAACGTGAGC |
|                  |       | 721                                  760 |
| Ile424-Ala433    | (721) | ACCGTGCAGTGCACCCACGGCATCCGCCCCGTGGTGAGCA |
| Trp427-Gly431    | (721) | ACCGTGCAGTGCACCCACGGCATCCGCCCCGTGGTGAGCA |
| Gln422-Tyr435B   | (721) | ACCGTGCAGTGCACCCACGGCATCCGCCCCGTGGTGAGCA |
| Arg426-Gly431    | (721) | ACCGTGCAGTGCACCCACGGCATCCGCCCCGTGGTGAGCA |
| Ile423-Met434    | (721) | ACCGTGCAGTGCACCCACGGCATCCGCCCCGTGGTGAGCA |
| Gln422-Tyr435    | (721) | ACCGTGCAGTGCACCCACGGCATCCGCCCCGTGGTGAGCA |
| Arg426-Lys432    | (721) | ACCGTGCAGTGCACCCACGGCATCCGCCCCGTGGTGAGCA |
| Arg426-Gly431B   | (721) | ACCGTGCAGTGCACCCACGGCATCCGCCCCGTGGTGAGCA |
| Asn425-Lys432    | (721) | ACCGTGCAGTGCACCCACGGCATCCGCCCCGTGGTGAGCA |
| Consensus        | (721) | ACCGTGCAGTGCACCCACGGCATCCGCCCCGTGGTGAGCA |
|                  |       | 761                                  800 |
| Ile424-Ala433    | (761) | CCCAGCTGCTGCTGAACGGCAGCCTGGCCGAGGAGGGCGT |
| Trp427-Gly431    | (761) | CCCAGCTGCTGCTGAACGGCAGCCTGGCCGAGGAGGGCGT |
| Gln422-Tyr435B   | (761) | CCCAGCTGCTGCTGAACGGCAGCCTGGCCGAGGAGGGCGT |
| Arg426-Gly431    | (761) | CCCAGCTGCTGCTGAACGGCAGCCTGGCCGAGGAGGGCGT |
| Ile423-Met434    | (761) | CCCAGCTGCTGCTGAACGGCAGCCTGGCCGAGGAGGGCGT |
| Gln422-Tyr435    | (761) | CCCAGCTGCTGCTGAACGGCAGCCTGGCCGAGGAGGGCGT |
| Arg426-Lys432    | (761) | CCCAGCTGCTGCTGAACGGCAGCCTGGCCGAGGAGGGCGT |
| Arg426-Gly431B   | (761) | CCCAGCTGCTGCTGAACGGCAGCCTGGCCGAGGAGGGCGT |
| Asn425-Lys432    | (761) | CCCAGCTGCTGCTGAACGGCAGCCTGGCCGAGGAGGGCGT |
| Consensus        | (761) | CCCAGCTGCTGCTGAACGGCAGCCTGGCCGAGGAGGGCGT |
|                  |       | 801                                  840 |
| Ile424-Ala433    | (801) | GGTGATCCGCAGCGAGAACTTCACCGACAACGCCAAGACC |
| Trp427-Gly431    | (801) | GGTGATCCGCAGCGAGAACTTCACCGACAACGCCAAGACC |
| Gln422-Tyr435B   | (801) | GGTGATCCGCAGCGAGAACTTCACCGACAACGCCAAGACC |
| Arg426-Gly431    | (801) | GGTGATCCGCAGCGAGAACTTCACCGACAACGCCAAGACC |
| Ile423-Met434    | (801) | GGTGATCCGCAGCGAGAACTTCACCGACAACGCCAAGACC |
| Gln422-Tyr435    | (801) | GGTGATCCGCAGCGAGAACTTCACCGACAACGCCAAGACC |
| Arg426-Lys432    | (801) | GGTGATCCGCAGCGAGAACTTCACCGACAACGCCAAGACC |

*FIG. 4D*

```
Arg426-Gly431B   (801)  GGTGATCCGCAGCGAGAACTTCACCGACAACGCCAAGACC
Asn425-Lys432    (801)  GGTGATCCGCAGCGAGAACTTCACCGACAACGCCAAGACC
    Consensus    (801)  GGTGATCCGCAGCGAGAACTTCACCGACAACGCCAAGACC
                        841                                     880
Ile424-Ala433    (841)  ATCATCGTGCAGCTGAAGGAGAGCGTGGAGATCAACTGCA
Trp427-Gly431    (841)  ATCATCGTGCAGCTGAAGGAGAGCGTGGAGATCAACTGCA
Gln422-Tyr435B   (841)  ATCATCGTGCAGCTGAAGGAGAGCGTGGAGATCAACTGCA
Arg426-Gly431    (841)  ATCATCGTGCAGCTGAAGGAGAGCGTGGAGATCAACTGCA
Ile423-Met434    (841)  ATCATCGTGCAGCTGAAGGAGAGCGTGGAGATCAACTGCA
Gln422-Tyr435    (841)  ATCATCGTGCAGCTGAAGGAGAGCGTGGAGATCAACTGCA
Arg426-Lys432    (841)  ATCATCGTGCAGCTGAAGGAGAGCGTGGAGATCAACTGCA
Arg426-Gly431B   (841)  ATCATCGTGCAGCTGAAGGACAGCGTGGAGATCAACTGCA
Asn425-Lys432    (841)  ATCATCGTGCAGCTGAAGGAGAGCGTGGAGATCAACTGCA
    Consensus    (841)  ATCATCGTGCAGCTGAAGGAGAGCGTGGAGATCAACTGCA
                        881                                     920
Ile424-Ala433    (881)  CCCGCCCCAACAACAACACCCGCAAGAGCATCACCATCGG
Trp427-Gly431    (881)  CCCGCCCCAACAACAACAGCCGCAAGAGCATCACCATCGG
Gln422-Tyr435B   (881)  CCCGCCCCAACAACAACACCCGCAAGAGCATCACCATCGG
Arg426-Gly431    (881)  CCCGCCCCAACAACAACACCCGCAAGAGCATCACCATCGG
Ile423-Met434    (881)  CCCGCCCCAACAACAACAGCCGCAAGAGCATCACCATCGG
Gln422-Tyr435    (881)  CCCGCCCCAACAACAACACCCGCAAGAGCATCACCATCGG
Arg426-Lys432    (881)  CCCGCCCCAACAACAACCGCAAGAGCATCACCATCGG
Arg426-Gly431B   (881)  CCCGCCCCAACAACAACACCCGCAAGAGCATCACCATCGG
Asn425-Lys432    (881)  CCCGCCCCAACAACAACACCCGCAAGAGCATCACCATCGG
    Consensus    (881)  CCCGCCCCAACAACAACACCCGCAAGAGCATCACCATCGG
                        921                                    960
Ile424-Ala433    (921)  CCCCGGCCGCGCCTTCTACGCCACCGGCGACATCATCGGC
Trp427-Gly431    (921)  CCCCGGCCGCGCCTTCTACGCCACCGGCGACATCATCGGC
Gln422-Tyr435B   (921)  CCCCGGCCGCGCCTTCTACGCCACCGGCGACATCATCGGC
Arg426-Gly431    (921)  CCCCGGCCGCGCCTTCTACGCCACCGGCGACATCATCGGC
Ile423-Met434    (921)  CCCCGGCCGCGCCTTCTACGCCACCGGCGACATCATCGGC
Gln422-Tyr435    (921)  CCCCGGCCGCGCCTTCTACGCCACCGGCGACATCATCGGC
Arg426-Lys432    (921)  CCCCGGCCGCGCCTTCTACGCCACCGGCGACATCATCGGC
Arg426-Gly431B   (921)  CCCCGGCCGCGCCTTCTACGCCACCGGCGACATCATCGGC
Asn425-Lys432    (921)  CCCCGGCCGCGCCTTCTACGCCACCGGCGACATCATCGGC
    Consensus    (921)  CCCCGGCCGCGCCTTCTACGCCACCGGCGACATCATCGGC
                        961                                    1000
Ile424-Ala433   (961)  GACATCCGCCAGGCCCACTGCAACATCAGCGGCGAGAAGT
Trp427-Gly431   (961)  GACATCCGCCAGGCCCACTGCAACATCAGCGGCGAGAAGT
Gln422-Tyr435B  (961)  GACATCCGCCAGGCCCACTGCAACATCAGCGGCGAGAAGT
Arg426-Gly431   (961)  GACATCCGCCAGGCCCACTGCAACATCAGCGGCGAGAAGT
Ile423-Met434   (961)  GACATCCGCCAGGCCCACTGCAACATCAGCGGCGAGAAGT
Gln422-Tyr435   (961)  GACATCCGCCAGGCCCACTGCAACATCAGCGGCGAGAAGT
Arg426-Lys432   (961)  GACATCCGCCAGGCCCACTGCAACATCAGCGGCGAGAAGT
Arg426-Gly431B  (961)  GACATCCGCCAGGCCCACTGCAACATCAGCGGCGAGAAGT
Asn425-Lys432   (961)  GACATCCGCCAGGCCCACTGCAACATCAGCGGCGAGAAGT
    Consensus   (961)  GACATCCGCCAGGCCCACTGCAACATCAGCGGCGAGAAGT
                        1001                                    1040
Ile424-Ala433  (1001)  GGAACAACACCCTGAAGCAGATCGTGACCAAGCTGCAGGC
Trp427-Gly431  (1001)  GGAACAACACCCTGAAGCAGATCGTGACCAAGCTGCAGGC
Gln422-Tyr435B (1001)  GGAACAACACCCTGAAGCAGATCGTGACCAAGCTGCAGGC
Arg426-Gly431  (1001)  GGAACAACACCCTGAAGCAGATCGTGACCAAGCTGCAGGC
Ile423-Met434  (1001)  GGAACAACACCCTGAAGCAGATCGTGACCAAGCTGCAGGC
Gln422-Tyr435  (1001)  GGAACAACACCCTGAAGCAGATCGTGACCAAGCTGCAGGC
Arg426-Lys432  (1001)  GGAACAACACCCTGAAGCAGATCGTGACCAAGCTGCAGGC
Arg426-Gly431B (1001)  GGAACAACACCCTGAAGCAGATCGTGACCAAGCTGCAGGC
Asn425-Lys432  (1001)  GGAACAACACCCTGAAGCAGATCGTGACCAAGCTGCAGGG
```

*FIG. 4E*

```
Consensus       (1001) GGAACAACACCCTGAAGCAGATCGTGACCAAGCTGCAGGC
                       1041                                    1080
Ile424-Ala433   (1041) CCAGTTCGGCAACAAGACCATCGTGTTCAAGCAGAGCAGC
Trp427-Gly431   (1041) CCAGTTCGGCAACAAGACCATCGTGTTCAAGCAGAGCAGC
Gln422-Tyr435B  (1041) CCAGTTCGGCAACAAGACCATCGTGTTCAAGCAGAGCAGC
Arg426-Gly431   (1041) CCAGTTCGGCAACAAGACCATCGTGTTCAAGCAGAGCAGC
Ile423-Met434   (1041) CCAGTTCGGCAACAAGACCATCGTGTTCAAGCAGAGCAGC
Gln422-Tyr435   (1041) CCAGTTCGGCAACAAGACCATCGTGTTCAAGCAGAGCAGC
Arg426-Lys432   (1041) CCAGTTCGGCAACAAGACCATCGTGTTCAAGCAGAGCAGC
Arg426-Gly431B  (1041) CCAGTTCGGCAACAAGACCATCGTGTTCAAGCAGAGCAGC
Asn425-Lys432   (1041) CCAGTTCGGCAACAAGACCATCGTGTTCAAGCAGAGCAGC
Consensus       (1041) CCAGTTCGGCAACAAGACCATCGTGTTCAAGCAGAGCAGC
                       1081                                    1120
Ile424-Ala433   (1081) GGCGGCGACCCCGAGATCGTGATGCACAGCTTCAACTGCG
Trp427-Gly431   (1081) GGCGGCGACCCCGAGATCGTGATGCACAGCTTCAACTGCG
Gln422-Tyr435B  (1081) GGCGGCGACCCCGAGATCGTGATGCACAGCTTCAACTGCG
Arg426-Gly431   (1081) GGCGGCGACCCCGAGATCGTGATGCACAGCTTCAACTGCG
Ile423-Met434   (1081) GGCGGCGACCCCGAGATCGTGATGCACAGCTTCAACTGCG
Gln422-Tyr435   (1081) GGCGGCGACCCCGAGATCGTGATGCACAGCTTCAACTGCG
Arg426-Lys432   (1081) GGCGGCGACCCCGAGATCGTGATGCACAGCTTCAACTGCG
Arg426-Gly431B  (1081) GGCGGCGACCCCGAGATCGTGATGCACAGCTTCAACTGCG
Asn425-Lys432   (1081) GGCGGCGACCCCGAGATCGTGATGCACAGCTTCAACTGCG
Consensus       (1081) GGCGGCGACCCCGAGATCGTGATGCACAGCTTCAACTGCG
                       1121                                    1160
Ile424-Ala433   (1121) GCGGCGAGTTCTTCTACTGCAACAGCACCCAGCTGTTCAA
Trp427-Gly431   (1121) GCGGCGAGTTCTTCTACTGCAACAGCACCCAGCTGTTCAA
Gln422-Tyr435B  (1121) GCGGCGAGTTCTTCTACTGCAACAGCACCCAGCTGTTCAA
Arg426-Gly431   (1121) GCGGCGAGTTCTTCTACTGCAACAGCACCCAGCTGTTCAA
Ile423-Met434   (1121) GCGGCGAGTTCTTCTACTGCAACAGCACCCAGCTGTTCAA
Gln422-Tyr435   (1121) GCGGCGAGTTCTTCTACTGCAACAGCACCCAGCTGTTCAA
Arg426-Lys432   (1121) GCGGCGAGTTCTTCTACTGCAACAGCACCCAGCTGTTCAA
Arg426-Gly431B  (1121) GCGGCGAGTTCTTCTACTGCAACAGCACCCAGCTGTTCAA
Asn425-Lys432   (1121) GCGGCGAGTTCTTCTACTGCAACAGCACCCAGCTGTTCAA
Consensus       (1121) GCGGCGAGTTCTTCTACTGCAACAGCACCCAGCTGTTCAA
                       1161                                    1200
Ile424-Ala433   (1161) CAGCACCTGGAACAACACCATCGGCCCCAACAACACCAAC
Trp427-Gly431   (1161) CAGCACCTGGAACAACACCATCGGCCCCAACAACACCAAC
Gln422-Tyr435B  (1161) CAGCACCTGGAACAACACCATCGGCCCCAACAACACCAAC
Arg426-Gly431   (1161) CAGCACCTGGAACAACACCATCGGCCCCAACAACACCAAC
Ile423-Met434   (1161) CAGCACCTGGAACAACACCATCGGCCCCAACAACACCAAC
Gln422-Tyr435   (1161) CAGCACCTGGAACAACACCATCGGCCCCAACAACACCAAC
Arg426-Lys432   (1161) CAGCACCTGGAACAACACCATCGGCCCCAACAACACCAAC
Arg426-Gly431B  (1161) CAGCACCTGGAACAACACCATCGGCCCCAACAACACCAAC
Asn425-Lys432   (1161) CAGCACCTGGAACAACACCATCGGCCCCAACAACACCAAC
Consensus       (1161) CAGCACCTGGAACAACACCATCGGCCCCAACAACACCAAC
                       1201                                    1240
Ile424-Ala433   (1201) GGCACCATCACCCTGCCCTGCCGCATCAAGCAGATCATC-
Trp427-Gly431   (1201) GGCACCATCACCCTGCCCTGCCGCATCAAGCAGATCATCA
Gln422-Tyr435B  (1201) GGCACCATCACCCTGCCCTGCCGCATCAAGCAG-------
Arg426-Gly431   (1201) GGCACCATCACCCTGCCCTGCCGCATCAAGCAGATCATCA
Ile423-Met434   (1201) GGCACCATCACCCTGCCCTGCCGCATCAAGCAGATC----
Gln422-Tyr435   (1201) GGCACCATCACCCTGCCCTGCCGCATCAAGCAG-------
Arg426-Lys432   (1201) GGCACCATCACCCTGCCCTGCCGCATCAAGCAGATCATCA
Arg426-Gly431B  (1201) GGCACCATCACCCTGCCCTGCCGCATCAAGCAGATCATCA
Asn425-Lys432   (1201) GGCACCATCACCCTGCCCTGCCGCATCAAGCAGATCATCA
Consensus       (1201) GGCACCATCACCCTGCCCTGCCGCATCAAGCAGATCATCA
                       1241                                    1280
```

*FIG. 4F*

| | | 1281 | 1320 |
|---|---|---|---|
| Ile424-Ala433 | (1240) | --------GGCGGC---G-CCATGTACGCCCCCCCCATCCG | |
| Trp427-Gly431 | (1241) | ACCGCTGGGGCGGCAAGGCCATGTACGGCCCCCCGATCCG | |
| Gln422-Tyr435B | (1234) | --------GCCCCG---------TACGCCCCCGGCATCCG | |
| Arg426-Gly431 | (1241) | ACCGCGGCGGCGGCAAGGCCATGTACGCGCCCCGCCATCCG | |
| Ile423-Met434 | (1237) | --------GGCGGC------ATGTACGCGCCCCGCATCCG | |
| Gln422-Tyr435 | (1234) | --------GGCGGC---------TACGCCCCCCGCATCCG | |
| Arg426-Lys432 | (1241) | ACCGCGGCGGCAACAAGGCCATGTACGCCCCCCCGATCCG | |
| Arg426-Gly431B | (1241) | ACGCGGCAGCGGCAAGGCCATGTACGCGCCCCGCCATCCG | |
| Asn425-Lys432 | (1241) | AC------GCCCCAAGGCCATGTACGCGCCCCCCATCCG | |
| Consensus | (1241) | AC      GGCGGCAAGGCCATGTACGCCCCCCCCATCCG | |

1281                                    1320

| | | 1281 | 1320 |
|---|---|---|---|
| Ile424-Ala433 | (1269) | CGGCCAGATCCGCTGCAGCAGCAACATCACCGGCCTGCTG | |
| Trp427-Gly431 | (1281) | CGGCCAGATCCGCTGCAGCAGCAACATCACCGGCCTGCTG | |
| Gln422-Tyr435B | (1257) | CGGCCAGATCCGCTGCAGCAGCAACATCACCGGCCTGCTG | |
| Arg426-Gly431 | (1281) | CGGCCAGATCCGCTGCAGCAGCAACATCACCGGCCTGCTG | |
| Ile423-Met434 | (1263) | CGGCCAGATCCGCTGCAGCAGCAACATCACCGGCCTGCTG | |
| Gln422-Tyr435 | (1257) | CGGCCAGATCCGCTGCAGCAGCAACATCACCGGCCTGCTG | |
| Arg426-Lys432 | (1281) | CGGCCAGATCCGCTGCAGCAGCAACATCACCGGCCTGCTG | |
| Arg426-Gly431B | (1281) | CGGCCAGATCCGCTGCAGCAGCAACATCACCGGCCTGCTG | |
| Asn425-Lys432 | (1275) | CGGCCAGATCCGCTGCAGCAGCAACATCACCGGCCTGCTG | |
| Consensus | (1281) | CGGCCAGATCCGCTGCAGCAGCAACATCACCGGCCTGCTG | |

1321                                    1360

| | | | |
|---|---|---|---|
| Ile424-Ala433 | (1309) | CTGACCCGCGACGGCGGCAAGGAGATCAGCAACACCACCG | |
| Trp427-Gly431 | (1321) | CTGACCCGCGACGGCGGCAAGGAGATCAGCAACACCACCG | |
| Gln422-Tyr435B | (1297) | CTGACCCGCGACGGCGGCAAGGAGATCAGCAACACCACCG | |
| Arg426-Gly431 | (1321) | CTGACCCGCGACGGCGGCAAGGAGATCAGCAACACCACCG | |
| Ile423-Met434 | (1303) | CTGACCCGCGACGGCGGCAAGGAGATCAGCAACACCACCG | |
| Gln422-Tyr435 | (1297) | CTGACCCGCGACGGCGGCAAGGAGATCAGCAACACCACCG | |
| Arg426-Lys432 | (1321) | CTGACCCGCGACGGCGGCAAGGAGATCAGCAACACCACCG | |
| Arg426-Gly431B | (1321) | CTGACCCGCGACGGCGGCAAGGAGATCAGCAACACCACCG | |
| Asn425-Lys432 | (1315) | CTGACCCGCGACGGCGGCAAGGAGATCAGCAACACCACCG | |
| Consensus | (1321) | CTGACCCGCGACGGCGGCAAGGAGATCAGCAACACCACCG | |

1361                                    1400

| | | | |
|---|---|---|---|
| Ile424-Ala433 | (1349) | AGATCTTCCGCCCCGGCGGCGGCGACATGCGCGACAACTG | |
| Trp427-Gly431 | (1361) | AGATCTTCCGCCCCGGCGGCGGCGACATGCGCGACAACTG | |
| Gln422-Tyr435B | (1337) | AGATCTTCCGCCCCGGCGGCGGCGACATGCGCGACAACTG | |
| Arg426-Gly431 | (1361) | AGATCTTCCGCCCCGGCGGCGGCGACATGCGCGACAACTG | |
| Ile423-Met434 | (1343) | AGATCTTCCGCCCCGGCGGCGGCGACATGCGCGACAACTG | |
| Gln422-Tyr435 | (1337) | AGATCTTCCGCCCCGGCGGCGGCGACATGCGCGACAACTG | |
| Arg426-Lys432 | (1361) | AGATCTTCCGCCCCGGCGGCGGCGACATGCGCGACAACTG | |
| Arg426-Gly431B | (1361) | AGATCTTCCGCCCCGGCGGCGGCGACATGCGCGACAACTG | |
| Asn425-Lys432 | (1355) | AGATCTTCCGCCCCGGCGGCGGCGACATGCGCGACAACTG | |
| Consensus | (1361) | AGATCTTCCGCCCCGGCGGCGGCGACATGCGCGACAACTG | |

1401                                    1440

| | | | |
|---|---|---|---|
| Ile424-Ala433 | (1389) | GCGCAGCGAGCTGTACAAGTACAAGGTGGTGAAGATCGAG | |
| Trp427-Gly431 | (1401) | GCGCAGCGAGCTGTACAAGTACAAGGTGGTGAAGATCGAG | |
| Gln422-Tyr435B | (1377) | GCGCAGCGAGCTGTACAAGTACAAGGTGGTGAAGATCGAG | |
| Arg426-Gly431 | (1401) | GCGCAGCGAGCTGTACAAGTACAAGGTGGTGAAGATCGAG | |
| Ile423-Met434 | (1383) | GCGCAGCGAGCTGTACAAGTACAAGGTGGTGAAGATCGAG | |
| Gln422-Tyr435 | (1377) | GCGCAGCGAGCTGTACAAGTACAAGGTGGTGAAGATCGAG | |
| Arg426-Lys432 | (1401) | GCGCAGCGAGCTGTACAAGTACAAGGTGGTGAAGATCGAG | |
| Arg426-Gly431B | (1401) | GCGCAGCGAGCTGTACAAGTACAAGGTGGTGAAGATCGAG | |
| Asn425-Lys432 | (1395) | GCGCAGCGAGCTGTACAAGTACAAGGTGGTGAAGATCGAG | |
| Consensus | (1401) | GCGCAGCGAGCTGTACAAGTACAAGGTGGTGAAGATCGAG | |

1441                                    1480

| | | | |
|---|---|---|---|
| Ile424-Ala433 | (1429) | CCCCTGGGCGTGGCCCCCACCAAGGCCAAGCGCCGCGTGG | |
| Trp427-Gly431 | (1441) | CCCCTGGGCGTGGCCCCCACCAAGGCCAAGCGCCGCGTGG | |

*FIG. 4G*

| | | 1441 1480 |
|---|---|---|
| Gln422-Tyr435B | (1417) | CCCCTGGGCGTGGCCCCCACCAAGGCCAAGCGCCGCGTGG |
| Arg426-Gly431 | (1441) | CCCCTGGGCGTGGCCCCCACCAAGGCCAAGCGCCGCGTGG |
| Ile423-Met434 | (1423) | CCCCTGGGCGTGGCCCCCACCAAGGCCAAGCGCCGCGTGG |
| Gln422-Tyr435 | (1417) | CCCCTGGGCGTGGCCCCCACCAAGGCCAAGCGCCGCGTGG |
| Arg426-Lys432 | (1441) | CCCCTGGGCGTGGCCCCCACCAAGGCCAAGCGCCGCGTGG |
| Arg426-Gly431B | (1441) | CCCCTGGGCGTGGCCCCCACCAAGGCCAAGCGCCGCGTGG |
| Asn425-Lys432 | (1435) | CCCCTGGGCGTGGCCCCCACCAAGGCCAAGCGCCGCGTGG |
| Consensus | (1441) | CCCCTGGGCGTGGCCCCCACCAAGGCCAAGCGCCGCGTGG |

| | | 1481 1520 |
|---|---|---|
| Ile424-Ala433 | (1469) | TGCAGCGCGAGAAGCGCGCCGTGACCCTGGGCGCCATGTT |
| Trp427-Gly431 | (1481) | TGCAGCGCGAGAAGCGCGCCGTGACCCTGGGCGCCATGTT |
| Gln422-Tyr435B | (1457) | TGCAGCGCGAGAAGCGCGCCGTGACCCTGGGCGCCATGTT |
| Arg426-Gly431 | (1481) | TGCAGCGCGAGAAGCGCGCCGTGACCCTGGGCGCCATGTT |
| Ile423-Met434 | (1463) | TGCAGCGCGAGAAGCGCGCCGTGACCCTGGGCGCCATGTT |
| Gln422-Tyr435 | (1457) | TGCAGCGCGAGAAGCGCGCCGTGACCCTGGGCGCCATGTT |
| Arg426-Lys432 | (1481) | TGCAGCGCGAGAAGCGCGCCGTGACCCTGGGCGCCATGTT |
| Arg426-Gly431B | (1481) | TGCAGCGCGAGAAGCGCGCCGTGACCCTGGGCGCCATGTT |
| Asn425-Lys432 | (1475) | TGCAGCGCGAGAAGCGCGCCGTGACCCTGGGCGCCATGTT |
| Consensus | (1481) | TGCAGCGCGAGAAGCGCGCCGTGACCCTGGGCGCCATGTT |

| | | 1521 1560 |
|---|---|---|
| Ile424-Ala433 | (1509) | CCTGGGCTTCCTGGGCGCCGCCGGCAGCACCATGGGCGCC |
| Trp427-Gly431 | (1521) | CCTGGGCTTCCTGGGCGCCGCCGGCAGCACCATGGGCGCC |
| Gln422-Tyr435B | (1497) | CCTGGGCTTCCTGGGCGCCGCCGGCAGCACCATGGGCGCC |
| Arg426-Gly431 | (1521) | CCTGGGCTTCCTGGGCGCCGCCGGCAGCACCATGGGCGCC |
| Ile423-Met434 | (1503) | CCTGGGCTTCCTGGGCGCCGCCGGCAGCACCATGGGCGCC |
| Gln422-Tyr435 | (1497) | CCTGGGCTTCCTGGGCGCCGCCGGCAGCACCATGGGCGCC |
| Arg426-Lys432 | (1521) | CCTGGGCTTCCTGGGCGCCGCCGGCAGCACCATGGGCGCC |
| Arg426-Gly431B | (1521) | CCTGGGCTTCCTGGGCGCCGCCGGCAGCACCATGGGCGCC |
| Asn425-Lys432 | (1515) | CCTGGGCTTCCTGGGCGCCGCCGGCAGCACCATGGGCGCC |
| Consensus | (1521) | CCTGGGCTTCCTGGGCGCCGCCGGCAGCACCATGGGCGCC |

| | | 1561 1600 |
|---|---|---|
| Ile424-Ala433 | (1549) | CGCAGCCTGACCCTGACCGTGCAGGCCCGCCAGCTGCTGA |
| Trp427-Gly431 | (1561) | CGCAGCCTGACCCTGACCGTGCAGGCCCGCCAGCTGCTGA |
| Gln422-Tyr435B | (1537) | CGCAGCCTGACCCTGACCGTGCAGGCCCGCCAGCTGCTGA |
| Arg426-Gly431 | (1561) | CGCAGCCTGACCCTGACCGTGCAGGCCCGCCAGCTGCTGA |
| Ile423-Met434 | (1543) | CGCAGCCTGACCCTGACCGTGCAGGCCCGCCAGCTGCTGA |
| Gln422-Tyr435 | (1537) | CGCAGCCTGACCCTGACCGTGCAGGCCCGCCAGCTGCTGA |
| Arg426-Lys432 | (1561) | CGCAGCCTGACCCTGACCGTGCAGGCCCGCCAGCTGCTGA |
| Arg426-Gly431B | (1561) | CGCAGCCTGACCCTGACCGTGCAGGCCCGCCAGCTGCTGA |
| Asn425-Lys432 | (1555) | CGCAGCCTGACCCTGACCGTGCAGGCCCGCCAGCTGCTGA |
| Consensus | (1561) | CGCAGCCTGACCCTGACCGTGCAGGCCCGCCAGCTGCTGA |

| | | 1601 1640 |
|---|---|---|
| Ile424-Ala433 | (1589) | GCGGCATCGTGCAGCAGCAGAACAACCTGCTGCGCGCCAT |
| Trp427-Gly431 | (1601) | GCGGCATCGTGCAGCAGCAGAACAACCTGCTGCGCGCCAT |
| Gln422-Tyr435B | (1577) | GCGGCATCGTGCAGCAGCAGAACAACCTGCTGCGCGCCAT |
| Arg426-Gly431 | (1601) | GCGGCATCGTGCAGCAGCAGAACAACCTGCTGCGCGCCAT |
| Ile423-Met434 | (1583) | GCGGCATCGTGCAGCAGCAGAACAACCTGCTGCGCGCCAT |
| Gln422-Tyr435 | (1577) | GCGGCATCGTGCAGCAGCAGAACAACCTGCTGCGCGCCAT |
| Arg426-Lys432 | (1601) | GCGGCATCGTGCAGCAGCAGAACAACCTGCTGCGCGCCAT |
| Arg426-Gly431B | (1601) | GCGGCATCGTGCAGCAGCAGAACAACCTGCTGCGCGCCAT |
| Asn425-Lys432 | (1595) | GCGGCATCGTGCAGCAGCAGAACAACCTGCTGCGCGCCAT |
| Consensus | (1601) | GCGGCATCGTGCAGCAGCAGAACAACCTGCTGCGCGCCAT |

| | | 1641 1680 |
|---|---|---|
| Ile424-Ala433 | (1629) | CGAGGCCCAGCAGCACCTGCTGCAGCTGACCGTGTGGGGC |
| Trp427-Gly431 | (1641) | CGAGGCCCAGCAGCACCTGCTGCAGCTGACCGTGTGGGGC |
| Gln422-Tyr435B | (1617) | CGAGGCCCAGCAGCACCTGCTGCAGCTGACCGTGTGGGGC |
| Arg426-Gly431 | (1641) | CGAGGCCCAGCAGCAGCTGGTGCAGCTGACCGTGTGGGGC |

*FIG. 4H*

| | | |
|---|---|---|
| Ile423-Met434 | (1623) | CGAGGCCCAGCAGCACCTGCTGCAGCTGACCGTGTGGGGC |
| Gln422-Tyr435 | (1617) | CGAGGCCCAGCAGCACCTGCTGCAGCTGACCGTGTGGGGC |
| Arg426-Lys432 | (1641) | CGAGGCCCAGCAGCACCTGCTGCAGCTGACCGTGTGGGGC |
| Arg426-Gly431B | (1641) | CGAGGCCCAGCAGCACCTGCTGCAGCTGACCGTGTGGGGC |
| Asn425-Lys432 | (1635) | CGAGGCCCAGCAGCACCTGCTGCAGCTGACCGTGTGGGGC |
| Consensus | (1641) | CGAGGCCCAGCAGCACCTGCTGCAGCTGACCGTGTGGGGC |
| | | 1681                              1720 |
| Ile424-Ala433 | (1669) | ATCAAGCAGCTGCAGGCCCGGGTGCTGGCCGTGGAGCGCT |
| Trp427-Gly431 | (1681) | ATCAAGCAGCTGCAGGCCCGGGTGCTGGCCGTGGAGCGCT |
| Gln422-Tyr435B | (1657) | ATCAAGCAGCTGCAGGCCCGGGTGCTGGCCGTGGAGCGCT |
| Arg426-Gly431 | (1681) | ATCAAGCAGCTGCAGGCCCGCGTGCTGGCCGTGGAGCGCT |
| Ile423-Met434 | (1663) | ATCAAGCAGCTGCAGGCCCGCGTGCTGGCCGTGGAGCGCT |
| Gln422-Tyr435 | (1657) | ATCAAGCAGCTGCAGGCCCGCGTGCTGGCCGTGGAGCGCT |
| Arg426-Lys432 | (1681) | ATCAAGCAGCTGCAGGCCCGCGTGCTGGCCGTGGAGCGCT |
| Arg426-Gly431B | (1681) | ATCAAGCAGCTGCAGGCCCGCGTGCTGGCCGTGGAGCGCT |
| Asn425-Lys432 | (1675) | ATCAAGCAGCTGCAGGCCCGCGTGCTGGCCGTGGAGCGCT |
| Consensus | (1681) | ATCAAGCAGCTGCAGGCCCGCGTGCTGGCCGTGGAGCGCT |
| | | 1721                                1760 |
| Ile424-Ala433 | (1709) | ACCTGAAGGACCAGCAGCTGCTGGGCATCTGGGGCTGCAG |
| Trp427-Gly431 | (1721) | ACCTGAAGGACCAGCAGCTGCTGGGCATCTGGGGCTGCAG |
| Gln422-Tyr435B | (1697) | ACCTGAAGGACCAGCAGCTGCTGGGCATCTGGGGCTGCAG |
| Arg426-Gly431 | (1721) | ACCTGAAGGACCAGCAGCTGCTGGGCATCTGGGGCTGCAG |
| Ile423-Met434 | (1703) | ACCTGAAGGACCAGCAGCTGCTGGGCATCTGGGGCTGCAG |
| Gln422-Tyr435 | (1697) | ACCTGAAGGACCAGCAGCTGCTGGGCATCTGGGGCTGCAG |
| Arg426-Lys432 | (1721) | ACCTGAAGGACCAGCAGCTGCTGGGCATCTGGGGCTGCAG |
| Arg426-Gly431B | (1721) | ACCTGAAGGACCAGCAGCTGCTGGGCATCTGGGGCTGCAG |
| Asn425-Lys432 | (1715) | ACCTGAAGGACCAGCAGCTGCTGGGCATCTGGGGCTGCAG |
| Consensus | (1721) | ACCTGAAGGACCAGCAGCTGCTGGGCATCTGGGGCTGCAG |
| | | 1761                                1800 |
| Ile424-Ala433 | (1749) | CGGCAAGCTGATCTGCACCACCGCCGTGCCCTGGAACGCC |
| Trp427-Gly431 | (1761) | CGGCAAGCTGATCTGGACCACCGCCGTGCCCTGGAACGCC |
| Gln422-Tyr435B | (1737) | CGGCAAGCTGATCTGCACCACCGCCGTGCCCTGGAACGCC |
| Arg426-Gly431 | (1761) | CGGCAAGCTGATCTGCACCACCGGCGTGCCCTGGAACGCC |
| Ile423-Met434 | (1743) | CGGCAAGCTGATCTGCACCACCGCCGTGCCCTGGAACGCC |
| Gln422-Tyr435 | (1737) | CGGCAAGCTGATCTGCACCACCGCCGTGCCCTGGAACGCC |
| Arg426-Lys432 | (1761) | CGGCAAGCTGATCTGCACCACCGCCGTGCCCTGGAACGCC |
| Arg426-Gly431B | (1761) | CGGCAAGCTGATCTGCACCACCGCCGTGCCCTGGAACGCC |
| Asn425-Lys432 | (1755) | CGGCAAGCTGATCTGCACCACCGCCGTGCCCTGGAACGCC |
| Consensus | (1761) | CGGCAAGCTGATCTGCACCACCGCCGTGCCCTGGAACGCC |
| | | 1801                                1840 |
| Ile424-Ala433 | (1789) | AGCTGGAGCAACAAGAGCCTGGACCAGATCTGGAACAACA |
| Trp427-Gly431 | (1801) | AGCTGGAGCAACAAGAGCCTGGACCAGATCTGGAACAACA |
| Gln422-Tyr435B | (1777) | AGCTGGAGCAACAAGAGCCTGGACCAGATCTGGAACAACA |
| Arg426-Gly431 | (1801) | AGCTGGAGCAACAAGAGCCTGGACCAGATCTGGAACAACA |
| Ile423-Met434 | (1783) | AGCTGGAGCAACAAGAGCCTGGACCAGATCTGGAACAACA |
| Gln422-Tyr435 | (1777) | AGCTGGAGCAACAAGAGCCTGGACCAGATCTGGAACAACA |
| Arg426-Lys432 | (1801) | AGCTGGAGCAACAAGAGCCTGGACCAGATCTGGAACAACA |
| Arg426-Gly431B | (1801) | AGCTGGAGCAACAAGAGCCTGGACCAGATCTGGAACAACA |
| Asn425-Lys432 | (1795) | AGCTGGAGCAACAAGAGCCTGGACCAGATCTGGAACAACA |
| Consensus | (1801) | AGCTGGAGCAACAAGAGCCTGGACCAGATCTGGAACAACA |
| | | 1841                                1880 |
| Ile424-Ala433 | (1829) | TGACCTGGATGGAGTGGGAGCGCGAGATCGACAACTACAC |
| Trp427-Gly431 | (1841) | TGACCTGGATGGAGTGGGAGCGCGAGATCGACAACTACAC |
| Gln422-Tyr435B | (1817) | TGACCTGGATGGAGTGGGAGCGCGAGATCGACAACTACAC |
| Arg426-Gly431 | (1841) | TGACCTGGATGGAGTGGGAGCGCGAGATCGACAACTACAC |
| Ile423-Met434 | (1823) | TGACCTGGATGGAGTGGGAGCGCGAGATCGACAACTACAC |
| Gln422-Tyr435 | (1817) | TGACCTGGATGGAGTGGGAGCGCGAGATCGACAACTACAC |

*FIG. 4I*

```
Arg426-Lys432    (1841) TGACCTGGATGGAGTGGGAGCGCGAGATCGACAACTACAC
Arg426-Gly431B   (1841) TGACCTGGATGGAGTGGGAGCGCGAGATCGACAACTACAC
Asn425-Lys432    (1835) TGACCTGGATGGAGTGGGAGCGCGAGATCGACAACTACAC
    Consensus    (1841) TGACCTGGATGGAGTGGGAGCGCGAGATCGACAACTACAC
                        1881                                    1920
Ile424-Ala433    (1869) CAACCTGATCTACACCCTGATCGAGGAGAGCCAGAACCAG
Trp427-Gly431    (1881) CAACCTGATCTACACCCTGATCGAGGAGAGCCAGAACCAG
Gln422-Tyr435B   (1857) CAACCTGATCTACACCCTGATCGAGGAGAGCCAGAACCAG
Arg426-Gly431    (1881) CAACCTGATCTACACCCTGATCGAGGAGAGCCAGAACCAG
Ile423-Met434    (1863) CAACCTGATCTACACCCTGATCGAGGAGAGCCAGAACCAG
Gln422-Tyr435    (1857) CAACCTGATCTACACCCTGATCGAGGAGAGCCAGAACCAG
Arg426-Lys432    (1881) CAACCTGATCTACACCCTGATCGAGGAGAGCCAGAACCAG
Arg426-Gly431B   (1881) CAACCTGATCTACACCCTGATCGAGGAGAGCCAGAACCAG
Asn425-Lys432    (1875) CAACCTGATCTACACCCTGATCGAGGAGAGCCAGAACCAG
    Consensus    (1881) CAACCTGATCTACACCCTGATCGAGGAGAGCCAGAACCAG
                        1921                                    1960
Ile424-Ala433    (1909) CAGGAGAAGAACGAGCAGGAGCTGCTGGAGCTGGACAAGT
Trp427-Gly431    (1921) CAGGAGAAGAACGAGCAGGAGCTGCTGGAGCTGGACAAGT
Gln422-Tyr435B   (1897) CAGGAGAAGAACGAGCAGGAGCTGCTGGAGCTGGACAAGT
Arg426-Gly431    (1921) CAGGAGAAGAACGAGCAGGAGCTGCTGGAGCTGGACAAGT
Ile423-Met434    (1903) CAGGAGAAGAACGAGCAGGAGCTGCTGGAGCTGGACAAGT
Gln422-Tyr435    (1897) CAGGAGAAGAACGAGCAGGAGCTGCTGGAGCTGGACAAGT
Arg426-Lys432    (1921) CAGGAGAAGAACGAGCAGGAGCTGCTGGAGCTGGACAAGT
Arg426-Gly431B   (1921) CAGGAGAAGAACGAGCAGGAGCTGCTGGAGCTGGACAAGT
Asn425-Lys432    (1915) CAGGAGAAGAACGAGCAGGAGCTGCTGGAGCTGGACAAGT
    Consensus    (1921) CAGGAGAAGAACGAGCAGGAGCTGCTGGAGCTGGACAAGT
                        1961                                    2000
Ile424-Ala433    (1949) GGGCCAGCCTGTGGAACTGGTTCGACATCAGCAAGTGGCT
Trp427-Gly431    (1961) GGGCCAGCCTGTGGAACTGGTTCGACATCAGCAAGTGGCT
Gln422-Tyr435B   (1937) GGGCCAGCCTGTGGAACTGGTTCGACATCAGCAAGTGGCT
Arg426-Gly431    (1961) GGGCCAGCCTGTGGAACTGGTTCGACATCAGCAAGTGGCT
Ile423-Met434    (1943) GGGCCAGCCTGTGGAACTGGTTCGACATCAGCAAGTGGCT
Gln422-Tyr435    (1937) GGGCCAGCCTGTGGAACTGGTTCGACATCAGCAAGTGGCT
Arg426-Lys432    (1961) GGGCCAGCCTGTGGAACTGGTTCGACATCAGCAAGTGGCT
Arg426-Gly431B   (1961) GGGCCAGCCTGTGGAACTGGTTCGACATCAGCAAGTGGCT
Asn425-Lys432    (1955) GGGCCAGCCTGTGGAACTGGTTCGACATCAGCAAGTGGCT
    Consensus    (1961) GGGCCAGCCTGTGGAACTGGTTCGACATCAGCAAGTGGCT
                        2001                                    2040
Ile424-Ala433    (1989) GTGGTACATCAAGATCTTCATCATGATCGTGGGCGGCCTG
Trp427-Gly431    (2001) GTGGTACATCAAGATCTTCATCATGATCGTGGGCGGCCTG
Gln422-Tyr435B   (1977) GTGGTACATCAAGATCTTCATCATGATCGTGGGCGGCCTG
Arg426-Gly431    (2001) GTGGTACATCAAGATCTTCATCATGATCGTGGGCGGCCTG
Ile423-Met434    (1983) GTGGTACATCAAGATCTTCATCATGATCGTGGGCGGCCTG
Gln422-Tyr435    (1977) GTGGTACATCAAGATCTTCATCATGATCGTGGGCGGCCTG
Arg426-Lys432    (2001) GTGGTACATCAAGATCTTCATCATGATCGTGGGCGGCCTG
Arg426-Gly431B   (2001) GTGGTACATCAAGATCTTCATCATGATCGTGGGCGGCCTG
Asn425-Lys432    (1995) GTGGTACATCAAGATCTTCATCATGATCGTGGGCGGCCTG
    Consensus    (2001) GTGGTACATCAAGATCTTCATCATGATCGTGGGCGGCCTG
                        2041                                    2080
Ile424-Ala433    (2029) GTGGGCCTGCGCATCGTGTTCACCGTGCTGAGCATCGTGA
Trp427-Gly431    (2041) GTGGGCCTGCGCATCGTGTTCACCGTGCTGAGCATCGTGA
Gln422-Tyr435B   (2017) GTGGGCCTGCGCATCGTGTTCACCGTGCTGAGCATCGTGA
Arg426-Gly431    (2041) GTGGGCCTGCGCATCGTGTTCACCGTGCTGAGCATCGTGA
Ile423-Met434    (2023) GTGGGCCTGCGCATCGTGTTCACCGTGCTGAGCATCGTGA
Gln422-Tyr435    (2017) GTGGGCCTGCGCATCGTGTTCACCGTGCTGAGCATCGTGA
Arg426-Lys432    (2041) GTGGGCCTGCGCATCGTGTTCACCGTGCTGAGCATCGTGA
Arg426-Gly431B   (2041) GTGGGCCTGCGCATCGTGTTCACCGTGCTGAGCATCGTGA
```

*FIG. 4J*

```
Asn425-Lys432     (2035) GTGGGCCTGCGCATCGTGTTCACCGTGCTGAGCATCGTGA
       Consensus  (2041) GTGGGCCTGCGCATCGTGTTCACCGTGCTGAGCATCGTGA
                         2081                                    2120
Ile424-Ala433     (2069) ACCGCGTGCGCCAGGGCTACAGCCCCCTGAGCTTCCAGAC
Trp427-Gly431     (2081) ACCGCGTGCGCCAGGGCTACAGCCCCCTGAGCTTCCAGAC
Gln422-Tyr435B    (2057) ACCGCGTGCGCCAGGGCTACAGCCCCCTGAGCTTCCAGAC
Arg426-Gly431     (2081) ACCGCGTGCGCCAGGGCTACAGCCCCCTGAGCTTCCAGAC
Ile423-Met434     (2063) ACCGCGTGCGCCAGGGCTACAGCCCCCTGAGCTTCCAGAC
Gln422-Tyr435     (2057) ACCGCGTGCGCCAGGGCTACAGCCCCCTGAGCTTCCAGAC
Arg426-Lys432     (2081) ACCGCGTGCGCCAGGGCTACAGCCCCCTGAGCTTCCAGAC
Arg426-Gly431B    (2081) ACCGCGTGCGCCAGGGCTACAGCCCCCTGAGCTTCCAGAC
Asn425-Lys432     (2075) ACCGCGTGCGCCAGGGCTACAGCCCCCTGAGCTTCCAGAC
       Consensus  (2081) ACCGCGTGCGCCAGGGCTACAGCCCCCTGAGCTTCCAGAC
                         2121                                    2160
Ile424-Ala433     (2109) CCGCTTCCCCGCCCCCGCGGCCCCGACCGCCCCGAGGGC
Trp427-Gly431     (2121) CCGCTTCCCCGCCCCCGCGGCCCCGACCGCCCCGAGGGC
Gln422-Tyr435B    (2097) CCGCTTCCCCGCCCCCGCGGCCCCGACCGCCCCGAGGGC
Arg426-Gly431     (2121) CCGCTTCCCCGCCCCCGCGGCCCCGACCGCCCCGAGGGC
Ile423-Met434     (2103) CCGCTTCCCCGCCCCCGCGGCCCCGACCGCCCCGAGGGC
Gln422-Tyr435     (2097) CCGCTTCCCCGCCCCCGCGGCCCCGACCGCCCCGAGGGC
Arg426-Lys432     (2121) CCGCTTCCCCGCCCCCGCGGCCCCGACCGCCCCGAGGGC
Arg426-Gly431B    (2121) CCGCTTCCCCGCCCCCGCGGCCCCGACCGCCCCGAGGGC
Asn425-Lys432     (2115) CCGCTTCCCCGCCCCCGCGGCCCCGACCGCCCCGAGGGC
       Consensus  (2121) CCGCTTCCCCGCCCCCGCGGCCCCGACCGCCCCGAGGGC
                         2161                                    2200
Ile424-Ala433     (2149) ATCGAGGAGGAGGGCGGCGAGCGCGACCGCGACCGCAGCA
Trp427-Gly431     (2161) ATCGAGGAGGAGGGCGGCGAGCGCGACCGCGACCGCAGCA
Gln422-Tyr435B    (2137) ATCGAGGAGGAGGGCGGCGAGCGCGACCGCGACCGCAGCA
Arg426-Gly431     (2161) ATCGAGGAGGAGGGCGGCGAGCGCGACCGCGACCGCAGCA
Ile423-Met434     (2143) ATCGAGGAGGAGGGCGGCGAGCGCGACCGCGACCGCAGCA
Gln422-Tyr435     (2137) ATCGAGGAGGAGGGCGGCGAGCGCGACCGCGACCGCAGCA
Arg426-Lys432     (2161) ATCGAGGAGGAGGGCGGCGAGCGCGACCGCGACCGCAGCA
Arg426-Gly431B    (2161) ATCGAGGAGGAGGGCGGCGAGCGCGACCGCGACCGCAGCA
Asn425-Lys432     (2155) ATCGAGGAGGAGGGCGGCGAGCGCGACCGCGACCGCAGCA
       Consensus  (2161) ATCGAGGAGGAGGGCGGCGAGCGCGACCGCGACCGCAGCA
                         2201                                    2240
Ile424-Ala433     (2189) GCCCCTGGTGCACGGCCTGCTGGCCCTGATCTGGGACGA
Trp427-Gly431     (2201) GCCCCTGGTGCACGGCCTGCTGGCCCTGATCTGGGACGA
Gln422-Tyr435B    (2177) GCCCCTGGTGCACGGCCTGCTGGCCCTGATCTGGGACGA
Arg426-Gly431     (2201) GCCCCTGGTGCACGGCCTGCTGGCCCTGATCTGGGACGA
Ile423-Met434     (2183) GCCCCTGGTGCACGGCCTGCTGGCCCTGATCTGGGACGA
Gln422-Tyr435     (2177) GCCCCTGGTGCACGGCCTGCTGGCCCTGATCTGGGACGA
Arg426-Lys432     (2201) GCCCCTGGTGCACGGCCTGCTGGCCCTGATCTGGGACGA
Arg426-Gly431B    (2201) GCCCCTGGTGCACGGCCTGCTGGCCCTGATCTGGGACGA
Asn425-Lys432     (2195) GCCCCTGGTGCACGGCCTGCTGGCCCTGATCTGGGACGA
       Consensus  (2201) GCCCCTGGTGCACGGCCTGCTGGCCCTGATCTGGGACGA
                         2241                                    2280
Ile424-Ala433     (2229) CCTGCGCAGCCTGTGCCTGTTCAGCTACCACGCCTGCGC
Trp427-Gly431     (2241) CCTGCGCAGCCTGTGCCTGTTCAGCTACCACGCCTGCGC
Gln422-Tyr435B    (2217) CCTGCGCAGCCTGTGCCTGTTCAGCTACCACGCCTGCGC
Arg426-Gly431     (2241) CCTGCGCAGCCTGTGCCTGTTCAGCTACCACGCCTGCGC
Ile423-Met434     (2223) CCTGCGCAGCCTGTGCCTGTTCAGCTACCACGCCTGCGC
Gln422-Tyr435     (2217) CCTGCGCAGCCTGTGCCTGTTCAGCTACCACGCCTGCGC
Arg426-Lys432     (2241) CCTGCGCAGCCTGTGCCTGTTCAGCTACCACGCCTGCGC
Arg426-Gly431B    (2241) CCTGCGCAGCCTGTGCCTGTTCAGCTACCACGCCTGCGC
Asn425-Lys432     (2235) CCTGCGCAGCCTGTGCCTGTTCAGCTACCACGCCTGCGC
       Consensus  (2241) CCTGCGCAGCCTGTGCCTGTTCAGCTACCACGCCTGCGC
```

*FIG. 4K*

|                    |        | 2281                                     2320 |
|---|---|---|
| Ile424-Ala433      | (2269) | GACCTGATCCTGATCGCCGCCCGCATCGTGGAGCTGCTGG |
| Trp427-Gly431      | (2281) | GACCTGATCCTGATCGCCGCCCGCATCGTGGAGCTGCTGG |
| Gln422-Tyr435B     | (2257) | GACCTGATCCTGATCGCCGCCCGCATCGTGGAGCTGCTGG |
| Arg426-Gly431      | (2281) | GACCTGATCCTGATCGCCGCCCGCATCGTGGAGCTGCTGG |
| Ile423-Met434      | (2263) | GACCTGATCCTGATCGCCGCCCGCATCGTGGAGCTGCTGG |
| Gln422-Tyr435      | (2257) | GACCTGATCCTGATCGCCGCCCGCATCGTGGAGCTGCTGG |
| Arg426-Lys432      | (2281) | GACCTGATCCTGATCGCCGCCCGCATCGTGGAGCTGCTGG |
| Arg426-Gly431B     | (2281) | GACCTGATCCTGATCGCCGCCCGCATCGTGGAGCTGCTGG |
| Asn425-Lys432      | (2275) | GACCTGATCCTGATCGCCGCCCGCATCGTGGAGCTGCTGG |
| Consensus          | (2281) | GACCTGATCCTGATCGCCGCCCGCATCGTGGAGCTGCTGG |
|                    |        | 2321                                     2360 |
| Ile424-Ala433      | (2309) | GCCGCCGCGGCTGGGAGGCCCTGAAGTACTGGGGCAACCT |
| Trp427-Gly431      | (2321) | GCCGCCGCGGCTGGGAGGCCCTGAAGTACTGGGGCAACCT |
| Gln422-Tyr435B     | (2297) | GCCGCCGCGGCTGGGAGGCCCTGAAGTACTGGGGCAACCT |
| Arg426-Gly431      | (2321) | GCCGCCGCGGCTGGGAGGCCCTGAAGTACTGGGGCAACCT |
| Ile423-Met434      | (2303) | GCCGCCGCGGCTGGGAGGCCCTGAAGTACTGGGGCAACCT |
| Gln422-Tyr435      | (2297) | GCCGCCGCGGCTGGGAGGCCCTGAAGTACTGGGGCAACCT |
| Arg426-Lys432      | (2321) | GCCGCCGCGGCTGGGAGGCCCTGAAGTACTGGGGCAACCT |
| Arg426-Gly431B     | (2321) | GCCGCCGCGGCTGGGAGGCCCTGAAGTACTGGGGCAACCT |
| Asn425-Lys432      | (2315) | GCCGCCGCGGCTGGGAGGCCCTGAAGTACTGGGGCAACCT |
| Consensus          | (2321) | GCCGCCGCGGCTGGGAGGCCCTGAAGTACTGGGGCAACCT |
|                    |        | 2361                                     2400 |
| Ile424-Ala433      | (2349) | GCTGCAGTACTGGATCCAGGAGCTGAAGAACAGCGCCGTG |
| Trp427-Gly431      | (2361) | GCTGCAGTACTGGATCCAGGAGCTGAAGAACAGCGCCGTG |
| Gln422-Tyr435B     | (2337) | GCTGCAGTACTGGATCCAGGAGCTGAAGAACAGCGCCGTG |
| Arg426-Gly431      | (2361) | GCTGCAGTACTGGATCCAGGAGCTGAAGAACAGCGCCGTG |
| Ile423-Met434      | (2343) | GCTGCAGTACTGGATCCAGGAGCTGAAGAACAGCGCCGTG |
| Gln422-Tyr435      | (2337) | GCTGCAGTACTGGATCCAGGAGCTGAAGAACAGCGCCGTG |
| Arg426-Lys432      | (2361) | GCTGCAGTACTGGATCCAGGAGCTGAAGAACAGCGCCGTG |
| Arg426-Gly431B     | (2361) | GCTGCAGTACTGGATCCAGGAGCTGAAGAACAGCGCCGTG |
| Asn425-Lys432      | (2355) | GCTGCAGTACTGGATCCAGGAGCTGAAGAACAGCGCCGTG |
| Consensus          | (2361) | GCTGCAGTACTGGATCCAGGAGCTGAAGAACAGCGCCGTG |
|                    |        | 2401                                     2440 |
| Ile424-Ala433      | (2389) | AGCCTGTTCGACGCCATCGGCATCGCCGTGGCCGAGGGCA |
| Trp427-Gly431      | (2401) | AGCCTGTTCGACGCCATCGGCATCGCCGTGGCCGAGGGCA |
| Gln422-Tyr435B     | (2377) | AGCCTGTTCGACGCCATCGGCATCGCCGTGGCCGAGGGCA |
| Arg426-Gly431      | (2401) | AGCCTGTTCGACGCCATCGGCATCGCCGTGGCCGAGGGCA |
| Ile423-Met434      | (2383) | AGCCTGTTCGACGCCATCGGCATCGCCGTGGCCGAGGGCA |
| Gln422-Tyr435      | (2377) | AGCCTGTTCGACGCCATCGGCATCGCCGTGGCCGAGGGCA |
| Arg426-Lys432      | (2401) | AGCCTGTTCGACGCCATCGGCATCGCCGTGGCCGAGGGCA |
| Arg426-Gly431B     | (2401) | AGCCTGTTCGACGCCATCGGCATCGCCGTGGCCGAGGGCA |
| Asn425-Lys432      | (2395) | AGCCTGTTCGACGCCATCGGCATCGCCGTGGCCGAGGGCA |
| Consensus          | (2401) | AGCCTGTTCGACGCCATCGGCATCGCCGTGGCCGAGGGCA |
|                    |        | 2441                                     2480 |
| Ile424-Ala433      | (2429) | CCGACCGCATCATCGAGGTGGCCCAGCGCATCGGCCGCGC |
| Trp427-Gly431      | (2441) | CCGACCGCATCATCGAGGTGGCCCAGCGCATCGGCCGCGC |
| Gln422-Tyr435B     | (2417) | CCGACCGCATCATCGAGGTGGCCCAGCGCATCGGCCGCGC |
| Arg426-Gly431      | (2441) | CCGACCGCATCATCGAGGTGGCCCAGCGCATCGGCCGCGC |
| Ile423-Met434      | (2423) | CCGACCGCATCATCGAGGTGGCCCAGCGCATCGGCCGCGC |
| Gln422-Tyr435      | (2417) | CCGACCGCATCATCGAGGTGGCCCAGCGCATCGGCCGCGC |
| Arg426-Lys432      | (2441) | CCGACCGCATCATCGAGGTGGCCCAGCGCATCGGCCGCGC |
| Arg426-Gly431B     | (2441) | CCGACCGCATCATCGAGGTGGCCCAGCGCATCGGCCGCGC |
| Asn425-Lys432      | (2435) | CCGACCGCATCATCGAGGTGGCCCAGCGCATCGGCCGCGC |
| Consensus          | (2441) | CCGACCGCATCATCGAGGTGGCCCAGCGCATCGGCCGCGC |
|                    |        | 2481                                     2520 |
| Ile424-Ala433      | (2469) | CTTCCTGCACATCGCCGGCGGCATCGGCCAGGGCTTCGAG |

*FIG. 4L*

| | | |
|---|---|---|
| Trp427-Gly431 | (2481) | CTTCCTGCACATCCCCCGCCGGCATCCGCCAGGGCTTCGAG |
| Gln422-Tyr435B | (2457) | CTTCCTGCACATCCCCCGCCGGCATCCGCCAGGGCTTCGAG |
| Arg426-Gly431 | (2481) | CTTCCTGCACATCCCCCGCCGGCATCCGCCAGGGCTTCGAG |
| Ile423-Met434 | (2463) | CTTCCTGCACATCCCCCGCCGGCATCCGCCAGGGCTTCGAG |
| Gln422-Tyr435 | (2457) | CTTCCTGCACATCCCCCGCCGGCATCCGCCAGGGCTTCGAG |
| Arg426-Lys432 | (2481) | CTTCCTGCACATCCCCCGCCGGCATCCGCCAGGGCTTCGAG |
| Arg426-Gly431B | (2481) | CTTCCTGCACATCCCCCGCCGGCATCCGCCAGGGCTTCGAG |
| Asn425-Lys432 | (2475) | CTTCCTGCACATCCCCCGCCGGCATCCGCCAGGGCTTCGAG |
| Consensus | (2481) | CTTCCTGCACATCCCCCGCCGCATCCGCCAGGGCTT CGAG |
| | | 2521              2541 |
| Ile424-Ala433 | (2509) | CGCGCCCTGCTGTAACTCGAG |
| Trp427-Gly431 | (2521) | CGCGCCCTGCTGTAACTCGAG |
| Gln422-Tyr435B | (2497) | CGCGCCCTGCTGTAACTCGAG |
| Arg426-Gly431 | (2521) | CGCGCCCTGCTGTAACTCGAG |
| Ile423-Met434 | (2503) | CGCGCCCTGCTGTAACTCGAG |
| Gln422-Tyr435 | (2497) | CGCGCCCTGCTGTAACTCGAG |
| Arg426-Lys432 | (2521) | CGCGCCCTGCTGTAACTCGAG |
| Arg426-Gly431B | (2521) | CGCGCCCTGCTGTAACTCGAG |
| Asn425-Lys432 | (2515) | CGCGCCCTGCTGTAACTCGAG |
| Consensus | (2521) | CGCGCCCTGCTGTAACTCGAG |

*FIG. 4M*

|   |   | 1 | 30 |
|---|---|---|---|
| Leu122-Ser199-Tryp427-Gly431 | (1) | GAATTCGCCACCATGGATGCAATGAAGAGA | |
| Val127-Asn195-Arg426-Gly431 | (1) | GAATTCGCCACCATGGATGCAATGAAGAGA | |
| Val120-Thr202-Ile424-Ala433 | (1) | GAATTCGCCACCATGGATGCAATGAAGAGA | |
| Leu122-Ser199-Arg426-Lys432 | (1) | GAATTCGCCACCATGGATGCAATGAAGAGA | |
| Leu122-Ser199-Arg426-Gly431 | (1) | GAATTCGCCACCATGGATGCAATGAAGAGA | |
| Lys121-Val200-Asn425-Lys432 | (1) | GAATTCGCCACCATGGATGCAATGAAGAGA | |
| Val120-Ile201-Ile424-Ala433 | (1) | GAATTCGCCACCATGGATGCAATGAAGAGA | |
| Val120-Ile201B-Ile424-Ala433 | (1) | GAATTCGCCACCATGGATGCAATGAAGAGA | |
| Consensus | (1) | GAATTCGCCACCATGGATGCAATGAAGAGA | |

|   |   | 31 | 60 |
|---|---|---|---|
| Leu122-Ser199-Tryp427-Gly431 | (31) | GGGCTCTGCTGTGTGCTGCTGCTGTGTGGA | |
| Val127-Asn195-Arg426-Gly431 | (31) | GGGCTCTGCTGTGTGCTGCTGCTGTGTGGA | |
| Val120-Thr202-Ile424-Ala433 | (31) | GGGCTCTGCTGTGTGCTGCTGCTGTGTGGA | |
| Leu122-Ser199-Arg426-Lys432 | (31) | GGGCTCTGCTGTGTGCTGCTGCTGTGTGGA | |
| Leu122-Ser199-Arg426-Gly431 | (31) | GGGCTCTGCTGTGTGCTGCTGCTGTGTGGA | |
| Lys121-Val200-Asn425-Lys432 | (31) | GGGCTCTGCTGTGTGCTGCTGCTGTGTGGA | |
| Val120-Ile201-Ile424-Ala433 | (31) | GGGCTCTGCTGTGTGCTGCTGCTGTGTGGA | |
| Val120-Ile201B-Ile424-Ala433 | (31) | GGGCTCTGCTGTGTGCTGCTGCTGTGTGGA | |
| Consensus | (31) | GGGCTCTGCTGTGTGCTGCTGCTGTGTGGA | |

|   |   | 61 | 90 |
|---|---|---|---|
| Leu122-Ser199-Tryp427-Gly431 | (61) | GCAGTCTTCGTTTCGCCCAGCGCCGTGGAG | |
| Val127-Asn195-Arg426-Gly431 | (61) | GCAGTCTTCGTTTCGCCCAGCGCCGTGGAG | |
| Val120-Thr202-Ile424-Ala433 | (61) | GCAGTCTTCGTTTCGCCCAGCGCCGTGGAG | |
| Leu122-Ser199-Arg426-Lys432 | (61) | GCAGTCTTCGTTTCGCCCAGCGCCGTGGAG | |
| Leu122-Ser199-Arg426-Gly431 | (61) | GCAGTCTTCGTTTCGCCCAGCGCCGTGGAG | |
| Lys121-Val200-Asn425-Lys432 | (61) | GCAGTCTTCGTTTCGCCCAGCGCCGTGGAG | |
| Val120-Ile201-Ile424-Ala433 | (61) | GCAGTCTTCGTTTCGCCCAGCGCCGTGGAG | |
| Val120-Ile201B-Ile424-Ala433 | (61) | GCAGTCTTCGTTTCGCCCAGCGCCGTGGAG | |
| Consensus | (61) | GCAGTCTTCGTTTCGCCCAGCGCCGTGGAG | |

|   |   | 91 | 120 |
|---|---|---|---|
| Leu122-Ser199-Tryp427-Gly431 | (91) | AAGCTGTGGGTGACCGTGTACTACGGCGTG | |
| Val127-Asn195-Arg426-Gly431 | (91) | AAGCTGTGGGTGACCGTGTACTACGGCGTG | |
| Val120-Thr202-Ile424-Ala433 | (91) | AAGCTGTGGGTGACCGTGTACTACGGCGTG | |
| Leu122-Ser199-Arg426-Lys432 | (91) | AAGCTGTGGGTGACCGTGTACTACGGCGTG | |
| Leu122-Ser199-Arg426-Gly431 | (91) | AAGCTGTGGGTGACCGTGTACTACGGCGTG | |
| Lys121-Val200-Asn425-Lys432 | (91) | AAGCTGTGGGTGACCGTGTACTACGGCGTG | |
| Val120-Ile201-Ile424-Ala433 | (91) | AAGCTGTGGGTGACCGTGTACTACGGCGTG | |
| Val120-Ile201B-Ile424-Ala433 | (91) | AAGCTGTGGGTGACCGTGTACTACGGCGTG | |
| Consensus | (91) | AAGCTGTGGGTGACCGTGTACTACGGCGTG | |

|   |   | 121 | 150 |
|---|---|---|---|
| Leu122-Ser199-Tryp427-Gly431 | (121) | CCCGTGTGGAAGGAGGCCACCACCACCCTG | |
| Val127-Asn195-Arg426-Gly431 | (121) | CCCGTGTGGAAGGAGGCCACCACCACCCTG | |
| Val120-Thr202-Ile424-Ala433 | (121) | CCCGTGTGGAAGGAGGCCACCACCACCCTG | |
| Leu122-Ser199-Arg426-Lys432 | (121) | CCCGTGTGGAAGGAGGCCACCACCACCCTG | |
| Leu122-Ser199-Arg426-Gly431 | (121) | CCCGTGTGGAAGGAGGCCACCACCACCCTG | |
| Lys121-Val200-Asn425-Lys432 | (121) | CCCGTGTGGAAGGAGGCCACCACCACCCTG | |
| Val120-Ile201-Ile424-Ala433 | (121) | CCCGTGTGGAAGGAGGCCACCACCACCCTG | |
| Val120-Ile201B-Ile424-Ala433 | (121) | CCCGTGTGGAAGGAGGCCACCACCACCCTG | |
| Consensus | (121) | CCCGTGTGGAAGGAGGCCACCACCACCCTG | |

|   |   | 151 | 180 |
|---|---|---|---|
| Leu122-Ser199-Tryp427-Gly431 | (151) | TTCTGCGCCAGCGACGCCAAGGCCTACGAC | |
| Val127-Asn195-Arg426-Gly431 | (151) | TTCTGCGCCAGCGACGCCAAGGCCTACGAC | |
| Val120-Thr202-Ile424-Ala433 | (151) | TTCTGCGCCAGCGACGCCAAGGCCTACGAC | |
| Leu122-Ser199-Arg426-Lys432 | (151) | TTCTGCGCCAGCGACGCCAAGGCCTACGAC | |
| Leu122-Ser199-Arg426-Gly431 | (151) | TTCTGCGCCAGCGACGCCAAGGCCTACGAC | |
| Lys121-Val200-Asn425-Lys432 | (151) | TTCTGCGCCAGCGACGCCAAGGCCTACGAC | |

*FIG. 5A*

|                                    |       |                                |
|------------------------------------|-------|--------------------------------|
| Val120-Ile201-Ile424-Ala433        | (151) | TTCTGCGCCAGCGACGCCAAGGCCTACGAC |
| Val120-Ile201B-Ile424-Ala433       | (151) | TTCTGCGCCAGCGACGCCAAGGCCTACGAC |
| Consensus                          | (151) | TTCTGCGCCAGCGACGCCAAGGCCTACGAC |
|                                    |       | 181                        210 |
| Leu122-Ser199-Tryp427-Gly431       | (181) | ACCGAGGTGCACAACGTGTGGGCCACCCAC |
| Val127-Asn195-Arg426-Gly431        | (181) | ACCGAGGTGCACAACGTGTGGGCCACCCAC |
| Val120-Thr202-Ile424-Ala433        | (181) | ACCGAGGTGCACAACGTGTGGGCCACCCAC |
| Leu122-Ser199-Arg426-Lys432        | (181) | ACCGAGGTGCACAACGTGTGGGCCACCCAC |
| Leu122-Ser199-Arg426-Gly431        | (181) | ACCGAGGTGCACAACGTGTGGGCCACCCAC |
| Lys121-Val200-Asn425-Lys432        | (181) | ACCGAGGTGCACAACGTGTGGGCCACCCAC |
| Val120-Ile201-Ile424-Ala433        | (181) | ACCGAGGTGCACAACGTGTGGGCCACCCAC |
| Val120-Ile201B-Ile424-Ala433       | (181) | ACCGAGGTGCACAACGTGTGGGCCACCCAC |
| Consensus                          | (181) | ACCGAGGTGCACAACGTGTGGGCCACCCAC |
|                                    |       | 211                        240 |
| Leu122-Ser199-Tryp427-Gly431       | (211) | GCCTGCGTGCCCACCGACCCCAACCCCCAG |
| Val127-Asn195-Arg426-Gly431        | (211) | GCCTGCGTGCCCACCGACCCCAACCCCCAG |
| Val120-Thr202-Ile424-Ala433        | (211) | GCCTGCGTGCCCACCGACCCCAACCCCCAG |
| Leu122-Ser199-Arg426-Lys432        | (211) | GCCTGCGTGCCCACCGACCCCAACCCCCAG |
| Leu122-Ser199-Arg426-Gly431        | (211) | GCCTGCGTGCCCACCGACCCCAACCCCCAG |
| Lys121-Val200-Asn425-Lys432        | (211) | GCCTGCGTGCCCACCGACCCCAACCCCCAG |
| Val120-Ile201-Ile424-Ala433        | (211) | GCCTGCGTGCCCACCGACCCCAACCCCCAG |
| Val120-Ile201B-Ile424-Ala433       | (211) | GCCTGCGTGCCCACCGACCCCAACCCCCAG |
| Consensus                          | (211) | GCCTGCGTGCCCACCGACCCCAACCCCCAG |
|                                    |       | 241                        270 |
| Leu122-Ser199-Tryp427-Gly431       | (241) | GAGATCGTGCTGGAGAACGTGACCGAGAAC |
| Val127-Asn195-Arg426-Gly431        | (241) | GAGATCGTGCTGGAGAACGTGACCGAGAAC |
| Val120-Thr202-Ile424-Ala433        | (241) | GAGATCGTGCTGGAGAACGTGACCGAGAAC |
| Leu122-Ser199-Arg426-Lys432        | (241) | GAGATCGTGCTGGAGAACGTGACCGAGAAC |
| Leu122-Ser199-Arg426-Gly431        | (241) | GAGATCGTGCTGGAGAACGTGACCGAGAAC |
| Lys121-Val200-Asn425-Lys432        | (241) | GAGATCGTGCTGGAGAACGTGACCGAGAAC |
| Val120-Ile201-Ile424-Ala433        | (241) | GAGATCGTGCTGGAGAACGTGACCGAGAAC |
| Val120-Ile201B-Ile424-Ala433       | (241) | GAGATCGTGCTGGAGAACGTGACCGAGAAC |
| Consensus                          | (241) | GAGATCGTGCTGGAGAACGTGACCGAGAAC |
|                                    |       | 271                        300 |
| Leu122-Ser199-Tryp427-Gly431       | (271) | TTCAACATGTGGAAGAACAACATGGTGGAG |
| Val127-Asn195-Arg426-Gly431        | (271) | TTCAACATGTGGAAGAACAACATGGTGGAG |
| Val120-Thr202-Ile424-Ala433        | (271) | TTCAACATGTGGAAGAACAACATGGTGGAG |
| Leu122-Ser199-Arg426-Lys432        | (271) | TTCAACATGTGGAAGAACAACATGGTGGAG |
| Leu122-Ser199-Arg426-Gly431        | (271) | TTCAACATGTGGAAGAACAACATGGTGGAG |
| Lys121-Val200-Asn425-Lys432        | (271) | TTCAACATGTGGAAGAACAACATGGTGGAG |
| Val120-Ile201-Ile424-Ala433        | (271) | TTCAACATGTGGAAGAACAACATGGTGGAG |
| Val120-Ile201B-Ile424-Ala433       | (271) | TTCAACATGTGGAAGAACAACATGGTGGAG |
| Consensus                          | (271) | TTCAACATGTGGAAGAACAACATGGTGGAG |
|                                    |       | 301                        330 |
| Leu122-Ser199-Tryp427-Gly431       | (301) | CAGATGCACGAGGACATCATCAGCCTGTGG |
| Val127-Asn195-Arg426-Gly431        | (301) | CAGATGCACGAGGACATCATCAGCCTGTGG |
| Val120-Thr202-Ile424-Ala433        | (301) | CAGATGCACGAGGACATCATCAGCCTGTGG |
| Leu122-Ser199-Arg426-Lys432        | (301) | CAGATGCACGAGGACATCATCAGCCTGTGG |
| Leu122-Ser199-Arg426-Gly431        | (301) | CAGATGCACGAGGACATCATCAGCCTGTGG |
| Lys121-Val200-Asn425-Lys432        | (301) | CAGATGCACGAGGACATCATCAGCCTGTGG |
| Val120-Ile201-Ile424-Ala433        | (301) | CAGATGCACGAGGACATCATCAGCCTGTGG |
| Val120-Ile201B-Ile424-Ala433       | (301) | CAGATGCACGAGGACATCATCAGCCTGTGG |
| Consensus                          | (301) | CAGATGCACGAGGACATCATCAGCCTGTGG |
|                                    |       | 331                        360 |
| Leu122-Ser199-Tryp427-Gly431       | (331) | GACCAGAGCCTGAAGCCCTGCGTGAAGCTG |
| Val127-Asn195-Arg426-Gly431        | (331) | GACCAGAGCCTGAAGCCCTGCGTGAAGCTG |
| Val120-Thr202-Ile424-Ala433        | (331) | GACCAGAGCCTGAAGCCCTGCGTG------ |

FIG. 5B

```
Leu122-Ser199-Arg426-Lys432      (331) GACCAGAGCCTGAAGCCCTGCGTGAAGCTG
Leu122-Ser199-Arg426-Gly431      (331) GACCAGAGCCTGAAGCCCTGCGTGAAGCTG
Lys121-Val200-Asn425-Lys432      (331) GACCAGAGCCTGAAGCCCTGCGTGAA----
Val120-Ile201-Ile424-Ala433      (331) GACCAGAGCCTGAAGCCCTGCGTG------
Val120-Ile201B-Ile424-Ala433     (331) GACCAGAGCCTGAAGCCCTGCGTG------
                    Consensus    (331) GACCAGAGCCTGAAGCCCTGCGTGAAGCTG
                                        361                          390
Leu122-Ser199-Tryp427-Gly431     (361) --------------GG--------------
Val127-Asn195-Arg426-Gly431      (361) ACCCCCCTGTGCGTGGGGGCAGGGAACTGC
Val120-Thr202-Ile424-Ala433      (355) --------------GG--------------
Leu122-Ser199-Arg426-Lys432      (361) --------------GG--------------
Leu122-Ser199-Arg426-Gly431      (361) --------------GG--------------
Lys121-Val200-Asn425-Lys432      (357) --------------GG--------------
Val120-Ile201-Ile424-Ala433      (355) ------------------------------
Val120-Ile201B-Ile424-Ala433     (355) ------------------------------
                    Consensus    (361)               GG
                                        391                          420
Leu122-Ser199-Tryp427-Gly431     (363) --CAACAGCGTGATCACCCAGGCCTGCCCC
Val127-Asn195-Arg426-Gly431      (391) AACACCAGCGTGATCACCCAGGCCTGCCCC
Val120-Thr202-Ile424-Ala433      (357) -----CGGCGC---CACCCAGGCCTGCCCC
Leu122-Ser199-Arg426-Lys432      (363) --CAACAGCGTGATCACCCAGGCCTGCCCC
Leu122-Ser199-Arg426-Gly431      (363) --CAACAGCGTGATCACCCAGGCCTGCCCC
Lys121-Val200-Asn425-Lys432      (359) ----CGCCGGTGATCACCCAGGCCTGCCCC
Val120-Ile201-Ile424-Ala433      (355) -------GGCGGCATCACCCAGGCCTGCCCC
Val120-Ile201B-Ile424-Ala433     (355) -------CCGGCATCACCCAGGCCTGCCCC
                    Consensus    (391)       CA CAGCGTGATCACCCAGGCCTGCCCC
                                        421                          450
Leu122-Ser199-Tryp427-Gly431     (391) AAGGTGAGCTTCGAGCCCATCCCCATCCAC
Val127-Asn195-Arg426-Gly431      (421) AAGGTGAGCTTCGAGCCCATCCCCATCCAC
Val120-Thr202-Ile424-Ala433      (379) AAGGTGAGCTTCGAGCCCATCCCCATCCAC
Leu122-Ser199-Arg426-Lys432      (391) AAGGTGAGCTTCGAGCCCATCCCCATCCAC
Leu122-Ser199-Arg426-Gly431      (391) AAGGTGAGCTTCGAGCCCATCCCCATCCAC
Lys121-Val200-Asn425-Lys432      (385) AAGGTGAGCTTCGAGCCCATCCCCATCCAC
Val120-Ile201-Ile424-Ala433      (379) AAGGTGAGCTTCGAGCCCATCCCCATCCAC
Val120-Ile201B-Ile424-Ala433     (379) AAGGTGAGCTTCGAGCCCATCCCCATCCAC
                    Consensus    (421) AAGGTGAGCTTCGAGCCCATCCCCATCCAC
                                        451                          480
Leu122-Ser199-Tryp427-Gly431     (421) TACTGCGCCCCCGCCGGCTTCGCCATCCTG
Val127-Asn195-Arg426-Gly431      (451) TACTGCGCCCCCGCCGGCTTCGCCATCCTG
Val120-Thr202-Ile424-Ala433      (409) TACTGCGCCCCCGCCGGCTTCGCCATCCTG
Leu122-Ser199-Arg426-Lys432      (421) TACTGCGCCCCCGCCGGCTTCGCCATCCTG
Leu122-Ser199-Arg426-Gly431      (421) TACTGCGCCCCCGCCGGCTTCGCCATCCTG
Lys121-Val200-Asn425-Lys432      (415) TACTGCGCCCCCGCCGGCTTCGCCATCCTG
Val120-Ile201-Ile424-Ala433      (409) TACTGCGCCCCCGCCGGCTTCGCCATCCTG
Val120-Ile201B-Ile424-Ala433     (409) TACTGCGCCCCCGCCGGCTTCGCCATCCTG
                    Consensus    (451) TACTGCGCCCCCGCCGGCTTCGCCATCCTG
                                        481                          510
Leu122-Ser199-Tryp427-Gly431     (451) AAGTGCAACGACAAGAAGTTCAACGGCAGC
Val127-Asn195-Arg426-Gly431      (481) AAGTGCAACGACAAGAAGTTCAACGGCAGC
Val120-Thr202-Ile424-Ala433      (439) AAGTGCAACGACAAGAAGTTCAACGGCAGC
Leu122-Ser199-Arg426-Lys432      (451) AAGTGCAACGACAAGAAGTTCAACGGCAGC
Leu122-Ser199-Arg426-Gly431      (451) AAGTGCAACGACAAGAAGTTCAACGGCAGC
Lys121-Val200-Asn425-Lys432      (445) AAGTGCAACGACAAGAAGTTCAACGGCAGC
Val120-Ile201-Ile424-Ala433      (439) AAGTGCAACGACAAGAAGTTCAACGGCAGC
Val120-Ile201B-Ile424-Ala433     (439) AAGTGCAACGACAAGAAGTTCAACGGCAGC
                    Consensus    (481) AAGTGCAACGACAAGAAGTTCAACGGCAGC
                                        511                          540
```

*FIG. 5C*

| | | |
|---|---|---|
| Leu122-Ser199-Tryp427-Gly431 | (481) | GGCCCCTGCACCAACGTGAGCACCGTGCAG |
| Val127-Asn195-Arg426-Gly431 | (511) | GGCCCCTGCACCAACGTGAGCACCGTGCAG |
| Val120-Thr202-Ile424-Ala433 | (469) | GGCCCCTGCACCAACGTGAGCACCGTGCAG |
| Leu122-Ser199-Arg426-Lys432 | (481) | GGCCCCTGCACCAACGTGAGCACCGTGCAG |
| Leu122-Ser199-Arg426-Gly431 | (481) | GGCCCCTGCACCAACGTGAGCACCGTGCAG |
| Lys121-Val200-Asn425-Lys432 | (475) | GGCCCCTGCACCAACGTGAGCACCGTGCAG |
| Val120-Ile201-Ile424-Ala433 | (469) | GGCCCCTGCACCAACGTGAGCACCGTGCAG |
| Val120-Ile201B-Ile424-Ala433 | (469) | GGCCCCTGCACCAACGTGAGCACCGTGCAG |
| Consensus | (511) | GGCCCCTGCACCAACGTGAGCACCGTGCAG |
| | | 541                        570 |
| Leu122-Ser199-Tryp427-Gly431 | (511) | TGCACCCACGGCATCCGCCCCGTGGTGAGC |
| Val127-Asn195-Arg426-Gly431 | (541) | TGCACCCACGGCATCCGCCCCGTGGTGAGC |
| Val120-Thr202-Ile424-Ala433 | (499) | TGCACCCACGGCATCCGCCCCGTGGTGAGC |
| Leu122-Ser199-Arg426-Lys432 | (511) | TGCACCCACGGCATCCGCCCCGTGGTGAGC |
| Leu122-Ser199-Arg426-Gly431 | (511) | TGCACCCACGGCATCCGCCCCGTGGTGAGC |
| Lys121-Val200-Asn425-Lys432 | (505) | TGCACCCACGGCATCCGCCCCGTGGTGAGC |
| Val120-Ile201-Ile424-Ala433 | (499) | TGCACCCACGGCATCCGCCCCGTGGTGAGC |
| Val120-Ile201B-Ile424-Ala433 | (499) | TGCACCCACGGCATCCGCCCCGTGGTGAGC |
| Consensus | (541) | TGCACCCACGGCATCCGCCCCGTGGTGAGC |
| | | 571                        600 |
| Leu122-Ser199-Tryp427-Gly431 | (541) | ACCCAGCTGCTGCTGAACGGCAGCCTGGCC |
| Val127-Asn195-Arg426-Gly431 | (571) | ACCCAGCTGCTGCTGAACGGCAGCCTGGCC |
| Val120-Thr202-Ile424-Ala433 | (529) | ACCCAGCTGCTGCTGAACGGCAGCCTGGCC |
| Leu122-Ser199-Arg426-Lys432 | (541) | ACGCAGCTGCTGCTGAACGGCAGCCTGGCC |
| Leu122-Ser199-Arg426-Gly431 | (541) | ACCCAGCTGCTGCTGAACGGCAGCCTGGCC |
| Lys121-Val200-Asn425-Lys432 | (535) | ACCCAGCTGCTGCTGAACGGCAGCCTGGCC |
| Val120-Ile201-Ile424-Ala433 | (529) | ACCCAGCTGCTGCTGAACGGCAGCCTGGCC |
| Val120-Ile201B-Ile424-Ala433 | (529) | ACCCAGCTGCTGCTGAACGGCAGCCTGGCC |
| Consensus | (571) | ACCCAGCTGCTGCTGAACGGCAGCCTGGCC |
| | | 601                        630 |
| Leu122-Ser199-Tryp427-Gly431 | (571) | GAGGAGGGCGTGGTGATCCGCAGCGAGAAC |
| Val127-Asn195-Arg426-Gly431 | (601) | GAGGAGGGCGTGGTGATCCGCAGCGAGAAC |
| Val120-Thr202-Ile424-Ala433 | (559) | GAGGAGGGCGTGGTGATCCGCAGCGAGAAC |
| Leu122-Ser199-Arg426-Lys432 | (571) | GAGGAGGGCGTGGTGATCCGCAGCGAGAAC |
| Leu122-Ser199-Arg426-Gly431 | (571) | GAGGAGGGCGTGGTGATCCGCAGCGAGAAC |
| Lys121-Val200-Asn425-Lys432 | (565) | GAGGAGGGCGTGGTGATCCGCAGCGAGAAC |
| Val120-Ile201-Ile424-Ala433 | (559) | GAGGAGGGCGTGGTGATCCGCAGCGAGAAC |
| Val120-Ile201B-Ile424-Ala433 | (559) | GAGGAGGGCGTGGTGATCCGCAGCGAGAAC |
| Consensus | (601) | GAGGAGGGCGTGGTGATCCGCAGCGAGAAC |
| | | 631                        660 |
| Leu122-Ser199-Tryp427-Gly431 | (601) | TTCACCGACAACGCCAAGACCATCATCGTG |
| Val127-Asn195-Arg426-Gly431 | (631) | TTCACCGACAACGCCAAGACCATCATCGTG |
| Val120-Thr202-Ile424-Ala433 | (589) | TTCACCGACAACGCCAAGACCATCATCGTG |
| Leu122-Ser199-Arg426-Lys432 | (601) | TTCACCGACAACGCCAAGACCATCATCGTG |
| Leu122-Ser199-Arg426-Gly431 | (601) | TTCACCGACAACGCCAAGACCATCATCGTG |
| Lys121-Val200-Asn425-Lys432 | (595) | TTCACCGACAACGCCAAGACCATCATCGTG |
| Val120-Ile201-Ile424-Ala433 | (589) | TTCACCGACAACGCCAAGACCATCATCGTG |
| Val120-Ile201B-Ile424-Ala433 | (589) | TTCACCGACAACGCCAAGACCATCATCGTG |
| Consensus | (631) | TTCACCGACAACGCCAAGACCATCATCGTG |
| | | 661                        690 |
| Leu122-Ser199-Tryp427-Gly431 | (631) | CAGCTGAAGGAGAGCGTGGAGATCAACTGC |
| Val127-Asn195-Arg426-Gly431 | (661) | CAGCTGAAGGAGAGCGTGGAGATCAACTGC |
| Val120-Thr202-Ile424-Ala433 | (619) | CAGCTGAAGGAGAGCGTGGAGATCAACTGC |
| Leu122-Ser199-Arg426-Lys432 | (631) | CAGCTGAAGGAGAGCGTGGAGATCAACTGC |
| Leu122-Ser199-Arg426-Gly431 | (631) | CAGCTGAAGGAGAGCGTGGAGATCAACTGC |
| Lys121-Val200-Asn425-Lys432 | (625) | CAGCTGAAGGAGAGCGTGGAGATCAACTGC |
| Val120-Ile201-Ile424-Ala433 | (619) | CAGCTGAAGGAGAGCGTGGAGATCAACTGC |

*FIG. 5D*

```
Val120-Ile201B-Ile424-Ala433    (619) CAGCTGAAGGAGAGCGTGGAGATCAACTGC
                     Consensus  (661) CAGCTGAAGGAGAGCGTGGAGATCAACTGC
                                      691                           720
Leu122-Ser199-Tryp427-Gly431    (661) ACCCGCCCCAACAACAACACCCGCAAGAGC
Val127-Asn195-Arg426-Gly431     (691) ACCCGCCCCAACAACAACACCCGCAAGAGC
Val120-Thr202-Ile424-Ala433     (649) ACCCGCCCCAACAACAACACCCGCAAGAGC
Leu122-Ser199-Arg426-Lys432     (661) ACCCGCCCCAACAACAACACCCGCAAGAGC
Leu122-Ser199-Arg426-Gly431     (661) ACCCGCCCCAACAACAACACCCGCAAGAGC
Lys121-Val200-Asn425-Lys432     (655) ACCCGCCCCAACAACAACACCCGCAAGAGC
Val120-Ile201-Ile424-Ala433     (649) ACCCGCCCCAACAACAACACCCGCAAGAGC
Val120-Ile201B-Ile424-Ala433    (649) ACCCGCCCCAACAACAACACCCGCAAGAGC
                     Consensus  (691) ACCCGCCCCAACAACAACACCCGCAAGAGC
                                      721                           750
Leu122-Ser199-Tryp427-Gly431    (691) ATCACCATCGGCCCCGGCCGCGCCTTCTAC
Val127-Asn195-Arg426-Gly431     (721) ATCACCATCGGCCCCGGCCGCGCCTTCTAC
Val120-Thr202-Ile424-Ala433     (679) ATCACCATCGGCCCCGGCCGCGCCTTCTAC
Leu122-Ser199-Arg426-Lys432     (691) ATCACCATCGGCCCCGGCCGCGCCTTCTAC
Leu122-Ser199-Arg426-Gly431     (691) ATCACCATCGGCCCCGGCCGCGCCTTCTAC
Lys121-Val200-Asn425-Lys432     (685) ATCACCATCGGCCCCGGCCGCGCCTTCTAC
Val120-Ile201-Ile424-Ala433     (679) ATCACCATCGGCCCCGGCCGCGCCTTCTAC
Val120-Ile201B-Ile424-Ala433    (679) ATCACCATCGGCCCCGGCCGCGCCTTCTAC
                     Consensus  (721) ATCACCATCGGCCCCGGCCGCGCCTTCTAC
                                      751                           780
Leu122-Ser199-Tryp427-Gly431    (721) GCCACCGGCGACATCATCGGCGACATCCGC
Val127-Asn195-Arg426-Gly431     (751) GCCACCGGCGACATCATCGGCGACATCCGC
Val120-Thr202-Ile424-Ala433     (709) GCCACCGGCGACATCATCGGCGACATCCGC
Leu122-Ser199-Arg426-Lys432     (721) GCCACCGGCGACATCATCGGCGACATCCGC
Leu122-Ser199-Arg426-Gly431     (721) GCCACCGGCGACATCATCGGCGACATCCGC
Lys121-Val200-Asn425-Lys432     (715) GCCACCGGCGACATCATCGGCGACATCCGC
Val120-Ile201-Ile424-Ala433     (709) GCCACCGGCGACATCATCGGCGACATCCGC
Val120-Ile201B-Ile424-Ala433    (709) GCCACCGGCGACATCATCGGCGACATCCGC
                     Consensus  (751) GCCACCGGCGACATCATCGGCGACATCCGC
                                      781                           810
Leu122-Ser199-Tryp427-Gly431    (751) CAGGCCCACTGCAACATCAGCGGCGAGAAG
Val127-Asn195-Arg426-Gly431     (781) CAGGCCCACTGCAACATCAGCGGCGAGAAG
Val120-Thr202-Ile424-Ala433     (739) CAGGCCCACTGCAACATCAGCGGCGAGAAG
Leu122-Ser199-Arg426-Lys432     (751) CAGGCCCACTGCAACATCAGCGGCGAGAAG
Leu122-Ser199-Arg426-Gly431     (751) CAGGCCCACTGCAACATCAGCGGCGAGAAG
Lys121-Val200-Asn425-Lys432     (745) CAGGCCCACTGCAACATCAGCGGCGAGAAG
Val120-Ile201-Ile424-Ala433     (739) CAGGCCCACTGCAACATCAGCGGCGAGAAG
Val120-Ile201B-Ile424-Ala433    (739) CAGGCCCACTGCAACATCAGCGGCGAGAAG
                     Consensus  (781) CAGGCCCACTGCAACATCAGCGGCGAGAAG
                                      811                           840
Leu122-Ser199-Tryp427-Gly431    (781) TGGAACAACACCCTGAAGCAGATCGTGACC
Val127-Asn195-Arg426-Gly431     (811) TGGAACAACACCCTGAAGCAGATCGTGACC
Val120-Thr202-Ile424-Ala433     (769) TGGAACAACACCCTGAAGCAGATCGTGACC
Leu122-Ser199-Arg426-Lys432     (781) TGGAACAACACCCTGAAGCAGATCGTGACC
Leu122-Ser199-Arg426-Gly431     (781) TGGAACAACACCCTGAAGCAGATCGTGACC
Lys121-Val200-Asn425-Lys432     (775) TGGAACAACACCCTGAAGCAGATCGTGACC
Val120-Ile201-Ile424-Ala433     (769) TGGAACAACACCCTGAAGCAGATCGTGACC
Val120-Ile201B-Ile424-Ala433    (769) TGGAACAACACCCTGAAGCAGATCGTGACC
                     Consensus  (811) TGGAACAACACCCTGAAGCAGATCGTGACC
                                      841                           870
Leu122-Ser199-Tryp427-Gly431    (811) AAGCTGCAGGCCCAGTTCGGCAACAAGACC
Val127-Asn195-Arg426-Gly431     (841) AAGCTGCAGGCCCAGTTCGGCAACAAGACC
Val120-Thr202-Ile424-Ala433     (799) AAGCTGCAGGCCCAGTTCGGCAACAAGACC
Leu122-Ser199-Arg426-Lys432     (811) AAGCTGCAGGCCCAGTTCGGCAACAAGACC
```

*FIG. 5E*

| Label | Pos | Sequence |
|---|---|---|
| Leu122-Ser199-Arg426-Gly431 | (811) | AAGCTGCAGGCCCAGTTCGGCAACAAGACC |
| Lys121-Val200-Asn425-Lys432 | (805) | AAGCTGCAGGCCCAGTTCGGCAACAAGACC |
| Val120-Ile201-Ile424-Ala433 | (799) | AAGCTGCAGGCCCAGTTCGGCAACAAGACC |
| Val120-Ile201B-Ile424-Ala433 | (799) | AAGCTGCAGGCCCAGTTCGGCAACAAGACC |
| Consensus | (841) | AAGCTGCAGGCCCAGTTCGGCAACAAGACC |

871 900

| Leu122-Ser199-Tryp427-Gly431 | (841) | ATCGTGTTCAAGCAGAGCAGCGGCGGCGAC |
| Val127-Asn195-Arg426-Gly431 | (871) | ATCGTGTTCAAGCAGAGCAGCGGCGGCGAC |
| Val120-Thr202-Ile424-Ala433 | (829) | ATCGTGTTCAAGCAGAGCAGCGGCGGCGAC |
| Leu122-Ser199-Arg426-Lys432 | (841) | ATCGTGTTCAAGCAGAGCAGCGGCGGCGAC |
| Leu122-Ser199-Arg426-Gly431 | (841) | ATCGTGTTCAAGCAGAGCAGCGGCGGCGAC |
| Lys121-Val200-Asn425-Lys432 | (835) | ATCGTGTTCAAGCAGAGCAGCGGCGGCGAC |
| Val120-Ile201-Ile424-Ala433 | (829) | ATCGTGTTCAAGCAGAGCAGCGGCGGCGAC |
| Val120-Ile201B-Ile424-Ala433 | (829) | ATCGTGTTCAAGCAGAGCAGCGGCGGCGAC |
| Consensus | (871) | ATCGTGTTCAAGCAGAGCAGCGGCGGCGAC |

901 930

| Leu122-Ser199-Tryp427-Gly431 | (871) | CCCGAGATCGTGATGCACAGCTTCAACTGC |
| Val127-Asn195-Arg426-Gly431 | (901) | CCCGAGATCGTGATGCACAGCTTCAACTGC |
| Val120-Thr202-Ile424-Ala433 | (859) | CCCGAGATCGTGATGCACAGCTTCAACTGC |
| Leu122-Ser199-Arg426-Lys432 | (871) | CCCGAGATCGTGATGCACAGCTTCAACTGC |
| Leu122-Ser199-Arg426-Gly431 | (871) | CCCGAGATCGTGATGCACAGCTTCAACTGC |
| Lys121-Val200-Asn425-Lys432 | (865) | CCCGAGATCGTGATGCACAGCTTCAACTGC |
| Val120-Ile201-Ile424-Ala433 | (859) | CCCGAGATCGTGATGCACAGCTTCAACTGC |
| Val120-Ile201B-Ile424-Ala433 | (859) | CCCGAGATCGTGATGCACAGCTTCAACTGC |
| Consensus | (901) | CCCGAGATCGTGATGCACAGCTTCAACTGC |

931 960

| Leu122-Ser199-Tryp427-Gly431 | (901) | GGCGGCGAGTTCTTCTACTGCAACAGCACC |
| Val127-Asn195-Arg426-Gly431 | (931) | GGCGGCGAGTTCTTCTACTGCAACAGCACC |
| Val120-Thr202-Ile424-Ala433 | (889) | GGCGGCGAGTTCTTCTACTGCAACAGCACC |
| Leu122-Ser199-Arg426-Lys432 | (901) | GGCGGCGAGTTCTTCTACTGCAACAGCACC |
| Leu122-Ser199-Arg426-Gly431 | (901) | GGCGGCGAGTTCTTCTACTGCAACAGCACC |
| Lys121-Val200-Asn425-Lys432 | (895) | GGCGGCGAGTTCTTCTACTGCAACAGCACC |
| Val120-Ile201-Ile424-Ala433 | (889) | GGCGGCGAGTTCTTCTACTGCAACAGCACC |
| Val120-Ile201B-Ile424-Ala433 | (889) | GGCGGCGAGTTCTTCTACTGCAACAGCACC |
| Consensus | (931) | GGCGGCGAGTTCTTCTACTGCAACAGCACC |

961 990

| Leu122-Ser199-Tryp427-Gly431 | (931) | CAGCTGTTCAACAGCACCTGGAACAACACC |
| Val127-Asn195-Arg426-Gly431 | (961) | CAGCTGTTCAACAGCACCTGGAACAACACC |
| Val120-Thr202-Ile424-Ala433 | (919) | CAGCTGTTCAACAGCACCTGGAACAACACC |
| Leu122-Ser199-Arg426-Lys432 | (931) | CAGCTGTTCAACAGCACCTGGAACAACACC |
| Leu122-Ser199-Arg426-Gly431 | (931) | CAGCTGTTCAACAGCACCTGGAACAACACC |
| Lys121-Val200-Asn425-Lys432 | (925) | CAGCTGTTCAACAGCACCTGGAACAACACC |
| Val120-Ile201-Ile424-Ala433 | (919) | CAGCTGTTCAACAGCACCTGGAACAACACC |
| Val120-Ile201B-Ile424-Ala433 | (919) | CAGCTGTTCAACAGCACCTGGAACAACACC |
| Consensus | (961) | CAGCTGTTCAACAGCACCTGGAACAACACC |

991 1020

| Leu122-Ser199-Tryp427-Gly431 | (961) | ATCGGCCCCAACAACACCAACGGCACCATC |
| Val127-Asn195-Arg426-Gly431 | (991) | ATCGGCCCCAACAACACCAACGGCACCATC |
| Val120-Thr202-Ile424-Ala433 | (949) | ATCGGCCCCAACAACACCAACGGCACCATC |
| Leu122-Ser199-Arg426-Lys432 | (961) | ATCGGCCCCAACAACACCAACGGCACCATC |
| Leu122-Ser199-Arg426-Gly431 | (961) | ATCGGCCCCAACAACACCAACGGCACCATC |
| Lys121-Val200-Asn425-Lys432 | (955) | ATCGGCCCCAACAACACCAACGGCACCATC |
| Val120-Ile201-Ile424-Ala433 | (949) | ATCGGCCCCAACAACACCAACGGCACCATC |
| Val120-Ile201B-Ile424-Ala433 | (949) | ATCGGCCCCAACAACACCAACGGCACCATC |
| Consensus | (991) | ATCGGCCCCAACAACACCAACGGCACCATC |

1021 1050

| Leu122-Ser199-Tryp427-Gly431 | (991) | ACCCTGCCCTGCCGGATCAAGCAGATCATC |

*FIG. 5F*

```
Val127-Asn195-Arg426-Gly431   (1021) ACCCTGCCCTGCCGCATCAAGCAGATCATC
Val120-Thr202-Ile424-Ala433    (979) ACCCTGCCCTGCCGCATCAAGCAGATCATC
Leu122-Ser199-Arg426-Lys432    (991) ACCCTGCCCTGCCGCATCAAGCAGATCATC
Leu122-Ser199-Arg426-Gly431    (991) ACCCTGCCCTGCCGCATCAAGCAGATCATC
Lys121-Val200-Asn425-Lys432    (985) ACCCTGCCCTGCCGCATCAAGCAGATCATC
Val120-Ile201-Ile424-Ala433    (979) ACCCTGCCCTGCCGCATCAAGCAGATCATC
Val120-Ile201B-Ile424-Ala433   (979) ACCCTGCCCTGCCGCATCAAGCAGATCATC
                    Consensus (1021) ACCCTGCCCTGCCGCATCAAGCAGATCATC
                                     1051                         1080
Leu122-Ser199 Tryp427-Gly431   (1021) AACCGCTGGGGCGGCAAGGCCATGTACGCC
Val127-Asn195-Arg426-Gly431   (1051) AACCGCGGCGGCGGCAAGGCCATGTACGCC
Val120-Thr202-Ile424-Ala433   (1009) ---------GGCGGC---GCCATGTACGCC
Leu122-Ser199-Arg426-Lys432   (1021) AACCGCGGCGGCAACAAGGCCATGTACGCC
Leu122-Ser199-Arg426-Gly431   (1021) AACCGCGGCAGCGGCAAGGCCATGTACGCC
Lys121-Val200-Asn425-Lys432   (1015) AAC------GCCCCAAGGCCATGTACGCC
Val120-Ile201-Ile424-Ala433   (1009) ---------GGCGGC---GCCATGTACGCC
Val120-Ile201B-Ile424-Ala433  (1009) ---------GGCGGC---GCCATGTACGCC
                    Consensus (1051) AACCGC G GGCGGCAAGGCCATGTACGCC
                                     1081                         1110
Leu122-Ser199 Tryp427-Gly431   (1051) CCCCCCATCCGCGGCCAGATCCGCTGCAGC
Val127-Asn195-Arg426-Gly431   (1081) CCCCCCATCCGCGGCCAGATCCGCTGCAGC
Val120-Thr202-Ile424-Ala433   (1027) CCCCCCATCCGCGGCCAGATCCGCTGCAGC
Leu122-Ser199-Arg426-Lys432   (1051) CCCCCCATCCGCGGCCAGATCCGCTGCAGC
Leu122-Ser199-Arg426-Gly431   (1051) CCCCCCATCCGCGGCCAGATCCGCTGCAGC
Lys121-Val200-Asn425-Lys432   (1039) CCCCCCATCCGCGGCCAGATCCGCTGCAGC
Val120-Ile201-Ile424-Ala433   (1027) CCCCCCATCCGCGGCCAGATCCGCTGCAGC
Val120-Ile201B-Ile424-Ala433  (1027) CCCCCCATCCGCGGCCAGATCCGCTGCAGC
                    Consensus (1081) CCCCCCATCCGCGGCCAGATCCGCTGCAGC
                                     1111                         1140
Leu122-Ser199 Tryp427-Gly431   (1081) AGCAACATCACCGGCCTGCTGCTGACCCGC
Val127-Asn195-Arg426-Gly431   (1111) AGCAACATCACCGGCCTGCTGCTGACCCGC
Val120-Thr202-Ile424-Ala433   (1057) AGCAACATCACCGGCCTGCTGCTGACCCGC
Leu122-Ser199-Arg426-Lys432   (1081) AGCAACATCACCGGCCTGCTGCTGACCCGC
Leu122-Ser199-Arg426-Gly431   (1081) AGCAACATCACCGGCCTGCTGCTGACCCGC
Lys121-Val200-Asn425-Lys432   (1069) AGCAACATCACCGGCCTGCTGCTGACCCGC
Val120-Ile201-Ile424-Ala433   (1057) AGCAACATCACCGGCCTGCTGCTGACCCGC
Val120-Ile201B-Ile424-Ala433  (1057) AGCAACATCACCGGCCTGCTGCTGACCCGC
                    Consensus (1111) AGCAACATCACCGGCCTGCTGCTGACCCGC
                                     1141                         1170
Leu122-Ser199 Tryp427-Gly431   (1111) GACGGCGGCAAGGAGATCAGCAACACCACC
Val127-Asn195-Arg426-Gly431   (1141) GACGGCGGCAAGGAGATCAGCAACACCACC
Val120-Thr202-Ile424-Ala433   (1087) GACGGCGGCAAGGAGATCAGCAACACCACC
Leu122-Ser199-Arg426-Lys432   (1111) GACGGCGGCAAGGAGATCAGCAACACCACC
Leu122-Ser199-Arg426-Gly431   (1111) GACGGCGGCAAGGAGATCAGCAACACCACC
Lys121-Val200-Asn425-Lys432   (1099) GACGGCGGCAAGGAGATCAGCAACACCACC
Val120-Ile201-Ile424-Ala433   (1087) GACGGCGGCAAGGAGATCAGCAACACCACC
Val120-Ile201B-Ile424-Ala433  (1087) GACGGCGGCAAGGAGATCAGCAACACCACC
                    Consensus (1141) GACGGCGGCAAGGAGATCAGCAACACCACC
                                     1171                         1200
Leu122-Ser199 Tryp427-Gly431   (1141) GAGATCTTCCGCCCCGGCGGCGGCGACATG
Val127-Asn195-Arg426-Gly431   (1171) GAGATCTTCCGCCCCGGCGGCGGCGACATG
Val120-Thr202-Ile424-Ala433   (1117) GAGATCTTCCGCCCCGGCGGCGGCGACATG
Leu122-Ser199-Arg426-Lys432   (1141) GAGATCTTCCGCCCCGGCGGCGGCGACATG
Leu122-Ser199-Arg426-Gly431   (1141) GAGATCTTCCGCCCCGGCGGCGGCGACATG
Lys121-Val200-Asn425-Lys432   (1129) GAGATCTTCCGCCCCGGCGGCGGCGACATG
Val120-Ile201-Ile424-Ala433   (1117) GAGATCTTCCGCCCCGGCGGCGGCGACATG
Val120-Ile201B-Ile424-Ala433  (1117) GAGATCTTCCGCCCCGGCGGCGGCGACATG
```

*FIG. 5G*

|                              |        |                                |
|------------------------------|--------|--------------------------------|
| Consensus                    | (1171) | GAGATCTTCCGCCCCGGCGGCGGCGACATG |

```
                                              1201                           1230
   Leu122-Ser199 Tryp427-Gly431    (1171)  CGCGACAACTGGCGCAGCGAGCTGTACAAG
   Val127-Asn195-Arg426-Gly431    (1201)  CGCGACAACTGGCGCAGCGAGCTGTACAAG
   Val120-Thr202-Ile424-Ala433    (1147)  CGCGACAACTGGCGCAGCGAGCTGTACAAG
   Leu122-Ser199-Arg426-Lys432    (1171)  CGCGACAACTGGCGCAGCGAGCTGTACAAG
   Leu122-Ser199-Arg426-Gly431    (1171)  CGCGACAACTGGCGCAGCGAGCTGTACAAG
   Lys121-Val200-Asn425-Lys432    (1159)  CGCGACAACTGGCGCAGCGAGCTGTACAAG
   Val120-Ile201-Ile424-Ala433    (1147)  CGCGACAACTGGCGCAGCGAGCTGTACAAG
  Val120-Ile201B-Ile424-Ala433    (1147)  CGCGACAACTGGCGCAGCGAGCTGTACAAG
                    Consensus    (1201)  CGCGACAACTGGCGCAGCGAGCTGTACAAG
                                              1231                           1260
   Leu122-Ser199 Tryp427-Gly431    (1201)  TACAAGGTGGTGAAGATCGAGCCCCTGGGC
   Val127-Asn195-Arg426-Gly431    (1231)  TACAAGGTGGTGAAGATCGAGCCCCTGGGC
   Val120-Thr202-Ile424-Ala433    (1177)  TACAAGGTGGTGAAGATCGAGCCCCTGGGC
   Leu122-Ser199-Arg426-Lys432    (1201)  TACAAGGTGGTGAAGATCGAGCCCCTGGGC
   Leu122-Ser199-Arg426-Gly431    (1201)  TACAAGGTGGTGAAGATCGAGCCCCTGGGC
   Lys121-Val200-Asn425-Lys432    (1189)  TACAAGGTGGTGAAGATCGAGCCCCTGGGC
   Val120-Ile201-Ile424-Ala433    (1177)  TACAAGGTGGTGAAGATCGAGCCCCTGGGC
  Val120-Ile201B-Ile424-Ala433    (1177)  TACAAGGTGGTGAAGATCGAGCCCCTGGGC
                    Consensus    (1231)  TACAAGGTGGTGAAGATCGAGCCCCTGGGC
                                              1261                           1290
   Leu122-Ser199 Tryp427-Gly431    (1231)  GTGGCCCCCACCAAGGCCAAGCGCCGCGTG
   Val127-Asn195-Arg426-Gly431    (1261)  GTGGCCCCCACCAAGGCCAAGCGCCGCGTG
   Val120-Thr202-Ile424-Ala433    (1207)  GTGGCCCCCACCAAGGCCAAGCGCCGCGTG
   Leu122-Ser199-Arg426-Lys432    (1231)  GTGGCCCCCACCAAGGCCAAGCGCCGCGTG
   Leu122-Ser199-Arg426-Gly431    (1231)  GTGGCCCCCACCAAGGCCAAGCGCCGCGTG
   Lys121-Val200-Asn425-Lys432    (1219)  GTGGCCCCCACCAAGGCCAAGCGCCGCGTG
   Val120-Ile201-Ile424-Ala433    (1207)  GTGGCCCCCACCAAGGCCAAGCGCCGCGTG
  Val120-Ile201B-Ile424-Ala433    (1207)  GTGGCCCCCACCAAGGCCAAGCGCCGCGTG
                    Consensus    (1261)  GTGGCCCCCACCAAGGCCAAGCGCCGCGTG
                                              1291                           1320
   Leu122-Ser199 Tryp427-Gly431    (1261)  GTGCAGCGCGAGAAGCGCGCCGTGACCCTG
   Val127-Asn195-Arg426-Gly431    (1291)  GTGCAGCGCGAGAAGCGCGCCGTGACCCTG
   Val120-Thr202-Ile424-Ala433    (1237)  GTGCAGCGCGAGAAGCGCGCCGTGACCCTG
   Leu122-Ser199-Arg426-Lys432    (1261)  GTGCAGCGCGAGAAGCGCGCCGTGACCCTG
   Leu122-Ser199-Arg426-Gly431    (1261)  GTGCAGCGCGAGAAGCGCGCCGTGACCCTG
   Lys121-Val200-Asn425-Lys432    (1249)  GTGCAGCGCGAGAAGCGCGCCGTGACCCTG
   Val120-Ile201-Ile424-Ala433    (1237)  GTGCAGCGCGAGAAGCGCGCCGTGACCCTG
  Val120-Ile201B-Ile424-Ala433    (1237)  GTGCAGCGCGAGAAGCGCGCCGTGACCCTG
                    Consensus    (1291)  GTGCAGCGCGAGAAGCGCGCCGTGACCCTG
                                              1321                           1350
   Leu122-Ser199 Tryp427-Gly431    (1291)  GGCGCCATGTTCCTGGGCTTCCTGGGCGCC
   Val127-Asn195-Arg426-Gly431    (1321)  GGCGCCATGTTCCTGGGCTTCCTGGGCGCC
   Val120-Thr202-Ile424-Ala433    (1267)  GGCGCCATGTTCCTGGGCTTCCTGGGCGCC
   Leu122-Ser199-Arg426-Lys432    (1291)  GGCGCCATGTTCCTGGGCTTCCTGGGCGCC
   Leu122-Ser199-Arg426-Gly431    (1291)  GGCGCCATGTTCCTGGGCTTCCTGGGCGCC
   Lys121-Val200-Asn425-Lys432    (1279)  GGCGCCATGTTCCTGGGCTTCCTGGGCGCC
   Val120-Ile201-Ile424-Ala433    (1267)  GGCGCCATGTTCCTGGGCTTCCTGGGCGCC
  Val120-Ile201B-Ile424-Ala433    (1267)  GGCGCCATGTTCCTGGGCTTCCTGGGCGCC
                    Consensus    (1321)  GGCGCCATGTTCCTGGGCTTCCTGGGCGCC
                                              1351                           1380
   Leu122-Ser199 Tryp427-Gly431    (1321)  GCCGGCAGCACCATGGGCGCCCGCAGCCTG
   Val127-Asn195-Arg426-Gly431    (1351)  GCCGGCAGCACCATGGGCGCCCGCAGCCTG
   Val120-Thr202-Ile424-Ala433    (1297)  GCCGGCAGCACCATGGGCGCCCGCAGCCTG
   Leu122-Ser199-Arg426-Lys432    (1321)  GCCGGCAGCACCATGGGCGCCCGCAGCCTG
   Leu122-Ser199-Arg426-Gly431    (1321)  GCCGGCAGCACCATGGGCGCCCGCAGCCTG
```

*FIG. 5H*

| | | |
|---|---|---|
| Leu121-Val200-Asn425-Lys432 | (1309) | GCCGGCAGCACCATGGGCGCCCGCAGCCTG |
| Val120-Ile201-Ile424-Ala433 | (1297) | GCCGGCAGCACCATGGGCGCCCGCAGCCTG |
| Val120-Ile201B-Ile424-Ala433 | (1297) | GCCGGCAGCACCATGGGCGCCCGCAGCCTG |
| Consensus | (1351) | GCCGGCAGCACCATGGGCGCCCGCAGCCTG |

```
                                         1381                           1410
Leu122-Ser199 Tryp427-Gly431      (1351) ACCCTGACCGTGCAGGCCCGCCAGCTGCTG
Val127-Asn195-Arg426-Gly431       (1381) ACCCTGACCGTGCAGGCCCGCCAGCTGCTG
Val120-Thr202-Ile424-Ala433       (1327) ACCCTGACCGTGCAGGCCCGCCAGCTGCTG
Leu122-Ser199-Arg426-Lys432       (1351) ACCCTGACCGTGCAGGCCCGCCAGCTGCTG
Leu122-Ser199-Arg426-Gly431       (1351) ACCCTGACCGTGCAGGCCCGCCAGCTGCTG
Lys121-Val200-Asn425-Lys432       (1339) ACCCTGACCGTGCAGGCCCGCCAGCTGCTG
Val120-Ile201-Ile424-Ala433       (1327) ACCCTGACCGTGCAGGCCCGCCAGCTGCTG
Val120-Ile201B-Ile424-Ala433      (1327) ACCCTGACCGTGCAGGCCCGCCAGCTGCTG
Consensus                         (1381) ACCCTGACCGTGCAGGCCCGCCAGCTGCTG
                                         1411                           1440
Leu122-Ser199 Tryp427-Gly431      (1381) AGCGGCATCGTGCAGCAGCAGAACAACCTG
Val127-Asn195-Arg426-Gly431       (1411) AGCGGCATCGTGCAGCAGCAGAACAACCTG
Val120-Thr202-Ile424-Ala433       (1357) AGCGGCATCGTGCAGCAGCAGAACAACCTG
Leu122-Ser199-Arg426-Lys432       (1381) AGCGGCATCGTGCAGCAGCAGAACAACCTG
Leu122-Ser199-Arg426-Gly431       (1381) AGCGGCATCGTGCAGCAGCAGAACAACCTG
Lys121-Val200-Asn425-Lys432       (1369) AGCGGCATCGTGCAGCAGCAGAACAACCTG
Val120-Ile201-Ile424-Ala433       (1357) AGCGGCATCGTGCAGCAGCAGAACAACCTG
Val120-Ile201B-Ile424-Ala433      (1357) AGCGGCATCGTGCAGCAGCAGAACAACCTG
Consensus                         (1411) AGCGGCATCGTGCAGCAGCAGAACAACCTG
                                         1441                           1470
Leu122-Ser199 Tryp427-Gly431      (1411) CTGCGCGCCATCGAGGCCCAGCAGCACCTG
Val127-Asn195-Arg426-Gly431       (1441) CTGCGCGCCATCGAGGCCCAGCAGCACCTG
Val120-Thr202-Ile424-Ala433       (1387) CTGCGCGCCATCGAGGCCCAGCAGCACCTG
Leu122-Ser199-Arg426-Lys432       (1411) CTGCGCGCCATCGAGGCCCAGCAGCACCTG
Leu122-Ser199-Arg426-Gly431       (1411) CTGCGCGCCATCGAGGCCCAGCAGCACCTG
Lys121-Val200-Asn425-Lys432       (1399) CTGCGCGCCATCGAGGCCCAGCAGCACCTG
Val120-Ile201-Ile424-Ala433       (1387) CTGCGCGCCATCGAGGCCCAGCAGCACCTG
Val120-Ile201B-Ile424-Ala433      (1387) CTGCGCGCCATCGAGGCCCAGCAGCACCTG
Consensus                         (1441) CTGCGCGCCATCGAGGCCCAGCAGCACCTG
                                         1471                           1500
Leu122-Ser199 Tryp427-Gly431      (1441) CTGCAGCTGACCGTGTGGGGCATCAAGCAG
Val127-Asn195-Arg426-Gly431       (1471) CTGCAGCTGACCGTGTGGGGCATCAAGCAG
Val120-Thr202-Ile424-Ala433       (1417) CTGCAGCTGACCGTGTGGGGCATCAAGCAG
Leu122-Ser199-Arg426-Lys432       (1441) CTGCAGCTGACCGTGTGGGGCATCAAGCAG
Leu122-Ser199-Arg426-Gly431       (1441) CTGCAGCTGACCGTGTGGGGCATCAAGCAG
Lys121-Val200-Asn425-Lys432       (1429) CTGCAGCTGACCGTGTGGGGCATCAAGCAG
Val120-Ile201-Ile424-Ala433       (1417) CTGCAGCTGACCGTGTGGGGCATCAAGCAG
Val120-Ile201B-Ile424-Ala433      (1417) CTGCAGCTGACCGTGTGGGGCATCAAGCAG
Consensus                         (1471) CTGCAGCTGACCGTGTGGGGCATCAAGCAG
                                         1501                           1530
Leu122-Ser199 Tryp427-Gly431      (1471) CTGCAGGCCCGCGTGCTGGCCGTGGAGCGC
Val127-Asn195-Arg426-Gly431       (1501) CTGCAGGCCCGCGTGCTGGCCGTGGAGCGC
Val120-Thr202-Ile424-Ala433       (1447) CTGCAGGCCCGCGTGCTGGCCGTGGAGCGC
Leu122-Ser199-Arg426-Lys432       (1471) CTGCAGGCCCGCGTGCTGGCCGTGGAGCGC
Leu122-Ser199-Arg426-Gly431       (1471) CTGCAGGCCCGCGTGCTGGCCGTGGAGCGC
Lys121-Val200-Asn425-Lys432       (1459) CTGCAGGCCCGCGTGCTGGCCGTGGAGCGC
Val120-Ile201-Ile424-Ala433       (1447) CTGCAGGCCCGCGTGCTGGCCGTGGAGCGC
Val120-Ile201B-Ile424-Ala433      (1447) CTGCAGGCCCGCGTGCTGGCCGTGGAGCGC
Consensus                         (1501) CTGCAGGCCCGCGTGCTGGCCGTGGAGCGC
                                         1531                           1560
Leu122-Ser199 Tryp427-Gly431      (1501) TACCTGAAGGACCAGCAGCTGCTGGGCATC
Val127-Asn195-Arg426-Gly431       (1531) TACCTGAAGGACCAGCAGCTGCTGGGCATC
```

FIG. 5I

```
Val120-Thr202-Ile424-Ala433    (1477) TACCTGAAGGACCAGCAGCTGCTGGGCATC
Leu122-Ser199-Arg426-Lys432    (1501) TACCTGAAGGACCAGCAGCTGCTGGGCATC
Leu122-Ser199-Arg426-Gly431    (1501) TACCTGAAGGACCAGCAGCTGCTGGGCATC
Lys121-Val200-Asn425-Lys432    (1489) TACCTGAAGGACCAGCAGCTGCTGGGCATC
Val120-Ile201-Ile424-Ala433    (1477) TACCTGAAGGACCAGCAGCTGCTGGGCATC
Val120-Ile201B-Ile424-Ala433   (1477) TACCTGAAGGACCAGCAGCTGCTGGGCATC
                    Consensus  (1531) TACCTGAAGGACCAGCAGCTGCTGGGCATC
                                      1561                        1590
Leu122-Ser199 Tryp427-Gly431   (1531) TGGGGCTGCAGCGGCAAGCTGATCTGCACC
Val127-Asn195-Arg426-Gly431    (1561) TGGGGCTGCAGCGGCAAGCTGATCTGCACC
Val120-Thr202-Ile424-Ala433    (1507) TGGGGCTGCAGCGGCAAGCTGATCTGCACC
Leu122-Ser199-Arg426-Lys432    (1531) TGGGGCTGCAGCGGCAAGCTGATCTGCACC
Leu122-Ser199-Arg426-Gly431    (1531) TGGGGCTGCAGCGGCAAGCTGATCTGCACC
Lys121-Val200-Asn425-Lys432    (1519) TGGGGCTGCAGCGGCAAGCTGATCTGCACC
Val120-Ile201-Ile424-Ala433    (1507) TGGGGCTGCAGCGGCAAGCTGATCTGCACC
Val120-Ile201B-Ile424-Ala433   (1507) TGGGGCTGCAGCGGCAAGCTGATCTGCACC
                    Consensus  (1561) TGGGGCTGCAGCGGCAAGCTGATCTGCACC
                                      1591                        1620
Leu122-Ser199 Tryp427-Gly431   (1561) ACCGCCGTGCCCTGGAACGCCAGCTGGAGC
Val127-Asn195-Arg426-Gly431    (1591) ACCGCCGTGCCCTGGAACGCCAGCTGGAGC
Val120-Thr202-Ile424-Ala433    (1537) ACCGCCGTGCCCTGGAACGCCAGCTGGAGC
Leu122-Ser199-Arg426-Lys432    (1561) ACCGCCGTGCCCTGGAACGCCAGCTGGAGC
Leu122-Ser199-Arg426-Gly431    (1561) ACCGCCGTGCCCTGGAACGCCAGCTGGAGC
Lys121-Val200-Asn425-Lys432    (1549) ACCGCCGTGCCCTGGAACGCCAGCTGGAGC
Val120-Ile201-Ile424-Ala433    (1537) ACCGCCGTGCCCTGGAACGCCAGCTGGAGC
Val120-Ile201B-Ile424-Ala433   (1537) ACCGCCGTGCCCTGGAACGCCAGCTGGAGC
                    Consensus  (1591) ACCGCCGTGCCCTGGAACGCCAGCTGGAGC
                                      1621                        1650
Leu122-Ser199 Tryp427-Gly431   (1591) AACAAGAGCCTGGACCAGATCTGGAACAAC
Val127-Asn195-Arg426-Gly431    (1621) AACAAGAGCCTGGACCAGATCTGGAACAAC
Val120-Thr202-Ile424-Ala433    (1567) AACAAGAGCCTGGACCAGATCTGGAACAAC
Leu122-Ser199-Arg426-Lys432    (1591) AACAAGAGCCTGGACCAGATCTGGAACAAC
Leu122-Ser199-Arg426-Gly431    (1591) AACAAGAGCCTGGACCAGATCTGGAACAAC
Lys121-Val200-Asn425-Lys432    (1579) AACAAGAGCCTGGACCAGATCTGGAACAAC
Val120-Ile201-Ile424-Ala433    (1567) AACAAGAGCCTGGACCAGATCTGGAACAAC
Val120-Ile201B-Ile424-Ala433   (1567) AACAAGAGCCTGGACCAGATCTGGAACAAC
                    Consensus  (1621) AACAAGAGCCTGGACCAGATCTGGAACAAC
                                      1651                        1680
Leu122-Ser199 Tryp427-Gly431   (1621) ATGACCTGGATGGAGTGGGAGCGCGAGATC
Val127-Asn195-Arg426-Gly431    (1651) ATGACCTGGATGGAGTGGGAGCGCGAGATC
Val120-Thr202-Ile424-Ala433    (1597) ATGACCTGGATGGAGTGGGAGCGCGAGATC
Leu122-Ser199-Arg426-Lys432    (1621) ATGACCTGGATGGAGTGGGAGCGCGAGATC
Leu122-Ser199-Arg426-Gly431    (1621) ATGACCTGGATGGAGTGGGAGCGCGAGATC
Lys121-Val200-Asn425-Lys432    (1609) ATGACCTGGATGGAGTGGGAGCGCGAGATC
Val120-Ile201-Ile424-Ala433    (1597) ATGACCTGGATGGAGTGGGAGCGCGAGATC
Val120-Ile201B-Ile424-Ala433   (1597) ATGACCTGGATGGAGTGGGAGCGCGAGATC
                    Consensus  (1651) ATGACCTGGATGGAGTGGGAGCGCGAGATC
                                      1681                        1710
Leu122-Ser199 Tryp427-Gly431   (1651) GACAACTACACCAACCTGATCTACACCCTG
Val127-Asn195-Arg426-Gly431    (1681) GACAACTACACCAACCTGATCTACACCCTG
Val120-Thr202-Ile424-Ala433    (1627) GACAACTACACCAACCTGATCTACACCCTG
Leu122-Ser199-Arg426-Lys432    (1651) GACAACTACACCAACCTGATCTACACCCTG
Leu122-Ser199-Arg426-Gly431    (1651) GACAACTACACCAACCTGATCTACACCCTG
Lys121-Val200-Asn425-Lys432    (1639) GACAACTACACCAACCTGATCTACACCCTG
Val120-Ile201-Ile424-Ala433    (1627) GACAACTACACCAACCTGATCTACACCCTG
Val120-Ile201B-Ile424-Ala433   (1627) GACAACTACACCAACCTGATCTACACCCTG
                    Consensus  (1681) GACAACTACACCAACCTGATCTACACCCTG
```

*FIG. 5J*

```
                                             1711                           1740
Leu122-Ser199 Tryp427-Gly431    (1681)  ATCGAGGAGAGCCAGAACCAGCAGGAGAAG
Val127-Asn195-Arg426-Gly431     (1711)  ATCGAGGAGAGCCAGAACCAGCAGGAGAAG
Val120-Thr202-Ile424-Ala433     (1657)  ATCGAGGAGAGCCAGAACCAGCAGGAGAAG
Leu122-Ser199-Arg426-Lys432     (1681)  ATCGAGGAGAGCCAGAACCAGCAGGAGAAG
Leu122-Ser199-Arg426-Gly431     (1681)  ATCGAGGAGAGCCAGAACCAGCAGGAGAAG
Lys121-Val200-Asn425-Lys432     (1669)  ATCGAGGAGAGCCAGAACCAGCAGGAGAAG
Val120-Ile201-Ile424-Ala433     (1657)  ATCGAGGAGAGCCAGAACCAGCAGGAGAAG
Val120-Ile201B-Ile424-Ala433    (1657)  ATCGAGGAGAGCCAGAACCAGCAGGAGAAG
                  Consensus     (1711)  ATCGAGGAGAGCCAGAACCAGCAGGAGAAG
                                             1741                           1770
Leu122-Ser199 Tryp427-Gly431    (1711)  AACGAGCAGGAGCTGCTGGAGCTGGACAAG
Val127-Asn195-Arg426-Gly431     (1741)  AACGAGCAGGAGCTGCTGGAGCTGGACAAG
Val120-Thr202-Ile424-Ala433     (1687)  AACGAGCAGGAGCTGCTGGAGCTGGACAAG
Leu122-Ser199-Arg426-Lys432     (1711)  AACGAGCAGGAGCTGCTGGAGCTGGACAAG
Leu122-Ser199-Arg426-Gly431     (1711)  AACGAGCAGGAGCTGCTGGAGCTGGACAAG
Lys121-Val200-Asn425-Lys432     (1699)  AACGAGCAGGAGCTGCTGGAGCTGGACAAG
Val120-Ile201-Ile424-Ala433     (1687)  AACGAGCAGGAGCTGCTGGAGCTGGACAAG
Val120-Ile201B-Ile424-Ala433    (1687)  AACGAGCAGGAGCTGCTGGAGCTGGACAAG
                  Consensus     (1741)  AACGAGCAGGAGCTGCTGGAGCTGGACAAG
                                             1771                           1800
Leu122-Ser199 Tryp427-Gly431    (1741)  TGGGCCAGCCTGTGGAACTGGTTCGACATC
Val127-Asn195-Arg426-Gly431     (1771)  TGGGCCAGCCTGTGGAACTGGTTCGACATC
Val120-Thr202-Ile424-Ala433     (1717)  TGGGCCAGCCTGTGGAACTGGTTCGACATC
Leu122-Ser199-Arg426-Lys432     (1741)  TGGGCCAGCCTGTGGAACTGGTTCGACATC
Leu122-Ser199-Arg426-Gly431     (1741)  TGGGCCAGCCTGTGGAACTGGTTCGACATC
Lys121-Val200-Asn425-Lys432     (1729)  TGGGCCAGCCTGTGGAACTGGTTCGACATC
Val120-Ile201-Ile424-Ala433     (1717)  TGGGCCAGCCTGTGGAACTGGTTCGACATC
Val120-Ile201B-Ile424-Ala433    (1717)  TGGGCCAGCCTGTGGAACTGGTTCGACATC
                  Consensus     (1771)  TGGGCCAGCCTGTGGAACTGGTTCGACATC
                                             1801                           1830
Leu122-Ser199 Tryp427-Gly431    (1771)  AGCAAGTGGCTGTGGTACATCAAGATCTTC
Val127-Asn195-Arg426-Gly431     (1801)  AGCAAGTGGCTGTGGTACATCAAGATCTTC
Val120-Thr202-Ile424-Ala433     (1747)  AGCAAGTGGCTGTGGTACATCAAGATCTTC
Leu122-Ser199-Arg426-Lys432     (1771)  AGCAAGTGGCTGTGGTACATCAAGATCTTC
Leu122-Ser199-Arg426-Gly431     (1771)  AGCAAGTGGCTGTGGTACATCAAGATCTTC
Lys121-Val200-Asn425-Lys432     (1759)  AGCAAGTGGCTGTGGTACATCAAGATCTTC
Val120-Ile201-Ile424-Ala433     (1747)  AGCAAGTGGCTGTGGTACATCAAGATCTTC
Val120-Ile201B-Ile424-Ala433    (1747)  AGCAAGTGGCTGTGGTACATCAAGATCTTC
                  Consensus     (1801)  AGCAAGTGGCTGTGGTACATCAAGATCTTC
                                             1831                           1860
Leu122-Ser199 Tryp427-Gly431    (1801)  ATCATGATCGTGGGCGGCCTGGTGGGCCTG
Val127-Asn195-Arg426-Gly431     (1831)  ATCATGATCGTGGGCGGCCTGGTGGGCCTG
Val120-Thr202-Ile424-Ala433     (1777)  ATCATGATCGTGGGCGGCCTGGTGGGCCTG
Leu122-Ser199-Arg426-Lys432     (1801)  ATCATGATCGTGGGCGGCCTGGTGGGCCTG
Leu122-Ser199-Arg426-Gly431     (1801)  ATCATGATCGTGGGCGGCCTGGTGGGCCTG
Lys121-Val200-Asn425-Lys432     (1789)  ATCATGATCGTGGGCGGCCTGGTGGGCCTG
Val120-Ile201-Ile424-Ala433     (1777)  ATCATGATCGTGGGCGGCCTGGTGGGCCTG
Val120-Ile201B-Ile424-Ala433    (1777)  ATCATGATCGTGGGCGGCCTGGTGGGCCTG
                  Consensus     (1831)  ATCATGATCGTGGGCGGCCTGGTGGGCCTG
                                             1861                           1890
Leu122-Ser199 Tryp427-Gly431    (1831)  CGCATCGTGTTCACCGTGCTGAGCATCGTG
Val127-Asn195-Arg426-Gly431     (1861)  CGCATCGTGTTCACCGTGCTGAGCATCGTG
Val120-Thr202-Ile424-Ala433     (1807)  CGCATCGTGTTCACCGTGCTGAGCATCGTG
Leu122-Ser199-Arg426-Lys432     (1831)  CGCATCGTGTTCACCGTGCTGAGCATCGTG
Leu122-Ser199-Arg426-Gly431     (1831)  CGCATCGTGTTCACCGTGCTGAGCATCGTG
Lys121-Val200-Asn425-Lys432     (1819)  CGCATCGTGTTCACCGTGCTGAGCATCGTG
```

*FIG. 5K*

| | | |
|---|---|---|
| Val120-Ile201-Ile424-Ala433 | (1807) | CGCATCGTGTTCACCGTGCTGAGCATCGTG |
| Val120-Ile201B-Ile424-Ala433 | (1807) | CGCATCGTGTTCACCGTGCTGAGCATCGTG |
| Consensus | (1861) | CGCATCGTGTTCACCGTGCTGAGCATCGTG |

```
              1891                           1920
```

| | | |
|---|---|---|
| Leu122-Ser199 Tryp427-Gly431 | (1861) | AACCGCGTGCGCCAGGGCTACAGCCCCCTG |
| Val127-Asn195-Arg426-Gly431 | (1891) | AACCGCGTGCGCCAGGGCTACAGCCCCCTG |
| Val120-Thr202-Ile424-Ala433 | (1837) | AACCGCGTGCGCCAGGGCTACAGCCCCCTG |
| Leu122-Ser199-Arg426-Lys432 | (1861) | AACCGCGTGCGCCAGGGCTACAGCCCCCTG |
| Leu122-Ser199-Arg426-Gly431 | (1861) | AACCGCGTGCGCCAGGGCTACAGCCCCCTG |
| Lys121-Val200-Asn425-Lys432 | (1849) | AACCGCGTGCGCCAGGGCTACAGCCCCCTG |
| Val120-Ile201-Ile424-Ala433 | (1837) | AACCGCGTGCGCCAGGGCTACAGCCCCCTG |
| Val120-Ile201B-Ile424-Ala433 | (1837) | AACCGCGTGCGCCAGGGCTACAGCCCCCTG |
| Consensus | (1891) | AACCGCGTGCGCCAGGGCTACAGCCCCCTG |

```
              1921                           1950
```

| | | |
|---|---|---|
| Leu122-Ser199 Tryp427-Gly431 | (1891) | AGCTTCCAGACCCGCTTCCCCGCCCCCCGC |
| Val127-Asn195-Arg426-Gly431 | (1921) | AGCTTCCAGACCCGCTTCCCCGCCCCCCGC |
| Val120-Thr202-Ile424-Ala433 | (1867) | AGCTTCCAGACCCGCTTCCCCGCCCCCCGC |
| Leu122-Ser199-Arg426-Lys432 | (1891) | AGCTTCCAGACCCGCTTCCCCGCCCCCCGC |
| Leu122-Ser199-Arg426-Gly431 | (1891) | AGCTTCCAGACCCGCTTCCCCGCCCCCCGC |
| Lys121-Val200-Asn425-Lys432 | (1879) | AGCTTCCAGACCCGCTTCCCCGCCCCCCGC |
| Val120-Ile201-Ile424-Ala433 | (1867) | AGCTTCCAGACCCGCTTCCCCGCCCCCCGC |
| Val120-Ile201B-Ile424-Ala433 | (1867) | AGCTTCCAGACCCGCTTCCCCGCCCCCCGC |
| Consensus | (1921) | AGCTTCCAGACCCGCTTCCCCGCCCCCCGC |

```
              1951                           1980
```

| | | |
|---|---|---|
| Leu122-Ser199 Tryp427-Gly431 | (1921) | GGCCCCGACCGCCCCGAGGGCATCGAGGAG |
| Val127-Asn195-Arg426-Gly431 | (1951) | GGCCCCGACCGCCCCGAGGGCATCGAGGAG |
| Val120-Thr202-Ile424-Ala433 | (1897) | GGCCCCGACCGCCCCGAGGGCATCGAGGAG |
| Leu122-Ser199-Arg426-Lys432 | (1921) | GGCCCCGACCGCCCCGAGGGCATCGAGGAG |
| Leu122-Ser199-Arg426-Gly431 | (1921) | GGCCCCGACCGCCCCGAGGGCATCGAGGAG |
| Lys121-Val200-Asn425-Lys432 | (1909) | GGCCCCGACCGCCCCGAGGGCATCGAGGAG |
| Val120-Ile201-Ile424-Ala433 | (1897) | GGCCCCGACCGCCCCGAGGGCATCGAGGAG |
| Val120-Ile201B-Ile424-Ala433 | (1897) | GGCCCCGACCGCCCCGAGGGCATCGAGGAG |
| Consensus | (1951) | GGCCCCGACCGCCCCGAGGGCATCGAGGAG |

```
              1981                           2010
```

| | | |
|---|---|---|
| Leu122-Ser199 Tryp427-Gly431 | (1951) | GAGGGCGGCGAGCGCGACCGCGACCGCAGC |
| Val127-Asn195-Arg426-Gly431 | (1981) | GAGGGCGGCGAGCGCGACCGCGACCGCAGC |
| Val120-Thr202-Ile424-Ala433 | (1927) | GAGGGCGGCGAGCGCGACCGCGACCGCAGC |
| Leu122-Ser199-Arg426-Lys432 | (1951) | GAGGGCGGCGAGCGCGACCGCGACCGCAGC |
| Leu122-Ser199-Arg426-Gly431 | (1951) | GAGGGCGGCGAGCGCGACCGCGACCGCAGC |
| Lys121-Val200-Asn425-Lys432 | (1939) | GAGGGCGGCGAGCGCGACCGCGACCGCAGC |
| Val120-Ile201-Ile424-Ala433 | (1927) | GAGGGCGGCGAGCGCGACCGCGACCGCAGC |
| Val120-Ile201B-Ile424-Ala433 | (1927) | GAGGGCGGCGAGCGCGACCGCGACCGCAGC |
| Consensus | (1981) | GAGGGCGGCGAGCGCGACCGCGACCGCAGC |

```
              2011                           2040
```

| | | |
|---|---|---|
| Leu122-Ser199 Tryp427-Gly431 | (1981) | AGCCCCCTGGTGCACGGCCTGCTGGCCCTG |
| Val127-Asn195-Arg426-Gly431 | (2011) | AGCCCCCTGGTGCACGGCCTGCTGGCCCTG |
| Val120-Thr202-Ile424-Ala433 | (1957) | AGCCCCCTGGTGCACGGCCTGCTGGCCCTG |
| Leu122-Ser199-Arg426-Lys432 | (1981) | AGCCCCCTGGTGCACGGCCTGCTGGCCCTG |
| Leu122-Ser199-Arg426-Gly431 | (1981) | AGCCCCCTGGTGCACGGCCTGCTGGCCCTG |
| Lys121-Val200-Asn425-Lys432 | (1969) | AGCCCCCTGGTGCACGGCCTGCTGGCCCTG |
| Val120-Ile201-Ile424-Ala433 | (1957) | AGCCCCCTGGTGCACGGCCTGCTGGCCCTG |
| Val120-Ile201B-Ile424-Ala433 | (1957) | AGCCCCCTGGTGCACGGCCTGCTGGCCCTG |
| Consensus | (2011) | AGCCCCCTGGTGCACGGCCTGCTGGCCCTG |

```
              2041                           2070
```

| | | |
|---|---|---|
| Leu122-Ser199 Tryp427-Gly431 | (2011) | ATCTGGGACGACCTGCGCAGCCTGTGCCTG |
| Val127-Asn195-Arg426-Gly431 | (2041) | ATCTGGGACGACCTGCGCAGCCTGTGCCTG |
| Val120-Thr202-Ile424-Ala433 | (1987) | ATCTGGGACGACCTGCGCAGCCTGTGCCTG |

*FIG. 5L*

```
Leu122-Ser199-Arg426-Lys432    (2011)  ATCTGGGACGACCTGCGCAGCCTGTGCCTG
Leu122-Ser199-Arg426-Gly431    (2011)  ATCTGGGACGACCTGCGCAGCCTGTGCCTG
Lys121-Val200-Asn425-Lys432    (1999)  ATCTGGGACGACCTGCGCAGCCTGTGCCTG
Val120-Ile201-Ile424-Ala433    (1987)  ATCTGGGACGACCTGCGCAGCCTGTGCCTG
Val120-Ile201B-Ile424-Ala433   (1987)  ATCTGGGACGAGCTGCGCAGCCTGTGCCTG
                    Consensus  (2041)  ATCTGGGACGACCTGCGCAGCCTGTGCCTG
                                       2071                         2100
Leu122-Ser199 Tryp427-Gly431   (2041)  TTCAGCTACCACCGCCTGCGCGACCTGATC
Val127-Asn195-Arg426-Gly431    (2071)  TTCAGCTACCACCGCCTGCGCGACCTGATC
Val120-Thr202-Ile424-Ala433    (2017)  TTCAGCTACCACCGCCTGCGCGACCTGATC
Leu122-Ser199-Arg426-Lys432    (2041)  TTCAGCTACCACCGCCTGCGCGACCTGATC
Leu122-Ser199-Arg426-Gly431    (2041)  TTCAGCTACCACCGCCTGCGCGACCTGATC
Lys121-Val200-Asn425-Lys432    (2029)  TTCAGCTACCACCGCCTGCGCGACCTGATC
Val120-Ile201-Ile424-Ala433    (2017)  TTCAGCTACCACCGCCTGCGCGACCTGATC
Val120-Ile201B-Ile424-Ala433   (2017)  TTCAGCTACCACCGCCTGCGCGACCTGATC
                    Consensus  (2071)  TTCAGCTACCACCGCCTGCGCGACCTGATC
                                       2101                         2130
Leu122-Ser199 Tryp427-Gly431   (2071)  CTGATCGCCGCCCGCATCGTGGAGCTGCTG
Val127-Asn195-Arg426-Gly431    (2101)  CTGATCGCCGCCCGCATCGTGGAGCTGCTG
Val120-Thr202-Ile424-Ala433    (2047)  CTGATCGCCGCCCGCATCGTGGAGCTGCTG
Leu122-Ser199-Arg426-Lys432    (2071)  CTGATCGCCGCCCGCATCGTGGAGCTGCTG
Leu122-Ser199-Arg426-Gly431    (2071)  CTGATCGCCGCCCGCATCGTGGAGCTGCTG
Lys121-Val200-Asn425-Lys432    (2059)  CTGATCGCCGCCCGCATCGTGGAGCTGCTG
Val120-Ile201-Ile424-Ala433    (2047)  CTGATCGCCGCCCGCATCGTGGAGCTGCTG
Val120-Ile201B-Ile424-Ala433   (2047)  CTGATCGCCGCCCGCATCGTGGAGCTGCTG
                    Consensus  (2101)  CTGATCGCCGCCCGCATCGTGGAGCTGCTG
                                       2131                         2160
Leu122-Ser199 Tryp427-Gly431   (2101)  GGCCGCCGCGGCTGGGAGGCCCTGAAGTAC
Val127-Asn195-Arg426-Gly431    (2131)  GGCCGCCGCGGCTGGGAGGCCCTGAAGTAC
Val120-Thr202-Ile424-Ala433    (2077)  GGCCGCCGCGGCTGGGAGGCCCTGAAGTAC
Leu122-Ser199-Arg426-Lys432    (2101)  GGCCGCCGCGGCTGGGAGGCCCTGAAGTAC
Leu122-Ser199-Arg426-Gly431    (2101)  GGCCGCCGCGGCTGGGAGGCCCTGAAGTAC
Lys121-Val200-Asn425-Lys432    (2089)  GGCCGCCGCGGCTGGGAGGCCCTGAAGTAC
Val120-Ile201-Ile424-Ala433    (2077)  GGCCGCCGCGGCTGGGAGGCCCTGAAGTAC
Val120-Ile201B-Ile424-Ala433   (2077)  GGCCGCCGCGGCTGGGAGGCCCTGAAGTAC
                    Consensus  (2131)  GGCCGCCGCGGCTGGGAGGCCCTGAAGTAC
                                       2161                         2190
Leu122-Ser199 Tryp427-Gly431   (2131)  TGGGGCAACCTGCTGCAGTACTGGATCCAG
Val127-Asn195-Arg426-Gly431    (2161)  TGGGGCAACCTGCTGCAGTACTGGATCCAG
Val120-Thr202-Ile424-Ala433    (2107)  TGGGGCAACCTGCTGCAGTACTGGATCCAG
Leu122-Ser199-Arg426-Lys432    (2131)  TGGGGCAACCTGCTGCAGTACTGGATCCAG
Leu122-Ser199-Arg426-Gly431    (2131)  TGGGGCAACCTGCTGCAGTACTGGATCCAG
Lys121-Val200-Asn425-Lys432    (2119)  TGGGGCAACCTGCTGCAGTACTGGATCCAG
Val120-Ile201-Ile424-Ala433    (2107)  TGGGGCAACCTGCTGCAGTACTGGATCCAG
Val120-Ile201B-Ile424-Ala433   (2107)  TGGGGCAACCTGCTGCAGTACTGGATCCAG
                    Consensus  (2161)  TGGGGCAACCTGCTGCAGTACTGGATCCAG
                                       2191                         2220
Leu122-Ser199 Tryp427-Gly431   (2161)  GAGCTGAAGAACAGCGCCGTGAGCCTGTTC
Val127-Asn195-Arg426-Gly431    (2191)  GAGCTGAAGAACAGCGCCGTGAGCCTGTTC
Val120-Thr202-Ile424-Ala433    (2137)  GAGCTGAAGAACAGCGCCGTGAGCCTGTTC
Leu122-Ser199-Arg426-Lys432    (2161)  GAGCTGAAGAACAGCGCCGTGAGCCTGTTC
Leu122-Ser199-Arg426-Gly431    (2161)  GAGCTGAAGAACAGCGCCGTGAGCCTGTTC
Lys121-Val200-Asn425-Lys432    (2149)  GAGCTGAAGAACAGCGCCGTGAGCCTGTTC
Val120-Ile201-Ile424-Ala433    (2137)  GAGCTGAAGAACAGCGCCGTGAGCCTGTTC
Val120-Ile201B-Ile424-Ala433   (2137)  GAGCTGAAGAACAGCGCCGTGAGCCTGTTC
                    Consensus  (2191)  GAGCTGAAGAACAGCGCCGTGAGCCTGTTC
                                       2221                         2250
```

*FIG. 5M*

```
Leu122-Ser199 Tryp427-Gly431    (2191) GACGCCATCGCCATCGCCGTGGCCGAGGGC
  Val127-Asn195-Arg426-Gly431   (2221) GACGCCATCGCCATCGCCGTGGCCGAGGGC
  Val120-Thr202-Ile424-Ala433   (2167) GACGCCATCGCCATCGCCGTGGCCGAGGGC
  Leu122-Ser199-Arg426-Lys432   (2191) GACGCCATCGCCATCGCCGTGGCCGAGGGC
  Leu122-Ser199-Arg426-Gly431   (2191) GACGCCATCGCCATCGCCGTGGCCGAGGGC
  Lys121-Val200-Asn425-Lys432   (2179) GACGCCATCGCCATCGCCGTGGCCGAGGGC
  Val120-Ile201-Ile424-Ala433   (2167) GACGCCATCGCCATCGCCGTGGCCGAGGGC
  Val120-Ile201B-Ile424-Ala433  (2167) GACGCCATCGCCATCGCCGTGGCCGAGGGC
                      Consensus (2221) GACGCCATCGCCATCGCCGTGGCCGAGGGC
                                       2251                       2280
Leu122-Ser199 Tryp427-Gly431    (2221) ACCGACCGCATCATCGAGGTGGCCCAGCGC
  Val127-Asn195-Arg426-Gly431   (2251) ACCGACCGCATCATCGAGGTGGCCCAGCGC
  Val120-Thr202-Ile424-Ala433   (2197) ACCGACCGCATCATCGAGGTGGCCCAGCGC
  Leu122-Ser199-Arg426-Lys432   (2221) ACCGACCGCATCATCGAGGTGGCCCAGCGC
  Leu122-Ser199-Arg426-Gly431   (2221) ACCGACCGCATCATCGAGGTGGCCCAGCGC
  Lys121-Val200-Asn425-Lys432   (2209) ACCGACCGCATCATCGAGGTGGCCCAGCGC
  Val120-Ile201-Ile424-Ala433   (2197) ACCGACCGCATCATCGAGGTGGCCCAGCGC
  Val120-Ile201B-Ile424-Ala433  (2197) ACCGACCGCATCATCGAGGTGGCCCAGCGC
                      Consensus (2251) ACCGACCGCATCATCGAGGTGGCCCAGCGC
                                       2281                       2310
Leu122-Ser199 Tryp427-Gly431    (2251) ATCGGCCGCGCCTTCCTGCACATCCCCCGC
  Val127-Asn195-Arg426-Gly431   (2281) ATCGGCCGCGCCTTCCTGCACATCCCCCGC
  Val120-Thr202-Ile424-Ala433   (2227) ATCGGCCGCGCCTTCCTGCACATCCCCCGC
  Leu122-Ser199-Arg426-Lys432   (2251) ATCGGCCGCGCCTTCCTGCACATCCCCCGC
  Leu122-Ser199-Arg426-Gly431   (2251) ATCGGCCGCGCCTTCCTGCACATCCCCCGC
  Lys121-Val200-Asn425-Lys432   (2239) ATCGGCCGCGCCTTCCTGCACATCCCCCGC
  Val120-Ile201-Ile424-Ala433   (2227) ATCGGCCGCGCCTTCCTGCACATCCCCCGC
  Val120-Ile201B-Ile424-Ala433  (2227) ATCGGCCGCGCCTTCCTGCACATCCCCCGC
                      Consensus (2281) ATCGGCCGCGCCTTCCTGCACATCCCCCGC
                                       2311                       2340
Leu122-Ser199 Tryp427-Gly431    (2281) CGCATCCGCCAGGGCTTCGAGCGCGCCCTG
  Val127-Asn195-Arg426-Gly431   (2311) CGCATCCGCCAGGGCTTCGAGCGCGCCCTG
  Val120-Thr202-Ile424-Ala433   (2257) CGCATCCGCCAGGGCTTCGAGCGCGCCCTG
  Leu122-Ser199-Arg426-Lys432   (2281) CGCATCCGCCAGGGCTTCGAGCGCGCCCTG
  Leu122-Ser199-Arg426-Gly431   (2281) CGCATCCGCCAGGGCTTCGAGCGCGCCCTG
  Lys121-Val200-Asn425-Lys432   (2269) CGCATCCGCCAGGGCTTCGAGCGCGCCCTG
  Val120-Ile201-Ile424-Ala433   (2257) CGCATCCGCCAGGGCTTCGAGCGCGCCCTG
  Val120-Ile201B-Ile424-Ala433  (2257) CGCATCCGCCAGGGCTTCGAGCGCGCCCTG
                      Consensus (2311) CGCATCCGCCAGGGCTTCGAGCGCGCCCTG
                                       2341     2352
Leu122-Ser199 Tryp427-Gly431    (2311) CTGTAACTCGAG
  Val127-Asn195-Arg426-Gly431   (2341) CTGTAACTCGAG
  Val120-Thr202-Ile424-Ala433   (2287) CTGTAACTCGAG
  Leu122-Ser199-Arg426-Lys432   (2311) CTGTAACTCGAG
  Leu122-Ser199-Arg426-Gly431   (2311) CTGTAACTCGAG
  Lys121-Val200-Asn425-Lys432   (2299) CTGTAACTCGAG
  Val120-Ile201-Ile424-Ala433   (2287) CTGTAACTCGAG
  Val120-Ile201B-Ile424-Ala433  (2287) CTGTAACTCGAG
                      Consensus (2341) CTGTAACTCGAG
```

*FIG. 5N*

SEQ ID NO:3 VAL120-ALA204

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGGGCGCCGGCGCCTGCCCCAA
GGTGAGCTTCGAGCCCATCCCCATCCACTACTGCGCCCCCGCCGGCTTCGCCATCCTGAAGTG
CAACGACAAGAAGTTCAACGGCAGCGGCCCCTGCACCAACGTGAGCACCGTGCAGTGCACCC
ACGGCATCCGCCCCGTGGTGAGCACCCAGCTGCTGCTGAACGGCAGCCTGGCCGAGGAGGGC
GTGGTGATCCGCAGCGAGAACTTCACCGACAACGCCAAGACCATCATCGTGCAGCTGAAGGA
GAGCGTGGAGATCAACTGCACCCGCCCCAACAACAACACCCGCAAGAGCATCACCATCGGCC
CCGGCCGCGCCTTCTACGCCACCGGCGACATCATCGGCGACATCCGCCAGGCCCACTGCAACA
TCAGCGGCGAGAAGTGGAACAACACCCTGAAGCAGATCGTGACCAAGCTGCAGGCCCAGTTC
GGCAACAAGACCATCGTGTTCAAGCAGAGCAGCGGCGGCGACCCCGAGATCGTGATGCACAG
CTTCAACTGCGGCGGCGAGTTCTTCTACTGCAACAGCACCCAGCTGTTCAACAGCACCTGGAA
CAACACCATCGGCCCCAACAACACCAACGGCACCATCACCCTGCCCTGCCGCATCAAGCAGA
TCATCAACCGCTGGCAGGAGGTGGGCAAGGCCATGTACGCCCCCCCCATCCGCGGCCAGATC
CGCTGCAGCAGCAACATCACCGGCCTGCTGCTGACCCGCGACGGCGGCAAGGAGATCAGCAA
CACCACCGAGATCTTCCGCCCCGGCGGCGGCGACATGCGCGACAACTGGCGCAGCGAGCTGT
ACAAGTACAAGGTGGTGAAGATCGAGCCCCTGGGCGTGGCCCCCACCAAGGCCAAGCGCCGC
GTGGTGCAGCGCGAGAAGCGCGCCGTGACCCTGGGCGCCATGTTCCTGGGCTTCCTGGGCGCC
GCCGGCAGCACCATGGGCGCCCCGCAGCCTGACCCTGACCGTGCAGGCCCGCCAGCTGCTGAG
CGGCATCGTGCAGCAGCAGAACAACCTGCTGCGCGCCATCGAGGCCCAGCAGCACCTGCTGC
AGCTGACCGTGTGGGGCATCAAGCAGCTGCAGGCCCGCGTGCTGGCCGTGGAGCGCTACCTG
AAGGACCAGCAGCTGCTGGGCATCTGGGGCTGCAGCGGCAAGCTGATCTGCACCACCGCCGT
GCCCTGGAACGCCAGCTGGAGCAACAAGAGCCTGGACCAGATCTGGAACAACATGACCTGGA
TGGAGTGGGAGCGCGAGATCGACAACTACACCAACCTGATCTACACCCTGATCGAGGAGAGC
CAGAACCAGCAGGAGAAGAACGAGCAGGAGCTGCTGGAGCTGGACAAGTGGGCCAGCCTGT
GGAACTGGTTCGACATCAGCAAGTGGCTGTGGTACATCAAGATCTTCATCATGATCGTGGGCG
GCCTGGTGGGCCTGCGCATCGTGTTCACCGTGCTGAGCATCGTGAACCGCGTGCGCCAGGGCT
ACAGCCCCCTGAGCTTCCAGACCCGCTTCCCCGCCCCCCGCGGCCCCGACCGCCCCGAGGGCA
TCGAGGAGGAGGGCGGCGAGCGCGACCGCGACCGCAGCAGCCCCTGGTGCACGGCCTGCTG
GCCCTGATCTGGGACGACCTGCGCAGCCTGTGCCTGTTCAGCTACCACCGCCTGCGCGACCTG
ATCCTGATCGCCGCCCGCATCGTGGAGCTGCTGGGCCGCCGCGGCTGGGAGGCCCTGAAGTAC
TGGGGCAACCTGCTGCAGTACTGGATCCAGGAGCTGAAGAACAGCGCCGTGAGCCTGTTCGA
CGCCATCGCCATCGCCGTGGCCGAGGGCACCGACCGCATCATCGAGGTGGCCCAGCGCATCG
GCCGCGCCTTCCTGCACATCCCCCGCCGCATCCGCCAGGGCTTCGAGCGCGCCCTGCTGTAAC
TCGAG

FIG. 6

SEQ ID NO:4 VAL120-ILE201

```
GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGGGCGGCATCACCCAGGCCTG
CCCCAAGGTGAGCTTCGAGCCCATCCCCATCCACTACTGCGCCCCCGCCGGCTTCGCCATCCT
GAAGTGCAACGACAAGAAGTTCAACGGCAGCGGCCCCTGCACCAACGTGAGCACCGTGCAGT
GCACCCACGGCATCCGCCCCGTGGTGAGCACCCAGCTGCTGCTGAACGGCAGCCTGGCCGAG
GAGGGCGTGGTGATCCGCAGCGAGAACTTCACCGACAACGCCAAGACCATCATCGTGCAGCT
GAAGGAGAGCGTGGAGATCAACTGCACCCGCCCCAACAACAACACCCGCAAGAGCATCACCA
TCGGCCCCGGCCGCGCCTTCTACGCCACCGGCGACATCATCGGCGACATCCGCCAGGCCCACT
GCAACATCAGCGGCGAGAAGTGGAACAACACCCTGAAGCAGATCGTGACCAAGCTGCAGGCC
CAGTTCGGCAACAAGACCATCGTGTTCAAGCAGAGCAGCGGCGGCGACCCCGAGATCGTGAT
GCACAGCTTCAACTGCGGCGGCGAGTTCTTCTACTGCAACAGCACCCAGCTGTTCAACAGCAC
CTGGAACAACACCATCGGCCCCAACAACACCAACGGCACCATCACCCTGCCCTGCCGCATCA
AGCAGATCATCAACCGCTGGCAGGAGGTGGGCAAGGCCATGTACGCCCCCCCCATCCGCGGC
CAGATCCGCTGCAGCAGCAACATCACCGGCCTGCTGCTGACCCGCGACGGCGGCAAGGAGAT
CAGCAACACCACCGAGATCTTCCGCCCCGGCGGCGGCGACATGCGCGACAACTGGCGCAGCG
AGCTGTACAAGTACAAGGTGGTGAAGATCGAGCCCCTGGGCGTGGCCCCCACCAAGGCCAAG
CGCCGCGTGGTGCAGCGCGAGAAGCGCGCCGTGACCCTGGGCGCCATGTTCCTGGGCTTCCTG
GGCGCCGCCGGCAGCACCATGGGCGCCCGCAGCCTGACCCTGACCGTGCAGGCCCGCCAGCT
GCTGAGCGGCATCGTGCAGCAGCAGAACAACCTGCTGCGCGCCATCGAGGCCCAGCAGCACC
TGCTGCAGCTGACCGTGTGGGGCATCAAGCAGCTGCAGGCCCGCGTGCTGGCCGTGGAGCGC
TACCTGAAGGACCAGCAGCTGCTGGGCATCTGGGGCTGCAGCGGCAAGCTGATCTGCACCAC
CGCCGTGCCCTGGAACGCCAGCTGGAGCAACAAGAGCCTGGACCAGATCTGGAACAACATGA
CCTGGATGGAGTGGGAGCGCGAGATCGACAACTACACCAACCTGATCTACACCCTGATCGAG
GAGAGCCAGAACCAGCAGGAGAAGAACGAGCAGGAGCTGCTGGAGCTGGACAAGTGGGCCA
GCCTGTGGAACTGGTTCGACATCAGCAAGTGGCTGTGGTACATCAAGATCTTCATCATGATCG
TGGGCGGCCTGGTGGGCCTGCGCATCGTGTTCACCGTGCTGAGCATCGTGAACCGCGTGCGCC
AGGGCTACAGCCCCCTGAGCTTCCAGACCCGCTTCCCCGCCCCCGCGGCCCCGACCGCCCCG
AGGGCATCGAGGAGGAGGGCGGCGAGCGCGACCGCGACCGCAGCAGCCCCCTGGTGCACGG
CCTGCTGGCCCTGATCTGGGACGACCTGCGCAGCCTGTGCCTGTTCAGCTACCACCGCCTGCG
CGACCTGATCCTGATCGCCGCCCGCATCGTGGAGCTGCTGGGCCGCCGCGGCTGGGAGGCCCT
GAAGTACTGGGGCAACCTGCTGCAGTACTGGATCCAGGAGCTGAAGAACAGCGCCGTGAGCC
TGTTCGACGCCATCGCCATCGCCGTGGCCGAGGGCACCGACCGCATCATCGAGGTGGCCCAGC
GCATCGGCCGCGCCTTCCTGCACATCCCCCGCCGCATCCGCCAGGGCTTCGAGCGCGCCCTGC
TGTAACTCGAG
```

*FIG. 7*

SEQ ID NO:5 VAL120-ILE201B

```
GAATTCGCCACCATGGATGCAATGAAGAGAGGGCTCTGCTGTGTGCTGCTGCTGTGTGGAGCAGTCTTCG
TTTCGCCCAGCGCCGTGGAGAAGCTGTGGGTGACCGTGTACTACGGCGTGCCCGTGTGGAAGGAGGCCA
CCACCACCCTGTTCTGCGCCAGCGACGCCAAGGCCTACGACACCGAGGTGCACAACGTGTGGGCCACCC
ACGCCTGCGTGCCCACCGACCCCAACCCCCAGGAGATCGTGCTGGAGAACGTGACCGAGAACTTCAACA
TGTGGAAGAACAACATGGTGGAGCAGATGCACGAGGACATCATCAGCCTGTGGGACCAGAGCCTGAAGC
CCTGCGTGCCCGGCATCACCCAGGCCTGCCCCAAGGTGAGCTTCGAGCCCATCCCCATCCACTACTGCG
CCCCGCCGGCTTCGCCATCCTGAAGTGCAACGACAAGAAGTTCAACGGCAGCGGCCCCTGCACCAACGT
GAGCACCGTGCAGTGCACCCACGGCATCCGCCCCGTGGTGAGCACCCAGCTGCTGCTGAACGGCAGCCT
GGCCGAGGAGGGCGTGGTGATCCGCAGCGAGAACTTCACCGACAACGCCAAGACCATCATCGTGCAGCT
GAAGGAGAGCGTGGAGATCAACTGCACCCGCCCCAACAACAACACCCGCAAGAGCATCACCATCGGCCC
CGGCCGCGCCTTCTACGCCACCGGCGACATCATCGGCGACATCCGCCAGGCCCACTGCAACATCAGCGGC
GAGAAGTGGAACAACACCCTGAAGCAGATCGTGACCAAGCTGCAGGCCCAGTTCGGCAACAAGACCATC
GTGTTCAAGCAGAGCAGCGGCGGCGACCCCGAGATCGTGATGCACAGCTTCAACTGCGGCGGCGAGTTC
TTCTACTGCAACAGCACCCAGCTGTTCAACAGCACCTGGAACAACACCATCGGCCCCAACAACACCAAC
GGCACCATCACCCTGCCCTGCCGCATCAAGCAGATCATCAACCGCTGGCAGGAGGTGGGCAAGGCCATG
TACGCCCCCCCCATCCGCGGCCAGATCCGCTGCAGCAGCAACATCACCGGCCTGCTGCTGACCCGCGACG
GCGGCAAGGAGATCAGCAACACCACCGAGATCTTCCGCCCCGGCGGCGGCGACATGCGCGACAACTGGC
GCAGCGAGCTGTACAAGTACAAGGTGGTGAAGATCGAGCCCCTGGGCGTGGCCCCCACCAAGGCCAAGC
GCCGCGTGGTGCAGCGCGAGAAGCGCGCCGTGACCCTGGGCGCCATGTTCCTGGGCTTCCTGGGCGCCG
CGGCAGCACCATGGGCGCCCGCAGCCTGACCCTGACCGTGCAGGCCCGCCAGCTGCTGAGCGGCATCGT
GCAGCAGCAGAACAACCTGCTGCGCGCCATCGAGGCCCAGCAGCACCTGCTGCAGCTGACCGTGTGGGG
CATCAAGCAGCTGCAGGCCCGCGTGCTGGCCGTGGAGCGCTACCTGAAGGACCAGCAGCTGCTGGGCAT
CTGGGGCTGCAGCGGCAAGCTGATCTGCACCACCGCCGTGCCCTGGAACGCCAGCTGGAGCAACAAGAG
CCTGGACCAGATCTGGAACAACATGACCTGGATGGAGTGGGAGCGCGAGATCGACAACTACACCAACCT
GATCTACACCCTGATCGAGGAGAGCCAGAACCAGCAGGAGAAGAACGAGCAGGAGCTGCTGGAGCTGG
ACAAGTGGGCCAGCCTGTGGAACTGGTTCGACATCAGCAAGTGGCTGTGGTACATCAAGATCTTCATCAT
GATCGTGGGCGGCCTGGTGGGCCTGCGCATCGTGTTCACCGTGCTGAGCATCGTGAACCGCGTGCGCCAG
GGCTACAGCCCCCTGAGCTTCCAGACCCGCTTCCCCGCCCCCGCGGCCCCGACCGCCCCGAGGGCATCG
AGGAGGAGGGCGGCGAGCGCGACCGCGACCGCAGCAGCCCCCTGGTGCACGGCCTGCTGGCCCTGATCT
GGGACGACCTGCGCAGCCTGTGCCTGTTCAGCTACCACCGCCTGCGCGACCTGATCCTGATCGCCGCCCG
CATCGTGGAGCTGCTGGGCCGCCGCGGCTGGGAGGCCCTGAAGTACTGGGGCAACCTGCTGCAGTACTG
GATCCAGGAGCTGAAGAACAGCGCCGTGAGCCTGTTCGACGCCATCGCCATCGCCGTGGCCGAGGGCAC
CGACCGCATCATCGAGGTGGCCCAGCGCATCGGCCGCGCCTTCCTGCACATCCCCCGCCGCATCCGCCAG
GGCTTCGAGCGCGCCCTGCTGTAACTCGAGCGTGCT
```

*FIG. 8*

SEQ ID NO:6 LYS121-VAL200

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGGCCCCCGTGATCACCCA
GGCCTGCCCCAAGGTGAGCTTCGAGCCCATCCCCATCCACTACTGCGCCCCCGCCGGCTTCGC
CATCCTGAAGTGCAACGACAAGAAGTTCAACGGCAGCGGCCCCTGCACCAACGTGAGCACCG
TGCAGTGCACCCACGGCATCCGCCCCGTGGTGAGCACCCAGCTGCTGCTGAACGGCAGCCTGG
CCGAGGAGGGCGTGGTGATCCGCAGCGAGAACTTCACCGACAACGCCAAGACCATCATCGTG
CAGCTGAAGGAGAGCGTGGAGATCAACTGCACCCGCCCCAACAACAACACCCGCAAGAGCAT
CACCATCGGCCCCGGCCGCGCCTTCTACGCCACCGGCGACATCATCGGCGACATCCGCCAGGC
CCACTGCAACATCAGCGGCGAGAAGTGGAACAACACCCTGAAGCAGATCGTGACCAAGCTGC
AGGCCCAGTTCGGCAACAAGACCATCGTGTTCAAGCAGAGCAGCGGCGGCGACCCCGAGATC
GTGATGCACAGCTTCAACTGCGGCGGCGAGTTCTTCTACTGCAACAGCACCCAGCTGTTCAAC
AGCACCTGGAACAACACCATCGGCCCCAACAACACCAACGGCACCATCACCCTGCCCTGCCG
CATCAAGCAGATCATCAACCGCTGGCAGGAGGTGGGCAAGGCCATGTACGCCCCCCCCATCC
GCGGCCAGATCCGCTGCAGCAGCAACATCACCGGCCTGCTGCTGACCCGCGACGGCGGCAAG
GAGATCAGCAACACCACCGAGATCTTCCGCCCCGGCGGCGGCGACATGCGCGACAACTGGCG
CAGCGAGCTGTACAAGTACAAGGTGGTGAAGATCGAGCCCCTGGGCGTGGCCCCCACCAAGG
CCAAGCGCCGCGTGGTGCAGCGCGAGAAGCGCGCCGTGACCCTGGGCGCCATGTTCCTGGGC
TTCCTGGGCGCCGCCGGCAGCACCATGGGCGCCCGCAGCCTGACCCTGACCGTGCAGGCCCGC
CAGCTGCTGAGCGGCATCGTGCAGCAGCAGAACAACCTGCTGCGCGCCATCGAGGCCCAGCA
GCACCTGCTGCAGCTGACCGTGTGGGGCATCAAGCAGCTGCAGGCCCGCGTGCTGGCCGTGG
AGCGCTACCTGAAGGACCAGCAGCTGCTGGGCATCTGGGGCTGCAGCGGCAAGCTGATCTGC
ACCACCGCCGTGCCCTGGAACGCCAGCTGGAGCAACAAGAGCCTGGACCAGATCTGGAACAA
CATGACCTGGATGGAGTGGGAGCGCGAGATCGACAACTACACCAACCTGATCTACACCCTGA
TCGAGGAGAGCCAGAACCAGCAGGAGAAGAACGAGCAGGAGCTGCTGGAGCTGGACAAGTG
GGCCAGCCTGTGGAACTGGTTCGACATCAGCAAGTGGCTGTGGTACATCAAGATCTTCATCAT
GATCGTGGGCGGCCTGGTGGGCCTGCGCATCGTGTTCACCGTGCTGAGCATCGTGAACCGCGT
GCGCCAGGGCTACAGCCCCCTGAGCTTCCAGACCCGCTTCCCCGCCCCCGCGGCCCCGACCG
CCCCGAGGGCATCGAGGAGGAGGGCGGCGAGCGCGACCGCGACCGCAGCAGCCCCCTGGTGC
ACGGCCTGCTGGCCCTGATCTGGGACGACCTGCGCAGCCTGTGCCTGTTCAGCTACCACCGCC
TGCGCGACCTGATCCTGATCGCCGCCCGCATCGTGGAGCTGCTGGGCCGCCGCGGCTGGGAGG
CCCTGAAGTACTGGGGCAACCTGCTGCAGTACTGGATCCAGGAGCTGAAGAACAGCGCCGTG
AGCCTGTTCGACGCCATCGCCATCGCCGTGGCCGAGGGCACCGACCGCATCATCGAGGTGGCC
CAGCGCATCGGCCGCGCCTTCCTGCACATCCCCGCCGCATCCGCCAGGGCTTCGAGCGCGCC
CTGCTGTAACTCGAGCGTGCT

FIG. 9

SEQ ID NO:7: LEU122-SER199

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGGGCAACAGCGTGAT
CACCCAGGCCTGCCCCAAGGTGAGCTTCGAGCCCATCCCCATCCACTACTGCGCCCCCGCCGG
CTTCGCCATCCTGAAGTGCAACGACAAGAAGTTCAACGGCAGCGGCCCCTGCACCAACGTGA
GCACCGTGCAGTGCACCCACGGCATCCGCCCCGTGGTGAGCACCCAGCTGCTGCTGAACGGC
AGCCTGGCCGAGGAGGGCGTGGTGATCCGCAGCGAGAACTTCACCGACAACGCCAAGACCAT
CATCGTGCAGCTGAAGGAGAGCGTGGAGATCAACTGCACCCGCCCCAACAACAACACCCGCA
AGAGCATCACCATCGGCCCCGGCCGCGCCTTCTACGCCACCGGCGACATCATCGGCGACATCC
GCCAGGCCCACTGCAACATCAGCGGCGAGAAGTGGAACAACACCCTGAAGCAGATCGTGACC
AAGCTGCAGGCCCAGTTCGGCAACAAGACCATCGTGTTCAAGCAGAGCAGCGGCGGCGACCC
CGAGATCGTGATGCACAGCTTCAACTGCGGCGGCGAGTTCTTCTACTGCAACAGCACCCAGCT
GTTCAACAGCACCTGGAACAACACCATCGGCCCCAACAACACCAACGGCACCATCACCCTGC
CCTGCCGCATCAAGCAGATCATCAACCGCTGGCAGGAGGTGGGCAAGGCCATGTACGCCCCC
CCCATCCGCGGCCAGATCCGCTGCAGCAGCAACATCACCGGCCTGCTGCTGACCCGCGACGGC
GGCAAGGAGATCAGCAACACCACCGAGATCTTCCGCCCCGGCGGCGGCGACATGCGCGACAA
CTGGCGCAGCGAGCTGTACAAGTACAAGGTGGTGAAGATCGAGCCCCTGGGCGTGGCCCCCA
CCAAGGCCAAGCGCCGCGTGGTGCAGCGCGAGAAGCGCGCCGTGACCCTGGGCGCCATGTTC
CTGGGCTTCCTGGGCGCCGCCGGCAGCACCATGGGCGCCCGCAGCCTGACCCTGACCGTGCAG
GCCCGCCAGCTGCTGAGCGGCATCGTGCAGCAGCAGAACAACCTGCTGCGCGCCATCGAGGC
CCAGCAGCACCTGCTGCAGCTGACCGTGTGGGGCATCAAGCAGCTGCAGGCCCGCGTGCTGG
CCGTGGAGCGCTACCTGAAGGACCAGCAGCTGCTGGGCATCTGGGGCTGCAGCGGCAAGCTG
ATCTGCACCACCGCCGTGCCCTGGAACGCCAGCTGGAGCAACAAGAGCCTGGACCAGATCTG
GAACAACATGACCTGGATGGAGTGGGAGCGCGAGATCGACAACTACACCAACCTGATCTACA
CCCTGATCGAGGAGAGCCAGAACCAGCAGGAGAAGAACGAGCAGGAGCTGCTGGAGCTGGA
CAAGTGGGCCAGCCTGTGGAACTGGTTCGACATCAGCAAGTGGCTGTGGTACATCAAGATCTT
CATCATGATCGTGGGCGGCCTGGTGGGCCTGCGCATCGTGTTCACCGTGCTGAGCATCGTGAA
CCGCGTGCGCCAGGGCTACAGCCCCCTGAGCTTCCAGACCCGCTTCCCCGCCCCCGCGGCCC
CGACCGCCCCGAGGGCATCGAGGAGGAGGGCGGCGAGCGCGACCGCGACCGCAGCAGCCCC
CTGGTGCACGGCCTGCTGGCCCTGATCTGGGACGACCTGCGCAGCCTGTGCCTGTTCAGCTAC
CACCGCCTGCGCGACCTGATCCTGATCGCCGCCCGCATCGTGGAGCTGCTGGGCCGCCGCGGC
TGGGAGGCCCTGAAGTACTGGGGCAACCTGCTGCAGTACTGGATCCAGGAGCTGAAGAACAG
CGCCGTGAGCCTGTTCGACGCCATCGCCATCGCCGTGGCCGAGGGCACCGACCGCATCATCGA
GGTGGCCCAGCGCATCGGCCGCGCCTTCCTGCACATCCCCCGCCGCATCCGCCAGGGCTTCGA
GCGCGCCCTGCTGTAACTCGAGCGTGCT

FIG. 10

SEQ ID NO:8 VAL120-THR202

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGGGCGGCGCCACCCAGGCCTG
CCCCAAGGTGAGCTTCGAGCCCATCCCCATCCACTACTGCGCCCCCGCCGGCTTCGCCATCCT
GAAGTGCAACGACAAGAAGTTCAACGGCAGCGGCCCCTGCACCAACGTGAGCACCGTGCAGT
GCACCCACGGCATCCGCCCCGTGGTGAGCACCCAGCTGCTGCTGAACGGCAGCCTGGCCGAG
GAGGGCGTGGTGATCCGCAGCGAGAACTTCACCGACAACGCCAAGACCATCATCGTGCAGCT
GAAGGAGAGCGTGGAGATCAACTGCACCCGCCCCAACAACAACACCCGCAAGAGCATCACCA
TCGGCCCCGGCCGCGCCTTCTACGCCACCGGCGACATCATCGGCGACATCCGCCAGGCCCACT
GCAACATCAGCGGCGAGAAGTGGAACAACACCCTGAAGCAGATCGTGACCAAGCTGCAGGCC
CAGTTCGGCAACAAGACCATCGTGTTCAAGCAGAGCAGCGGCGGCGACCCCGAGATCGTGAT
GCACAGCTTCAACTGCGGCGGCGAGTTCTTCTACTGCAACAGCACCCAGCTGTTCAACAGCAC
CTGGAACAACACCATCGGCCCCAACAACACCAACGGCACCATCACCCTGCCCTGCCGCATCA
AGCAGATCATCAACCGCTGGCAGGAGGTGGGCAAGGCCATGTACGCCCCCCCCATCCGCGGC
CAGATCCGCTGCAGCAGCAACATCACCGGCCTGCTGCTGACCCGCGACGGCGGCAAGGAGAT
CAGCAACACCACCGAGATCTTCCGCCCCGGCGGCGGCGACATGCGCGACAACTGGCGCAGCG
AGCTGTACAAGTACAAGGTGGTGAAGATCGAGCCCCTGGGCGTGGCCCCCACCAAGGCCAAG
CGCCGCGTGGTGCAGCGCGAGAAGCGCGCCGTGACCCTGGGCGCCATGTTCCTGGGCTTCCTG
GGCGCCGCCGGCAGCACCATGGGCGCCCGCAGCCTGACCCTGACCGTGCAGGCCCGCCAGCT
GCTGAGCGGCATCGTGCAGCAGCAGAACAACCTGCTGCGCGCCATCGAGGCCCAGCAGCACC
TGCTGCAGCTGACCGTGTGGGGCATCAAGCAGCTGCAGGCCCGCGTGCTGGCCGTGGAGCGC
TACCTGAAGGACCAGCAGCTGCTGGGCATCTGGGGCTGCAGCGGCAAGCTGATCTGCACCAC
CGCCGTGCCCTGGAACGCCAGCTGGAGCAACAAGAGCCTGGACCAGATCTGGAACAACATGA
CCTGGATGGAGTGGGAGCGCGAGATCGACAACTACACCAACCTGATCTACACCCTGATCGAG
GAGAGCCAGAACCAGCAGGAGAAGAACGAGCAGGAGCTGCTGGAGCTGGACAAGTGGGCCA
GCCTGTGGAACTGGTTCGACATCAGCAAGTGGCTGTGGTACATCAAGATCTTCATCATGATCG
TGGGCGGCCTGGTGGGCCTGCGCATCGTGTTCACCGTGCTGAGCATCGTGAACCGCGTGCGCC
AGGGCTACAGCCCCCTGAGCTTCCAGACCCGCTTCCCCGCCCCCCGCGGCCCCGACCGCCCCG
AGGGCATCGAGGAGGAGGGCGGCGAGCGCGACCGCGACCGCAGCAGCCCCCTGGTGCACGG
CCTGCTGGCCCTGATCTGGGACGACCTGCGCAGCCTGTGCCTGTTCAGCTACCACCGCCTGCG
CGACCTGATCCTGATCGCCGCCCGCATCGTGGAGCTGCTGGGCCGCCGCGGCTGGGAGGCCCT
GAAGTACTGGGGCAACCTGCTGCAGTACTGGATCCAGGAGCTGAAGAACAGCGCCGTGAGCC
TGTTCGACGCCATCGCCATCGCCGTGGCCGAGGGCACCGACCGCATCATCGAGGTGGCCCAGC
GCATCGGCCGCGCCTTCCTGCACATCCCCCGCCGCATCCGCCAGGGCTTCGAGCGCGCCCTGC
TGTAACTCGAG

SEQ ID NO:9 TRP427-GLY431

```
GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGACCCCCCTGTGCGTG
ACCCTGCACTGCACCAACCTGAAGAACGCCACCAACACCAAGAGCAGCAACTGGAAGGAGAT
GGACCGCGGCGAGATCAAGAACTGCAGCTTCAAGGTGACCACCAGCATCCGCAACAAGATGC
AGAAGGAGTACGCCCTGTTCTACAAGCTGGACGTGGTGCCCATCGACAACGACAACACCAGC
TACAAGCTGATCAACTGCAACACCAGCGTGATCACCCAGGCCTGCCCCAAGGTGAGCTTCGA
GCCCATCCCCATCCACTACTGCGCCCCCGCCGGCTTCGCCATCCTGAAGTGCAACGACAAGAA
GTTCAACGGCAGCGGCCCCTGCACCAACGTGAGCACCGTGCAGTGCACCCACGGCATCCGCC
CCGTGGTGAGCACCCAGCTGCTGCTGAACGGCAGCCTGGCCGAGGAGGGCGTGGTGATCCGC
AGCGAGAACTTCACCGACAACGCCAAGACCATCATCGTGCAGCTGAAGGAGAGCGTGGAGAT
CAACTGCACCCGCCCCAACAACAACACCCGCAAGAGCATCACCATCGGCCCCGGCCGCGCCT
TCTACGCCACCGGCGACATCATCGGCGACATCCGCCAGGCCCACTGCAACATCAGCGGCGAG
AAGTGGAACAACACCCTGAAGCAGATCGTGACCAAGCTGCAGGCCCAGTTCGGCAACAAGAC
CATCGTGTTCAAGCAGAGCAGCGGCGGCGACCCCGAGATCGTGATGCACAGCTTCAACTGCG
GCGGCGAGTTCTTCTACTGCAACAGCACCCAGCTGTTCAACAGCACCTGGAACAACACCATCG
GCCCCAACAACACCAACGGCACCATCACCCTGCCCTGCCGCATCAAGCAGATCATCAACCGCT
GGGGCGGCAAGGCCATGTACGCCCCCCCCATCCGCGGCCAGATCCGCTGCAGCAGCAACATC
ACCGGCCTGCTGCTGACCCGCGACGGCGGCAAGGAGATCAGCAACACCACCGAGATCTTCCG
CCCCGGCGGCGGCGACATGCGCGACAACTGGCGCAGCGAGCTGTACAAGTACAAGGTGGTGA
AGATCGAGCCCCTGGGCGTGGCCCCCACCAAGGCCAAGCGCCGCGTGGTGCAGCGCGAGAAG
CGCGCCGTGACCCTGGGCGCCATGTTCCTGGGCTTCCTGGGCGCCGCCGGCAGCACCATGGGC
GCCCGCAGCCTGACCCTGACCGTGCAGGCCCGCCAGCTGCTGAGCGGCATCGTGCAGCAGCA
GAACAACCTGCTGCGCGCCATCGAGGCCCAGCAGCACCTGCTGCAGCTGACCGTGTGGGGCA
TCAAGCAGCTGCAGGCCCGCGTGCTGGCCGTGGAGCGCTACCTGAAGGACCAGCAGCTGCTG
GGCATCTGGGGCTGCAGCGGCAAGCTGATCTGCACCACCGCCGTGCCCTGGAACGCCAGCTG
GAGCAACAAGAGCCTGGACCAGATCTGGAACAACATGACCTGGATGGAGTGGGAGCGCGAG
ATCGACAACTACACCAACCTGATCTACACCCTGATCGAGGAGAGCCAGAACCAGCAGGAGAA
GAACGAGCAGGAGCTGCTGGAGCTGGACAAGTGGGCCAGCCTGTGGAACTGGTTCGACATCA
GCAAGTGGCTGTGGTACATCAAGATCTTCATCATGATCGTGGGCGGCCTGGTGGGCCTGCGCA
TCGTGTTCACCGTGCTGAGCATCGTGAACCGCGTGCGCCAGGGCTACAGCCCCCTGAGCTTCC
AGACCCGCTTCCCCGCCCCCCGCGGCCCCGACCGCCCCGAGGGCATCGAGGAGGAGGGCGGC
GAGCGCGACCGCGACCGCAGCAGCCCCTGGTGCACGGCCTGCTGGCCCTGATCTGGGACGA
CCTGCGCAGCCTGTGCCTGTTCAGCTACCACCGCCTGCGCGACCTGATCCTGATCGCCGCCCG
CATCGTGGAGCTGCTGGGCCGCCGCGGCTGGGAGGCCCTGAAGTACTGGGGCAACCTGCTGC
AGTACTGGATCCAGGAGCTGAAGAACAGCGCCGTGAGCCTGTTCGACGCCATCGCCATCGCC
GTGGCCGAGGGCACCGACCGCATCATCGAGGTGGCCCAGCGCATCGGCCGCGCCTTCCTGCA
CATCCCCCGCCGCATCCGCCAGGGCTTCGAGCGCGCCCTGCTGTAACTCGAG
```

FIG. 12

SEQ ID NO:10 ARG426-GLY431

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGACCCCCCTGTGCGTG
ACCCTGCACTGCACCAACCTGAAGAACGCCACCAACACCAAGAGCAGCAACTGGAAGGAGAT
GGACCGCGGCGAGATCAAGAACTGCAGCTTCAAGGTGACCACCAGCATCCGCAACAAGATGC
AGAAGGAGTACGCCCTGTTCTACAAGCTGGACGTGGTGCCCATCGACAACGACAACACCAGC
TACAAGCTGATCAACTGCAACACCAGCGTGATCACCCAGGCCTGCCCCAAGGTGAGCTTCGA
GCCCATCCCCATCCACTACTGCGCCCCCGCCGGCTTCGCCATCCTGAAGTGCAACGACAAGAA
GTTCAACGGCAGCGGCCCCTGCACCAACGTGAGCACCGTGCAGTGCACCCACGGCATCCGCC
CCGTGGTGAGCACCCAGCTGCTGCTGAACGGCAGCCTGGCCGAGGAGGGCGTGGTGATCCGC
AGCGAGAACTTCACCGACAACGCCAAGACCATCATCGTGCAGCTGAAGGAGAGCGTGGAGAT
CAACTGCACCCGCCCCAACAACAACACCCGCAAGAGCATCACCATCGGCCCCGGCCGCGCCT
TCTACGCCACCGGCGACATCATCGGCGACATCCGCCAGGCCCACTGCAACATCAGCGGCGAG
AAGTGGAACAACACCCTGAAGCAGATCGTGACCAAGCTGCAGGCCCAGTTCGGCAACAAGAC
CATCGTGTTCAAGCAGAGCAGCGGCGGCGACCCCGAGATCGTGATGCACAGCTTCAACTGCG
GCGGCGAGTTCTTCTACTGCAACAGCACCCAGCTGTTCAACAGCACCTGGAACAACACCATCG
GCCCCAACAACACCAACGGCACCATCACCCTGCCCTGCCGCATCAAGCAGATCATCAACCGC
GGCGGCGGCAAGGCCATGTACGCCCCCCCCATCCGCGGCCAGATCCGCTGCAGCAGCAACAT
CACCGGCCTGCTGCTGACCCGCGACGGCGGCAAGGAGATCAGCAACACCACCGAGATCTTCC
GCCCCGGCGGCGGCGACATGCGCGACAACTGGCGCAGCGAGCTGTACAAGTACAAGGTGGTG
AAGATCGAGCCCCTGGGCGTGGCCCCCACCAAGGCCAAGCGCCGCGTGGTGCAGCGCGAGAA
GCGCGCCGTGACCCTGGGCGCCATGTTCCTGGGCTTCCTGGGCGCCGCCGGCAGCACCATGGG
CGCCCGCAGCCTGACCCTGACCGTGCAGGCCCGCCAGCTGCTGAGCGGCATCGTGCAGCAGC
AGAACAACCTGCTGCGCGCCATCGAGGCCCAGCAGCACCTGCTGCAGCTGACCGTGTGGGGC
ATCAAGCAGCTGCAGGCCCGCGTGCTGGCCGTGGAGCGCTACCTGAAGGACCAGCAGCTGCT
GGGCATCTGGGGCTGCAGCGGCAAGCTGATCTGCACCACCGCCGTGCCCTGGAACGCCAGCT
GGAGCAACAAGAGCCTGGACCAGATCTGGAACAACATGACCTGGATGGAGTGGGAGCGCGA
GATCGACAACTACACCAACCTGATCTACACCCTGATCGAGGAGAGCCAGAACCAGCAGGAGA
AGAACGAGCAGGAGCTGCTGGAGCTGGACAAGTGGGCCAGCCTGTGGAACTGGTTCGACATC
AGCAAGTGGCTGTGGTACATCAAGATCTTCATCATGATCGTGGGCGGCCTGGTGGGCCTGCGC
ATCGTGTTCACCGTGCTGAGCATCGTGAACCGCGTGCGCCAGGGCTACAGCCCCCTGAGCTTC
CAGACCCGCTTCCCCGCCCCCGCGGCCCCGACCGCCCCGAGGGCATCGAGGAGGAGGGCGG
CGAGCGCGACCGCGACCGCAGCAGCCCCTGGTGCACGGCCTGCTGGCCCTGATCTGGGACG
ACCTGCGCAGCCTGTGCCTGTTCAGCTACCACCGCCTGCGCGACCTGATCCTGATCGCCGCCC
GCATCGTGGAGCTGCTGGGCCGCCGCGGCTGGGAGGCCCTGAAGTACTGGGGCAACCTGCTG
CAGTACTGGATCCAGGAGCTGAAGAACAGCGCCGTGAGCCTGTTCGACGCCATCGCCATCGC
CGTGGCCGAGGGCACCGACCGCATCATCGAGGTGGCCCAGCGCATCGGCCGCGCCTTCCTGC
ACATCCCCCGCCGCATCCGCCAGGGCTTCGAGCGCGCCCTGCTGTAACTCGAG

*FIG. 13*

SEQ ID NO:11 ARG426-GLY431B

```
GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGACCCCCCTGTGCGTG
ACCCTGCACTGCACCAACCTGAAGAACGCCACCAACACCAAGAGCAGCAACTGGAAGGAGAT
GGACCGCGGCGAGATCAAGAACTGCAGCTTCAAGGTGACCACCAGCATCCGCAACAAGATGC
AGAAGGAGTACGCCCTGTTCTACAAGCTGGACGTGGTGCCCATCGACAACGACAACACCAGC
TACAAGCTGATCAACTGCAACACCAGCGTGATCACCCAGGCCTGCCCCAAGGTGAGCTTCGA
GCCCATCCCCATCCACTACTGCGCCCCCGCCGGCTTCGCCATCCTGAAGTGCAACGACAAGAA
GTTCAACGGCAGCGGCCCCTGCACCAACGTGAGCACCGTGCAGTGCACCCACGGCATCCGCC
CCGTGGTGAGCACCCAGCTGCTGCTGAACGGCAGCCTGGCCGAGGAGGGCGTGGTGATCCGC
AGCGAGAACTTCACCGACAACGCCAAGACCATCATCGTGCAGCTGAAGGAGAGCGTGGAGAT
CAACTGCACCCGCCCCAACAACAACACCCGCAAGAGCATCACCATCGGCCCCGGCCGCGCCT
TCTACGCCACCGGCGACATCATCGGCGACATCCGCCAGGCCCACTGCAACATCAGCGGCGAG
AAGTGGAACAACACCCTGAAGCAGATCGTGACCAAGCTGCAGGCCCAGTTCGGCAACAAGAC
CATCGTGTTCAAGCAGAGCAGCGGCGGCGACCCCGAGATCGTGATGCACAGCTTCAACTGCG
GCGGCGAGTTCTTCTACTGCAACAGCACCCAGCTGTTCAACAGCACCTGGAACAACACCATCG
GCCCCAACAACACCAACGGCACCATCACCCTGCCCTGCCGCATCAAGCAGATCATCAACCGC
GGCAGCGGCAAGGCCATGTACGCCCCCCCCATCCGCGGCCAGATCCGCTGCAGCAGCAACAT
CACCGGCCTGCTGCTGACCCGCGACGGCGGCAAGGAGATCAGCAACACCACCGAGATCTTCC
GCCCCGGCGGCGGCGACATGCGCGACAACTGGCGCAGCGAGCTGTACAAGTACAAGGTGGTG
AAGATCGAGCCCCTGGGCGTGGCCCCCACCAAGGCCAAGCGCCGCGTGGTGCAGCGCGAGAA
GCGCGCCGTGACCCTGGGCGCCATGTTCCTGGGCTTCCTGGGCGCCGCCGGCAGCACCATGGG
CGCCCGCAGCCTGACCCTGACCGTGCAGGCCCGCCAGCTGCTGAGCGGCATCGTGCAGCAGC
AGAACAACCTGCTGCGCGCCATCGAGGCCCAGCAGCACCTGCTGCAGCTGACCGTGTGGGGC
ATCAAGCAGCTGCAGGCCCGCGTGCTGGCCGTGGAGCGCTACCTGAAGGACCAGCAGCTGCT
GGGCATCTGGGGCTGCAGCGGCAAGCTGATCTGCACCACCGCCGTGCCCTGGAACGCCAGCT
GGAGCAACAAGAGCCTGGACCAGATCTGGAACAACATGACCTGGATGGAGTGGGAGCGCGA
GATCGACAACTACACCAACCTGATCTACACCCTGATCGAGGAGAGCCAGAACCAGCAGGAGA
GAACGAGCAGGAGCTGCTGGAGCTGGACAAGTGGGCCAGCCTGTGGAACTGGTTCGACATC
AGCAAGTGGCTGTGGTACATCAAGATCTTCATCATGATCGTGGGCGGCCTGGTGGGCCTGCGC
ATCGTGTTCACCGTGCTGAGCATCGTGAACCGCGTGCGCCAGGGCTACAGCCCCCTGAGCTTC
CAGACCCGCTTCCCCGCCCCCGCGGCCCCGACCGCCCCGAGGGCATCGAGGAGGAGGGCGG
CGAGCGCGACCGCGACCGCAGCAGCCCCTGGTGCACGGCCTGCTGGCCCTGATCTGGGACG
ACCTGCGCAGCCTGTGCCTGTTCAGCTACCACCGCCTGCGCGACCTGATCCTGATCGCCGCCC
GCATCGTGGAGCTGCTGGGCCGCCGCGGCTGGGAGGCCCTGAAGTACTGGGGCAACCTGCTG
CAGTACTGGATCCAGGAGCTGAAGAACAGCGCCGTGAGCCTGTTCGACGCCATCGCCATCGC
CGTGGCCGAGGGCACCGACCGCATCATCGAGGTGGCCCAGCGCATCGGCCGCGCCTTCCTGC
ACATCCCCCGCCGCATCCGCCAGGGCTTCGAGCGCGCCCTGCTGTAACTCGAG
```

FIG. 14

SEQ ID NO:12 ARG426-LYS432

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGACCCCCCTGTGCGTG
ACCCTGCACTGCACCAACCTGAAGAACGCCACCAACACCAAGAGCAGCAACTGGAAGGAGAT
GGACCGCGGCGAGATCAAGAACTGCAGCTTCAAGGTGACCACCAGCATCCGCAACAAGATGC
AGAAGGAGTACGCCCTGTTCTACAAGCTGGACGTGGTGCCCATCGACAACGACAACACCAGC
TACAAGCTGATCAACTGCAACACCAGCGTGATCACCCAGGCCTGCCCCAAGGTGAGCTTCGA
GCCCATCCCCATCCACTACTGCGCCCCCGCCGGCTTCGCCATCCTGAAGTGCAACGACAAGAA
GTTCAACGGCAGCGGCCCCTGCACCAACGTGAGCACCGTGCAGTGCACCCACGGCATCCGCC
CCGTGGTGAGCACCCAGCTGCTGCTGAACGGCAGCCTGGCCGAGGAGGGCGTGGTGATCCGC
AGCGAGAACTTCACCGACAACGCCAAGACCATCATCGTGCAGCTGAAGGAGAGCGTGGAGAT
CAACTGCACCCGCCCCAACAACAACACCCGCAAGAGCATCACCATCGGCCCCGGCCGCGCCT
TCTACGCCACCGGCGACATCATCGGCGACATCCGCCAGGCCCACTGCAACATCAGCGGCGAG
AAGTGGAACAACACCCTGAAGCAGATCGTGACCAAGCTGCAGGCCCAGTTCGGCAACAAGAC
CATCGTGTTCAAGCAGAGCAGCGGCGGCGACCCCGAGATCGTGATGCACAGCTTCAACTGCG
GCGGCGAGTTCTTCTACTGCAACAGCACCCAGCTGTTCAACAGCACCTGGAACAACACCATCG
GCCCCAACAACACCAACGGCACCATCACCCTGCCCTGCCGCATCAAGCAGATCATCAACCGC
GGCGGCAACAAGGCCATGTACGCCCCCCCCATCCGCGGCCAGATCCGCTGCAGCAGCAACAT
CACCGGCCTGCTGCTGACCCGCGACGGCGGCAAGGAGATCAGCAACACCACCGAGATCTTCC
GCCCCGGCGGCGGCGACATGCGCGACAACTGGCGCAGCGAGCTGTACAAGTACAAGGTGGTG
AAGATCGAGCCCCTGGGCGTGGCCCCCACCAAGGCCAAGCGCCGCGTGGTGCAGCGCGAGAA
GCGCGCCGTGACCCTGGGCGCCATGTTCCTGGGCTTCCTGGGCGCCGCCGGCAGCACCATGGG
CGCCCGCAGCCTGACCCTGACCGTGCAGGCCCGCCAGCTGCTGAGCGGCATCGTGCAGCAGC
AGAACAACCTGCTGCGCGCCATCGAGGCCCAGCAGCACCTGCTGCAGCTGACCGTGTGGGGC
ATCAAGCAGCTGCAGGCCCGCGTGCTGGCCGTGGAGCGCTACCTGAAGGACCAGCAGCTGCT
GGGCATCTGGGGCTGCAGCGGCAAGCTGATCTGCACCACCGCCGTGCCCTGGAACGCCAGCT
GGAGCAACAAGAGCCTGGACCAGATCTGGAACAACATGACCTGGATGGAGTGGGAGCGCGA
GATCGACAACTACACCAACCTGATCTACACCCTGATCGAGGAGAGCCAGAACCAGCAGGAGA
AGAACGAGCAGGAGCTGCTGGAGCTGGACAAGTGGGCCAGCCTGTGGAACTGGTTCGACATC
AGCAAGTGGCTGTGGTACATCAAGATCTTCATCATGATCGTGGGCGGCCTGGTGGGCCTGCGC
ATCGTGTTCACCGTGCTGAGCATCGTGAACCGCGTGCGCCAGGGCTACAGCCCCCTGAGCTTC
CAGACCCGCTTCCCCGCCCCCGCGGCCCCGACCGCCCCGAGGGCATCGAGGAGGAGGGCGG
CGAGCGCGACCGCGACCGCAGCAGCCCCTGGTGCACGGCCTGCTGGCCCTGATCTGGGACG
ACCTGCGCAGCCTGTGCCTGTTCAGCTACCACCGCCTGCGCGACCTGATCCTGATCGCCGCCC
GCATCGTGGAGCTGCTGGGCCGCCGCGGCTGGAGGCCCTGAAGTACTGGGGCAACCTGCTG
CAGTACTGGATCCAGGAGCTGAAGAACAGCGCCGTGAGCCTGTTCGACGCCATCGCCATCGC
CGTGGCCGAGGGCACCGACCGCATCATCGAGGTGGCCCAGCGCATCGGCCGCGCCTTCCTGC
ACATCCCCCGCCGCATCCGCCAGGGCTTCGAGCGCGCCCTGCTGTAACTCGAG

*FIG. 15*

SEQ ID NO:13 ASN425-LYS432

```
GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGACCCCCCTGTGCGTG
ACCCTGCACTGCACCAACCTGAAGAACGCCACCAACACCAAGAGCAGCAACTGGAAGGAGAT
GGACCGCGGCGAGATCAAGAACTGCAGCTTCAAGGTGACCACCAGCATCCGCAACAAGATGC
AGAAGGAGTACGCCCTGTTCTACAAGCTGGACGTGGTGCCCATCGACAACGACAACACCAGC
TACAAGCTGATCAACTGCAACACCAGCGTGATCACCCAGGCCTGCCCCAAGGTGAGCTTCGA
GCCCATCCCCATCCACTACTGCGCCCCCGCCGGCTTCGCCATCCTGAAGTGCAACGACAAGAA
GTTCAACGGCAGCGGCCCCTGCACCAACGTGAGCACCGTGCAGTGCACCCACGGCATCCGCC
CCGTGGTGAGCACCCAGCTGCTGCTGAACGGCAGCCTGGCCGAGGAGGGCGTGGTGATCCGC
AGCGAGAACTTCACCGACAACGCCAAGACCATCATCGTGCAGCTGAAGGAGAGCGTGGAGAT
CAACTGCACCCGCCCCAACAACAACACCCGCAAGAGCATCACCATCGGCCCCGGCCGCGCCT
TCTACGCCACCGGCGACATCATCGGCGACATCCGCCAGGCCCACTGCAACATCAGCGGCGAG
AAGTGGAACAACACCCTGAAGCAGATCGTGACCAAGCTGCAGGCCCAGTTCGGCAACAAGAC
CATCGTGTTCAAGCAGAGCAGCGGCGGCGACCCCGAGATCGTGATGCACAGCTTCAACTGCG
GCGGCGAGTTCTTCTACTGCAACAGCACCCAGCTGTTCAACAGCACCTGGAACAACACCATCG
GCCCCAACAACACCAACGGCACCATCACCCTGCCCTGCCGCATCAAGCAGATCATCAACGCCC
CCAAGGCCATGTACGCCCCCCCCATCCGCGGCCAGATCCGCTGCAGCAGCAACATCACCGGCC
TGCTGCTGACCCGCGACGGCGGCAAGGAGATCAGCAACACCACCGAGATCTTCCGCCCCGGC
GGCGGCGACATGCGCGACAACTGGCGCAGCGAGCTGTACAAGTACAAGGTGGTGAAGATCGA
GCCCCTGGGCGTGGCCCCCACCAAGGCCAAGCGCCGCGTGGTGCAGCGCGAGAAGCGCGCCG
TGACCCTGGGCGCCATGTTCCTGGGCTTCCTGGGCGCCGCCGGCAGCACCATGGGCGCCCGCA
GCCTGACCCTGACCGTGCAGGCCCGCCAGCTGCTGAGCGGCATCGTGCAGCAGCAGAACAAC
CTGCTGCGCGCCATCGAGGCCCAGCAGCACCTGCTGCAGCTGACCGTGTGGGGCATCAAGCA
GCTGCAGGCCCGCGTGCTGGCCGTGGAGCGCTACCTGAAGGACCAGCAGCTGCTGGGCATCT
GGGGCTGCAGCGGCAAGCTGATCTGCACCACCGCCGTGCCCTGGAACGCCAGCTGGAGCAAC
AAGAGCCTGGACCAGATCTGGAACAACATGACCTGGATGGAGTGGGAGCGCGAGATCGACAA
CTACACCAACCTGATCTACACCCTGATCGAGGAGAGCCAGAACCAGCAGGAGAAGAACGAGC
AGGAGCTGCTGGAGCTGGACAAGTGGGCCAGCCTGTGGAACTGGTTCGACATCAGCAAGTGG
CTGTGGTACATCAAGATCTTCATCATGATCGTGGGCGGCCTGGTGGGCCTGCGCATCGTGTTC
ACCGTGCTGAGCATCGTGAACCGCGTGCGCCAGGGCTACAGCCCCCTGAGCTTCCAGACCCGC
TTCCCCGCCCCCGCGGCCCCGACCGCCCCGAGGGCATCGAGGAGGAGGGCGGCGAGCGCGA
CCGCGACCGCAGCAGCCCCCTGGTGCACGGCCTGCTGGCCCTGATCTGGGACGACCTGCGCAG
CCTGTGCCTGTTCAGCTACCACCGCCTGCGCGACCTGATCCTGATCGCCGCCCGCATCGTGGA
GCTGCTGGGCCGCCGCGGCTGGGAGGCCCTGAAGTACTGGGGCAACCTGCTGCAGTACTGGA
TCCAGGAGCTGAAGAACAGCGCCGTGAGCCTGTTCGACGCCATCGCCATCGCCGTGGCCGAG
GGCACCGACCGCATCATCGAGGTGGCCCAGCGCATCGGCCGCGCCTTCCTGCACATCCCCCGC
CGCATCCGCCAGGGCTTCGAGCGCGCCCTGCTGTAACTCGAG
```

FIG. 16

SEQ ID NO:14 ILE424-ALA433

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGACCCCCCTGTGCGTG
ACCCTGCACTGCACCAACCTGAAGAACGCCACCAACACCAAGAGCAGCAACTGGAAGGAGAT
GGACCGCGGCGAGATCAAGAACTGCAGCTTCAAGGTGACCACCAGCATCCGCAACAAGATGC
AGAAGGAGTACGCCCTGTTCTACAAGCTGGACGTGGTGCCCATCGACAACGACAACACCAGC
TACAAGCTGATCAACTGCAACACCAGCGTGATCACCCAGGCCTGCCCCAAGGTGAGCTTCGA
GCCCATCCCCATCCACTACTGCGCCCCCGCCGGCTTCGCCATCCTGAAGTGCAACGACAAGAA
GTTCAACGGCAGCGGCCCCTGCACCAACGTGAGCACCGTGCAGTGCACCCACGGCATCCGCC
CCGTGGTGAGCACCCAGCTGCTGCTGAACGGCAGCCTGGCCGAGGAGGGCGTGGTGATCCGC
AGCGAGAACTTCACCGACAACGCCAAGACCATCATCGTGCAGCTGAAGGAGAGCGTGGAGAT
CAACTGCACCCGCCCCAACAACAACACCCGCAAGAGCATCACCATCGGCCCCGGCCGCGCCT
TCTACGCCACCGGCGACATCATCGGCGACATCCGCCAGGCCCACTGCAACATCAGCGGCGAG
AAGTGGAACAACACCCTGAAGCAGATCGTGACCAAGCTGCAGGCCCAGTTCGGCAACAAGAC
CATCGTGTTCAAGCAGAGCAGCGGCGGCGACCCCGAGATCGTGATGCACAGCTTCAACTGCG
GCGGCGAGTTCTTCTACTGCAACAGCACCCAGCTGTTCAACAGCACCTGGAACAACACCATCG
GCCCCAACAACACCAACGGCACCATCACCCTGCCCTGCCGCATCAAGCAGATCATCGGCGGC
GCCATGTACGCCCCCCCCATCCGCGGCCAGATCCGCTGCAGCAGCAACATCACCGGCCTGCTG
CTGACCCGCGACGGCGGCAAGGAGATCAGCAACACCACCGAGATCTTCCGCCCCGGCGGCGG
CGACATGCGCGACAACTGGCGCAGCGAGCTGTACAAGTACAAGGTGGTGAAGATCGAGCCCC
TGGGCGTGGCCCCCACCAAGGCCAAGCGCCGCGTGGTGCAGCGCGAGAAGCGCGCCGTGACC
CTGGGCGCCATGTTCCTGGGCTTCCTGGGCGCCGCCGGCAGCACCATGGGCGCCCGCAGCCTG
ACCCTGACCGTGCAGGCCCGCCAGCTGCTGAGCGGCATCGTGCAGCAGCAGAACAACCTGCT
GCGCGCCATCGAGGCCCAGCAGCACCTGCTGCAGCTGACCGTGTGGGGCATCAAGCAGCTGC
AGGCCCGCGTGCTGGCCGTGGAGCGCTACCTGAAGGACCAGCAGCTGCTGGGCATCTGGGGC
TGCAGCGGCAAGCTGATCTGCACCACCGCCGTGCCCTGGAACGCCAGCTGGAGCAACAAGAG
CCTGGACCAGATCTGGAACAACATGACCTGGATGGAGTGGGAGCGCGAGATCGACAACTACA
CCAACCTGATCTACACCCTGATCGAGGAGAGCCAGAACCAGCAGGAGAAGAACGAGCAGGA
GCTGCTGGAGCTGGACAAGTGGGCCAGCCTGTGGAACTGGTTCGACATCAGCAAGTGGCTGT
GGTACATCAAGATCTTCATCATGATCGTGGGCGGCCTGGTGGGCCTGCGCATCGTGTTCACCG
TGCTGAGCATCGTGAACCGCGTGCGCCAGGGCTACAGCCCCCTGAGCTTCCAGACCCGCTTCC
CCGCCCCCGCGGCCCCGACCGCCCCGAGGGCATCGAGGAGGAGGGCGGCGAGCGCGACCGC
GACCGCAGCAGCCCCTGGTGCACGGCCTGCTGGCCCTGATCTGGGACGACCTGCGCAGCCTG
TGCCTGTTCAGCTACCACCGCCTGCGCGACCTGATCCTGATCGCCGCCCGCATCGTGGAGCTG
CTGGGCCGCCGCGGCTGGGAGGCCCTGAAGTACTGGGGCAACCTGCTGCAGTACTGGATCCA
GGAGCTGAAGAACAGCGCCGTGAGCCTGTTCGACGCCATCGCCATCGCCGTGGCCGAGGGCA
CCGACCGCATCATCGAGGTGGCCCAGCGCATCGGCCGCGCCTTCCTGCACATCCCCCGCCGCA
TCCGCCAGGGCTTCGAGCGCGCCCTGCTGTAACTCGAG

FIG. 17

SEQ ID NO:15 ILE423-MET434

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGACCCCCCTGTGCGTG
ACCCTGCACTGCACCAACCTGAAGAACGCCACCAACACCAAGAGCAGCAACTGGAAGGAGAT
GGACCGCGGCGAGATCAAGAACTGCAGCTTCAAGGTGACCACCAGCATCCGCAACAAGATGC
AGAAGGAGTACGCCCTGTTCTACAAGCTGGACGTGGTGCCCATCGACAACGACAACACCAGC
TACAAGCTGATCAACTGCAACACCAGCGTGATCACCCAGGCCTGCCCCAAGGTGAGCTTCGA
GCCCATCCCCATCCACTACTGCGCCCCCGCCGGCTTCGCCATCCTGAAGTGCAACGACAAGAA
GTTCAACGGCAGCGGCCCCTGCACCAACGTGAGCACCGTGCAGTGCACCCACGGCATCCGCC
CCGTGGTGAGCACCCAGCTGCTGCTGAACGGCAGCCTGGCCGAGGAGGGCGTGGTGATCCGC
AGCGAGAACTTCACCGACAACGCCAAGACCATCATCGTGCAGCTGAAGGAGAGCGTGGAGAT
CAACTGCACCCGCCCCAACAACAACACCCGCAAGAGCATCACCATCGGCCCCGGCCGCGCCT
TCTACGCCACCGGCGACATCATCGGCGACATCCGCCAGGCCCACTGCAACATCAGCGGCGAG
AAGTGGAACAACACCCTGAAGCAGATCGTGACCAAGCTGCAGGCCCAGTTCGGCAACAAGAC
CATCGTGTTCAAGCAGAGCAGCGGCGGCGACCCCGAGATCGTGATGCACAGCTTCAACTGCG
GCGGCGAGTTCTTCTACTGCAACAGCACCCAGCTGTTCAACAGCACCTGGAACAACACCATCG
GCCCCAACAACACCAACGGCACCATCACCCTGCCCTGCCGCATCAAGCAGATCGGCGGCATG
TACGCCCCCCCCATCCGCGGCCAGATCCGCTGCAGCAGCAACATCACCGGCCTGCTGCTGACC
CGCGACGGCGGCAAGGAGATCAGCAACACCACCGAGATCTTCCGCCCCGGCGGCGGCGACAT
GCGCGACAACTGGCGCAGCGAGCTGTACAAGTACAAGGTGGTGAAGATCGAGCCCCTGGGCG
TGGCCCCCACCAAGGCCAAGCGCCGCGTGGTGCAGCGCGAGAAGCGCGCCGTGACCCTGGGC
GCCATGTTCCTGGGCTTCCTGGGCGCCGCCGGCAGCACCATGGGCGCCCGCAGCCTGACCCTG
ACCGTGCAGGCCCGCCAGCTGCTGAGCGGCATCGTGCAGCAGCAGAACAACCTGCTGCGCGC
CATCGAGGCCCAGCAGCACCTGCTGCAGCTGACCGTGTGGGGCATCAAGCAGCTGCAGGCCC
GCGTGCTGGCCGTGGAGCGCTACCTGAAGGACCAGCAGCTGCTGGGCATCTGGGGCTGCAGC
GGCAAGCTGATCTGCACCACCGCCGTGCCCTGGAACGCCAGCTGGAGCAACAAGAGCCTGGA
CCAGATCTGGAACAACATGACCTGGATGGAGTGGGAGCGCGAGATCGACAACTACACCAACC
TGATCTACACCCTGATCGAGGAGAGCCAGAACCAGCAGGAGAAGAACGAGCAGGAGCTGCTG
GAGCTGGACAAGTGGGCCAGCCTGTGGAACTGGTTCGACATCAGCAAGTGGCTGTGGTACAT
CAAGATCTTCATCATGATCGTGGGCGGCCTGGTGGGCCTGCGCATCGTGTTCACCGTGCTGAG
CATCGTGAACCGCGTGCGCCAGGGCTACAGCCCCCTGAGCTTCCAGACCCGCTTCCCCGCCCC
CCGCGGCCCCGACCGCCCCGAGGGCATCGAGGAGGAGGGCGGCGAGCGCGACCGCGACCGC
AGCAGCCCCCTGGTGCACGGCCTGCTGGCCCTGATCTGGGACGACCTGCGCAGCCTGTGCCTG
TTCAGCTACCACCGCCTGCGCGACCTGATCCTGATCGCCGCCCGCATCGTGGAGCTGCTGGGC
CGCCGCGGCTGGGAGGCCCTGAAGTACTGGGGCAACCTGCTGCAGTACTGGATCCAGGAGCT
GAAGAACAGCGCCGTGAGCCTGTTCGACGCCATCGCCATCGCCGTGGCCGAGGGCACCGACC
GCATCATCGAGGTGGCCCAGCGCATCGGCCGCGCCTTCCTGCACATCCCCCGCCGCATCCGCC
AGGGCTTCGAGCGCGCCCTGCTGTAACTCGAG

FIG. 18

SEQ ID NO:16 GLN422-TYR435

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGACCCCCCTGTGCGTG
ACCCTGCACTGCACCAACCTGAAGAACGCCACCAACACCAAGAGCAGCAACTGGAAGGAGAT
GGACCGCGGCGAGATCAAGAACTGCAGCTTCAAGGTGACCACCAGCATCCGCAACAAGATGC
AGAAGGAGTACGCCCTGTTCTACAAGCTGGACGTGGTGCCCATCGACAACGACAACACCAGC
TACAAGCTGATCAACTGCAACACCAGCGTGATCACCCAGGCCTGCCCCAAGGTGAGCTTCGA
GCCCATCCCCATCCACTACTGCGCCCCCGCCGGCTTCGCCATCCTGAAGTGCAACGACAAGAA
GTTCAACGGCAGCGGCCCCTGCACCAACGTGAGCACCGTGCAGTGCACCCACGGCATCCGCC
CCGTGGTGAGCACCCAGCTGCTGCTGAACGGCAGCCTGGCCGAGGAGGGCGTGGTGATCCGC
AGCGAGAACTTCACCGACAACGCCAAGACCATCATCGTGCAGCTGAAGGAGAGCGTGGAGAT
CAACTGCACCCGCCCCAACAACAACACCCGCAAGAGCATCACCATCGGCCCCGGCCGCGCCT
TCTACGCCACCGGCGACATCATCGGCGACATCCGCCAGGCCCACTGCAACATCAGCGGCGAG
AAGTGGAACAACACCCTGAAGCAGATCGTGACCAAGCTGCAGGCCCAGTTCGGCAACAAGAC
CATCGTGTTCAAGCAGAGCAGCGGCGGCGACCCCGAGATCGTGATGCACAGCTTCAACTGCG
GCGGCGAGTTCTTCTACTGCAACAGCACCCAGCTGTTCAACAGCACCTGGAACAACACCATCG
GCCCCAACAACACCAACGGCACCATCACCCTGCCCTGCCGCATCAAGCAGGGCGGCTACGCC
CCCCCCATCCGCGGCCAGATCCGCTGCAGCAGCAACATCACCGGCCTGCTGCTGACCCGCGAC
GGCGGCAAGGAGATCAGCAACACCACCGAGATCTTCCGCCCCGGCGGCGGCGACATGCGCGA
CAACTGGCGCAGCGAGCTGTACAAGTACAAGGTGGTGAAGATCGAGCCCCTGGGCGTGGCCC
CCACCAAGGCCAAGCGCCGCGTGGTGCAGCGCGAGAAGCGCGCCGTGACCCTGGGCGCCATG
TTCCTGGGCTTCCTGGGCGCCGCCGGCAGCACCATGGGCGCCCGCAGCCTGACCCTGACCGTG
CAGGCCCGCCAGCTGCTGAGCGGCATCGTGCAGCAGCAGAACAACCTGCTGCGCGCCATCGA
GGCCCAGCAGCACCTGCTGCAGCTGACCGTGTGGGGCATCAAGCAGCTGCAGGCCCGCGTGC
TGGCCGTGGAGCGCTACCTGAAGGACCAGCAGCTGCTGGGCATCTGGGGCTGCAGCGGCAAG
CTGATCTGCACCACCGCCGTGCCCTGGAACGCCAGCTGGAGCAACAAGAGCCTGGACCAGAT
CTGGAACAACATGACCTGGATGGAGTGGGAGCGCGAGATCGACAACTACACCAACCTGATCT
ACACCCTGATCGAGGAGAGCCAGAACCAGCAGGAGAAGAACGAGCAGGAGCTGCTGGAGCT
GGACAAGTGGGCCAGCCTGTGGAACTGGTTCGACATCAGCAAGTGGCTGTGGTACATCAAGA
TCTTCATCATGATCGTGGGCGGCCTGGTGGGCCTGCGCATCGTGTTCACCGTGCTGAGCATCG
TGAACCGCGTGCGCCAGGGCTACAGCCCCCTGAGCTTCCAGACCCGCTTCCCCGCCCCCCGCG
GCCCCGACCGCCCCGAGGGCATCGAGGAGGAGGGCGGCGAGCGCGACCGCGACCGCAGCAG
CCCCCTGGTGCACGGCCTGCTGGCCCTGATCTGGGACGACCTGCGCAGCCTGTGCCTGTTCAG
CTACCACCGCCTGCGCGACCTGATCCTGATCGCCGCCCGCATCGTGGAGCTGCTGGGCCGCCG
CGGCTGGGAGGCCCTGAAGTACTGGGGCAACCTGCTGCAGTACTGGATCCAGGAGCTGAAGA
ACAGCGCCGTGAGCCTGTTCGACGCCATCGCCATCGCCGTGGCCGAGGGCACCGACCGCATC
ATCGAGGTGGCCCAGGCGCATCGGCCGCGCCTTCCTGCACATCCCCCGCCGCATCCGCCAGGGC
TTCGAGCGCGCCCTGCTGTAACTCGAG

FIG. 19

SEQ ID NO:17 GLN422-TYR435B

```
GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGACCCCCCTGTGCGTG
ACCCTGCACTGCACCAACCTGAAGAACGCCACCAACACCAAGAGCAGCAACTGGAAGGAGAT
GGACCGCGGCGAGATCAAGAACTGCAGCTTCAAGGTGACCACCAGCATCCGCAACAAGATGC
AGAAGGAGTACGCCCTGTTCTACAAGCTGGACGTGGTGCCCATCGACAACGACAACACCAGC
TACAAGCTGATCAACTGCAACACCAGCGTGATCACCCAGGCCTGCCCCAAGGTGAGCTTCGA
GCCCATCCCCATCCACTACTGCGCCCCCGCCGGCTTCGCCATCCTGAAGTGCAACGACAAGAA
GTTCAACGGCAGCGGCCCCTGCACCAACGTGAGCACCGTGCAGTGCACCCACGGCATCCGCC
CCGTGGTGAGCACCCAGCTGCTGCTGAACGGCAGCCTGGCCGAGGAGGGCGTGGTGATCCGC
AGCGAGAACTTCACCGACAACGCCAAGACCATCATCGTGCAGCTGAAGGAGAGCGTGGAGAT
CAACTGCACCCGCCCCAACAACAACACCCGCAAGAGCATCACCATCGGCCCCGGCCGCGCCT
TCTACGCCACCGGCGACATCATCGGCGACATCCGCCAGGCCCACTGCAACATCAGCGGCGAG
AAGTGGAACAACACCCTGAAGCAGATCGTGACCAAGCTGCAGGCCCAGTTCGGCAACAAGAC
CATCGTGTTCAAGCAGAGCAGCGGCGGCGACCCCGAGATCGTGATGCACAGCTTCAACTGCG
GCGGCGAGTTCTTCTACTGCAACAGCACCCAGCTGTTCAACAGCACCTGGAACAACACCATCG
GCCCCAACAACACCAACGGCACCATCACCCTGCCCTGCCGCATCAAGCAGGCCCCCTACGCCC
CCCCCATCCGCGGCCAGATCCGCTGCAGCAGCAACATCACCGGCCTGCTGCTGACCCGCGACG
GCGGCAAGGAGATCAGCAACACCACCGAGATCTTCCGCCCCGGCGGCGGCGACATGCGCGAC
AACTGGCGCAGCGAGCTGTACAAGTACAAGGTGGTGAAGATCGAGCCCCTGGGCGTGGCCCC
CACCAAGGCCAAGCGCCGCGTGGTGCAGCGCGAGAAGCGCGCCGTGACCCTGGGCGCCATGT
TCCTGGGCTTCCTGGGCGCCGCCGGCAGCACCATGGGCGCCCGCAGCCTGACCCTGACCGTGC
AGGCCCGCCAGCTGCTGAGCGGCATCGTGCAGCAGCAGAACAACCTGCTGCGCGCCATCGAG
GCCCAGCAGCACCTGCTGCAGCTGACCGTGTGGGGCATCAAGCAGCTGCAGGCCCGCGTGCT
GGCCGTGGAGCGCTACCTGAAGGACCAGCAGCTGCTGGGCATCTGGGGCTGCAGCGGCAAGC
TGATCTGCACCACCGCCGTGCCCTGGAACGCCAGCTGGAGCAACAAGAGCCTGGACCAGATC
TGGAACAACATGACCTGGATGGAGTGGGAGCGCGAGATCGACAACTACACCAACCTGATCTA
CACCCTGATCGAGGAGAGCCAGAACCAGCAGGAGAAGAACGAGCAGGAGCTGCTGGAGCTG
GACAAGTGGGCCAGCCTGTGGAACTGGTTCGACATCAGCAAGTGGCTGTGGTACATCAAGAT
CTTCATCATGATCGTGGGCGGCCTGGTGGGCCTGCGCATCGTGTTCACCGTGCTGAGCATCGT
GAACCGCGTGCGCCAGGGCTACAGCCCCCTGAGCTTCCAGACCCGCTTCCCCGCCCCCCGCGG
CCCCGACCGCCCCGAGGGCATCGAGGAGGAGGGCGGCGAGCGCGACCGCGACCGCAGCAGC
CCCCTGGTGCACGGCCTGCTGGCCCTGATCTGGGACGACCTGCGCAGCCTGTGCCTGTTCAGC
TACCACCGCCTGCGCGACCTGATCCTGATCGCCGCCCGCATCGTGGAGCTGCTGGGCCGCCGC
GGCTGGGAGGCCCTGAAGTACTGGGGCAACCTGCTGCAGTACTGGATCCAGGAGCTGAAGAA
CAGCGCCGTGAGCCTGTTCGACGCCATCGCCATCGCCGTGGCCGAGGGCACCGACCGCATCAT
CGAGGTGGCCCAGCGCATCGGCCGCGCCTTCCTGCACATCCCCCGCCGCATCCGCCAGGGCTT
CGAGCGCGCCCTGCTGTAACTCGAG
```

FIG. 20

SEQ ID NO:18: LEU122-SER199; ARG426-GLY431

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGGGCAACAGCGTGAT
CACCCAGGCCTGCCCCAAGGTGAGCTTCGAGCCCATCCCCATCCACTACTGCGCCCCCGCCGG
CTTCGCCATCCTGAAGTGCAACGACAAGAAGTTCAACGGCAGCGGCCCCTGCACCAACGTGA
GCACCGTGCAGTGCACCCACGGCATCCGCCCCGTGGTGAGCACCCAGCTGCTGCTGAACGGC
AGCCTGGCCGAGGAGGGCGTGGTGATCCGCAGCGAGAACTTCACCGACAACGCCAAGACCAT
CATCGTGCAGCTGAAGGAGAGCGTGGAGATCAACTGCACCCGCCCCAACAACAACACCCGCA
AGAGCATCACCATCGGCCCCGGCCGCGCCTTCTACGCCACCGGCGACATCATCGGCGACATCC
GCCAGGCCCACTGCAACATCAGCGGCGAGAAGTGGAACAACACCCTGAAGCAGATCGTGACC
AAGCTGCAGGCCCAGTTCGGCAACAAGACCATCGTGTTCAAGCAGAGCAGCGGCGGCGACCC
CGAGATCGTGATGCACAGCTTCAACTGCGGCGGCGAGTTCTTCTACTGCAACAGCACCCAGCT
GTTCAACAGCACCTGGAACAACACCATCGGCCCCAACAACACCAACGGCACCATCACCCTGC
CCTGCCGCATCAAGCAGATCATCAACCGCGGCGGCGGCAAGGCCATGTACGCCCCCCCCATCC
GCGGCCAGATCCGCTGCAGCAGCAACATCACCGGCCTGCTGCTGACCCGCGACGGCGGCAAG
GAGATCAGCAACACCACCGAGATCTTCCGCCCCGGCGGCGGCGACATGCGCGACAACTGGCG
CAGCGAGCTGTACAAGTACAAGGTGGTGAAGATCGAGCCCCTGGGCGTGGCCCCCACCAAGG
CCAAGCGCCGCGTGGTGCAGCGCGAGAAGCGCGCCGTGACCCTGGGCGCCATGTTCCTGGGC
TTCCTGGGCGCCGCCGGCAGCACCATGGGCGCCCGCAGCCTGACCCTGACCGTGCAGGCCCGC
CAGCTGCTGAGCGGCATCGTGCAGCAGCAGAACAACCTGCTGCGCGCCATCGAGGCCCAGCA
GCACCTGCTGCAGCTGACCGTGTGGGGCATCAAGCAGCTGCAGGCCCGCGTGCTGGCCGTGG
AGCGCTACCTGAAGGACCAGCAGCTGCTGGGCATCTGGGGCTGCAGCGGCAAGCTGATCTGC
ACCACCGCCGTGCCCTGGAACGCCAGCTGGAGCAACAAGAGCCTGGACCAGATCTGGAACAA
CATGACCTGGATGGAGTGGGAGCGCGAGATCGACAACTACACCAACCTGATCTACACCCTGA
TCGAGGAGAGCCAGAACCAGCAGGAGAAGAACGAGCAGGAGCTGCTGGAGCTGGACAAGTG
GGCCAGCCTGTGGAACTGGTTCGACATCAGCAAGTGGCTGTGGTACATCAAGATCTTCATCAT
GATCGTGGGCGGCCTGGTGGGCCTGCGCATCGTGTTCACCGTGCTGAGCATCGTGAACCGCGT
GCGCCAGGGCTACAGCCCCCTGAGCTTCCAGACCCGCTTCCCCGCCCCCCGCGGCCCCGACCG
CCCCGAGGGCATCGAGGAGGAGGGCGGCGAGCGCGACCGCGACCGCAGCAGCCCCTGGTGC
ACGGCCTGCTGGCCCTGATCTGGGACGACCTGCGCAGCCTGTGCCTGTTCAGCTACCACCGCC
TGCGCGACCTGATCCTGATCGCCGCCCGCATCGTGGAGCTGCTGGGCCGCCGCGGCTGGGAGG
CCCTGAAGTACTGGGGCAACCTGCTGCAGTACTGGATCCAGGAGCTGAAGAACAGCGCCGTG
AGCCTGTTCGACGCCATCGCCATCGCCGTGGCCGAGGGCACCGACCGCATCATCGAGGTGGCC
CAGCGCATCGGCCGCGCCTTCCTGCACATCCCCCGCCGCATCCGCCAGGGCTTCGAGCGCGCC
CTGCTGTAACTCGAG

FIG. 21

SEQ ID NO:19 LEU122-SER199; ARG426-LYS432

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGGGCAACAGCGTGAT
CACCCAGGCCTGCCCCAAGGTGAGCTTCGAGCCCATCCCCATCCACTACTGCGCCCCCGCCGG
CTTCGCCATCCTGAAGTGCAACGACAAGAAGTTCAACGGCAGCGGCCCCTGCACCAACGTGA
GCACCGTGCAGTGCACCCACGGCATCCGCCCCGTGGTGAGCACCCAGCTGCTGCTGAACGGC
AGCCTGGCCGAGGAGGGCGTGGTGATCCGCAGCGAGAACTTCACCGACAACGCCAAGACCAT
CATCGTGCAGCTGAAGGAGAGCGTGGAGATCAACTGCACCCGCCCCAACAACAACACCCGCA
AGAGCATCACCATCGGCCCCGGCCGCGCCTTCTACGCCACCGGCGACATCATCGGCGACATCC
GCCAGGCCCACTGCAACATCAGCGGCGAGAAGTGGAACAACACCCTGAAGCAGATCGTGACC
AAGCTGCAGGCCCAGTTCGGCAACAAGACCATCGTGTTCAAGCAGAGCAGCGGCGGCGACCC
CGAGATCGTGATGCACAGCTTCAACTGCGGCGGCGAGTTCTTCTACTGCAACAGCACCCAGCT
GTTCAACAGCACCTGGAACAACACCATCGGCCCCAACAACACCAACGGCACCATCACCCTGC
CCTGCCGCATCAAGCAGATCATCAACCGCGGCGGCAACAAGGCCATGTACGCCCCCCCCATCC
GCGGCCAGATCCGCTGCAGCAGCAACATCACCGGCCTGCTGCTGACCCGCGACGGCGGCAAG
GAGATCAGCAACACCACCGAGATCTTCCGCCCCGGCGGCGGCGACATGCGCGACAACTGGCG
CAGCGAGCTGTACAAGTACAAGGTGGTGAAGATCGAGCCCCTGGGCGTGGCCCCCACCAAGG
CCAAGCGCCGCGTGGTGCAGCGCGAGAAGCGCGCCGTGACCCTGGGCGCCATGTTCCTGGGC
TTCCTGGGCGCCGCCGGCAGCACCATGGGCGCCCGCAGCCTGACCCTGACCGTGCAGGCCCGC
CAGCTGCTGAGCGGCATCGTGCAGCAGCAGAACAACCTGCTGCGCGCCATCGAGGCCCAGCA
GCACCTGCTGCAGCTGACCGTGTGGGGCATCAAGCAGCTGCAGGCCCGCGTGCTGGCCGTGG
AGCGCTACCTGAAGGACCAGCAGCTGCTGGGCATCTGGGGCTGCAGCGGCAAGCTGATCTGC
ACCACCGCCGTGCCCTGGAACGCCAGCTGGAGCAACAAGAGCCTGGACCAGATCTGGAACAA
CATGACCTGGATGGAGTGGGAGCGCGAGATCGACAACTACACCAACCTGATCTACACCCTGA
TCGAGGAGAGCCAGAACCAGCAGGAGAAGAACGAGCAGGAGCTGCTGGAGCTGGACAAGTG
GGCCAGCCTGTGGAACTGGTTCGACATCAGCAAGTGGCTGTGGTACATCAAGATCTTCATCAT
GATCGTGGGCGGCCTGGTGGGCCTGCGCATCGTGTTCACCGTGCTGAGCATCGTGAACCGCGT
GCGCCAGGGCTACAGCCCCCTGAGCTTCCAGACCCGCTTCCCCGCCCCCCGCGGCCCCGACCG
CCCCGAGGGCATCGAGGAGGAGGGCGGCGAGCGCGACCGCGACCGCAGCAGCCCCCTGGTGC
ACGGCCTGCTGGCCCTGATCTGGGACGACCTGCGCAGCCTGTGCCTGTTCAGCTACCACCGCC
TGCGCGACCTGATCCTGATCGCCGCCCGCATCGTGGAGCTGCTGGGCCGCCGCGGCTGGGAGG
CCCTGAAGTACTGGGGCAACCTGCTGCAGTACTGGATCCAGGAGCTGAAGAACAGCGCCGTG
AGCCTGTTCGACGCCATCGCCATCGCCGTGGCCGAGGGCACCGACCGCATCATCGAGGTGGCC
CAGCGCATCGGCCGCGCCTTCCTGCACATCCCCCGCCGCATCCGCCAGGGCTTCGAGCGCGCC
CTGCTGTAACTCGAG

FIG. 22

SEQ ID NO: 20: LEU122-SER199; TRP427-GLY431

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGGGCAACAGCGTGAT
CACCCAGGCCTGCCCCAAGGTGAGCTTCGAGCCCATCCCCATCCACTACTGCGCCCCCGCCGG
CTTCGCCATCCTGAAGTGCAACGACAAGAAGTTCAACGGCAGCGGCCCCTGCACCAACGTGA
GCACCGTGCAGTGCACCCACGGCATCCGCCCCGTGGTGAGCACCCAGCTGCTGCTGAACGGC
AGCCTGGCCGAGGAGGGCGTGGTGATCCGCAGCGAGAACTTCACCGACAACGCCAAGACCAT
CATCGTGCAGCTGAAGGAGAGCGTGGAGATCAACTGCACCCGCCCCAACAACAACACCCGCA
AGAGCATCACCATCGGCCCCGGCCGCGCCTTCTACGCCACCGGCGACATCATCGGCGACATCC
GCCAGGCCCACTGCAACATCAGCGGCGAGAAGTGGAACAACACCCTGAAGCAGATCGTGACC
AAGCTGCAGGCCCAGTTCGGCAACAAGACCATCGTGTTCAAGCAGAGCAGCGGCGGCGACCC
CGAGATCGTGATGCACAGCTTCAACTGCGGCGGCGAGTTCTTCTACTGCAACAGCACCCAGCT
GTTCAACAGCACCTGGAACAACACCATCGGCCCCAACAACACCAACGGCACCATCACCCTGC
CCTGCCGCATCAAGCAGATCATCAACCGCTGGGGCGGCAAGGCCATGTACGCCCCCCCCATCC
GCGGCCAGATCCGCTGCAGCAGCAACATCACCGGCCTGCTGCTGACCCGCGACGGCGGCAAG
GAGATCAGCAACACCACCGAGATCTTCCGCCCCGGCGGCGGCGACATGCGCGACAACTGGCG
CAGCGAGCTGTACAAGTACAAGGTGGTGAAGATCGAGCCCCTGGGCGTGGCCCCCACCAAGG
CCAAGCGCCGCGTGGTGCAGCGCGAGAAGCGCGCCGTGACCCTGGGCGCCATGTTCCTGGGC
TTCCTGGGCGCCGCCGGCAGCACCATGGGCGCCCGCAGCCTGACCCTGACCGTGCAGGCCCGC
CAGCTGCTGAGCGGCATCGTGCAGCAGCAGAACAACCTGCTGCGCGCCATCGAGGCCCAGCA
GCACCTGCTGCAGCTGACCGTGTGGGGCATCAAGCAGCTGCAGGCCCGCGTGCTGGCCGTGG
AGCGCTACCTGAAGGACCAGCAGCTGCTGGGCATCTGGGGCTGCAGCGGCAAGCTGATCTGC
ACCACCGCCGTGCCCTGGAACGCCAGCTGGAGCAACAAGAGCCTGGACCAGATCTGGAACAA
CATGACCTGGATGGAGTGGGAGCGCGAGATCGACAACTACACCAACCTGATCTACACCCTGA
TCGAGGAGAGCCAGAACCAGCAGGAGAAGAACGAGCAGGAGCTGCTGGAGCTGGACAAGTG
GGCCAGCCTGTGGAACTGGTTCGACATCAGCAAGTGGCTGTGGTACATCAAGATCTTCATCAT
GATCGTGGGCGGCCTGGTGGGCCTGCGCATCGTGTTCACCGTGCTGAGCATCGTGAACCGCGT
GCGCCAGGGCTACAGCCCCCTGAGCTTCCAGACCCGCTTCCCCGCCCCCCGCGGCCCCGACCG
CCCCGAGGGCATCGAGGAGGAGGGCGGCGAGCGCGACCGCGACCGCAGCAGCCCCCTGGTGC
ACGGCCTGCTGGCCCTGATCTGGGACGACCTGCGCAGCCTGTGCCTGTTCAGCTACCACCGCC
TGCGCGACCTGATCCTGATCGCCGCCCGCATCGTGGAGCTGCTGGGCCGCCGCGGCTGGAGG
CCCTGAAGTACTGGGGCAACCTGCTGCAGTACTGGATCCAGGAGCTGAAGAACAGCGCCGTG
AGCCTGTTCGACGCCATCGCCATCGCCGTGGCCGAGGGCACCGACCGCATCATCGAGGTGGCC
CAGCGCATCGGCCGCGCCTTCCTGCACATCCCCCGCCGCATCCGCCAGGGCTTCGAGCGCGCC
CTGCTGTAACTCGAG

SEQ ID NO:21 LYS121-VAL200; ASN425-LYS432

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGGCCCCCGTGATCACCCA
GGCCTGCCCCAAGGTGAGCTTCGAGCCCATCCCCATCCACTACTGCGCCCCCGCCGGCTTCGC
CATCCTGAAGTGCAACGACAAGAAGTTCAACGGCAGCGGCCCTGCACCAACGTGAGCACCG
TGCAGTGCACCCACGGCATCCGCCCCGTGGTGAGCACCCAGCTGCTGCTGAACGGCAGCCTGG
CCGAGGAGGGCGTGGTGATCCGCAGCGAGAACTTCACCGACAACGCCAAGACCATCATCGTG
CAGCTGAAGGAGAGCGTGGAGATCAACTGCACCCGCCCCAACAACAACACCCGCAAGAGCAT
CACCATCGGCCCCGGCCGCGCCTTCTACGCCACCGGCGACATCATCGGCGACATCCGCCAGGC
CCACTGCAACATCAGCGGCGAGAAGTGGAACAACACCCTGAAGCAGATCGTGACCAAGCTGC
AGGCCCAGTTCGGCAACAAGACCATCGTGTTCAAGCAGAGCAGCGGCGGCGACCCCGAGATC
GTGATGCACAGCTTCAACTGCGGCGGCGAGTTCTTCTACTGCAACAGCACCCAGCTGTTCAAC
AGCACCTGGAACAACACCATCGGCCCCAACAACACCAACGGCACCATCACCCTGCCCTGCCG
CATCAAGCAGATCATCAACGCCCCCAAGGCCATGTACGCCCCCCCCATCCGCGGCCAGATCCG
CTGCAGCAGCAACATCACCGGCCTGCTGCTGACCCGCGACGGCGGCAAGGAGATCAGCAACA
CCACCGAGATCTTCCGCCCCGGCGGCGGCGACATGCGCGACAACTGGCGCAGCGAGCTGTAC
AAGTACAAGGTGGTGAAGATCGAGCCCCTGGGCGTGGCCCCCACCAAGGCCAAGCGCCGCGT
GGTGCAGCGCGAGAAGCGCGCCGTGACCCTGGGCGCCATGTTCCTGGGCTTCCTGGGCGCCG
CCGGCAGCACCATGGGCGCCCGCAGCCTGACCCTGACCGTGCAGGCCCGCCAGCTGCTGAGCG
GCATCGTGCAGCAGCAGAACAACCTGCTGCGCGCCATCGAGGCCCAGCAGCACCTGCTGCAG
CTGACCGTGTGGGGCATCAAGCAGCTGCAGGCCCGCGTGCTGGCCGTGGAGCGCTACCTGAA
GGACCAGCAGCTGCTGGGCATCTGGGGCTGCAGCGGCAAGCTGATCTGCACCACCGCCGTGC
CCTGGAACGCCAGCTGGAGCAACAAGAGCCTGGACCAGATCTGGAACAACATGACCTGGATG
GAGTGGGAGCGCGAGATCGACAACTACACCAACCTGATCTACACCCTGATCGAGGAGAGCCA
GAACCAGCAGGAGAAGAACGAGCAGGAGCTGCTGGAGCTGGACAAGTGGGCCAGCCTGTGG
AACTGGTTCGACATCAGCAAGTGGCTGTGGTACATCAAGATCTTCATCATGATCGTGGGCGGC
CTGGTGGGCCTGCGCATCGTGTTCACCGTGCTGAGCATCGTGAACCGCGTGCGCCAGGGCTAC
AGCCCCCTGAGCTTCCAGACCCGCTTCCCCGCCCCCGCGGCCCCGACCGCCCCGAGGGCATC
GAGGAGGAGGGCGGCGAGCGCGACCGCGACCGCAGCAGCCCCCTGGTGCACGGCCTGCTGGC
CCTGATCTGGGACGACCTGCGCAGCCTGTGCCTGTTCAGCTACCACCGCCTGCGCGACCTGAT
CCTGATCGCCGCCCGCATCGTGGAGCTGCTGGGCCGCCGCGGCTGGGAGGCCCTGAAGTACTG
GGGCAACCTGCTGCAGTACTGGATCCAGGAGCTGAAGAACAGCGCCGTGAGCCTGTTCGACG
CCATCGCCATCGCCGTGGCCGAGGGCACCGACCGCATCATCGAGGTGGCCCAGCGCATCGGC
CGCGCCTTCCTGCACATCCCCCGCCGCATCCGCCAGGGCTTCGAGCGCGCCCTGCTGTAACTC
GAG

SEQ ID NO:22 VAL120-ILE201; ILE 424-ALA433

```
GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGGGCGGCATCACCCAGGCCTG
CCCCAAGGTGAGCTTCGAGCCCATCCCCATCCACTACTGCGCCCCCGCCGGCTTCGCCATCCT
GAAGTGCAACGACAAGAAGTTCAACGGCAGCGGCCCCTGCACCAACGTGAGCACCGTGCAGT
GCACCCACGGCATCCGCCCCGTGGTGAGCACCCAGCTGCTGCTGAACGGCAGCCTGGCCGAG
GAGGGCGTGGTGATCCGCAGCGAGAACTTCACCGACAACGCCAAGACCATCATCGTGCAGCT
GAAGGAGAGCGTGGAGATCAACTGCACCCGCCCCAACAACAACACCCGCAAGAGCATCACCA
TCGGCCCCGGCCGCGCCTTCTACGCCACCGGCGACATCATCGGCGACATCCGCCAGGCCCACT
GCAACATCAGCGGCGAGAAGTGGAACAACACCCTGAAGCAGATCGTGACCAAGCTGCAGGCC
CAGTTCGGCAACAAGACCATCGTGTTCAAGCAGAGCAGCGGCGGCGACCCCGAGATCGTGAT
GCACAGCTTCAACTGCGGCGGCGAGTTCTTCTACTGCAACAGCACCCAGCTGTTCAACAGCAC
CTGGAACAACACCATCGGCCCCAACAACACCAACGGCACCATCACCCTGCCCTGCCGCATCA
AGCAGATCATCGGCGGCGCCATGTACGCCCCCCCCATCCGCGGCCAGATCCGCTGCAGCAGC
AACATCACCGGCCTGCTGCTGACCCGCGACGGCGGCAAGGAGATCAGCAACACCACCGAGAT
CTTCCGCCCCGGCGGCGGCGACATGCGCGACAACTGGCGCAGCGAGCTGTACAAGTACAAGG
TGGTGAAGATCGAGCCCCTGGGCGTGGCCCCCACCAAGGCCAAGCGCCGCGTGGTGCAGCGC
GAGAAGCGCGCCGTGACCCTGGGCGCCATGTTCCTGGGCTTCCTGGGCGCCGCCGGCAGCACC
ATGGGCGCCCGCAGCCTGACCCTGACCGTGCAGGCCCGCCAGCTGCTGAGCGGCATCGTGCA
GCAGCAGAACAACCTGCTGCGCGCCATCGAGGCCCAGCAGCACCTGCTGCAGCTGACCGTGT
GGGGCATCAAGCAGCTGCAGGCCCGCGTGCTGGCCGTGGAGCGCTACCTGAAGGACCAGCAG
CTGCTGGGCATCTGGGGCTGCAGCGGCAAGCTGATCTGCACCACCGCCGTGCCCTGGAACGCC
AGCTGGAGCAACAAGAGCCTGGACCAGATCTGGAACAACATGACCTGGATGGAGTGGGAGCG
CGAGATCGACAACTACACCAACCTGATCTACACCCTGATCGAGGAGAGCCAGAACCAGCAGG
AGAAGAACGAGCAGGAGCTGCTGGAGCTGGACAAGTGGGCCAGCCTGTGGAACTGGTTCGAC
ATCAGCAAGTGGCTGTGGTACATCAAGATCTTCATCATGATCGTGGGCGGCCTGGTGGGCCTG
CGCATCGTGTTCACCGTGCTGAGCATCGTGAACCGCGTGCGCCAGGGCTACAGCCCCCTGAGC
TTCCAGACCCGCTTCCCCGCCCCCCGCGGCCCCGACCGCCCCGAGGGCATCGAGGAGGAGGG
CGGCGAGCGCGACCGCGACCGCAGCAGCCCCCTGGTGCACGGCCTGCTGGCCCTGATCTGGG
ACGACCTGCGCAGCCTGTGCCTGTTCAGCTACCACCGCCTGCGCGACCTGATCCTGATCGCCG
CCCGCATCGTGGAGCTGCTGGGCCGCCGCGGCTGGGAGGCCCTGAAGTACTGGGGCAACCTG
CTGCAGTACTGGATCCAGGAGCTGAAGAACAGCGCCGTGAGCCTGTTCGACGCCATCGCCATC
GCCGTGGCCGAGGGCACCGACCGCATCATCGAGGTGGCCCAGCGCATCGGCCGCGCCTTCCT
GCACATCCCCCGCCGCATCCGCCAGGGCTTCGAGCGCGCCCTGCTGTAACTCGAG
```

FIG. 25

SEQ ID NO:23: VAL120-ILE201B; ILE424-ALA433

```
GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGCCCGGCATCACCCAGGCCTGC
CCCAAGGTGAGCTTCGAGCCCATCCCCATCCACTACTGCGCCCCCGCCGGCTTCGCCATCCTG
AAGTGCAACGACAAGAAGTTCAACGGCAGCGGCCCCTGCACCAACGTGAGCACCGTGCAGTG
CACCCACGGCATCCGCCCCGTGGTGAGCACCCAGCTGCTGCTGAACGGCAGCCTGGCCGAGG
AGGGCGTGGTGATCCGCAGCGAGAACTTCACCGACAACGCCAAGACCATCATCGTGCAGCTG
AAGGAGAGCGTGGAGATCAACTGCACCCGCCCCAACAACAACACCCGCAAGAGCATCACCAT
CGGCCCCGGCCGCGCCTTCTACGCCACCGGCGACATCATCGGCGACATCCGCCAGGCCCACTG
CAACATCAGCGGCGAGAAGTGGAACAACACCCTGAAGCAGATCGTGACCAAGCTGCAGGCCC
AGTTCGGCAACAAGACCATCGTGTTCAAGCAGAGCAGCGGCGGCGACCCCGAGATCGTGATG
CACAGCTTCAACTGCGGCGGCGAGTTCTTCTACTGCAACAGCACCCAGCTGTTCAACAGCACC
TGGAACAACACCATCGGCCCCAACAACACCAACGGCACCATCACCCTGCCCTGCCGCATCAA
GCAGATCATCGGCGGCGCCATGTACGCCCCCCCCATCCGCGGCCAGATCCGCTGCAGCAGCA
ACATCACCGGCCTGCTGCTGACCCGCGACGGCGGCAAGGAGATCAGCAACACCACCGAGATC
TTCCGCCCCGGCGGCGGCGACATGCGCGACAACTGGCGCAGCGAGCTGTACAAGTACAAGGT
GGTGAAGATCGAGCCCCTGGGCGTGGCCCCCACCAAGGCCAAGCGCCGCGTGGTGCAGCGCG
AGAAGCGCGCCGTGACCCTGGGCGCCATGTTCCTGGGCTTCCTGGGCGCCGCCGGCAGCACCA
TGGGCGCCCGCAGCCTGACCCTGACCGTGCAGGCCCGCCAGCTGCTGAGCGGCATCGTGCAG
CAGCAGAACAACCTGCTGCGCGCCATCGAGGCCCAGCAGCACCTGCTGCAGCTGACCGTGTG
GGGCATCAAGCAGCTGCAGGCCCGCGTGCTGGCCGTGGAGCGCTACCTGAAGGACCAGCAGC
TGCTGGGCATCTGGGGCTGCAGCGGCAAGCTGATCTGCACCACCGCCGTGCCCTGGAACGCCA
GCTGGAGCAACAAGAGCCTGGACCAGATCTGGAACAACATGACCTGGATGGAGTGGGAGCGC
GAGATCGACAACTACACCAACCTGATCTACACCCTGATCGAGGAGAGCCAGAACCAGCAGGA
GAAGAACGAGCAGGAGCTGCTGGAGCTGGACAAGTGGGCCAGCCTGTGGAACTGGTTCGACA
TCAGCAAGTGGCTGTGGTACATCAAGATCTTCATCATGATCGTGGGCGGCCTGGTGGGCCTGC
GCATCGTGTTCACCGTGCTGAGCATCGTGAACCGCGTGCGCCAGGGCTACAGCCCCCTGAGCT
TCCAGACCCGCTTCCCCGCCCCCGCGGCCCCGACCGCCCCGAGGGCATCGAGGAGGAGGGC
GGCGAGCGCGACCGCGACCGCAGCAGCCCCTGGTGCACGGCCTGCTGGCCCTGATCTGGGA
CGACCTGCGCAGCCTGTGCCTGTTCAGCTACCACGCCTGCGCGACCTGATCCTGATCGCCGC
CCGCATCGTGGAGCTGCTGGGCCGCCGCGGCTGGGAGGCCCTGAAGTACTGGGGCAACCTGC
TGCAGTACTGGATCCAGGAGCTGAAGAACAGCGCCGTGAGCCTGTTCGACGCCATCGCCATC
GCCGTGGCCGAGGGCACCGACCGCATCATCGAGGTGGCCCAGCGCATCGGCCGCGCCTTCCT
GCACATCCCCCGCCGCATCCGCCAGGGCTTCGAGCGCGCCCTGCTGTAACTCGAG
```

FIG. 26

SEQ ID NO:24 VAL120-THR202; ILE424-ALA433

```
GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGGGCGGCGCCACCCAGGCCTG
CCCCAAGGTGAGCTTCGAGCCCATCCCCATCCACTACTGCGCCCCCGCCGGCTTCGCCATCCT
GAAGTGCAACGACAAGAAGTTCAACGGCAGCGGCCCCTGCACCAACGTGAGCACCGTGCAGT
GCACCCACGGCATCCGCCCCGTGGTGAGCACCCAGCTGCTGCTGAACGGCAGCCTGGCCGAG
GAGGGCGTGGTGATCCGCAGCGAGAACTTCACCGACAACGCCAAGACCATCATCGTGCAGCT
GAAGGAGAGCGTGGAGATCAACTGCACCCGCCCCAACAACAACACCCGCAAGAGCATCACCA
TCGGCCCCGGCCGCGCCTTCTACGCCACCGGCGACATCATCGGCGACATCCGCCAGGCCACT
GCAACATCAGCGGCGAGAAGTGGAACAACACCCTGAAGCAGATCGTGACCAAGCTGCAGGCC
CAGTTCGGCAACAAGACCATCGTGTTCAAGCAGAGCAGCGGCGGCGACCCCGAGATCGTGAT
GCACAGCTTCAACTGCGGCGGCGAGTTCTTCTACTGCAACAGCACCCAGCTGTTCAACAGCAC
CTGGAACAACACCATCGGCCCCAACAACACCAACGGCACCATCACCCTGCCCTGCCGCATCA
AGCAGATCATCGGCGGCGCCATGTACGCCCCCCCCATCCGCGGCCAGATCCGCTGCAGCAGC
AACATCACCGGCCTGCTGCTGACCCGCGACGGCGGCAAGGAGATCAGCAACACCACCGAGAT
CTTCCGCCCCGGCGGCGGCGACATGCGCGACAACTGGCGCAGCGAGCTGTACAAGTACAAGG
TGGTGAAGATCGAGCCCCTGGGCGTGGCCCCCACCAAGGCCAAGCGCCGCGTGGTGCAGCGC
GAGAAGCGCGCCGTGACCCTGGGCGCCATGTTCCTGGGCTTCCTGGGCGCCGCCGGCAGCACC
ATGGGCGCCCGCAGCCTGACCCTGACCGTGCAGGCCCGCCAGCTGCTGAGCGGCATCGTGCA
GCAGCAGAACAACCTGCTGCGCGCCATCGAGGCCCAGCAGCACCTGCTGCAGCTGACCGTGT
GGGGCATCAAGCAGCTGCAGGCCCGCGTGCTGGCCGTGGAGCGCTACCTGAAGGACCAGCAG
CTGCTGGGCATCTGGGGCTGCAGCGGCAAGCTGATCTGCACCACCGCCGTGCCCTGGAACGCC
AGCTGGAGCAACAAGAGCCTGGACCAGATCTGGAACAACATGACCTGGATGGAGTGGGAGCG
CGAGATCGACAACTACACCAACCTGATCTACACCCTGATCGAGGAGAGCCAGAACCAGCAGG
AGAAGAACGAGCAGGAGCTGCTGGAGCTGGACAAGTGGGCCAGCCTGTGGAACTGGTTCGAC
ATCAGCAAGTGGCTGTGGTACATCAAGATCTTCATCATGATCGTGGGCGGCCTGGTGGGCCTG
CGCATCGTGTTCACCGTGCTGAGCATCGTGAACCGCGTGCGCCAGGGCTACAGCCCCCTGAGC
TTCCAGACCCGCTTCCCCGCCCCCGCGGCCCCGACCGCCCCGAGGGCATCGAGGAGGAGGG
CGGCGAGCGCGACCGCGACCGCAGCAGCCCCCTGGTGCACGGCCTGCTGGCCCTGATCTGGG
ACGACCTGCGCAGCCTGTGCCTGTTCAGCTACCACCGCCTGCGCGACCTGATCCTGATCGCCG
CCCGCATCGTGGAGCTGCTGGGCCGCCGCGGCTGGGAGGCCCTGAAGTACTGGGGCAACCTG
CTGCAGTACTGGATCCAGGAGCTGAAGAACAGCGCCGTGAGCCTGTTCGACGCCATCGCCATC
GCCGTGGCCGAGGGCACCGACCGCATCATCGAGGTGGCCCAGCGCATCGGCCGCGCCTTCCT
GCACATCCCCCGCCGCATCCGCCAGGGCTTCGAGCGCGCCCTGCTGTAACTCGAG
```

FIG. 27

SEQ ID NO:25 VAL127-ASN195

```
GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGACCCCCCTGTGCGTG
GGGGCAGGGAACTGCAACACCAGCGTGATCACCCAGGCCTGCCCCAAGGTGAGCTTCGAGCC
CATCCCCATCCACTACTGCGCCCCCGCCGGCTTCGCCATCCTGAAGTGCAACGACAAGAAGTT
CAACGGCAGCGGCCCCTGCACCAACGTGAGCACCGTGCAGTGCACCCACGGCATCCGCCCCG
TGGTGAGCACCCAGCTGCTGCTGAACGGCAGCCTGGCCGAGGAGGGCGTGGTGATCCGCAGC
GAGAACTTCACCGACAACGCCAAGACCATCATCGTGCAGCTGAAGGAGAGCGTGGAGATCAA
CTGCACCCGCCCCAACAACAACACCCGCAAGAGCATCACCATCGGCCCCGGCCGCGCCTTCTA
CGCCACCGGCGACATCATCGGCGACATCCGCCAGGCCCACTGCAACATCAGCGGCGAGAAGT
GGAACAACACCCTGAAGCAGATCGTGACCAAGCTGCAGGCCCAGTTCGGCAACAAGACCATC
GTGTTCAAGCAGAGCAGCGGCGGCGACCCCGAGATCGTGATGCACAGCTTCAACTGCGGCGG
CGAGTTCTTCTACTGCAACAGCACCCAGCTGTTCAACAGCACCTGGAACAACACCATCGGCCC
CAACAACACCAACGGCACCATCACCCTGCCCTGCCGCATCAAGCAGATCATCAACCGCTGGC
AGGAGGTGGGCAAGGCCATGTACGCCCCCCCCATCCGCGGCCAGATCCGCTGCAGCAGCAAC
ATCACCGGCCTGCTGCTGACCCGCGACGGCGGCAAGGAGATCAGCAACACCACCGAGATCTT
CCGCCCCGGCGGCGGCGACATGCGCGACAACTGGCGCAGCGAGCTGTACAAGTACAAGGTGG
TGAAGATCGAGCCCCTGGGCGTGGCCCCCACCAAGGCCAAGCGCCGCGTGGTGCAGCGCGAG
AAGCGCGCCGTGACCCTGGGCGCCATGTTCCTGGGCTTCCTGGGCGCCGCCGGCAGCACCATG
GGCGCCCGCAGCCTGACCCTGACCGTGCAGGCCCGCCAGCTGCTGAGCGGCATCGTGCAGCA
GCAGAACAACCTGCTGCGCGCCATCGAGGCCCAGCAGCACCTGCTGCAGCTGACCGTGTGGG
GCATCAAGCAGCTGCAGGCCCGCGTGCTGGCCGTGGAGCGCTACCTGAAGGACCAGCAGCTG
CTGGGCATCTGGGGCTGCAGCGGCAAGCTGATCTGCACCACCGCCGTGCCCTGGAACGCCAG
CTGGAGCAACAAGAGCCTGGACCAGATCTGGAACAACATGACCTGGATGGAGTGGGAGCGCG
AGATCGACAACTACACCAACCTGATCTACACCCTGATCGAGGAGAGCCAGAACCAGCAGGAG
AAGAACGAGCAGGAGCTGCTGGAGCTGGACAAGTGGGCCAGCCTGTGGAACTGGTTCGACAT
CAGCAAGTGGCTGTGGTACATCAAGATCTTCATCATGATCGTGGGCGGCCTGGTGGGCCTGCG
CATCGTGTTCACCGTGCTGAGCATCGTGAACCGCGTGCGCCAGGGCTACAGCCCCCTGAGCTT
CCAGACCCGCTTCCCCGCCCCCGCGGCCCCGACCGCCCCGAGGGCATCGAGGAGGAGGGCG
GCGAGCGCGACCGCGACCGCAGCAGCCCCCTGGTGCACGGCCTGCTGGCCCTGATCTGGGAC
GACCTGCGCAGCCTGTGCCTGTTCAGCTACCACCGCCTGCGCGACCTGATCCTGATCGCCGCC
CGCATCGTGGAGCTGCTGGGCCGCCGCGGCTGGAGGCCCTGAAGTACTGGGGCAACCTGCT
GCAGTACTGGATCCAGGAGCTGAAGAACAGCGCCGTGAGCCTGTTCGACGCCATCGCCATCG
CCGTGGCCGAGGGCACCGACCGCATCATCGAGGTGGCCCAGCGCATCGGCCGCGCCTTCCTGC
ACATCCCCCGCCGCATCCGCCAGGGCTTCGAGCGCGCCCTGCTGTAACTCGAG
```

FIG. 28

SEQ ID NO:26 VAL127-ASN195; ARG426-GLY431

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGACCCCCTGTGCGTG
GGGGCAGGGAACTGCAACACCAGCGTGATCACCCAGGCCTGCCCCAAGGTGAGCTTCGAGCC
CATCCCCATCCACTACTGCGCCCCCGCCGGCTTCGCCATCCTGAAGTGCAACGACAAGAAGTT
CAACGGCAGCGGCCCCTGCACCAACGTGAGCACCGTGCAGTGCACCCACGGCATCCGCCCCG
TGGTGAGCACCCAGCTGCTGCTGAACGGCAGCCTGGCCGAGGAGGGCGTGGTGATCCGCAGC
GAGAACTTCACCGACAACGCCAAGACCATCATCGTGCAGCTGAAGGAGAGCGTGGAGATCAA
CTGCACCCGCCCCAACAACAACACCCGCAAGAGCATCACCATCGGCCCCGGCCGCGCCTTCTA
CGCCACCGGCGACATCATCGGCGACATCCGCCAGGCCCACTGCAACATCAGCGGCGAGAAGT
GGAACAACACCCTGAAGCAGATCGTGACCAAGCTGCAGGCCCAGTTCGGCAACAAGACCATC
GTGTTCAAGCAGAGCAGCGGCGGCGACCCCGAGATCGTGATGCACAGCTTCAACTGCGGCGG
CGAGTTCTTCTACTGCAACAGCACCCAGCTGTTCAACAGCACCTGGAACAACACCATCGGCCC
CAACAACACCAACGGCACCATCACCCTGCCCTGCCGCATCAAGCAGATCATCAACCGCGGCG
GCGGCAAGGCCATGTACGCCCCCCCCATCCGCGGCCAGATCCGCTGCAGCAGCAACATCACC
GGCCTGCTGCTGACCCGCGACGGCGGCAAGGAGATCAGCAACACCACCGAGATCTTCCGCCC
CGGGGGCGGCGACATGCGCGACAACTGGCGCAGCGAGCTGTACAAGTACAAGGTGGTGAAG
ATCGAGCCCCTGGGCGTGGCCCCCACCAAGGCCAAGCGCCGCGTGGTGCAGCGCGAGAAGCG
CGCCGTGACCCTGGGCGCCATGTTCCTGGGCTTCCTGGGCGCCGCCGGCAGCACCATGGGCGC
CCGCAGCCTGACCCTGACCGTGCAGGCCCGCCAGCTGCTGAGCGGCATCGTGCAGCAGCAGA
ACAACCTGCTGCGCGCCATCGAGGCCCAGCAGCACCTGCTGCAGCTGACCGTGTGGGGCATC
AAGCAGCTGCAGGCCCGCGTGCTGGCCGTGGAGCGCTACCTGAAGGACCAGCAGCTGCTGGG
CATCTGGGGCTGCAGCGGCAAGCTGATCTGCACCACCGCCGTGCCCTGGAACGCCAGCTGGA
GCAACAAGAGCCTGGACCAGATCTGGAACAACATGACCTGGATGGAGTGGGAGCGCGAGATC
GACAACTACACCAACCTGATCTACACCCTGATCGAGGAGAGCCAGAACCAGCAGGAGAAGAA
CGAGCAGGAGCTGCTGGAGCTGGACAAGTGGGCCAGCCTGTGGAACTGGTTCGACATCAGCA
AGTGGCTGTGGTACATCAAGATCTTCATCATGATCGTGGGCGGCCTGGTGGGCCTGCGCATCG
TGTTCACCGTGCTGAGCATCGTGAACCGCGTGCGCCAGGGCTACAGCCCCCTGAGCTTCCAGA
CCCGCTTCCCCGCCCCCGCGGCCCCGACCGCCCCGAGGGCATCGAGGAGGAGGGCGGCGAG
CGCGACCGCGACCGCAGCAGCCCCCTGGTGCACGGCCTGCTGGCCCTGATCTGGGACGACCTG
CGCAGCCTGTGCCTGTTCAGCTACCACCGCCTGCGCGACCTGATCCTGATCGCCGCCCGCATC
GTGGAGCTGCTGGGCCGCCGCGGCTGGGAGGCCCTGAAGTACTGGGGCAACCTGCTGCAGTA
CTGGATCCAGGAGCTGAAGAACAGCGCCGTGAGCCTGTTCGACGCCATCGCCATCGCCGTGG
CCGAGGGCACCGACCGCATCATCGAGGTGGCCCAGCGCATCGGCCGCGCCTTCCTGCACATCC
CCCGCCGCATCCGCCAGGGCTTCGAGCGCGCCCTGCTGTAACTCGAG

SEQUENCE LISTING

<160> NUMBER OF SEQ ID NOS: 26

<210> SEQ ID NO 1
<211> LENGTH: 856
<212> TYPE: PRT
<213> ORGANISM: Human immunodeficiency virus

<400> SEQUENCE: 1

Met Arg Val Lys Glu Lys Tyr Gln His Leu Trp Arg Trp Gly Trp Arg
 1               5                  10                  15

Trp Gly Thr Met Leu Leu Gly Met Leu Met Ile Cys Ser Ala Thr Glu
                20                  25                  30

Lys Leu Trp Val Thr Val Tyr Tyr Gly Val Pro Val Trp Lys Glu Ala
            35                  40                  45

Thr Thr Thr Leu Phe Cys Ala Ser Asp Ala Lys Ala Tyr Asp Thr Glu
        50                  55                  60

Val His Asn Val Trp Ala Thr His Ala Cys Val Pro Thr Asp Pro Asn
 65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Glu Val Val Ile
            260                 265                 270

-continued

```
Arg Ser Val Asn Phe Thr Asp Asn Ala Lys Thr Ile Ile Val Gln Leu
        275                 280                 285

Asn Thr Ser Val Glu Ile Asn Cys Thr Arg Pro Asn Asn Asn Thr Arg
        290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                    325                 330                 335

Lys Trp Asn Asn Thr Leu Lys Gln Ile Ala Ser Lys Leu Arg Glu Gln
                340                 345                 350

Phe Gly Asn Asn Lys Thr Ile Ile Phe Lys Gln Ser Ser Gly Gly Asp
            355                 360                 365

Pro Glu Ile Val Thr His Ser Phe Asn Cys Gly Gly Glu Phe Phe Tyr
        370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                    405                 410                 415

Pro Cys Arg Ile Lys Gln Ile Ile Asn Met Trp Gln Lys Val Gly Lys
                420                 425                 430

Ala Met Tyr Ala Pro Pro Ile Ser Gly Gln Ile Arg Cys Ser Ser Asn
            435                 440                 445

Ile Thr Gly Leu Leu Leu Thr Arg Asp Gly Gly Asn Ser Asn Asn Glu
        450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                    485                 490                 495

Ala Pro Thr Lys Ala Lys Arg Arg Val Val Gln Arg Glu Lys Arg Ala
                500                 505                 510

Val Gly Ile Gly Ala Leu Phe Leu Gly Phe Leu Gly Ala Ala Gly Ser
            515                 520                 525

Thr Met Gly Ala Ala Ser Met Thr Leu Thr Val Gln Ala Arg Gln Leu
        530                 535                 540

Leu Ser Gly Ile Val Gln Gln Gln Asn Asn Leu Leu Arg Ala Ile Glu
545                 550                 555                 560

Ala Gln Gln His Leu Leu Gln Leu Thr Val Trp Gly Ile Lys Gln Leu
                    565                 570                 575

Gln Ala Arg Ile Leu Ala Val Glu Arg Tyr Leu Lys Asp Gln Gln Leu
                580                 585                 590

Leu Gly Ile Trp Gly Cys Ser Gly Lys Leu Ile Cys Thr Thr Ala Val
            595                 600                 605

Pro Trp Asn Ala Ser Trp Ser Asn Lys Ser Leu Glu Gln Ile Trp Asn
        610                 615                 620

His Thr Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
                    645                 650                 655

Glu Gln Glu Leu Leu Glu Leu Asp Lys Trp Ala Ser Leu Trp Asn Trp
                660                 665                 670

Phe Asn Ile Thr Asn Trp Leu Trp Tyr Ile Lys Leu Phe Ile Met Ile
            675                 680                 685
```

```
Val Gly Gly Leu Val Gly Leu Arg Ile Val Phe Ala Val Leu Ser Ile
    690             695                 700

Val Asn Arg Val Arg Gln Gly Tyr Ser Pro Leu Ser Phe Gln Thr His
705             710                 715                 720

Leu Pro Thr Pro Arg Gly Pro Asp Arg Pro Glu Gly Ile Glu Glu Glu
                725                 730                 735

Gly Gly Glu Arg Asp Arg Asp Arg Ser Ile Arg Leu Val Asn Gly Ser
            740                 745                 750

Leu Ala Leu Ile Trp Asp Asp Leu Arg Ser Leu Cys Leu Phe Ser Tyr
        755                 760                 765

His Arg Leu Arg Asp Leu Leu Leu Ile Val Thr Arg Ile Val Glu Leu
    770                 775                 780

Leu Gly Arg Arg Gly Trp Glu Ala Leu Lys Tyr Trp Trp Asn Leu Leu
785             790                 795                 800

Gln Tyr Trp Ser Gln Glu Leu Lys Asn Ser Ala Val Ser Leu Leu Asn
                805                 810                 815

Ala Thr Ala Ile Ala Val Ala Glu Gly Thr Asp Arg Val Ile Glu Val
            820                 825                 830

Val Gln Gly Ala Cys Arg Ala Ile Arg His Ile Pro Arg Arg Ile Arg
        835                 840                 845

Gln Gly Leu Glu Arg Ile Leu Leu
    850                 855

<210> SEQ ID NO 2
<211> LENGTH: 847
<212> TYPE: PRT
<213> ORGANISM: Human immunodeficiency virus

<400> SEQUENCE: 2

Met Arg Val Lys Gly Ile Arg Lys Asn Tyr Gln His Leu Trp Arg Gly
  1               5                  10                  15

Gly Thr Leu Leu Leu Gly Met Leu Met Ile Cys Ser Ala Val Glu Lys
                 20                  25                  30

Leu Trp Val Thr Val Tyr Tyr Gly Val Pro Val Trp Lys Glu Ala Thr
             35                  40                  45

Thr Thr Leu Phe Cys Ala Ser Asp Ala Lys Ala Tyr Asp Thr Glu Val
         50                  55                  60

His Asn Val Trp Ala Thr His Ala Cys Val Pro Thr Asp Pro Asn Pro
 65                  70                  75                  80

Gln Glu Ile Val Leu Glu Asn Val Thr Glu Asn Phe Asn Met Trp Lys
                 85                  90                  95

Asn Asn Met Val Glu Gln Met His Glu Asp Ile Ile Ser Leu Trp Asp
                100                 105                 110

Gln Ser Leu Lys Pro Cys Val Lys Leu Thr Pro Leu Cys Val Thr Leu
            115                 120                 125

His Cys Thr Asn Leu Lys Asn Ala Thr Asn Thr Lys Ser Ser Asn Trp
        130                 135                 140

Lys Glu Met Asp Arg Gly Glu Ile Lys Asn Cys Ser Phe Lys Val Thr
145                 150                 155                 160

Thr Ser Ile Arg Asn Lys Met Gln Lys Glu Tyr Ala Leu Phe Tyr Lys
                165                 170                 175

Leu Asp Val Val Pro Ile Asp Asn Asp Asn Thr Ser Tyr Lys Leu Ile
            180                 185                 190

Asn Cys Asn Thr Ser Val Ile Thr Gln Ala Cys Pro Lys Val Ser Phe
        195                 200                 205
```

-continued

```
Glu Pro Ile Pro Ile His Tyr Cys Ala Pro Ala Gly Phe Ala Ile Leu
210                 215                 220

Lys Cys Asn Asp Lys Lys Phe Asn Gly Ser Gly Pro Cys Thr Asn Val
225                 230                 235                 240

Ser Thr Val Gln Cys Thr His Gly Ile Arg Pro Val Val Ser Thr Gln
                245                 250                 255

Leu Leu Leu Asn Gly Ser Leu Ala Glu Glu Gly Val Val Ile Arg Ser
                260                 265                 270

Glu Asn Phe Thr Asp Asn Ala Lys Thr Ile Ile Val Gln Leu Lys Glu
                275                 280                 285

Ser Val Glu Ile Asn Cys Thr Arg Pro Asn Asn Asn Thr Arg Lys Ser
290                 295                 300

Ile Thr Ile Gly Pro Gly Arg Ala Phe Tyr Ala Thr Gly Asp Ile Ile
305                 310                 315                 320

Gly Asp Ile Arg Gln Ala His Cys Asn Ile Ser Gly Glu Lys Trp Asn
                325                 330                 335

Asn Thr Leu Lys Gln Ile Val Thr Lys Leu Gln Ala Gln Phe Gly Asn
                340                 345                 350

Lys Thr Ile Val Phe Lys Gln Ser Ser Gly Gly Asp Pro Glu Ile Val
                355                 360                 365

Met His Ser Phe Asn Cys Gly Gly Glu Phe Phe Tyr Cys Asn Ser Thr
                370                 375                 380

Gln Leu Phe Asn Ser Thr Trp Asn Asn Thr Ile Gly Pro Asn Asn Thr
385                 390                 395                 400

Asn Gly Thr Ile Thr Leu Pro Cys Arg Ile Lys Gln Ile Ile Asn Arg
                405                 410                 415

Trp Gln Glu Val Gly Lys Ala Met Tyr Ala Pro Pro Ile Arg Gly Gln
                420                 425                 430

Ile Arg Cys Ser Ser Asn Ile Thr Gly Leu Leu Leu Thr Arg Asp Gly
                435                 440                 445

Gly Lys Glu Ile Ser Asn Thr Thr Glu Ile Phe Arg Pro Gly Gly Gly
                450                 455                 460

Asp Met Arg Asp Asn Trp Arg Ser Glu Leu Tyr Lys Tyr Lys Val Val
465                 470                 475                 480

Lys Ile Glu Pro Leu Gly Val Ala Pro Thr Lys Ala Lys Arg Arg Val
                485                 490                 495

Val Gln Arg Glu Lys Arg Ala Val Thr Leu Gly Ala Met Phe Leu Gly
                500                 505                 510

Phe Leu Gly Ala Ala Gly Ser Thr Met Gly Ala Arg Ser Leu Thr Leu
                515                 520                 525

Thr Val Gln Ala Arg Gln Leu Leu Ser Gly Ile Val Gln Gln Gln Asn
                530                 535                 540

Asn Leu Leu Arg Ala Ile Glu Ala Gln Gln His Leu Leu Gln Leu Thr
545                 550                 555                 560

Val Trp Gly Ile Lys Gln Leu Gln Ala Arg Val Leu Ala Val Glu Arg
                565                 570                 575

Tyr Leu Lys Asp Gln Gln Leu Leu Gly Ile Trp Gly Cys Ser Gly Lys
                580                 585                 590

Leu Ile Cys Thr Thr Ala Val Pro Trp Asn Ala Ser Trp Ser Asn Lys
                595                 600                 605

Ser Leu Asp Gln Ile Trp Asn Asn Met Thr Trp Met Glu Trp Glu Arg
610                 615                 620
```

```
Glu Ile Asp Asn Tyr Thr Asn Leu Ile Tyr Thr Leu Ile Glu Glu Ser
625                 630                 635                 640

Gln Asn Gln Gln Glu Lys Asn Glu Gln Glu Leu Leu Glu Leu Asp Lys
            645                 650                 655

Trp Ala Ser Leu Trp Asn Trp Phe Asp Ile Ser Lys Trp Leu Trp Tyr
                660                 665                 670

Ile Lys Ile Phe Ile Met Ile Val Gly Gly Leu Val Gly Leu Arg Ile
            675                 680                 685

Val Phe Thr Val Leu Ser Ile Val Asn Arg Val Arg Gln Gly Tyr Ser
690                 695                 700

Pro Leu Ser Phe Gln Thr Arg Phe Pro Ala Pro Arg Gly Pro Asp Arg
705                 710                 715                 720

Pro Glu Gly Ile Glu Glu Gly Gly Glu Arg Asp Arg Asp Arg Ser
                725                 730                 735

Ser Pro Leu Val His Gly Leu Leu Ala Leu Ile Trp Asp Asp Leu Arg
            740                 745                 750

Ser Leu Cys Leu Phe Ser Tyr His Arg Leu Arg Asp Leu Ile Leu Ile
            755                 760                 765

Ala Ala Arg Ile Val Glu Leu Leu Gly Arg Arg Gly Trp Glu Ala Leu
            770                 775                 780

Lys Tyr Trp Gly Asn Leu Leu Gln Tyr Trp Ile Gln Glu Leu Lys Asn
785                 790                 795                 800

Ser Ala Val Ser Leu Phe Asp Ala Ile Ala Ile Ala Val Ala Glu Gly
                805                 810                 815

Thr Asp Arg Ile Ile Glu Val Ala Gln Arg Ile Gly Arg Ala Phe Leu
            820                 825                 830

His Ile Pro Arg Arg Ile Arg Gln Gly Phe Glu Arg Ala Leu Leu
            835                 840                 845

<210> SEQ ID NO 3
<211> LENGTH: 2310
<212> TYPE: DNA
<213> ORGANISM: Artificial Sequence
<220> FEATURE:
<223> OTHER INFORMATION: Description of Artificial Sequence:
      Val120-Ala204

<400> SEQUENCE: 3
gaattcgcca ccatggatgc aatgaagaga gggctctgct gtgtgctgct gctgtgtgga      60
gcagtcttcg tttcgcccag cgccgtggag aagctgtggg tgaccgtgta ctacggcgtg     120
cccgtgtgga aggaggccac caccaccctg ttctgcgcca gcgacgccaa ggcctacgac     180
accgaggtgc acaacgtgtg gccacccac gcctgcgtgc ccaccgaccc caaccccag     240 gagatcgtgc tggagaacgt gaccgagaac ttcaacatgt ggaagaacaa catggtggag     300
cagatgcacg aggacatcat cagcctgtgg gaccagagcc tgaagccctg cgtgggcgcc     360
ggcgcctgcc ccaaggtgag cttcgagccc atccccatcc actactgcgc cccgccggc     420 ttcgccatcc tgaagtgcaa cgacaagaag ttcaacggca cgggcccctg caccaacgtg     480
agcaccgtgc agtgcaccca cggcatccgc ccgtggtga gcacccagct gctgctgaac     540
ggcagcctgg ccgaggaggg cgtggtgatc cgcagcgaga acttcaccga caacgccaag     600
accatcatcg tgcagctgaa ggagagcgtg gagatcaact gcacccgccc caacaacaac     660
acccgcaaga gcatcaccat cggccccggc cgcgccttct acgccaccgg cgacatcatc     720
ggcgacatcc gccaggccca ctgcaacatc agcggcgaga agtggaacaa caccctgaag     780
```

-continued

```
cagatcgtga ccaagctgca ggcccagttc ggcaacaaga ccatcgtgtt caagcagagc      840
agcggcggcg accccgagat cgtgatgcac agcttcaact gcggcggcga gttcttctac      900
tgcaacagca cccagctgtt caacagcacc tggaacaaca ccatcggccc caacaacacc      960
aacggcacca tcaccctgcc ctgccgcatc aagcagatca tcaaccgctg gcaggaggtg     1020
ggcaaggcca tgtacgcccc ccccatccgc ggccagatcc gctgcagcag caacatcacc     1080
ggcctgctgc tgacccgcga cggcggcaag gagatcagca caccaccga gatcttccgc      1140
cccggcggcg cgacatgcg cgacaactgg cgcagcgagc tgtacaagta caaggtggtg      1200
aagatcgagc ccctgggcgt ggcccccacc aaggccaagc gccgcgtggt gcagcgcgag     1260
aagcgcgccg tgaccctggg cgccatgttc ctgggcttcc tgggcgccgc cggcagcacc     1320
atgggcgccc gcagcctgac cctgaccgtg caggcccgcc agctgctgag cggcatcgtg     1380
cagcagcaga caacctgct gcgcgccatc gaggcccagc agcacctgct gcagctgacc      1440
gtgtgggca tcaagcagct gcaggcccgc gtgctggccg tggagcgcta cctgaaggac      1500
cagcagctgc tgggcatctg gggctgcagc ggcaagctga tctgcaccac cgccgtgccc     1560
tggaacgcca gctggagcaa caagagcctg accagatct ggaacaacat gacctggatg      1620
gagtgggagc gcgagatcga caactacacc aacctgatct acccctgat cgaggagagc      1680
cagaaccagc aggagaagaa cgagcaggag ctgctggagc tggacaagtg ggccagcctg     1740
tggaactggt tcgacatcag caagtggctg tggtacatca agatcttcat catgatcgtg     1800
ggcggcctgg tgggcctgcg catcgtgttc accgtgctga gcatcgtgaa ccgcgtgcgc     1860
cagggctaca gccccctgag cttccagacc cgcttccccg cccccgcgg ccccgaccgc      1920
cccgagggca tcgaggagga gggcggcgag cgcgaccgcg accgcagcag cccccctggtg    1980
cacggcctgc tggccctgat ctgggacgac ctgcgcagcc tgtgcctgtt cagctaccac     2040
cgcctgcgcg acctgatcct gatcgccgcc cgcatcgtgg agctgctggg ccgccgcggc     2100
tgggaggccc tgaagtactg gggcaacctg ctgcagtact ggatccagga gctgaagaac     2160
agcgccgtga cctgttcga cgccatcgcc atcgccgtgg ccgagggcac cgaccgcatc     2220
atcgaggtgg cccagcgcat cggccgcgcc ttcctgcaca tcccccgccg catccgccag     2280
ggcttcgagc gcgccctgct gtaactcgag                                       2310
```

<210> SEQ ID NO 4
<211> LENGTH: 2316
<212> TYPE: DNA
<213> ORGANISM: Artificial Sequence
<220> FEATURE:
<223> OTHER INFORMATION: Description of Artificial Sequence: Val120-Ile201

<400> SEQUENCE: 4

```
gaattcgcca ccatggatgc aatgaagaga gggctctgct gtgtgctgct gctgtgtgga       60
gcagtcttcg tttcgcccag cgccgtggag aagctgtggg tgaccgtgta ctacggcgtg      120
cccgtgtgga aggaggccac caccaccctg ttctgcgcca gcgacgccaa ggcctacgac      180
accgaggtgc acaacgtgtg gccacccac gcctgcgtgc ccaccgaccc caaccccag      240
gagatcgtgc tggagaacgt gaccgagaac ttcaacatgt ggaagaacaa catggtggag      300
cagatgcacg aggacatcat cagcctgtgg gaccagagcc tgaagccctg cgtgggcggc      360
atcacccagg cctgccccaa ggtgagcttc gagcccatcc ccatccacta ctgcgccccc      420
gccggcttcg ccatcctgaa gtgcaacgac aagaagttca cggcagcgg ccctgcacc       480
```

| | |
|---|---|
| aacgtgagca ccgtgcagtg cacccacggc atccgccccg tggtgagcac ccagctgctg | 540 |
| ctgaacggca gcctggccga ggagggcgtg gtgatccgcg cgagaacttc accgacaac | 600 |
| gccaagacca tcatcgtgca gctgaaggag agcgtggaga tcaactgcac ccgcccaac | 660 |
| aacaacaccc gcaagagcat caccatcggc cccggccgcg ccttctacgc caccggcgac | 720 |
| atcatcggcg acatccgcca ggcccactgc aacatcagcg gcgagaagtg gaacaacacc | 780 |
| ctgaagcaga tcgtgaccaa gctgcaggcc cagttcggca caagaccat cgtgttcaag | 840 |
| cagagcagcg gcggcgaccc cgagatcgtg atgcacagct tcaactgcgg cggcgagttc | 900 |
| ttctactgca acagcaccca gctgttcaac agcacctgga caacaccat cggccccaac | 960 |
| aacaccaacg gcaccatcac cctgccctgc cgcatcaagc agatcatcaa ccgctggcag | 1020 |
| gaggtgggca aggccatgta cgcccccccc atccgcggcc agatccgctg cagcagcaac | 1080 |
| atcaccggcc tgctgctgac ccgcgacggc ggcaaggaga tcagcaacac caccgagatc | 1140 |
| ttccgccccg cgcgcggcga catgcgcgac aactggcgca gcgagctgta caagtacaag | 1200 |
| gtggtgaaga tcgagcccct gggcgtggcc cccaccaagg ccaagcgccg cgtggtgcag | 1260 |
| cgcgagaagc gcgccgtgac cctgggcgcc atgttcctgg gcttcctggg cgccgccggc | 1320 |
| agcaccatgg gcgcccgcag cctgacccctg accgtgcagg cccgccagct gctgagcggc | 1380 |
| atcgtgcagc agcagaacaa cctgctgcgc gccatcgagg cccagcagca cctgctgcag | 1440 |
| ctgaccgtgt ggggcatcaa gcagctgcag gcccgcgtgc tggccgtgga gcgctacctg | 1500 |
| aaggaccagc agctgctggg catctggggc tgcagcggca gctgatctg caccaccgcc | 1560 |
| gtgccctgga acgccagctg gagcaacaag agcctggacc agatctggaa caacatgacc | 1620 |
| tggatggagt gggagcgcga gatcgacaac tacaccaacc tgatctacac cctgatcgag | 1680 |
| gagagccaga accagcagga agaacgag caggagctgc tggagctgga caagtgggcc | 1740 |
| agcctgtgga actggttcga catcagcaag tggctgtggt acatcaagat cttcatcatg | 1800 |
| atcgtgggcg gcctggtggg cctgcgcatc gtgttcaccg tgctgagcat cgtgaaccgc | 1860 |
| gtgcgccagg gctacagccc cctgagcttc cagacccgct tccccgcccc cgcggccc | 1920 |
| gaccgccccg agggcatcga ggaggagggc ggcgagcgcg accgcgaccg cagcagcccc | 1980 |
| ctggtgcacg gcctgctggc cctgatctgg gacgacctgc gcagcctgtg cctgttcagc | 2040 |
| taccaccgcc tgcgcgacct gatcctgatc gccgcccgca tcgtggagct gctgggccgc | 2100 |
| cgcggctggg aggccctgaa gtactggggc aacctgctgc agtactggat ccaggagctg | 2160 |
| aagaacagcg ccgtgagcct gttcgacgcc atcgccatcc ccgtggccga gggcaccgac | 2220 |
| cgcatcatcg aggtggccca gcgcatcggc gcgccttcc tgcacatccc ccgccgcatc | 2280 |
| cgccagggct cgagcgcgc cctgctgtaa ctcgag | 2316 |

<210> SEQ ID NO 5
<211> LENGTH: 2322
<212> TYPE: DNA
<213> ORGANISM: Artificial Sequence
<220> FEATURE:
<223> OTHER INFORMATION: Description of Artificial Sequence:
    Val120-Ile201B

<400> SEQUENCE: 5

| | |
|---|---|
| gaattcgcca ccatggatgc aatgaagaga gggctctgct gtgtgctgct gctgtgtgga | 60 |
| gcagtcttcg tttcgcccag cgccgtggag aagctgtggg tgaccgtgta ctacggcgtg | 120 |
| cccgtgtgga aggaggccac caccaccctg ttctgcgcca gcgacgccaa ggcctacgac | 180 |

-continued

```
accgaggtgc acaacgtgtg ggccacccac gcctgcgtgc ccaccgaccc caacccccag      240
gagatcgtgc tggagaacgt gaccgagaac ttcaacatgt ggaagaacaa catggtggag      300
cagatgcacg aggacatcat cagcctgtgg gaccagagcc tgaagccctg cgtgcccggc      360
atcacccagg cctgccccaa ggtgagcttc gagcccatcc ccatccacta ctgcgccccc      420
gccggcttcg ccatcctgaa gtgcaacgac aagaagttca acggcagcgg ccoctgcacc      480 aacgtgagca ccgtgcagtg cacccacggc atccgccccg tggtgagcac ccagctgctg      540
ctgaacggca gcctggccga ggagggcgtg gtgatccgca gcgagaactt caccgacaac      600
gccaagacca tcatcgtgca gctgaaggag agcgtggaga tcaactgcac ccgccccaac      660
aacaacaccc gcaagagcat caccatcggc cccggccgcg ccttctacgc caccggcgac      720
atcatcggcg acatccgcca ggcccactgc aacatcagcg cgcgagaagtg gaacaacacc      780 ctgaagcaga tcgtgaccaa gctgcaggcc cagttcggca acaagaccat cgtgttcaag      840
cagagcagcg gcggcgaccc cgagatcgtg atgcacagct tcaactgcgg cggcgagttc      900
ttctactgca acagcaccca gctgttcaac agcacctgga acaacaccat cggccccaac      960
aacaccaacg gcaccatcac cctgccctgc cgcatcaagc agatcatcaa ccgctggcag     1020
gaggtgggca aggccatgta cgccccccc atccgcggcc agatccgctg cagcagcaac     1080
atcaccggcc tgctgctgac ccgcgacggc ggcaaggaga tcagcaacac caccgagatc     1140
ttccgccccg gcggcggcga catgcgcgac aactggcgca gcgagctgta caagtacaag     1200
gtggtgaaga tcgagcccct gggcgtggcc cccaccaagg ccaagcgccg cgtggtgcag     1260
cgcgagaagc gcgccgtgac cctgggcgcc atgttcctgg gcttcctggg cgccgccggc     1320
agcaccatgg gcgcccgcag cctgacccty accgtgcagg cccgccagct gctgagcggc     1380
atcgtgcagc agcagaacaa cctgctgcgc gccatcgagg cccagcagca cctgctgcag     1440
ctgaccgtgt ggggcatcaa gcagctgcag gcccgcgtgc tggccgtgga gcgctacctg     1500
aaggaccagc agctgctggg catctggggc tgcagcggca gctgatctg caccaccgcc     1560 gtgccctgga acgccagctg gagcaacaag agcctggacc agatctggaa caacatgacc     1620
tggatggagt gggagcgcga gatcgacaac tacaccaacc tgatctacac cctgatcgag     1680
gagagccaga accagcagga gaagaacgag caggagctgc tggagctgga caagtgggcc     1740
agcctgtgga actggttcga catcagcaag tggctgtggt acatcaagat cttcatcatg     1800
atcgtgggcg gcctggtggg cctgcgcatc gtgttcaccg tgctgagcat cgtgaaccgc     1860
gtgcgccagg gctacagccc cctgagcttc cagacccgct cccccgcccc ccgcggcccc     1920
gaccgccccg agggcatcga ggaggagggc ggcgagcgcg accgcgaccg cagcagcccc     1980
ctggtgcacg gcctgctggc cctgatctgg gacgacctgc gcagcctgtg cctgttcagc     2040
taccaccgcc tgcgcgacct gatcctgatc gccgcccgca tcgtggagct gctgggccgc     2100
cgcggctggg aggccctgaa gtactgggc aacctgctgc agtactggat ccaggagctg     2160
aagaacagcg ccgtgagcct gttcgacgcc atcgccatcg ccgtggccga gggcaccgac     2220
cgcatcatcg aggtggccca gcgcatcggc cgcgccttcc tgcacatccc cgccgcatc     2280 cgccagggct tcgagcgcgc cctgctgtaa ctcgagcgtg ct                        2322
```

<210> SEQ ID NO 6
<211> LENGTH: 2328
<212> TYPE: DNA
<213> ORGANISM: Artificial Sequence
<220> FEATURE:
<223> OTHER INFORMATION: Description of Artificial Sequence:

-continued

Lys121-Val200

<400> SEQUENCE: 6

| | | | | | |
|---|---|---|---|---|---|
| gaattcgcca | ccatggatgc | aatgaagaga | gggctctgct | gtgtgctgct | gctgtgtgga | 60 |
| gcagtcttcg | tttcgcccag | cgccgtggag | aagctgtggg | tgaccgtgta | ctacggcgtg | 120 |
| cccgtgtgga | aggaggccac | caccaccctg | ttctgcgcca | gcgacgccaa | ggcctacgac | 180 |
| accgaggtgc | acaacgtgtg | gccaccccac | gcctgcgtgc | ccaccgaccc | caaccccag | 240 |
| gagatcgtgc | tggagaacgt | gaccgagaac | ttcaacatgt | ggaagaacaa | catggtggag | 300 |
| cagatgcacg | aggacatcat | cagcctgtgg | gaccagagcc | tgaagccctg | cgtgaaggcc | 360 |
| cccgtgatca | cccaggcctg | ccccaaggtg | agcttcgagc | ccatccccat | ccactactgc | 420 |
| gcccccgccg | gcttcgccat | cctgaagtgc | aacgacaaga | agttcaacgg | cagcggcccc | 480 |
| tgcaccaacg | tgagcaccgt | gcagtgcacc | cacggcatcc | gccccgtggt | gagcacccag | 540 |
| ctgctgctga | acggcagcct | ggccgaggag | ggcgtggtga | tccgcagcga | gaacttcacc | 600 |
| gacaacgcca | agaccatcat | cgtgcagctg | aaggagagcg | tggagatcaa | ctgcacccgc | 660 |
| cccaacaaca | cacccgcaa | gagcatcacc | atcggccccg | gccgcgcctt | ctacgccacc | 720 |
| ggcgacatca | tcggcgacat | ccgccaggcc | cactgcaaca | tcagcggcga | gaagtggaac | 780 |
| aaccccctga | gcagatcgt | gaccaagctg | caggcccagt | tcggcaacaa | gaccatcgtg | 840 |
| ttcaagcaga | gcagcggcgg | cgaccccgag | atcgtgatgc | acagcttcaa | ctgcggcggc | 900 |
| gagttcttct | actgcaacag | cacccagctg | ttcaacagca | cctggaacaa | caccatcggc | 960 |
| cccaacaaca | ccaacggcac | catcaccctg | ccctgccgca | tcaagcagat | catcaaccgc | 1020 |
| tggcaggagg | tgggcaaggc | catgtacgcc | cccccatcc | gcggccagat | ccgctgcagc | 1080 |
| agcaacatca | ccggcctgct | gctgacccgc | gacgcggca | aggagatcag | caacaccacc | 1140 |
| gagatcttcc | gccccggcgg | cggcgacatg | cgcgacaact | ggcgcagcga | gctgtacaag | 1200 |
| tacaaggtgg | tgaagatcga | gcccctgggc | gtggcccca | ccaaggccaa | cgccgcgtg | 1260 |
| gtgcagcgcg | agaagcgcgc | cgtgaccctg | ggcgccatgt | tcctgggctt | cctgggcgcc | 1320 |
| gccggcagca | ccatgggcgc | ccgcagcctg | accctgaccg | tgcaggcccg | ccagctgctg | 1380 |
| agcggcatcg | tgcagcagca | gaacaacctg | ctgcgcgcca | tcgaggccca | gcagcacctg | 1440 |
| ctgcagctga | ccgtgtgggg | catcaagcag | ctgcaggccc | gcgtgctggc | cgtggagcgc | 1500 |
| tacctgaagg | accagcagct | gctgggcatc | tggggctgca | gcggcaagct | gatctgcacc | 1560 |
| accgccgtgc | cctggaacgc | cagctggagc | aacaagagcc | tggaccagat | ctggaacaac | 1620 |
| atgacctgga | tggagtggga | gcgcgagatc | gacaactaca | ccaacctgat | ctacaccctg | 1680 |
| atcgaggaga | gccagaacca | gcaggagaag | aacgagcagg | agctgctgga | gctggacaag | 1740 |
| tgggccagcc | tgtggaactg | gttcgacatc | agcaagtggc | tgtggtacat | caagatcttc | 1800 |
| atcatgatcg | tgggcggcct | ggtgggcctg | cgcatcgtgt | tcaccgtgct | gagcatcgtg | 1860 |
| aaccgcgtgc | gccagggcta | cagccccctg | agcttccaga | cccgcttccc | cgcccccgc | 1920 |
| ggcccccgacc | gccccgaggg | catcgaggag | gagggcggcg | agcgcgaccg | cgaccgcagc | 1980 |
| agccccctgg | tgcacggcct | gctggccctg | atctgggacg | acctgcgcag | cctgtgcctg | 2040 |
| ttcagctacc | accgcctgcg | cgacctgatc | ctgatcgccg | cccgcatcgt | ggagctgctg | 2100 |
| ggccgccgcg | gctgggaggc | cctgaagtac | tggggcaacc | tgctgcagta | ctggatccag | 2160 |
| gagctgaaga | acagcgccgt | gagcctgttc | gacgccatcg | ccatcgccgt | ggccgagggc | 2220 |
| accgaccgca | tcatcgaggt | ggcccagcgc | atcggccgcg | ccttcctgca | catccccgc | 2280 | cgcatccgcc agggcttcga gcgcgccctg ctgtaactcg agcgtgct                2328

<210> SEQ ID NO 7
<211> LENGTH: 2334
<212> TYPE: DNA
<213> ORGANISM: Artificial Sequence
<220> FEATURE:
<223> OTHER INFORMATION: Description of Artificial Sequence:
      Leu122-Ser199

<400> SEQUENCE: 7

| | | | | | |
|---|---|---|---|---|---|
| gaattcgcca | ccatggatgc | aatgaagaga | gggctctgct | gtgtgctgct | gctgtgtgga |   60 |
| gcagtcttcg | tttcgcccag | cgccgtggag | aagctgtggg | tgaccgtgta | ctacggcgtg |  120 |
| cccgtgtgga | aggaggccac | caccaccctg | ttctgcgcca | cgacgccaa | ggcctacgac |  180 |
| accgaggtgc | acaacgtgtg | gccaccac | gcctgcgtgc | caccgaccc | caaccccag |  240 |
| gagatcgtgc | tggagaacgt | gaccgagaac | ttcaacatgt | ggaagaacaa | catggtggag |  300 |
| cagatgcacg | aggacatcat | cagcctgtgg | gaccagagcc | tgaagccctg | cgtgaagctg |  360 |
| ggcaacagcg | tgatcaccca | ggcctgcccc | aaggtgagct | cgagcccat | ccccatccac |  420 |
| tactgcgccc | ccgccggctt | cgccatcctg | aagtgcaacg | acaagaagtt | caacggcagc |  480 |
| ggcccctgca | ccaacgtgag | caccgtgcag | tgcacccacg | gcatccgccc | cgtggtgagc |  540 |
| acccagctgc | tgctgaacgg | cagcctggcc | gaggagggcg | tggtgatccg | cagcgagaac |  600 |
| ttcaccgaca | acgccaagac | catcatcgtg | cagctgaagg | agagcgtgga | gatcaactgc |  660 |
| acccgcccca | caacaacac | ccgcaagagc | atcaccatcg | ccccggccg | cgccttctac |  720 |
| gccaccggcg | acatcatcgg | cgacatccgc | caggcccact | gcaacatcag | cggcgagaag |  780 |
| tggaacaaca | ccctgaagca | gatcgtgacc | aagctgcagg | cccagttcgg | caacaagacc |  840 |
| atcgtgttca | gcagagcag | cggcggcgac | cccgagatcg | tgatgcacag | cttcaactgc |  900 |
| ggcggcgagt | tcttctactg | caacagcacc | cagctgttca | acagcacctg | gaacaacacc |  960 |
| atcggcccca | caacaccaa | cggcaccatc | accctgccct | gccgcatcaa | gcagatcatc | 1020 |
| aaccgctggc | aggaggtggg | caaggccatg | tacgcccccc | ccatccgcgg | ccagatccgc | 1080 |
| tgcagcagca | acatcaccgg | cctgctgctg | accgcgacg | gcggcaagga | gatcagcaac | 1140 |
| accaccgaga | tcttccgccc | cggcggcggc | gacatgcgcg | acaactggcg | cagcgagctg | 1200 |
| tacaagtaca | aggtggtgaa | gatcgagccc | ctgggcgtgg | cccccaccaa | ggccaagcgc | 1260 |
| cgcgtggtgc | agcgcgagaa | gcgcgccgtg | accctgggcg | ccatgttcct | gggcttcctg | 1320 |
| ggcgccgccg | gcagcaccat | gggcgcccgc | agcctgaccc | tgaccgtgca | ggcccgccag | 1380 |
| ctgctgagcg | gcatcgtgca | gcagcagaac | aacctgctgc | gcgccatcga | ggcccagcag | 1440 |
| cacctgctgc | agctgaccgt | gtggggcatc | aagcagctgc | aggcccgcgt | gctggccgtg | 1500 |
| gagcgctacc | tgaaggacca | gcagctgctg | ggcatctggg | gctgcagcgg | caagctgatc | 1560 |
| tgcaccaccg | ccgtgccctg | gaacgccagc | tggagcaaca | agagcctgga | ccagatctgg | 1620 |
| aacaacatga | cctggatgga | gtgggagcgc | gagatcgaca | actacaccaa | cctgatctac | 1680 |
| accctgatcg | aggagagcca | gaaccagcag | gagaagaacg | agcaggagct | gctggagctg | 1740 |
| gacaagtggg | ccagcctgtg | gaactggttc | gacatcagca | gtggctgtg | gtacatcaag | 1800 |
| atcttcatca | tgatcgtggg | cggcctggtg | ggcctgcgca | tcgtgttcac | cgtgctgagc | 1860 |
| atcgtgaacc | gcgtgcgcca | gggctacagc | cccctgagct | ccagacccg | cttccccgcc | 1920 |
| ccccgcggcc | ccgaccgccc | cgagggcatc | gaggaggagg | gcggcgagcg | cgaccgcgac | 1980 |

-continued

```
cgcagcagcc ccctggtgca cggcctgctg gccctgatct gggacgacct gcgcagcctg    2040
tgcctgttca gctaccaccg cctgcgcgac ctgatcctga tcgccgcccg catcgtggag    2100
ctgctgggcc gccgcggctg ggaggccctg aagtactggg caacctgct gcagtactgg     2160 atccaggagc tgaagaacag cgccgtgagc ctgttcgacg ccatcgccat cgccgtggcc    2220
gagggcaccg accgcatcat cgaggtggcc cagcgcatcg gccgcgcctt cctgcacatc    2280
ccccgccgca tccgccaggg cttcgagcgc gccctgctgt aactcgagcg tgct           2334
```

<210> SEQ ID NO 8
<211> LENGTH: 2316
<212> TYPE: DNA
<213> ORGANISM: Artificial Sequence
<220> FEATURE:
<223> OTHER INFORMATION: Description of Artificial Sequence:
      Val120-Thr202

<400> SEQUENCE: 8

```
gaattcgcca ccatggatgc aatgaagaga gggctctgct gtgtgctgct gctgtgtgga     60
gcagtcttcg tttcgcccag cgccgtggag aagctgtggg tgaccgtgta ctacggcgtg    120
cccgtgtgga aggaggccac caccaccctg ttctgcgcca gcgacgccaa ggcctacgac    180
accgaggtgc acaacgtgtg gccaccacc gcctgcgtgc ccaccgaccc caaccccag    240 gagatcgtgc tggagaacgt gaccgagaac ttcaacatgt ggaagaacaa catggtggag    300
cagatgcacg aggacatcat cagcctgtgg gaccagagcc tgaagccctg cgtgggcggc    360
gccacccagg cctgccccaa ggtgagcttc gagcccatcc catccacta ctgcgccccc    420 gccggcttcg ccatcctgaa gtgcaacgac aagaagttca cggcagcgg cccctgcacc    480 aacgtgagca ccgtgcagtg cacccacggc atccgccccg tggtgagcac ccagctgctg    540
ctgaacggca gcctggccga ggagggcgtg gtgatccgca cgagaacttt caccgacaac    600
gccaagacca tcatcgtgca gctgaaggag agcgtggaga tcaactgcac ccgccccaac    660
aacaacaccc gcaagagcat caccatcggc cccggccgcg ccttctacgc caccggcgac    720
atcatcggcg acatccgcca ggcccactgc aacatcagcg cgagaagtg aacaacacc    780 ctgaagcaga tcgtgaccaa gctgcaggcc cagttcggca acaagaccat cgtgttcaag    840
cagagcagcg gcggcgaccc cgagatcgtg atgcacagct caactgcgg cggcgagttc    900 ttctactgca acagcaccca gctgttcaac agcacctgga caacaccat cggccccaac    960 aacaccaacg caccatcac cctgccctgc cgcatcaagc agatcatcaa ccgctggcag    1020
gaggtgggca aggccatgta cgccccccc atccgcggcc agatccgctg cagcagcaac    1080
atcaccggcc tgctgctgac ccgcgacggc ggcaaggaga tcagcaacac caccgagatc    1140
ttccgccccg gcggcggcga catgcgcgac aactggcgca gcgagctgta caagtacaag    1200
gtggtgaaga tcgagcccct gggcgtggcc ccaccaagg ccaagcgccg cgtggtgcag    1260
cgcgagaagc gcgccgtgac cctgggcgcc atgttcctgg gcttcctggg cgccgccggc    1320
agcaccatgg gcgcccgcag cctgaccctg accgtgcagg cccgccagct gctgagcggc    1380
atcgtgcagc agcagaacaa cctgctgcgc gccatcgagg cccagcagca cctgctgcag    1440
ctgaccgtgt ggggcatcaa gcagctgcag gcccgcgtgc tggccgtgga gcgctacctg    1500
aaggaccagc agctgctggg catctgggc tgcagcggca gctgatctg caccaccgcc    1560 gtgccctgga acgccagctg gagcaacaag agcctggacc agatctggaa caacatgacc    1620
tggatggagt gggagcgcga gatcgacaac tacaccaacc tgatctacac cctgatcgag    1680
```

```
gagagccaga accagcagga gaagaacgag caggagctgc tggagctgga caagtgggcc    1740
agcctgtgga actggttcga catcagcaag tggctgtggt acatcaagat cttcatcatg    1800
atcgtgggcg gcctggtggg cctgcgcatc gtgttcaccg tgctgagcat cgtgaaccgc    1860
gtgcgccagg gctacagccc cctgagcttc cagacccgct cccccgcccc ccgcggcccc    1920
gaccgccccg agggcatcga ggaggagggc ggcgagcgcg accgcgaccg cagcagcccc    1980
ctggtgcacg gcctgctggc cctgatctgg gacgacctgc gcagcctgtg cctgttcagc    2040
taccaccgcc tgcgcgacct gatcctgatc gccgcccgca tcgtggagct gctgggccgc    2100
cgcggctggg aggccctgaa gtactggggc aacctgctgc agtactggat ccaggagctg    2160
aagaacagcg ccgtgagcct gttcgacgcc atcgccatcg ccgtggccga gggcaccgac    2220
cgcatcatcg aggtggccca cgcatcggc cgcgccttcc tgcacatccc ccgccgcatc    2280
cgccagggct cgagcgcgc cctgctgtaa ctcgag                              2316
```

<210> SEQ ID NO 9
<211> LENGTH: 2541
<212> TYPE: DNA
<213> ORGANISM: Artificial Sequence
<220> FEATURE:
<223> OTHER INFORMATION: Description of Artificial Sequence:
      Trp427-Gly431

<400> SEQUENCE: 9

```
gaattcgcca ccatggatgc aatgaagaga gggctctgct gtgtgctgct gctgtgtgga      60
gcagtcttcg tttcgcccag cgccgtggag aagctgtggg tgaccgtgta ctacggcgtg     120
cccgtgtgga aggaggccac caccaccctg ttctgcgcca gcgacgccaa ggcctacgac     180
accgaggtgc acaacgtgtg gcccaccac gcctgcgtgc ccaccgaccc caaccccag      240 gagatcgtgc tggagaacgt gaccgagaac ttcaacatgt ggaagaacaa catggtggag     300
cagatgcacg aggacatcat cagcctgtgg gaccagagcc tgaagccctg cgtgaagctg     360 accccctgt gcgtgaccct gcactgcacc aacctgaaga cgccaccaa caccaagagc      420 agcaactgga aggagatgga ccgcggcgag atcaagaact gcagcttcaa ggtgaccacc     480
agcatccgca caagatgca aaggagtac gccctgttct acaagctgga cgtggtgccc      540
atcgacaacg acaacaccag ctacaagctg atcaactgca caccagcgt gatcacccag     600 gcctgcccca aggtgagctt cgagcccatc cccatccact actgcgcccc cgccggcttc     660
gccatcctga gtgcaacga caagaagttc aacggcagcg cccctgcac aacgtgagc       720 accgtgcagt gcacccacgg catccgcccc gtggtgagca cccagctgct gctgaacggc     780
agcctggccg aggagggcgt ggtgatccgc agcgagaact tcaccgacaa cgccaagacc     840
atcatcgtgc agctgaagga gagcgtggag atcaactgca cccgccccaa caacaacacc     900
cgcaagagca tcaccatcgg ccccggccgc gccttctacg ccaccggcga catcatcggc     960
gacatccgcc aggccactg caacatcagc ggcgagaagt ggaacaacac cctgaagcag    1020
atcgtgacca gctgcaggc ccagttcggc aacaagacca tcgtgttcaa gcagagcagc    1080
ggcggcgacc ccgagatcgt gatgcacagc ttcaactgcg gcggcgagtt cttctactgc    1140
aacagcaccc agctgttcaa cagcacctgg aacaacacca tcggcccaa caacaccaac    1200 ggcaccatca ccctgccctg ccgcatcaag cagatcatca accgctgggg cggcaaggcc    1260
atgtacgccc ccccatccg cggccagatc cgctgcagca gcaacatcac cggcctgctg    1320
ctgacccgcg acggcggcaa ggagatcagc aacaccaccg agatcttccg ccccggcggc    1380
```

```
ggcgacatgc gcgacaactg gcgcagcgag ctgtacaagt acaaggtggt gaagatcgag    1440
cccctgggcg tggcccccac caaggccaag cgccgcgtgg tgcagcgcga aagcgcgcc     1500 gtgaccctgg cgccatgtt cctgggcttc ctgggcgccg ccggcagcac catgggcgcc     1560
cgcagcctga ccctgaccgt gcaggcccgc cagctgctga gcggcatcgt gcagcagcag    1620
aacaacctgc tgcgcgccat cgaggcccag cagcacctgc tgcagctgac cgtgtggggc    1680
atcaagcagc tgcaggcccg cgtgctggcc gtggagcgct acctgaagga ccagcagctg    1740
ctgggcatct ggggctgcag cggcaagctg atctgcacca ccgccgtgcc ctggaacgcc    1800
agctggagca acaagagcct ggaccagatc tggaacaaca tgacctggat ggagtgggag    1860
cgcgagatcg acaactacac caacctgatc tacaccctga tcgaggagag ccagaaccag    1920
caggagaaga acgagcagga gctgctggag ctggacaagt gggccagcct gtggaactgg    1980
ttcgacatca gcaagtggct gtggtacatc aagatcttca tcatgatcgt gggcggcctg    2040
gtgggcctgc gcatcgtgtt caccgtgctg agcatcgtga accgcgtgcg ccagggctac    2100 agcccctga gcttccagac ccgcttcccc gccccccgcg gccccgaccg ccccgagggc    2160
atcgaggagg agggcggcga gcgcgaccgc gaccgcagca gccccctggt gcacggcctg    2220
ctggccctga tctgggacga cctgcgcagc ctgtgcctgt tcagctacca ccgcctgcgc    2280
gacctgatcc tgatcgccgc ccgcatcgtg gagctgctgg gccgccgcgg ctgggaggcc    2340
ctgaagtact ggggcaacct gctgcagtac tggatccagg agctgaagaa cagcgccgtg    2400
agcctgttcg acgccatcgc catcgccgtg gccgagggcc ccgaccgcat catcgaggtg    2460
gcccagcgca tcggccgcgc cttcctgcac atcccccgcc gcatccgcca gggcttcgag    2520
cgcgccctgc tgtaactcga g                                              2541
```

<210> SEQ ID NO 10
<211> LENGTH: 2541
<212> TYPE: DNA
<213> ORGANISM: Artificial Sequence
<220> FEATURE:
<223> OTHER INFORMATION: Description of Artificial Sequence:
      Arg426-Gly431

<400> SEQUENCE: 10

```
gaattcgcca ccatggatgc aatgaagaga gggctctgct gtgtgctgct gctgtgtgga     60
gcagtcttcg tttcgcccag cgccgtggag aagctgtggg tgaccgtgta ctacggcgtg    120
cccgtgtgga aggaggccac caccaccctg ttctgcgcca gcgacgccaa ggcctacgac    180
accgaggtgc acaacgtgtg gccaccac gcctgcgtgc ccaccgaccc caacccccag    240
gagatcgtgt tggagaacgt gaccgagaac ttcaacatgt ggaagaacaa catggtggag    300
cagatgcacg aggacatcat cagcctgtgg gaccagagcc tgaagccctg cgtgaagctg    360
acccccctgt gcgtgaccct gcactgcacc aacctgaaga cgccaccaa caccaagagc    420 agcaactgga aggagatgga ccgcggcgag atcaagaact gcagcttcaa ggtgaccacc    480
agcatccgca caagatgca aggagtac gccctgttct acaagctgga cgtggtgccc    540
atcgacaacg acaacaccag ctacaagctg atcaactgca acaccagcgt gatcacccag    600
gcctgcccca aggtgagctt cgagcccatc cccatccact actgcgcccc cgccggcttc    660
gccatcctga gtgcaacga caagaagttc aacggcagcg gccctgcac aacgtgagc    720 accgtgcagt gcacccacgg catccgcccc gtggtgagca cccagctgct gctgaacggc    780
agcctggccg aggagggcgt ggtgatccgc agcgagaact tcaccgacaa cgccaagacc    840
```

```
atcatcgtgc agctgaagga gagcgtggag atcaactgca cccgcccaa caacaacacc    900
cgcaagagca tcaccatcgg ccccggccgc gccttctacg ccaccggcga catcatcggc    960
gacatccgcc aggcccactg caacatcagc ggcgagaagt ggaacaacac cctgaagcag   1020
atcgtgacca agctgcaggc ccagttcggc aacaagacca tcgtgttcaa gcagagcagc   1080
ggcggcgacc ccgagatcgt gatgcacagc ttcaactgcg gcggcgagtt cttctactgc   1140
aacagcaccc agctgttcaa cagcacctgg aacaacacca tcggccccaa caacaccaac   1200
ggcaccatca ccctgccctg ccgcatcaag cagatcatca accgcggcgg cggcaaggcc   1260
atgtacgccc ccccatccg cggccagatc cgctgcagca gcaacatcac cggcctgctg   1320
ctgacccgcg acggcggcaa ggagatcagc aacaccaccg agatcttccg ccccggcggc   1380
ggcgacatgc gcgacaactg gcgcagcgag ctgtacaagt acaaggtggt gaagatcgag   1440
cccctgggcg tggcccccac caaggccaag cgccgcgtgg tgcagcgcga aagcgcgcc    1500
gtgaccctgg gcgccatgtt cctgggcttc ctgggcgccg ccggcagcac catgggcgcc   1560
cgcagcctga ccctgaccgt gcaggcccgc cagctgctga gcggcatcgt gcagcagcag   1620
aacaacctgc tgcgcgccat cgaggcccag cagcacctgc tgcagctgac cgtgtggggc   1680
atcaagcagc tgcaggcccg cgtgctggcc gtggagcgct acctgaagga ccagcagctg   1740
ctgggcatct ggggctgcag cggcaagctg atctgcacca ccgccgtgcc ctggaacgcc   1800
agctggagca acaagagcct ggaccagatc tggaacaaca tgacctggat ggagtgggag   1860
cgcgagatcg acaactacac caacctgatc tacaccctga tcgaggagag ccagaaccag   1920
caggagaaga cgagcagga gctgctggag ctggacaagt gggccagcct gtggaactgg   1980
ttcgacatca gcaagtggct gtggtacatc aagatcttca tcatgatcgt gggcggcctg   2040
gtgggcctgc gcatcgtgtt caccgtgctg agcatcgtga accgcgtgcg ccagggctac   2100
agcccctga gcttccagac ccgcttcccc gcccccgcg gccccgaccg ccccgagggc   2160
atcgaggagg agggcggcga gcgcgaccgc gaccgcagca gccccctggt gcacggcctg   2220
ctggccctga tctgggacga cctgcgcagc ctgtgcctgt tcagctacca ccgcctgcgc   2280
gacctgatcc tgatcgccgc ccgcatcgtg gagctgctgg gccgccgcgg ctgggaggcc   2340
ctgaagtact ggggcaacct gctgcagtac tggatccagg agctgaagaa cagcgccgtg   2400
agcctgttcg acgccatcgc catcgccgtg gccgagggca ccgaccgcat catcgaggtg   2460
gcccagcgca tcgccgcgc cttcctgcac atccccgcc gcatccgcca gggcttcgag   2520
cgcgccctgc tgtaactcga g                                             2541
```

<210> SEQ ID NO 11
<211> LENGTH: 2541
<212> TYPE: DNA
<213> ORGANISM: Artificial Sequence
<220> FEATURE:
<223> OTHER INFORMATION: Description of Artificial Sequence:
      Arg426-Gly431B

<400> SEQUENCE: 11

```
gaattcgcca ccatggatgc aatgaagaga gggctctgct gtgtgctgct gctgtgtgga     60
gcagtcttcg tttcgcccag cgccgtggag aagctgtggg tgaccgtgta ctacggcgtg    120
cccgtgtgga aggaggccac caccaccctg ttctgcgcca gcgacgccaa ggcctacgac    180
accgaggtgc acaacgtgtg gccacccac gcctgcgtgc ccaccgaccc caacccccag    240
gagatcgtgc tggagaacgt gaccgagaac ttcaacatgt ggaagaacaa catggtggag    300
```

| | |
|---|---|
| cagatgcacg aggacatcat cagcctgtgg gaccagagcc tgaagccctg cgtgaagctg | 360 |
| acccccctgt gcgtgacect gcactgcacc aacctgaaga cgccaccaa caccaagagc | 420 |
| agcaactgga aggagatgga ccgcggcgag atcaagaact gcagcttcaa ggtgaccacc | 480 |
| agcatccgca acaagatgca aaggagtac gccctgttct acaagctgga cgtggtgccc | 540 |
| atcgacaacg acaacaccag ctacaagctg atcaactgca acaccagcgt gatcacccag | 600 |
| gcctgcccca aggtgagctt cgagcccatc cccatccact actgcgcccc cgccggcttc | 660 |
| gccatcctga agtgcaacga caagaagttc aacggcagcg cccctgcac caacgtgagc | 720 |
| accgtgcagt gcacccacgg catccgcccc gtggtgagca cccagctgct gctgaacggc | 780 |
| agcctggccg aggagggcgt ggtgatccgc agcgagaact tcaccgacaa cgccaagacc | 840 |
| atcatcgtgc agctgaagga gagcgtggag atcaactgca cccgccccaa caacaacacc | 900 |
| cgcaagagca tcaccatcgg ccccggccgc gccttctacg ccaccggcga catcatcggc | 960 |
| gacatccgcc aggcccactg caacatcagc ggcgagaagt ggaacaacac cctgaagcag | 1020 |
| atcgtgacca gctgcaggc ccagttcggc aacaagacca tcgtgttcaa gcagagcagc | 1080 |
| ggcggcgacc ccgagatcgt gatgcacagc ttcaactgcg gcggcgagtt cttctactgc | 1140 |
| aacagcaccc agctgttcaa cagcacctgg aacaacacca tcggccccaa caacaccaac | 1200 |
| ggcaccatca ccctgccctg ccgcatcaag cagatcatca accgcggcag cggcaaggcc | 1260 |
| atgtacgccc cccccatccg cggccagatc cgctgcagca gcaacatcac cggcctgctg | 1320 |
| ctgacccgcg acggcggcaa ggagatcagc aacaccaccg agatcttccg ccccggcggc | 1380 |
| ggcgacatgc gcgacaactg gcgcagcgag ctgtacaagt acaaggtggt gaagatcgag | 1440 |
| cccctgggcg tggcccccac caaggccaag cgccgcgtgg tgcagcgcga aagcgcgcc | 1500 |
| gtgaccctgg gcgccatgtt cctgggcttc ctgggcgccg ccggcagcac catgggcgcc | 1560 |
| cgcagcctga ccctgaccgt gcaggcccgc cagctgctga cggcatcgt gcagcagcag | 1620 |
| aacaacctgc tgcgcgccat cgaggcccag cagcacctgc tgcagctgac cgtgtggggc | 1680 |
| atcaagcagc tgcaggcccg cgtgctggcc gtggagcgct acctgaagga ccagcagctg | 1740 |
| ctgggcatct ggggctgcag cggcaagctg atctgcacca ccgccgtgcc ctggaacgcc | 1800 |
| agctggagca acaagagcct ggaccagatc tggaacaaca tgacctggat ggagtgggag | 1860 |
| cgcgagatcg acaactacac caacctgatc tacaccctga tcgaggagag ccagaaccag | 1920 |
| caggagaaga acgagcagga gctgctggag ctggacaagt gggccagcct gtggaactgg | 1980 |
| ttcgacatca gcaagtggct gtggtacatc aagatcttca tcatgatcgt gggcggcctg | 2040 |
| gtgggcctgc gcatcgtgtt caccgtgctg agcatcgtga accgcgtgcg ccagggctac | 2100 |
| agccccctga gcttccagac ccgcttcccc gcccccgcg ccccgaccg ccccgagggc | 2160 |
| atcgaggagg agggcggcga gcgcgaccgc gaccgcagca gccccctggt gcacggcctg | 2220 |
| ctggccctga tctgggacga cctgcgcagc ctgtgcctgt tcagctacca ccgcctgcgc | 2280 |
| gacctgatcc tgatcgcccgc ccgcatcgtg gagctgctgg gccgccgcgg ctgggaggcc | 2340 |
| ctgaagtact ggggcaacct gctgcagtac tggatccagg agctgaagaa cagcgccgtg | 2400 |
| agcctgttcg acgccatcgc catcgccgtg gccgagggca ccgaccgcat catcgaggtg | 2460 |
| gcccagcgca tcggccgcgc cttcctgcac atccccgcc gcatccgcca gggcttcgag | 2520 |
| cgcgcccctgc tgtaactcga g | 2541 |

<210> SEQ ID NO 12

<211> LENGTH: 2541
<212> TYPE: DNA
<213> ORGANISM: Artificial Sequence
<220> FEATURE:
<223> OTHER INFORMATION: Description of Artificial Sequence:
      Arg426-Lys432

<400> SEQUENCE: 12

| | | | | | |
|---|---|---|---|---|---|
| gaattcgcca | ccatggatgc | aatgaagaga | gggctctgct | gtgtgctgct | gctgtgtgga | 60 |
| gcagtcttcg | tttcgcccag | cgccgtggag | aagctgtggg | tgaccgtgta | ctacggcgtg | 120 |
| cccgtgtgga | aggaggccac | caccaccctg | ttctgcgcca | cgacgccaa | ggcctacgac | 180 |
| accgaggtgc | acaacgtgtg | gccacccac | gcctgcgtgc | caccgaccc | caacccccag | 240 |
| gagatcgtgc | tggagaacgt | gaccgagaac | ttcaacatgt | ggaagaacaa | catggtggag | 300 |
| cagatgcacg | aggacatcat | cagcctgtgg | gaccagagcc | tgaagccctg | cgtgaagctg | 360 |
| acccccctgt | gcgtgaccct | gcactgcacc | aacctgaaga | cgccaccaa | caccaagagc | 420 |
| agcaactgga | aggagatgga | ccgcggcgag | atcaagaact | gcagcttcaa | ggtgaccacc | 480 |
| agcatccgca | acaagatgca | gaaggagtac | gccctgttct | acaagctgga | cgtggtgccc | 540 |
| atcgacaacg | acaacaccag | ctacaagctg | atcaactgca | acaccagcgt | gatcacccag | 600 |
| gcctgcccca | aggtgagctt | cgagcccatc | cccatccact | actgcgcccc | cgccggcttc | 660 |
| gccatcctga | agtgcaacga | caagaagttc | aacggcagcg | cccctgcac | caacgtgagc | 720 |
| accgtgcagt | gcacccacgg | catccgcccc | gtggtgagca | cccagctgct | gctgaacggc | 780 |
| agcctggccg | aggagggcgt | ggtgatccgc | agcgagaact | tcaccgacaa | cgccaagacc | 840 |
| atcatcgtgc | agctgaagga | gagcgtggag | atcaactgca | cccgccccaa | caacaacacc | 900 |
| cgcaagagca | tcaccatcgg | ccccggccgc | gccttctacg | ccaccggcga | catcatcggc | 960 |
| gacatccgcc | aggcccactg | caacatcagc | ggcgagaagt | ggaacaacac | cctgaagcag | 1020 |
| atcgtgacca | agctgcaggc | ccagttcggc | aacaagacca | tcgtgttcaa | gcagagcagc | 1080 |
| ggcggcgacc | ccgagatcgt | gatgcacagc | ttcaactgcg | gcggcgagtt | cttctactgc | 1140 |
| aacagcaccc | agctgttcaa | cagcacctgg | aacaacacca | tcggccccaa | caacaccaac | 1200 |
| ggcaccatca | ccctgccctg | ccgcatcaag | cagatcatca | accgcggcgg | caacaaggcc | 1260 |
| atgtacgccc | ccccatccg | cggccagatc | cgctgcagca | gcaacatcac | cggcctgctg | 1320 |
| ctgacccgcg | acggcggcaa | ggagatcagc | aacaccaccg | agatcttccg | ccccggcggc | 1380 |
| ggcgacatgc | gcgacaactg | gcgcagcgag | ctgtacaagt | acaaggtggt | gaagatcgag | 1440 |
| cccctgggcg | tggcccccac | caaggccaag | cgccgcgtgg | tgcagcgcga | aagcgcgcc | 1500 |
| gtgaccctgg | gcgccatgtt | cctgggcttc | ctgggcgccg | ccggcagcac | catgggcgcc | 1560 |
| cgcagcctga | ccctgaccgt | gcaggcccgc | cagctgctga | gcggcatcgt | gcagcagcag | 1620 |
| aacaacctgc | tgcgcgccat | cgaggcccag | cagcacctgc | tgcagctgac | cgtgtggggc | 1680 |
| atcaagcagc | tgcaggcccg | cgtgctggcc | gtggagcgct | acctgaagga | ccagcagctg | 1740 |
| ctgggcatct | ggggctgcag | cggcaagctg | atctgcacca | ccgccgtgcc | ctggaacgcc | 1800 |
| agctggagca | acaagagcct | ggaccagatc | tggaacaaca | tgacctggat | ggagtgggag | 1860 |
| cgcgagatcg | acaactacac | caacctgatc | tacaccctga | tcgaggagag | ccagaaccag | 1920 |
| caggagaaga | acgagcagga | gctgctggag | ctggacaagt | gggccagcct | gtggaactgg | 1980 |
| ttcgacatca | gcaagtggct | gtggtacatc | aagatcttca | tcatgatcgt | gggcggcctg | 2040 |
| gtgggcctgc | gcatcgtgtt | caccgtgctg | agcatcgtga | accgcgtgcg | ccagggctac | 2100 |

```
agcccectga gcttccagac ccgcttcccc gcccccccgcg gccccgaccg ccccgagggc        2160
atcgaggagg agggcggcga gcgcgaccgc gaccgcagca gcccectggt gcacggcctg        2220 ctggccctga tctgggacga cctgcgcagc ctgtgcctgt tcagctacca ccgcctgcgc        2280
gacctgatcc tgatcgccgc ccgcatcgtg gagctgctgg gccgccgcgg ctgggaggcc        2340
ctgaagtact ggggcaacct gctgcagtac tggatccagg agctgaagaa cagcgccgtg        2400
agcctgttcg acgccatcgc catcgccgtg gccgagggca ccgaccgcat catcgaggtg        2460
gcccagcgca tcggccgcgc cttcctgcac atcccccgcc gcatccgcca gggcttcgag        2520
cgcgccctgc tgtaactcga g                                                  2541
```

<210> SEQ ID NO 13
<211> LENGTH: 2535
<212> TYPE: DNA
<213> ORGANISM: Artificial Sequence
<220> FEATURE:
<223> OTHER INFORMATION: Description of Artificial Sequence:
      Asn425-Lys432

<400> SEQUENCE: 13

```
gaattcgcca ccatggatgc aatgaagaga gggctctgct gtgtgctgct gctgtgtgga         60
gcagtcttcg tttcgcccag cgccgtggag aagctgtggg tgaccgtgta ctacggcgtg        120
cccgtgtgga aggaggccac caccaccctg ttctgcgcca gcgacgccaa ggcctacgac        180
accgaggtgc acaacgtgtg gccaccac gcctgcgtgc ccaccgaccc caaccccag          240 gagatcgtgc tggagaacgt gaccgagaac ttcaacatgt ggaagaacaa catggtggag        300
cagatgcacg aggacatcat cagcctgtgg gaccagagcc tgaagccctg cgtgaagctg        360 accccccctgt gcgtgaccct gcactgcacc aacctgaaga cgccaccaa caccaagagc        420 agcaactgga aggagatgga ccgcggcgag atcaagaact gcagcttcaa ggtgaccacc        480
agcatccgca caagatgca aggagtac gccctgttct acaagctgga cgtggtgccc          540
atcgacaacg acaacaccag ctacaagctg atcaactgca caccagcgt gatcacccag         600 gcctgcccca aggtgagctt cgagcccatc cccatccact actgcgcccc cgccggcttc        660
gccatcctga agtgcaacga caagaagttc aacggcagcg gcccctgcac caacgtgagc        720
accgtgcagt gcacccacgg catccgcccc gtggtgagca cccagctgct gctgaacggc        780
agcctggccg aggagggcgt ggtgatccgc agcgagaact tcaccgacaa cgccaagacc        840
atcatcgtgc agctgaagga gagcgtggag atcaactgca cccgcccaa caacaacacc         900 cgcaagagca tcaccatcgg ccccggccgc gccttctacg ccaccggcga catcatcggc        960
gacatccgcc aggcccactg caacatcagc ggcgagaagt ggaacaacac cctgaagcag       1020
atcgtgacca agctgcaggc ccagttcggc aacaagacca tcgtgttcaa gcagagcagc       1080
ggcggcgacc ccgagatcgt gatgcacagc ttcaactgcg gcggcgagtt cttctactgc       1140
aacagcaccc agctgttcaa cagcacctgg aacaacacca tcggccccaa caccaccac       1200 ggcaccatca ccctgccctg ccgcatcaag cagatcatca acgcccccaa ggccatgtac       1260 gccccccca tccgcggcca gatccgctgc agcagcaaca tcaccggcct gctgctgacc       1320
cgcgacggcg gcaaggagat cagcaacacc accgagatct ccgcccccgg cggcggcgac       1380
atgcgcgaca actggcgcag cgagctgtac aagtacaagg tggtgaagat cgagcccctg       1440
ggcgtggccc ccaccaaggc caagcgccgc gtggtgcagc gcgagaagcg cgccgtgacc       1500
ctgggcgcca tgttcctggg cttcctgggc gccgccggca gcaccatggg cgcccgcagc       1560
```

-continued

```
ctgaccctga ccgtgcaggc ccgccagctg ctgagcggca tcgtgcagca gcagaacaac    1620
ctgctgcgcg ccatcgaggc ccagcagcac ctgctgcagc tgaccgtgtg gggcatcaag    1680
cagctgcagg cccgcgtgct ggccgtggag cgctacctga aggaccagca gctgctgggc    1740
atctggggct gcagcggcaa gctgatctgc accaccgccg tgccctggaa cgccagctgg    1800
agcaacaaga gcctggacca gatctggaac aacatgacct ggatggagtg ggagcgcgag    1860
atcgacaact acaccaacct gatctacacc ctgatcgagg agagccagaa ccagcaggag    1920
aagaacgagc aggagctgct ggagctggac aagtgggcca gcctgtggaa ctggttcgac    1980
atcagcaagt ggctgtggta catcaagatc ttcatcatga tcgtgggcgg cctggtgggc    2040
ctgcgcatcg tgttcaccgt gctgagcatc gtgaaccgcg tgcgccaggg ctacagcccc    2100
ctgagcttcc agacccgctt ccccgccccc cgcggcccg accgcccga gggcatcgag    2160
gaggagggcg gcgagcgcga ccgcgaccgc agcagccccc tggtgcacgg cctgctggcc    2220
ctgatctggg acgacctgcg cagcctgtgc ctgttcagct accaccgcct gcgcgacctg    2280
atcctgatcg ccgcccgcat cgtggagctg ctgggccgcc gcggctggga ggccctgaag    2340
tactggggca acctgctgca gtactggatc caggagctga agaacagcgc cgtgagcctg    2400
ttcgacgcca tcgccatcgc cgtggccgag ggcaccgacc gcatcatcga ggtggcccag    2460
cgcatcggcc gcgccttcct gcacatcccc cgccgcatcc gccagggctt cgagcgcgcc    2520
ctgctgtaac tcgag                                                    2535
```

<210> SEQ ID NO 14
<211> LENGTH: 2529
<212> TYPE: DNA
<213> ORGANISM: Artificial Sequence
<220> FEATURE:
<223> OTHER INFORMATION: Description of Artificial Sequence: Ile424-Ala433

<400> SEQUENCE: 14

```
gaattcgcca ccatggatgc aatgaagaga gggctctgct gtgtgctgct gctgtgtgga      60
gcagtcttcg tttcgcccag cgccgtggag aagctgtggg tgaccgtgta ctacggcgtg     120
cccgtgtgga aggaggccac caccaccctg ttctgcgcca gcgacgccaa ggcctacgac     180
accgaggtgc acaacgtgtg gaccacccac gcctgcgtgc ccaccgaccc caaccccccag   240
gagatcgtgc tggagaacgt gaccgagaac ttcaacatgt ggaagaacaa catggtggag    300
cagatgcacg aggacatcat cagcctgtgg gaccagagcc tgaagccctg cgtgaagctg   360
accccccctgt gcgtgacccct gcactgcacc aacctgaaga cgccaccaa caccaagagc   420
agcaactgga aggagatgga ccgcggcgag atcaagaact gcagcttcaa ggtgaccacc   480
agcatccgca caagatgca aaggagtac gccctgttct acaagctgga cgtggtgccc    540
atcgacaacg acaacaccag ctacaagctg atcaactgca caccagcgt gatcacccag    600
gcctgcccca aggtgagctt cgagcccatc cccatccact actgcgcccc cgccggcttc    660
gccatcctga gtgcaacga caagaagttc aacggcagcg gccccctgca caacgtgagc    720
accgtgcagt gcacccacgg catccgcccc gtggtgagca cccagctgct gctgaacggc    780
agcctggccg aggagggcgt ggtgatccgc agcgagaact tcaccgacaa cgccaagacc    840
atcatcgtgc agctgaagga gagcgtggag atcaactgca cccgccccaa caacaacacc    900
cgcaagagca tcaccatcgg ccccggccgc gccttctacg ccaccggcga catcatcggc    960
gacatccgcc aggcccactg caacatcagc ggcgagaagt ggaacaacac cctgaagcag   1020
```

-continued

| | |
|---|---|
| atcgtgacca agctgcaggc ccagttcggc aacaagacca tcgtgttcaa gcagagcagc | 1080 |
| ggcggcgacc ccgagatcgt gatgcacagc ttcaactgcg gcggcgagtt cttctactgc | 1140 |
| aacagcaccc agctgttcaa cagcacctgg aacaacacca tcggcCccaa caacaccaac | 1200 |
| ggcaccatca ccctgccctg ccgcatcaag cagatcatcg gcggcgccat gtacgccccc | 1260 |
| cccatccgcg ccagatccg ctgcagcagc aacatcaccg gcctgctgct gacccgcgac | 1320 |
| ggcggcaagg agatcagcaa caccaccgag atcttccgcc ccggcggcgg cgacatgcgc | 1380 |
| gacaactggc gcagcgagct gtacaagtac aaggtggtga agatcgagcc cctgggcgtg | 1440 |
| gcccccacca aggccaagcg ccgcgtggtg cagcgcgaga gcgcgccgt gaccctgggc | 1500 |
| gccatgttcc tgggcttcct gggcgccgcc ggcagcacca tgggcgcccg cagcctgacc | 1560 |
| ctgaccgtgc aggcccgcca gctgctgagc ggcatcgtgc agcagcagaa caacctgctg | 1620 |
| cgcgccatcg aggcccagca gcacctgctg cagctgaccg tgtggggcat caagcagctg | 1680 |
| caggcccgcg tgctggccgt ggagcgctac ctgaaggacc agcagctgct gggcatctgg | 1740 |
| ggctgcagcg gcaagctgat ctgcaccacc gccgtgccct ggaacgccag ctggagcaac | 1800 |
| aagagcctgg accagatctg gaacaacatg acctggatgg agtgggagcg cgagatcgac | 1860 |
| aactacacca acctgatcta cacctgatc gaggagagcc agaaccagca ggagaagaac | 1920 |
| gagcaggagc tgctggagct ggacaagtgg gccagcctgt ggaactggtt cgacatcagc | 1980 |
| aagtggctgt ggtacatcaa gatcttcatc atgatcgtgg gcggcctggt gggcctgcgc | 2040 |
| atcgtgttca ccgtgctgag catcgtgaac cgcgtgcgcc agggctacag cccctgagc | 2100 |
| ttccagaccc gcttccccgc ccccgcggc cccgaccgcc ccgagggcat cgaggaggag | 2160 |
| ggcggcgagc gcgaccgcga ccgcagcagc cccctggtgc acggcctgct ggccctgatc | 2220 |
| tgggacgacc tgcgcagcct gtgcctgttc agctaccacc gcctgcgcga cctgatcctg | 2280 |
| atcgccgccc gcatcgtgga gctgctgggc cgccgcggct gggaggccct gaagtactgg | 2340 |
| ggcaacctgc tgcagtactg gatccaggag ctgaagaaca gcgccgtgag cctgttcgac | 2400 |
| gccatcgcca tcgccgtggc cgagggcacc gaccgcatca tcgaggtggc ccagcgcatc | 2460 |
| ggccgcgcct tcctgcacat ccccgccgc atccgccagg gcttcgagcg cgccctgctg | 2520 |
| taactcgag | 2529 |

<210> SEQ ID NO 15
<211> LENGTH: 2523
<212> TYPE: DNA
<213> ORGANISM: Artificial Sequence
<220> FEATURE:
<223> OTHER INFORMATION: Description of Artificial Sequence:
      Ile423-Met434

<400> SEQUENCE: 15

| | |
|---|---|
| gaattcgcca ccatggatgc aatgaagaga gggctctgct gtgtgctgct gctgtgtgga | 60 |
| gcagtcttcg tttcgcccag cgccgtggag aagctgtggg tgaccgtgta ctacggcgtg | 120 |
| cccgtgtgga aggaggccac caccaccctg ttctgcgcca gcgacgccaa ggcctacgac | 180 |
| accgaggtgc acaacgtgtg gccaccac gcctgcgtgc ccaccgaccc caaccccag | 240 |
| gagatcgtgc tggagaacgt gaccgagaac ttcaacatgt ggaagaacaa catggtggag | 300 |
| cagatgcacg aggacatcat cagcctgtgg gaccagagcc tgaagccctg cgtgaagctg | 360 |
| accccctgt gcgtgaccct gcactgcacc aacctgaaga acgccaccaa caccaagagc | 420 |
| agcaactgga aggagatgga ccgcggcgag atcaagaact gcagcttcaa ggtgaccacc | 480 |

-continued

```
agcatccgca acaagatgca gaaggagtac gccctgttct acaagctgga cgtggtgccc    540
atcgacaacg acaacaccag ctacaagctg atcaactgca acaccagcgt gatcacccag    600
gcctgcccca aggtgagctt cgagcccatc cccatccact actgcgcccc cgccggcttc    660
gccatcctga agtgcaacga caagaagttc aacggcagcg gcccctgcac caacgtgagc    720
accgtgcagt gcacccacgg catccgcccc gtggtgagca cccagctgct gctgaacggc    780
agcctggccg aggagggcgt ggtgatccgc agcgagaact tcaccgacaa cgccaagacc    840
atcatcgtgc agctgaagga gagcgtggag atcaactgca cccgccccaa caacaacacc    900
cgcaagagca tcaccatcgg ccccggccgc gccttctacg ccaccggcga catcatcggc    960
gacatccgcc aggcccactg caacatcagc ggcgagaagt ggaacaacac cctgaagcag    1020
atcgtgacca gctgcaggc ccagttcggc aacaagacca tcgtgttcaa gcagagcagc    1080
ggcggcgacc ccgagatcgt gatgcacagc ttcaactgcg gcggcgagtt cttctactgc    1140
aacagcaccc agctgttcaa cagcacctgg aacaacacca tcggcccaa caacaccaac    1200 ggcaccatca ccctgccctg ccgcatcaag cagatcggcg gcatgtacgc cccccccatc    1260
cgcggccaga tccgctgcag cagcaacatc accggcctgc tgctgacccg cgacggcggc    1320
aaggagatca gcaacaccac cgagatcttc cgccccggcg gcggcgacat gcgcgacaac    1380
tggcgcagcg agctgtacaa gtacaaggtg gtgaagatcg agcccctggg cgtggccccc    1440
accaaggcca gcgccgcgt ggtgcagcgc gagaagcgcg ccgtgaccct gggcgccatg    1500
ttcctgggct tcctgggcgc cgccggcagc accatgggcg cccgcagcct gacctgacc    1560 gtgcaggccc gccagctgct gagcggcatc gtgcagcagc agaacaacct gctgcgcgcc    1620
atcgaggccc agcagcacct gctgcagctg accgtgtggg gcatcaagca gctgcaggcc    1680
cgcgtgctgg ccgtggagcg ctacctgaag gaccagcagc tgctgggcat ctggggctgc    1740
agcggcaagc tgatctgcac caccgccgtg ccctggaacg ccagctggag caacaagagc    1800
ctggaccaga tctggaacaa catgacctgg atggagtggg agcgcgagat cgacaactac    1860
accaacctga tctacaccct gatcgaggag agccagaacc agcaggagaa gaacgagcag    1920
gagctgctgg agctggacaa gtgggccagc ctgtggaact ggttcgacat cagcaagtgg    1980
ctgtggtaca tcaagatctt catcatgatc gtgggcggcc tggtgggcct gcgcatcgtg    2040
ttcaccgtgc tgagcatcgt gaaccgcgtg cgccagggct acagccccct gagcttccag    2100
acccgcttcc ccgccccccg cggccccgac cgccccgagg catcgagga ggagggcggc    2160 gagcgcgacc gcgaccgcag cagcccctg gtgcacggc tgctggccct gatctgggac    2220
gacctgcgca gcctgtgcct gttcagctac accgcctgc gcgacctgat cctgatcgcc    2280
gcccgcatcg tggagctgct gggccgccgc ggctggagg ccctgaagta ctggggcaac    2340
ctgctgcagt actggatcca ggagctgaag aacagcgccg tgagcctgtt cgacgccatc    2400
gccatcgccg tggccgaggg caccgaccgc atcatcgagg tggcccagcg catcggccgc    2460
gccttcctgc acatcccccg ccgcatccgc cagggcttcg agcgcgccct gctgtaactc    2520
gag                                                                  2523
```

<210> SEQ ID NO 16
<211> LENGTH: 2517
<212> TYPE: DNA
<213> ORGANISM: Artificial Sequence
<220> FEATURE:
<223> OTHER INFORMATION: Description of Artificial Sequence:
    Gln422-Tyr435

<400> SEQUENCE: 16

```
gaattcgcca ccatggatgc aatgaagaga gggctctgct gtgtgctgct gctgtgtgga      60
gcagtcttcg tttcgcccag cgccgtggag aagctgtggg tgaccgtgta ctacggcgtg     120
cccgtgtgga aggaggccac caccaccctg ttctgcgcca gcgacgccaa ggcctacgac     180
accgaggtgc acaacgtgtg gccaccac gcctgcgtgc ccaccgaccc caaccccag        240
```

<400> SEQUENCE: 16

```
gaattcgcca ccatggatgc aatgaagaga gggctctgct gtgtgctgct gctgtgtgga      60
gcagtcttcg tttcgcccag cgccgtggag aagctgtggg tgaccgtgta ctacggcgtg     120
cccgtgtgga aggaggccac caccaccctg ttctgcgcca gcgacgccaa ggcctacgac     180
accgaggtgc acaacgtgtg gccaccac gcctgcgtgc ccaccgaccc caaccccag        240
gagatcgtgc tggagaacgt gaccgagaac ttcaacatgt ggaagaacaa catggtggag     300
cagatgcacg aggacatcat cagcctgtgg gaccagagcc tgaagccctg cgtgaagctg     360
accccctgt gcgtgaccct gcactgcacc aacctgaaga cgccaccaa caccaagagc       420
agcaactgga aggagatgga ccgcggcgag atcaagaact gcagcttcaa ggtgaccacc     480
agcatccgca caagatgca aggagtac gccctgttct acaagctgga cgtggtgccc        540
atcgacaacg acaacaccag ctacaagctg atcaactgca acaccagcgt gatcacccag     600
gcctgcccca aggtgagctt cgagcccatc cccatccact actgcgcccc cgccggcttc     660
gccatcctga agtgcaacga caagaagttc aacggcagcg gccctgcac caacgtgagc      720
accgtgcagt gcacccacgg catccgcccc gtggtgagca cccagctgct gctgaacggc     780
agcctggccg aggagggcgt ggtgatccgc agcgagaact tcaccgacaa cgccaagacc     840
atcatcgtgc agctgaagga gagcgtggag atcaactgca cccgccccaa caacaacacc    900
cgcaagagca tcaccatcgg ccccggccgc gccttctacg ccaccggcga catcatcggc     960
gacatccgcc aggcccactg caacatcagc ggcgagaagt ggaacaacac cctgaagcag    1020
atcgtgacca agctgcaggc ccagttcggc aacaagacca tcgtgttcaa gcagagcagc    1080
ggcggcgacc ccgagatcgt gatgcacagc ttcaactgcg gcggcgagtt cttctactgc    1140
aacagcaccc agctgttcaa cagcacctgg aacaacacca tcggccccaa caacaccaac    1200
ggcaccatca ccctgccctg ccgcatcaag cagggcggct acgcccccc catccgcggc     1260
cagatccgct gcagcagcaa catcaccggc ctgctgctga cccgcgacgg cggcaaggag    1320
atcagcaaca ccaccgagat cttccgcccc ggcggcggcg acatgcgcga caactggcgc    1380
agcgagctgt acaagtacaa ggtggtgaag atcgagcccc tgggcgtggc ccccaccaag    1440
gccaagcgcc gcgtggtgca gcgcgagaag cgcgccgtga ccctgggcgc catgttcctg    1500
ggcttcctgg gcgccgccgg cagcaccatg ggcgcccgca gcctgaccct gaccgtgcag    1560
gcccgccagc tgctgagcgg catcgtgcag cagcagaaca acctgctgcg cgccatcgag    1620
gcccagcagc acctgctgca gctgaccgtg tggggcatca agcagctgca ggcccgcgtg    1680
ctggccgtgg agcgctacct gaaggaccag cagctgctgg gcatctgggg ctgcagcggc    1740
aagctgatct gcaccaccgc cgtgccctgg aacgccagct ggagcaacaa gagcctggac    1800
cagatctgga acaacatgac ctggatggag tgggagcgcg agatcgacaa ctacaccaac    1860
ctgatctaca ccctgatcga ggagagccag aaccagcagg agaagaacga gcaggagctg    1920
ctggagctgg acaagtgggc cagcctgtgg aactggttcg acatcagcaa gtggctgtgg    1980
tacatcaaga tcttcatcat gatcgtgggc ggcctggtgg gcctgcgcat cgtgttcacc    2040
gtgctgagca tcgtgaaccg cgtgcgccag ggctacagcc ccctgagctt ccagacccgc    2100
ttccccgccc ccgcggcccc cgaccgcccc gagggcatcg aggaggaggg cggcgagcgc    2160
gaccgcgacc gcagcagccc cctggtgcac ggcctgctgg ccctgatctg ggacgacctg    2220
cgcagcctgt gcctgttcag ctaccaccgc ctgcgcgacc tgatcctgat cgccgcccgc    2280
atcgtggagc tgctgggccg ccgcggctgg gaggccctga gtactgggg caacctgctg    2340
```

-continued

| | |
|---|---|
| cagtactgga tccaggagct gaagaacagc gccgtgagcc tgttcgacgc catcgccatc | 2400 |
| gccgtggccg agggcaccga ccgcatcatc gaggtggccc agcgcatcgg ccgcgccttc | 2460 |
| ctgcacatcc cccgccgcat ccgccagggc ttcgagcgcg ccctgctgta actcgag | 2517 |

<210> SEQ ID NO 17
<211> LENGTH: 2517
<212> TYPE: DNA
<213> ORGANISM: Artificial Sequence
<220> FEATURE:
<223> OTHER INFORMATION: Description of Artificial Sequence:
    Gln422-Tyr435B

<400> SEQUENCE: 17

| | |
|---|---|
| gaattcgcca ccatggatgc aatgaagaga gggctctgct gtgtgctgct gctgtgtgga | 60 |
| gcagtcttcg tttcgcccag cgccgtggag aagctgtggg tgaccgtgta ctacggcgtg | 120 |
| cccgtgtgga aggaggccac caccaccctg ttctgcgcca cgacgccaa ggcctacgac | 180 |
| accgaggtgc acaacgtgtg gccaccac gcctgcgtgc ccaccgaccc caaccccag | 240 |
| gagatcgtgt ggagaacgt gaccgagaac ttcaacatgt ggaagaacaa catggtggag | 300 |
| cagatgcacg aggacatcat cagcctgtgg gaccagagcc tgaagccctg cgtgaagctg | 360 |
| accccctgt gcgtgaccct gcactgcacc aacctgaaga cgccaccaa caccaagagc | 420 |
| agcaactgga aggagatgga ccgcggcgag atcaagaact gcagcttcaa ggtgaccacc | 480 |
| agcatccgca caagatgca gaaggagtac gccctgttct acaagctgga cgtggtgccc | 540 |
| atcgacaacg acaacaccag ctacaagctg atcaactgca caccagcgt gatcacccag | 600 |
| gcctgcccca aggtgagctt cgagcccatc cccatccact actgcgcccc cgccggcttc | 660 |
| gccatcctga agtgcaacga caagaagttc aacggcagcg gcccctgcac caacgtgagc | 720 |
| accgtgcagt gcacccacgg catccgcccc gtggtgagca cccagctgct gctgaacggc | 780 |
| agcctggccg aggagggcgt ggtgatccgc agcgagaact tcaccgacaa cgccaagacc | 840 |
| atcatcgtgc agctgaagga gagcgtggag atcaactgca cccgccccaa caacaacacc | 900 |
| cgcaagagca tcaccatcgg ccccggccgc gccttctacg ccaccggcga catcatcggc | 960 |
| gacatccgcc aggcccactg caacatcagc ggcgagaagt ggaacaacac cctgaagcag | 1020 |
| atcgtgacca agctgcaggc ccagttcggc aacaagacca tcgtgttcaa gcagagcagc | 1080 |
| ggcggcgacc ccgagatcgt gatgcacagc ttcaactgcg gcggcgagtt cttctactgc | 1140 |
| aacagcaccc agctgttcaa cagcacctgg aacaacacca tcggccccaa caacaccaac | 1200 |
| ggcaccatca ccctgccctg ccgcatcaag caggccccct acgcccccc catccgcggc | 1260 |
| cagatccgct gcagcagcaa catcaccggc ctgctgctga cccgcgacgg cggcaaggag | 1320 |
| atcagcaaca ccaccgagat cttccgcccc ggcggcggcg acatgcgcga caactggcgc | 1380 |
| agcgagctgt acaagtacaa ggtggtgaag atcgagcccc tgggcgtggc ccccaccaag | 1440 |
| gccaagcgcc gcgtggtgca gcgcgagaag cgcgccgtga ccctgggcgc catgttcctg | 1500 |
| ggcttcctgg gcgccgccgg cagcaccatg ggcgcccgca gctgaccct gaccgtgcag | 1560 |
| gcccgccagc tgctgagcgg catcgtgcag cagcagaaca acctgctgcg cgccatcgag | 1620 |
| gcccagcagc acctgctgca gctgaccgtg tggggcatca gcagctgca ggcccgcgtg | 1680 |
| ctggccgtgg agcgctacct gaaggaccag cagctgctgg gcatctgggg ctgcagcggc | 1740 |
| aagctgatct gcaccaccgc cgtgccctgg aacgccagct ggagcaacaa gagcctggac | 1800 |
| cagatctgga acaacatgac ctggatggag tgggagcgcg agatcgacaa ctacaccaac | 1860 |

-continued

```
ctgatctaca ccctgatcga ggagagccag aaccagcagg agaagaacga gcaggagctg   1920
ctggagctgg acaagtgggc cagcctgtgg aactggttcg acatcagcaa gtggctgtgg   1980
tacatcaaga tcttcatcat gatcgtgggc ggcctggtgg cctgcgcat cgtgttcacc    2040 gtgctgagca tcgtgaaccg cgtgcgccag ggctacagcc ccctgagctt ccagacccgc   2100
ttccccgccc ccgcggccc cgaccgcccc gagggcatcg aggaggaggg cggcgagcgc    2160
gaccgcgacc gcagcagccc cctggtgcac ggcctgctgg ccctgatctg ggacgacctg   2220
cgcagcctgt gcctgttcag ctaccaccgc ctgcgcgacc tgatcctgat cgccgcccgc   2280
atcgtggagc tgctgggccg ccgcggctgg gaggccctga gtactgggg caacctgctg    2340 cagtactgga tccaggagct gaagaacagc gccgtgagcc tgttcgacgc catcgccatc   2400
gccgtggccg agggcaccga ccgcatcatc gaggtggccc agcgcatcgg ccgcgccttc   2460
ctgcacatcc ccgccgcat ccgccagggc ttcgagcgcg ccctgctgta actcgag      2517
```

<210> SEQ ID NO 18
<211> LENGTH: 2322
<212> TYPE: DNA
<213> ORGANISM: Artificial Sequence
<220> FEATURE:
<223> OTHER INFORMATION: Description of Artificial Sequence:
      Leu122-Ser199; Arg426-Gly431

<400> SEQUENCE: 18

```
gaattcgcca ccatggatgc aatgaagaga gggctctgct gtgtgctgct gctgtgtgga     60
gcagtcttcg tttcgcccag cgccgtggag aagctgtggg tgaccgtgta ctacggcgtg   120
cccgtgtgga aggaggccac caccaccctg ttctgcgcca cgacgccaa ggcctacgac    180 accgaggtgc acaacgtgtg ggccacccac gcctgcgtgc ccaccgaccc caacccccag   240
gagatcgtgc tggagaacgt gaccgagaac ttcaacatgt ggaagaacaa catggtggag   300
cagatgcacg aggacatcat cagcctgtgg gaccagagcc tgaagccctg cgtgaagctg    360
ggcaacagcg tgatcaccca ggcctgcccc aaggtgagct cgagcccat ccccatccac    420 tactgcgccc ccgccggctt cgccatcctg aagtgcaacg acaagaagtt caacggcagc   480
ggcccctgca ccaacgtgag caccgtgcag tgcacccacg gcatccgccc cgtggtgagc   540
acccagctgc tgctgaacgg cagcctggcc gaggagggcg tggtgatccg cagcgagaac   600
ttcaccgaca cgccaagac catcatcgtg cagctgaagg agagcgtgga gatcaactgc    660
acccgcccca acaacaacac ccgcaagagc atcaccatcg gccccggccg cgccttctac   720
gccaccggcg acatcatcgg cgacatccgc caggcccact gcaacatcag cggcgagaag   780
tggaacaaca ccctgaagca gatcgtgacc aagctgcagg cccagttcgg caacaagacc    840
atcgtgttca gcagagcag cggcggcgac cccgagatcg tgatgcacag cttcaactgc    900
ggcggcgagt tcttctactg caacagcacc cagctgttca cagcacctg gaacaacacc    960 atcggcccca caacaccaa cggcaccatc accctgccct gccgcatcaa gcagatcatc   1020
aaccgcggcg cggcaaggc catgtacgcc cccccatcc gcggccagat ccgctgcagc    1080
agcaacatca ccggcctgct gctgacccgc gacggcggca aggagatcag caacaccacc   1140
gagatcttcc gccccggcgg cggcgacatg cgcgacaact ggcgcagcga gctgtacaag   1200
tacaaggtgg tgaagatcga gcccctgggc gtggccccca ccaaggccaa gcgccgcgtg   1260
gtgcagcgcg agaagcgcgc cgtgaccctg ggcgccatgt tcctgggctt cctgggcgcc   1320
gccggcagca ccatgggcgc cgcagcctg accctgaccg tgcaggcccg ccagctgctg   1380
```

-continued

```
agcggcatcg tgcagcagca gaacaacctg ctgcgcgcca tcgaggccca gcagcacctg   1440
ctgcagctga ccgtgtgggg catcaagcag ctgcaggccc gcgtgctggc cgtggagcgc   1500
tacctgaagg accagcagct gctgggcatc tgggctgca gcggcaagct gatctgcacc    1560
accgccgtgc cctggaacgc cagctggagc aacaagagcc tggaccagat ctggaacaac   1620
atgacctgga tggagtggga gcgcgagatc gacaactaca ccaacctgat ctacaccctg   1680
atcgaggaga gccagaacca gcaggagaag aacgagcagg agctgctgga gctggacaag   1740
tgggccagcc tgtggaactg gttcgacatc agcaagtggc tgtggtacat caagatcttc   1800
atcatgatcg tgggcggcct ggtgggcctg cgcatcgtgt tcaccgtgct gagcatcgtg   1860
aaccgcgtgc gccagggcta cagcccctg agcttccaga cccgcttccc cgcccccgc    1920 ggccccgacc gccccgaggg catcgaggag gagggcggcg agcgcgaccg cgaccgcagc   1980 agcccctgg tgcacggcct gctggccctg atctgggacg acctgcgcag cctgtgcctg    2040
ttcagctacc accgcctgcg cgacctgatc ctgatcgccg cccgcatcgt ggagctgctg   2100
ggccgccgcg gctgggaggc cctgaagtac tggggcaacc tgctgcagta ctggatccag   2160
gagctgaaga acagcgccgt gagcctgttc gacgccatcg ccatcgccgt ggccgagggc   2220
accgaccgca tcatcgaggt ggcccagcgc atcggccgcg ccttcctgca catccccgc    2280 cgcatccgcc agggcttcga gcgcgccctg ctgtaactcg ag                      2322
```

<210> SEQ ID NO 19
<211> LENGTH: 2322
<212> TYPE: DNA
<213> ORGANISM: Artificial Sequence
<220> FEATURE:
<223> OTHER INFORMATION: Description of Artificial Sequence:
      Leu122-Ser199; Arg426-Lys432

<400> SEQUENCE: 19

```
gaattcgcca ccatggatgc aatgaagaga gggctctgct gtgtgctgct gctgtgtgga   60
gcagtcttcg tttcgcccag cgccgtggag aagctgtggg tgaccgtgta ctacggcgtg   120
cccgtgtgga aggaggccac caccaccctg ttctgcgcca gcgacgccaa ggcctacgac   180
accgaggtgc acaacgtgtg ggccacccac gcctgcgtgc ccaccgaccc caaccccag   240 gagatcgtgc tggagaacgt gaccgagaac ttcaacatgt ggaagaacaa catggtggag   300
cagatgcacg aggacatcat cagcctgtgg gaccagagcc tgaagccctg cgtgaagctg   360
ggcaacagcg tgatcaccca ggcctgcccc aaggtgagct cgagcccat ccccatccac   420 tactgcgccc ccgccggctt cgccatcctg aagtgcaacg acaagaagtt caacggcagc   480 ggccctgca ccaacgtgag caccgtgcag tgcacccacg catccgccc cgtggtgagc   540 acccagctgc tgctgaacgg cagcctggcc gaggagggcg tggtgatccg cagcgagaac   600
ttcaccgaca acgccaagac catcatcgtg cagctgaagg agagcgtgga gatcaactgc   660
acccgcccca caacaacac ccgcaagagc atcaccatcg gccccggccg cgccttctac   720
gccaccggcg acatcatcgg cgacatccgc caggcccact gcaacatcag cggcgagaag   780
tggaacaaca ccctgaagca gatcgtgacc aagctgcagg cccagttcgg caacaagacc   840
atcgtgttca gcagagcag cggcggcgac ccgagatct tgatgcacag cttcaactgc   900
ggcggcgagt tcttctactg caacagcacc cagctgttca acagcacctg gaacaacacc   960
atcgccccca caacaccaa cggcaccatc accctgccct gccgcatcaa gcagatcatc   1020
aaccgcggcg gcaacaaggc catgtacgcc ccccccatcc gcggccagat ccgctgcagc   1080
```

-continued

```
agcaacatca ccggcctgct gctgacccgc gacggcggca aggagatcag caacaccacc    1140
gagatcttcc gccccggcgg cggcgacatg cgcgacaact ggcgcagcga gctgtacaag    1200
tacaaggtgg tgaagatcga gcccctgggc gtggccccca ccaaggccaa cgccgcgtg     1260 gtgcagcgcg agaagcgcgc cgtgaccctg gcgccatgt tcctgggctt cctgggcgcc    1320
gccggcagca ccatgggcgc ccgcagcctg accctgaccg tgcaggcccg ccagctgctg    1380
agcggcatcg tgcagcagca gaacaacctg ctgcgcgcca tcgaggccca gcagcacctg    1440
ctgcagctga ccgtgtgggg catcaagcag ctgcaggccc gcgtgctggc cgtggagcgc    1500
tacctgaagg accagcagct gctgggcatc tggggctgca gcggcaagct gatctgcacc    1560
accgccgtgc cctggaacgc cagctggagc aacaagagcc tggaccagat ctggaacaac    1620
atgacctgga tggagtggga gcgcgagatc gacaactaca ccaacctgat ctacacccg    1680 atcgaggaga ccagaaccca gcaggagaag aacgagcagg agctgctgga gctggacaag    1740
tgggccagcc tgtggaactg gttcgacatc agcaagtggc tgtggtacat caagatcttc    1800
atcatgatcg tgggcggcct ggtgggcctg cgcatcgtgt tcaccgtgct gagcatcgtg    1860
aaccgcgtgc gccagggcta cagcccctg agcttccaga cccgcttccc cgccccccgc     1920
ggccccgacc gccccgaggg catcgaggag gagggcggcg agcgcgaccg cgaccgcagc    1980
agccccctgg tgcacggcct gctggcccg atctgggacg acctgcgcag cctgtgcctg    2040
ttcagctacc accgcctgcg cgacctgatc ctgatcgccg cccgcatcgt ggagctgctg    2100
ggccgccgcg gctgggaggc cctgaagtac tggggcaacc tgctgcagta ctggatccag    2160
gagctgaaga cagcgccgt gagcctgttc gacgccatcg ccatcgccgt ggccgagggc    2220
accgaccgca tcatcgaggt ggcccagcgc atcggccgcg ccttcctgca catccccgc    2280 cgcatccgcc agggcttcga gcgcgccctg ctgtaactcg ag                      2322
```

<210> SEQ ID NO 20
<211> LENGTH: 2322
<212> TYPE: DNA
<213> ORGANISM: Artificial Sequence
<220> FEATURE:
<223> OTHER INFORMATION: Description of Artificial Sequence:
      Leu122-Ser199; Trp427-Gly431

<400> SEQUENCE: 20

```
gaattcgcca ccatggatgc aatgaagaga gggctctgct gtgtgctgct gctgtgtgga     60
gcagtcttcg tttcgcccag cgccgtggag aagctgtggg tgaccgtgta ctacggcgtg    120
cccgtgtgga aggaggccac caccaccctg ttctgcgcca gcgacgccaa ggcctacgac    180
accgaggtgc acaacgtgtg gaccacccac gcctgcgtgc caccgaccc caaccccag    240 gagatcgtgc tggagaacgt gaccgagaac ttcaacatgt ggaagaacaa catggtggag    300
cagatgcacg aggacatcat cagcctgtgg gaccagagcc tgaagccctg cgtgaagctg    360
ggcaacagcg tgatcaccca ggcctgcccc aaggtgagct cgagcccat ccccatccac    420 tactgcgccc ccgccggctt cgccatcctg aagtgcaacg acaagaagtt caacggcagc    480 ggccctgca ccaacgtgag caccgtgcag tgcacccacg gcatccgccc cgtggtgagc    540
acccagctgc tgctgaacgg cagcctggcc gaggagggc tggtgatccg cagcgagaac    600
ttcaccgaca cgccaagac catcatcgtg cagctgaagg agagcgtgga gatcaactgc    660
accgccccca caacaacac ccgcaagagc atcaccatcg gccccggccg cgccttctac    720
gccaccggcg acatcatcgg cgacatccgc caggcccact gcaacatcag cggcgagaag    780
```

```
tggaacaaca ccctgaagca gatcgtgacc aagctgcagg cccagttcgg caacaagacc    840
atcgtgttca agcagagcag cggcggcgac cccgagatcg tgatgcacag cttcaactgc    900
ggcggcgagt tcttctactg caacagcacc cagctgttca acagcacctg gaacaacacc    960
atcggcccca acaacaccaa cggcaccatc accctgccct gccgcatcaa gcagatcatc   1020
aaccgctggg gcggcaaggc catgtacgcc cccccatcc gcggccagat ccgctgcagc    1080
agcaacatca ccggcctgct gctgacccgc gacggcggca aggagatcag caacaccacc   1140
gagatcttcc gccccggcgg cggcgacatg cgcgacaact ggcgcagcga gctgtacaag   1200
tacaaggtgg tgaagatcga gcccctgggc gtggccccca ccaaggccaa cgccgcgtg    1260 gtgcagcgcg agaagcgcgc cgtgaccctg gcgccatgt tcctgggctt cctgggcgcc    1320
gccggcagca ccatgggcgc ccgcagcctg accctgaccg tgcaggcccg ccagctgctg   1380
agcggcatcg tgcagcagca gaacaacctg ctgcgcgcca tcgaggccca gcagcacctg   1440
ctgcagctga ccgtgtgggg catcaagcag ctgcaggccc gcgtgctggc cgtggagcgc   1500
tacctgaagg accagcagct gctgggcatc tgggctgca gcggcaagct gatctgcacc    1560
accgccgtgc cctggaacgc cagctggagc aacaagagcc tggaccagat ctggaacaac   1620
atgacctgga tggagtggga gcgcgagatc gacaactaca ccaacctgat ctacaccctg   1680
atcgaggaga gccagaacca gcaggagaag aacgagcagg agctgctgga gctggacaag   1740
tgggccagcc tgtggaactg gttcgacatc agcaagtggc tgtggtacat caagatcttc   1800
atcatgatcg tgggcggcct ggtggcctg cgcatcgtgt tcaccgtgct gagcatcgtg    1860
aaccgcgtgc gccagggcta cagccccctg agcttccaga cccgcttccc cgccccccgc   1920
ggccccgacc gccccgaggg catcgaggag agggcggcg agcgcgaccg cgaccgcagc    1980
agccccctgg tgcacggcct gctggccctg atctgggacg acctgcgcag cctgtgcctg   2040
ttcagctacc accgcctgcg cgacctgatc ctgatcgccg cccgcatcgt ggagctgctg   2100
ggccgccgcg gctgggaggc cctgaagtac tggggcaacc tgctgcagta ctggatccag   2160
gagctgaaga acagcgccgt gagcctgttc gacgccatcg ccatcgccgt ggccgagggc   2220
accgaccgca tcatcgaggt ggcccagcgc atcggccgcg ccttcctgca catccccgc    2280 cgcatccgcc agggcttcga gcgcgccctg ctgtaactcg ag                      2322
```

<210> SEQ ID NO 21
<211> LENGTH: 2310
<212> TYPE: DNA
<213> ORGANISM: Artificial Sequence
<220> FEATURE:
<223> OTHER INFORMATION: Description of Artificial Sequence:
      Lys121-Val200; Asn425-Lys432

<400> SEQUENCE: 21

```
gaattcgcca ccatggatgc aatgaagaga gggctctgct gtgtgctgct gctgtgtgga     60
gcagtcttcg tttcgcccag cgccgtggag aagctgtggg tgaccgtgta ctacggcgtg    120
cccgtgtgga aggaggccac caccaccctg ttctgcgcca gcgacgccaa ggcctacgac    180
accgaggtgc acaacgtgtg gccaccca cgctgcgtgc ccaccgaccc caaccccag     240 gagatcgtgt tggagaacgt gaccgagaac ttcaacatgt ggaagaacaa catggtggag    300
cagatgcacg aggacatcat cagcctgtgg gaccagagcc tgaagccctg cgtgaaggcc    360
cccgtgatca cccaggcctg ccccaaggtg agcttcgagc ccatccccat ccactactgc    420
gcccccgccg gcttcgccat cctgaagtgc aacgacaaga agttcaacgg cagcggcccc    480
```

-continued

```
tgcaccaacg tgagcaccgt gcagtgcacc cacggcatcc gccccgtggt gagcacccag      540
ctgctgctga acggcagcct ggccgaggag ggcgtggtga tccgcagcga gaacttcacc      600
gacaacgcca agaccatcat cgtgcagctg aaggagagcg tggagatcaa ctgcacccgc      660
cccaacaaca cacccgcaa gagcatcacc atcggccccg gccgcgcctt ctacgccacc       720
ggcgacatca tcggcgacat ccgccaggcc cactgcaaca tcagcggcga aagtggaac       780 aacaccctga agcagatcgt gaccaagctg caggcccagt tcggcaacaa gaccatcgtg      840
ttcaagcaga gcagcggcgg cgaccccgag atcgtgatgc acagcttcaa ctgcggcggc      900
gagttcttct actgcaacag cacccagctg ttcaacagca cctggaacaa caccatcggc      960
cccaacaaca ccaacggcac catcaccctg ccctgccgca tcaagcagat catcaacgcc     1020
cccaaggcca tgtacgcccc ccccatccgc ggccagatcc gctgcagcag caacatcacc     1080
ggcctgctgc tgacccgcga cggcggcaag gagatcagca acaccaccga gatcttccgc     1140
cccggcggcg gcgacatgcg cgacaactgg cgcagcgagc tgtacaagta caaggtggtg     1200
aagatcgagc ccctgggcgt ggccccacc aaggccaagc gccgcgtggt gcagcgcgag      1260
aagcgcgccg tgaccctggg cgccatgttc ctgggcttcc tgggcgccgc cggcagcacc     1320
atgggcgccc gcagcctgac cctgaccgtg caggcccgcc agctgctgag cggcatcgtg     1380
cagcagcaga acaacctgct gcgcgccatc gaggcccagc agcacctgct gcagctgacc     1440
gtgtggggca tcaagcagct gcaggcccgc gtgctggccg tggagcgcta cctgaaggac     1500
cagcagctgc tgggcatctg gggctgcagc ggcaagctga tctgcaccac cgccgtgccc     1560
tggaacgcca gctggagcaa caagagcctg gaccagatct ggaacaacat gacctggatg     1620
gagtgggagc gcgagatcga caactacacc aacctgatct acaccctgat cgaggagagc     1680
cagaaccagc aggagaagaa cgagcaggag ctgctggagc tggacaagtg gccagcctg      1740 tggaactggt tcgacatcag caagtggctg tggtacatca gatcttcat catgatcgtg      1800 ggcggcctgg tgggcctgcg catcgtgttc accgtgctga gcatcgtgaa ccgcgtgcgc     1860
cagggctaca gcccctgag cttccagacc cgcttcccg cccccgcgg ccccgaccgc        1920 cccgagggca tcgaggagga gggcggcgag cgcgaccgcg accgcagcag ccccctggtg     1980
cacggcctgc tggccctgat ctgggacgac ctgcgcagcc tgtgcctgtt cagctaccac     2040
cgcctgcgcg acctgatcct gatcgccgcc cgcatcgtgg agctgctggg ccgccgcggc     2100
tgggaggccc tgaagtactg gggcaacctg ctgcagtact ggatccagga gctgaagaac     2160
agcgccgtga gcctgttcga cgccatcgcc atcgccgtgg ccgagggcac cgaccgcatc     2220
atcgaggtgg cccagcgcat cggccgcgcc ttcctgcaca tcccccgccg catccgccag     2280
ggcttcgagc gcgccctgct gtaactcgag                                     2310
```

<210> SEQ ID NO 22
<211> LENGTH: 2298
<212> TYPE: DNA
<213> ORGANISM: Artificial Sequence
<220> FEATURE:
<223> OTHER INFORMATION: Description of Artificial Sequence:
      Val120-Ile201; Ile424-Ala433

<400> SEQUENCE: 22

```
gaattcgcca ccatggatgc aatgaagaga gggctctgct gtgtgctgct gctgtgtgga      60
gcagtcttcg tttcgcccag cgccgtggag aagctgtggg tgaccgtgta ctacggcgtg     120
cccgtgtgga aggaggccac caccacccctg ttctgcgcca gcgacgccaa ggcctacgac      180
```

```
accgaggtgc acaacgtgtg ggccacccac gcctgcgtgc ccaccgaccc caaccccag      240 gagatcgtgc tggagaacgt gaccgagaac ttcaacatgt ggaagaacaa catggtggag     300
cagatgcacg aggacatcat cagcctgtgg gaccagagcc tgaagccctg cgtgggcggc     360
atcacccagg cctgccccaa ggtgagcttc gagcccatcc ccatccacta ctgcgccccc     420
gccggcttcg ccatcctgaa gtgcaacgac aagaagttca acggcagcgg ccctgcacc      480 aacgtgagca ccgtgcagtg cacccacggc atccgccccg tggtgagcac ccagctgctg     540
ctgaacggca gcctggccga ggagggcgtg gtgatccgca gcgagaactt caccgacaac     600
gccaagacca tcatcgtgca gctgaaggag agcgtggaga tcaactgcac ccgccccaac     660
aacaacaccc gcaagagcat caccatcggc cccggccgcg ccttctacgc caccggcgac     720
atcatcggcg acatccgcca ggcccactgc aacatcagcg gcgagaagtg gaacaacacc     780
ctgaagcaga tcgtgaccaa gctgcaggcc cagttcggca acaagaccat cgtgttcaag     840
cagagcagcg gcggcgaccc cgagatcgtg atgcacagct tcaactgcgg cggcgagttc     900
ttctactgca acagcaccca gctgttcaac agcacctgga caacaccat cggccccaac      960 aacaccaacg gcaccatcac cctgccctgc cgcatcaagc agatcatcgg cggcgccatg    1020
tacgcccccc ccatccgcgg ccagatccg tgcagcagca catcaccgg cctgctgctg       1080 acccgcgacg gcggcaagga gatcagcaac accaccgaga tcttccgccc cggcggcggc    1140
gacatgcgcg acaactggcg cagcgagctg tacaagtaca aggtggtgaa gatcgagccc    1200
ctgggcgtgg cccccaccaa ggccaagcgc cgcgtggtgc agcgcgagaa gcgcgccgtg    1260
accctgggcg ccatgttcct gggcttcctg ggcgccgccg cagcaccat gggcgcccgc     1320 agcctgaccc tgaccgtgca ggcccgccag ctgctgagcg gcatcgtgca gcagcagaac    1380
aacctgctgc gcgccatcga ggcccagcag cacctgctgc agctgaccgt gtgggcatc    1440 aagcagctgc aggcccgcgt gctggccgtg gagcgctacc tgaaggacca gcagctgctg    1500
ggcatctggg gctgcagcgg caagctgatc tgcaccaccg ccgtgccctg gaacgccagc    1560
tggagcaaca agagcctgga ccagatctgg aacaacatga cctggatgga gtgggagcgc    1620
gagatcgaca actacaccaa cctgatctac accctgatcg aggagagcca gaaccagcag    1680
gagaagaacg agcaggagct gctggagctg gacaagtggg ccagcctgtg gaactggttc    1740
gacatcagca gtggctgtg gtacatcaag atcttcatca tgatcgtggg cggcctggtg    1800
ggcctgcgca tcgtgttcac cgtgctgagc atcgtgaacc gcgtgcgcca gggctacagc    1860
cccctgagct tccagacccg cttccccgcc cccgcggcc ccgaccgccc cgagggcatc     1920
gaggaggagg gcggcgagcg cgaccgcgac cgcagcagcc ccctggtgca cggcctgctg    1980
gccctgatct gggacgacct cgcagcctg tgcctgttca gctaccaccg cctgcgcgac     2040
ctgatcctga tcgccgcccg catcgtggag ctgctgggcc gccgcggctg ggaggccctg    2100
aagtactggg gcaacctgct gcagtactgg atccaggagc tgaagaacag cgccgtgagc    2160
ctgttcgacg ccatcgccat cgccgtggcc gagggcaccg accgcatcat cgaggtggcc    2220
cagcgcatcg gccgcgcctt cctgcacatc ccccgccgca tccgccaggg cttcgagcgc    2280
gccctgctgt aactcgag                                                  2298
```

<210> SEQ ID NO 23
<211> LENGTH: 2298
<212> TYPE: DNA
<213> ORGANISM: Artificial Sequence
<220> FEATURE:

<223> OTHER INFORMATION: Description of Artificial Sequence:
Val120-Ile201B; Ile424-Ala433

<400> SEQUENCE: 23

| | | | | | |
|---|---|---|---|---|---|
| gaattcgcca | ccatggatgc | aatgaagaga | gggctctgct | gtgtgctgct | gctgtgtgga | 60 |
| gcagtcttcg | tttcgcccag | cgccgtggag | aagctgtggg | tgaccgtgta | ctacggcgtg | 120 |
| cccgtgtgga | aggaggccac | caccaccctg | ttctgcgcca | cgacgccaa | ggcctacgac | 180 |
| accgaggtgc | acaacgtgtg | gccacccac | gcctgcgtgc | caccgaccc | caaccccag | 240 |
| gagatcgtgc | tggagaacgt | gaccgagaac | ttcaacatgt | ggaagaacaa | catggtggag | 300 |
| cagatgcacg | aggacatcat | cagcctgtgg | gaccagagcc | tgaagccctg | cgtgcccggc | 360 |
| atcacccagg | cctgccccaa | ggtgagcttc | gagcccatcc | ccatccacta | ctgcgccccc | 420 |
| gccggcttcg | ccatcctgaa | gtgcaacgac | aagaagttca | acggcagcgg | ccctgcacc | 480 |
| aacgtgagca | ccgtgcagtg | cacccacggc | atccgcccg | tggtgagcac | ccagctgctg | 540 |
| ctgaacggca | gcctggccga | ggagggcgtg | gtgatccgca | gcgagaactt | caccgacaac | 600 |
| gccaagacca | tcatcgtgca | gctgaaggag | agcgtggaga | tcaactgcac | ccgccccaac | 660 |
| aacaacaccc | gcaagagcat | caccatcggc | cccggccgcg | ccttctacgc | caccggcgac | 720 |
| atcatcggcg | acatccgcca | ggcccactgc | aacatcagcg | gcgagaagtg | gaacaacacc | 780 |
| ctgaagcaga | tcgtgaccaa | gctgcaggcc | cagttcggca | caagaccat | cgtgttcaag | 840 |
| cagagcagcg | gcggcgaccc | cgagatcgtg | atgcacagct | tcaactgcgg | cggcgagttc | 900 |
| ttctactgca | acagcaccca | gctgttcaac | agcacctgga | caacaccat | cggccccaac | 960 |
| aacaccaacg | gcaccatcac | cctgccctgc | cgcatcaagc | agatcatcgg | cggcgccatg | 1020 |
| tacgcccccc | ccatccgcgg | ccagatccg | tgcagcagca | acatcaccgg | cctgctgctg | 1080 |
| acccgcgacg | gcggcaagga | gatcagcaac | accaccgaga | tcttccgccc | cggcggcggc | 1140 |
| gacatgcgcg | acaactggcg | cagcgagctg | tacaagtaca | aggtggtgaa | gatcgagccc | 1200 |
| ctgggcgtgg | ccccaccaa | ggccaagcgc | cgcgtggtgc | agcgcgagaa | cgcgccgtg | 1260 |
| accctgggcg | ccatgttcct | gggcttcctg | ggcgccgccg | gcagcaccat | gggcgcccgc | 1320 |
| agcctgaccc | tgaccgtgca | ggccgccag | ctgctgagcg | gcatcgtgca | gcagcagaac | 1380 |
| aacctgctgc | gcgccatcga | ggcccagcag | cacctgctgc | agctgaccgt | gtgggcatc | 1440 |
| aagcagctgc | aggcccgcgt | gctggccgtg | gagcgctacc | tgaaggacca | gcagctgctg | 1500 |
| ggcatctggg | gctgcagcgg | caagctgatc | tgcaccaccg | ccgtgccctg | gaacgccagc | 1560 |
| tggagcaaca | agagcctgga | ccagatctgg | aacaacatga | cctggatgga | gtgggagcgc | 1620 |
| gagatcgaca | actacaccaa | cctgatctac | accctgatcg | aggagagcca | gaaccagcag | 1680 |
| gagaagaacg | agcaggagct | gctggagctg | gacaagtggg | ccagcctgtg | gaactggttc | 1740 |
| gacatcagca | gtggctgtg | gtacatcaag | atcttcatca | tgatcgtggg | cggcctggtg | 1800 |
| ggcctgcgca | tcgtgttcac | cgtgctgagc | atcgtgaacc | gcgtgcgcca | gggctacagc | 1860 |
| cccctgagct | tccagacccg | cttccccgcc | cccgcggcc | ccgaccgccc | cgagggcatc | 1920 |
| gaggaggagg | gcggcgagcg | cgaccgcgac | cgcagcagcc | cctggtgca | cggcctgctg | 1980 |
| gccctgatct | gggacgacct | cgcagcctg | tgcctgttca | gctaccaccg | cctgcgcgac | 2040 |
| ctgatcctga | tcgccgcccg | catcgtggag | ctgctgggcc | gccggctg | ggaggccctg | 2100 |
| aagtactggg | gcaacctgct | gcagtactgg | atccaggagc | tgaagaacag | cgccgtgagc | 2160 |
| ctgttcgacg | ccatcgccat | cgccgtggcc | gagggcaccg | accgcatcat | cgaggtggcc | 2220 | cagcgcatcg gccgcgcctt cctgcacatc ccccgccgca tccgccaggg cttcgagcgc    2280 gccctgctgt aactcgag                                                  2298

<210> SEQ ID NO 24
<211> LENGTH: 2298
<212> TYPE: DNA
<213> ORGANISM: Artificial Sequence
<220> FEATURE:
<223> OTHER INFORMATION: Description of Artificial Sequence:
      Val120-Thr202; Ile424-Ala433

<400> SEQUENCE: 24
gaattcgcca ccatggatgc aatgaagaga gggctctgct gtgtgctgct gctgtgtgga     60
gcagtcttcg tttcgcccag cgccgtggag aagctgtggg tgaccgtgta ctacggcgtg    120
cccgtgtgga aggaggccac caccaccctg ttctgcgcca gcgacgccaa ggcctacgac    180
accgaggtgc acaacgtgtg gccacccac gcctgcgtgc ccaccgaccc caaccccag     240 gagatcgtgc tggagaacgt gaccgagaac ttcaacatgt ggaagaacaa catggtggag    300
cagatgcacg aggacatcat cagcctgtgg gaccagagcc tgaagccctg cgtgggcggc    360
gccacccagg cctgccccaa ggtgagcttc gagcccatcc ccatccacta ctgcgccccc    420
gccggcttcg ccatcctgaa gtgcaacgac aagaagttca cggcagcgg ccctgcacc     480 aacgtgagca ccgtgcagtg cacccacggc atccgccccg tggtgagcac ccagctgctg    540
ctgaacggca gcctggccga ggagggcgtg gtgatccgca gcgagaactt caccgacaac    600
gccaagacca tcatcgtgca gctgaaggag agcgtggaga tcaactgcac ccgccccaac    660
aacaacaccc gcaagagcat caccatcggc cccggccgcg ccttctacgc caccggcgac    720
atcatcggcg acatccgcca ggcccactgc aacatcagcg cgagaagtg gaacaacacc    780 ctgaagcaga tcgtgaccaa gctgcaggcc cagttcggca acaagaccat cgtgttcaag    840
cagagcagcg gcggcgaccc cgagatcgtg atgcacagct caactgcgg cggcgagttc    900 ttctactgca acagcacccc agctgttcaac agcacctgga caacaccat cggccccaac    960 aacaccaacg gcaccatcac cctgccctgc cgcatcaagc agatcatcgg cggcgccatg   1020
tacgcccccc ccatccgcgg ccagatccgc tgcagcagca acatcaccgg cctgctgctg   1080
acccgcgacg gcggcaagga gatcagcaac accaccgaga tcttccgccc cggcggcggc   1140
gacatgcgcg acaactggcg cagcgagctg tacaagtaca aggtggtgaa gatcgagccc   1200
ctgggcgtgg cccccaccaa ggccaagcgc cgcgtggtgc agcgcgagaa gcgcgccgtg   1260
accctgggcg ccatgttcct gggcttcctg ggcgccgccg gcagcaccat gggcgcccgc   1320
agcctgaccc tgaccgtgca ggcccgccag ctgctgagcg gcatcgtgca gcagcagaac   1380
aacctgctgc gcgccatcga ggcccagcag cacctgctgc agctgaccgt gtggggcatc   1440
aagcagctgc aggcccgcgt gctggccgtg gagcgctacc tgaaggacca gcagctgctg   1500
ggcatctggg gctgcagcgg caagctgatc tgcaccaccg ccgtgccctg gaacgccagc   1560
tggagcaaca agagcctgga ccagatctgg aacaacatga cctggatgga gtgggagcgc   1620
gagatcgaca actacaccaa cctgatctac accctgatcg aggagagcca gaaccagcag   1680
gagaagaacg agcaggagct gctggagctg gacaagtggg ccagcctgtg gaactggttc   1740
gacatcagca gtggctgtg gtacatcaag atcttcatca tgatcgtggg cggcctggtg   1800
ggcctgcgca tcgtgttcac cgtgctgagc atcgtgaacc gcgtgcgcca gggctacagc   1860
cccctgagct tccagacccg cttccccgcc cccgcgcggcc ccgaccgccc cgagggcatc   1920

-continued

| | |
|---|---|
| gaggaggagg gcggcgagcg cgaccgcgac cgcagcagcc ccctggtgca cggcctgctg | 1980 |
| gccctgatct gggacgacct gcgcagcctg tgcctgttca gctaccaccg cctgcgcgac | 2040 |
| ctgatcctga tcgccgcccg catcgtggag ctgctgggcc gccgcggctg ggaggccctg | 2100 |
| aagtactggg gcaacctgct gcagtactgg atccaggagc tgaagaacag cgccgtgagc | 2160 |
| ctgttcgacg ccatcgccat cgccgtggcc gagggcaccg accgcatcat cgaggtggcc | 2220 |
| cagcgcatcg gccgcgcctt cctgcacatc ccccgccgca tccgccaggg cttcgagcgc | 2280 |
| gccctgctgt aactcgag | 2298 |

<210> SEQ ID NO 25
<211> LENGTH: 2358
<212> TYPE: DNA
<213> ORGANISM: Artificial Sequence
<220> FEATURE:
<223> OTHER INFORMATION: Description of Artificial Sequence:
      Val127-Asn195

<400> SEQUENCE: 25

| | |
|---|---|
| gaattcgcca ccatggatgc aatgaagaga gggctctgct gtgtgctgct gctgtgtgga | 60 |
| gcagtcttcg tttcgcccag cgccgtggag aagctgtggg tgaccgtgta ctacggcgtg | 120 |
| cccgtgtgga aggaggccac caccaccctg ttctgcgcca gcgacgccaa ggcctacgac | 180 |
| accgaggtgc acaacgtgtg gcccacccac gcctgcgtgc ccaccgaccc caaccccag | 240 |
| gagatcgtgc tggagaacgt gaccgagaac ttcaacatgt ggaagaacaa catggtggag | 300 |
| cagatgcacg aggacatcat cagcctgtgg gaccagagcc tgaagccctg cgtgaagctg | 360 |
| acccccctgt gcgtgggggc agggaactgc aacaccagcg tgatcaccca ggcctgcccc | 420 |
| aaggtgagct tcgagcccat ccccatccac tactgcgccc ccgccggctt cgccatcctg | 480 |
| aagtgcaacg acaagaagtt caacggcagc ggcccctgca ccaacgtgag caccgtgcag | 540 |
| tgcacccacg gcatccgccc cgtggtgagc acccagctgc tgctgaacgg cagcctggcc | 600 |
| gaggagggcg tggtgatccg cagcgagaac ttcaccgaca acgccaagac catcatcgtg | 660 |
| cagctgaagg agagcgtgga gatcaactgc acccgcccca acaacaacac ccgcaagagc | 720 |
| atcaccatcg cccccggccg cgccttctac gccaccggcg acatcatcgg cgacatccgc | 780 |
| caggcccact gcaacatcag cggcgagaag tggaacaaca ccctgaagca gatcgtgacc | 840 |
| aagctgcagg cccagttcgg caacaagacc atcgtgttca gcagagcag cggcggcgac | 900 |
| cccgagatct gatgcacag cttcaactgc ggcggcgagt tcttctactg caacagcacc | 960 |
| cagctgttca acagcacctg gaacaacacc atcggcccca caacaccaa cggcaccatc | 1020 |
| accctgcct gccgcatcaa gcagatcatc aaccgctggc aggaggtggg caaggccatg | 1080 |
| tacgcccccc ccatccgcgg ccagatccgc tgcagcagca acatcaccgg cctgctgctg | 1140 |
| acccgcgacg gcggcaagga gatcagcaac accaccgaga tcttccgccc cggcggcggc | 1200 |
| gacatgcgcg acaactggcg cagcgagctg tacaagtaca aggtggtgaa gatcgagccc | 1260 |
| ctgggcgtgg cccccaccaa ggccaagcgc gcgtggtgc agcgcgagaa gcgcgccgtg | 1320 |
| accctgggcg ccatgttcct gggcttcctg ggcgccgccg gcagcaccat gggcgcccgc | 1380 |
| agcctgaccc tgaccgtgca ggcccgccag ctgctgagcg gcatcgtgca gcagcagaac | 1440 |
| aacctgctgc gcgccatcga ggcccagcag cacctgctgc agctgaccgt gtggggcatc | 1500 |
| aagcagctgc aggcccgcgt gctggccgtg gagcgctacc tgaaggacca gcagctgctg | 1560 |
| ggcatctggg gctgcagcgg caagctgatc tgcaccaccg ccgtgccctg gaacgccagc | 1620 |

| | |
|---|---:|
| tggagcaaca agagcctgga ccagatctgg aacaacatga cctggatgga gtgggagcgc | 1680 |
| gagatcgaca actacaccaa cctgatctac accctgatcg aggagagcca gaaccagcag | 1740 |
| gagaagaacg agcaggagct gctggagctg gacaagtggg ccagcctgtg gaactggttc | 1800 |
| gacatcagca agtggctgtg gtacatcaag atcttcatca tgatcgtggg cggcctggtg | 1860 |
| ggcctgcgca tcgtgttcac cgtgctgagc atcgtgaacc gcgtgcgcca gggctacagc | 1920 |
| cccctgagct tccagacccg cttccccgcc ccccgcggcc ccgaccgccc cgagggcatc | 1980 |
| gaggaggagg cggcgagcg cgaccgcgac cgcagcagcc cctggtgca cggcctgctg | 2040 |
| gccctgatct gggacgacct gcgcagcctg tgcctgttca gctaccaccg cctgcgcgac | 2100 |
| ctgatcctga tcgccgcccg catcgtggag ctgctgggcc gccgcggctg ggaggccctg | 2160 |
| aagtactggg gcaacctgct gcagtactgg atccaggagc tgaagaacag cgccgtgagc | 2220 |
| ctgttcgacg ccatcgccat cgccgtggcc gagggcaccg accgcatcat cgaggtggcc | 2280 |
| cagcgcatcg gccgcgcctt cctgcacatc cccgccgca tccgccaggg cttcgagcgc | 2340 |
| gccctgctgt aactcgag | 2358 |

<210> SEQ ID NO 26
<211> LENGTH: 2352
<212> TYPE: DNA
<213> ORGANISM: Artificial Sequence
<220> FEATURE:
<223> OTHER INFORMATION: Description of Artificial Sequence:
      Val127-Asn195; Arg426-Gly431

<400> SEQUENCE: 26

| | |
|---|---:|
| gaattcgcca ccatggatgc aatgaagaga gggctctgct gtgtgctgct gctgtgtgga | 60 |
| gcagtcttcg tttcgcccag cgccgtggag aagctgtggg tgaccgtgta ctacggcgtg | 120 |
| cccgtgtgga aggaggccac caccaccctg ttctgcgcca gcgacgccaa ggcctacgac | 180 |
| accgaggtgc acaacgtgtg gccacccac gcctgcgtgc ccaccgaccc caaccccag | 240 |
| gagatcgtgc tggagaacgt gaccgagaac ttcaacatgt ggaagaacaa catggtggag | 300 |
| cagatgcacg aggacatcat cagcctgtgg gaccagagcc tgaagccctg cgtgaagctg | 360 |
| accccctgt gcgtgggggc agggaactgc aacaccagcg tgatcaccca ggcctgcccc | 420 |
| aaggtgagct tcgagcccat ccccatccac tactgcgccc ccgccggctt cgccatcctg | 480 |
| aagtgcaacg acaagaagtt caacggcagc ggcccctgca ccaacgtgag caccgtgcag | 540 |
| tgcacccacg gcatccgccc cgtggtgagc acccagctgc tgctgaacgg cagcctggcc | 600 |
| gaggagggcg tggtgatccg cagcgagaac ttcaccgaca cgccaagac catcatcgtg | 660 |
| cagctgaagg agagcgtgga gatcaactgc acccgcccca caacaacac ccgcaagagc | 720 |
| atcaccatcg gccccggccg cgccttctac gccaccggcg acatcatcgg cgacatccgc | 780 |
| caggcccact gcaacatcag cggcgagaag tggaacaaca ccctgaagca gatcgtgacc | 840 |
| aagctgcagg cccagttcgg caacaagacc atcgtgttca gcagagcag cggcggcgac | 900 |
| cccgagatcg tgatgcacag cttcaactgc ggcggcgagt tcttctactg caacagcacc | 960 |
| cagctgttca acagcacctg gaacaacac atcgccccca caacaccaa cggcaccatc | 1020 |
| accctgccct gccgcatcaa gcagatcatc aaccgcggcg cggcaaggc catgtacgcc | 1080 |
| cccccatcc gcggccagat ccgctgcagc agcaacatca ccggcctgct gctgacccgc | 1140 |
| gacggcggca aggagatcag caacaccacc gagatcttcc gccccggggg cggcgacatg | 1200 |
| cgcgacaact ggcgcagcga gctgtacaag tacaaggtgg tgaagatcga gcccctgggc | 1260 |

-continued

```
gtggccccca ccaaggccaa gcgccgcgtg gtgcagcgcg agaagcgcgc cgtgaccctg      1320
ggcgccatgt tcctgggctt cctgggcgcc gccggcagca ccatgggcgc ccgcagcctg      1380
accctgaccg tgcaggcccg ccagctgctg agcggcatcg tgcagcagca gaacaacctg      1440
ctgcgcgcca tcgaggccca gcagcacctg ctgcagctga ccgtgtgggg catcaagcag      1500
ctgcaggccc gcgtgctggc cgtggagcgc tacctgaagg accagcagct gctgggcatc      1560
tggggctgca gcggcaagct gatctgcacc accgccgtgc cctggaacgc cagctggagc      1620
aacaagagcc tggaccagat ctggaacaac atgacctgga tggagtggga gcgcgagatc      1680
gacaactaca ccaacctgat ctacaccctg atcgaggaga gccagaacca gcaggagaag      1740
aacgagcagg agctgctgga gctggacaag tgggccagcc tgtggaactg gttcgacatc      1800
agcaagtggc tgtggtacat caagatcttc atcatgatcg tgggcggcct ggtgggcctg      1860
cgcatcgtgt tcaccgtgct gagcatcgtg aaccgcgtgc gccagggcta cagcccctg      1920 agcttccaga cccgcttccc cgcccccgc ggccccgacc gccccgaggg catcgaggag      1980
gagggcggcg agcgcgaccg cgaccgcagc agcccctgg tgcacggcct gctggccctg      2040
atctgggacg acctgcgcag cctgtgcctg ttcagctacc accgcctgcg cgacctgatc      2100
ctgatcgccg cccgcatcgt ggagctgctg ggccgccgcg gctgggaggc cctgaagtac      2160
tggggcaacc tgctgcagta ctggatccag gagctgaaga acagcgccgt gagcctgttc      2220
gacgccatcg ccatcgccgt ggccgagggc accgaccgca tcatcgaggt ggcccagcgc      2280
atcggccgcg ccttcctgca catcccccgc cgcatccgcc agggcttcga gcgcgccctg      2340
ctgtaactcg ag                                                          2352
```

MODIFIED HIV ENV POLYPEPTIDES

CROSS-REFERENCE TO RELATED APPLICATIONS

This application is a continuation of U.S. Ser. No. 09/476,242, filed Dec. 30, 1999, now U.S. Pat. No. 6,689,879. U.S. Ser. No. 09/476,242 claims the benefit of provisional patent application Ser. Nos. 60/114,495, filed Dec. 31, 1998 and 60/156,670, filed Sep. 29, 1999. All the aforementioned applications are incorporated herein by reference in their entireties.

TECHNICAL FIELD

The invention relates generally to modified HIV envelope (Env) polypeptides which are useful as immunizing agents or for generating an immune response in a subject, for example a cellular immune response or a protective immune response. More particularly, the invention relates Env polypeptides such as gp120, gp140 or gp160, wherein at least one of the native β-sheet configurations has been modified. The invention also pertains to methods of using these polypeptides to elicit an immune response against a broad range of HIV subtypes.

BACKGROUND OF THE INVENTION

The human immunodeficiency virus (HIV-1, also referred to as HTLV-III, LAV or HTLV-III/LAV) is the etiological agent of the acquired immune deficiency syndrome (AIDS) and related disorders. (see, e.g., Barre-Sinoussi, et al., (1983) *Science* 220:868-871; Gallo et al. (1984) *Science* 224:500-503; Levy et al., (1984) *Science* 225:840-842; Siegal et al., (1981) *N. Engl. J. Med.* 305:1439-1444). AIDS patients usually have a long asymptomatic period followed by the progressive degeneration of the immune system and the central nervous system. Replication of the virus is highly regulated, and both latent and lytic infection of the CD4 positive helper subset of T-lymphocytes occur in tissue culture (Zagury et al., (1986) Science 231:850-853). Molecular studies of HIV-1 show that it encodes a number of genes (Ratner et al., (1985) *Nature* 313:277-284; Sanchez-Pescador et al., (1985) *Science* 227:484-492), including three structural genes—gag, pol and env—that are common to all retroviruses. Nucleotide sequences from viral genomes of other retroviruses, particularly HIV-2 and simian immunodeficiency viruses, SIV (previously referred to as STLV-III), also contain these structural genes. (Guyader et al., (1987) *Nature* 326:662-669; Chakrabarti et al., (1987) *Nature*

The envelope protein of HIV-1, HIV-2 and SIV is a glycoprotein of about 160 kd (gp160). During virus infection of the host cell, gp160 is cleaved by host cell proteases to form gp120 and the integral membrane protein, gp41. The gp41 portion is anchored in the membrane bilayer of virion, while the gp120 segment protrudes into the surrounding environment. gp120 and gp41 are more covalently associated and free gp120 can be released from the surface of virions and infected cells.

As depicted in FIG. 1, crystallography studies of the gp120 core polypeptide indicate that this polypeptide is folded into two major domains having certain emanating structures. The inner domain (inner with respect to the N and C terminus) features a two-helix, two-stranded bundle with a small five-stranded β-sandwich at its termini-proximal end and a projection at the distal end from which the V1/V2 stem emanates. The outer domain is a staked double barrel that lies along side the inner domain so that the outer barrel and inner bundle axes are approximately parallel. Between the distal inner domain and the distal outer domain is a four-stranded bridging sheet which holds a peculiar minidomain in contact with, but distinct from, the inner, the outer domain, and the V1/V2 domain. The bridging sheet is composed of four β-strand structures (β-3, β-2, β-21, β-20, shown in FIG. 1). The bridging region can be seen in FIG. 1 packing primarily over the inner domain, although some surface residues of the outer domain, such as Phe 382, reach into the bridging sheet to form part of its hydrophobic core.

The basic unit of the β-sheet conformation of the bridging sheet region is the β-strand which exists as a less tightly coiled helix, with 2.0 residues per turn. The β-strand conformation is only stable when incorporated into a β-sheet, where hydrogen bonds with close to optimal geometry are formed between the peptide groups on adjacent β-strands; the dipole moments of the strands are also aligned favorably. Side chains from adjacent residues of the same strand protrude from opposite sides of the sheet and do not interact with each other, but have significant interactions with their backbone and with the side chains of neighboring strands. For a general description of β-sheets, see, e.g., T. E. Creighton, Proteins: Structures and Molecular Properties (W. H. Freeman and Company, 1993); and A. L. Lehninger, *Biochemistry* (Worth Publishers, Inc., 1975).

The gp120 polypeptide is instrumental in mediating entry into the host cell. Recent studies have indicated that binding of CD4 to gp120 induces a conformational change in Env that allows for binding to a co-receptor (e.g., a chemokine receptor) and subsequent entry of the virus into the cell. (Wyatt, R., et al. (1998) *Nature* 393:705-711; Kwong, P., et al.(1998) *Nature* 393:648-659). Referring again to FIG. 1, CD4 is bound into a depression formed at the interface of the outer domain, the inner domain and the bridging sheet of gp120.

Immunogenicity of the gp120 polypeptide has also been studied. For example, individuals infected by HIV-1 usually develop antibodies that can neutralize the virus in in vitro assays, and this response is directed primarily against linear neutralizing determinants in the third variable loop of gp120 glycoprotein (Javaherian, K., et al. (1989) *Proc. Natl. Acad. Sci.* 86:6786-6772; Matsushita, M., et al. (1988) *J. Virol.* 62:2107-2144; Putney, S., et al. (1986) *Science* 234:1392-1395; Rushe, J. R., et al. (1988) *Proc. Nat. Acad. Sci. USA* 85: 3198-3202.). However, these antibodies generally exhibit the ability to neutralize only a limited number of HIV-1 strains (Matthews, T. (1986) *Proc. Natl. Acad. Sci. USA.* 83:9709-9713; Nara, P. L., et al. (1988) *J. Virol.* 62:2622-2628; Palker, T. J., et al. (1988) *Proc. Natl. Acad. Sci. USA.* 85:1932-1936). Later in the course of HIV infection in humans, antibodies capable of neutralizing a wider range of HIV-1 isolates appear (Barre-Sinoussi, F., et al. (1983) *Science* 220:868-871; Robert-Guroff, M., et al. (1985) *Nature* (London) 316:72-74; Weis, R., et al. (1985) *Nature* (London) 316:69-72; Weis, R., et al. (1986) *Nature* (London) 324:572-575).

Recent work done by Stamatatos et al (1998) *AIDS Res Hum Retroviruses* 14(13):1129-39, shows that a deletion of the variable region 2 from a HIV-1$_{SF162}$ virus, which utilizes the CCR-5 co-receptor for virus entry, rendered the virus highly susceptible to serum-mediated neutralization. This V2 deleted virus was also neutralized by sera obtained from patients infected not only with clade B HIV-1 isolates but also with clade A, C, D and F HIV-1 isolates. However, deletion of the variable region 1 had no effect. Deletion of the variable regions 1 and 2 from a LAI isolate HIV-1$_{IIIB}$ also increased the susceptibility to neutralization by monoclonal antibodies whose epitopes are located within the V3 loop, the CD4- binding site, and conserved gp120 regions (Wyatt, R., et al. (1995) *J. Virol.* 69:5723-5733). Rabbit immunogenicity studies done with the HIV-1 virus with deletions in the V1/V2 and V3 region from the LAI strain, which uses the CXCR4 co-receptor for virus entry, showed no improvement in the ability of Env to raise neutralizing antibodies (Leu et al. (1998) AIDS Res. and Human Retroviruses. 14:151-155).

Further, a subset of the broadly reactive antibodies, found in most infected individuals, interferes with the binding of gp120 and CD4 (Kang, C.-Y., et al. (1991) *Proc. Natl. Acad. Sci. USA.* 88:6171-6175; McDougal, J. S., et al. (1986) *J. Immunol.* 137:2937-2944). Other antibodies are believed to bind to the chemokine receptor binding region after CD4 has bound to Env (Thali et al. (1993) *J. Virol.* 67:3978-3988). The fact that neutralizing antibodies generated during the course of HIV infection do not provide permanent antiviral effect may in part be due to the generation of "neutralization escapes" virus mutants and to the general decline in the host immune system associated with pathogenesis. In contrast, the presence of pre-existing neutralizing antibodies upon initial HIV-1 exposure will likely have a protective effect.

It is widely thought that a successful vaccine should be able to induce a strong, broadly neutralizing antibody response against diverse HIV-1 strains (Montefiori and Evans (1999) *AIDS Res. Hum. Ret.* 15(8):689-698; Bolognesi, D., P., et al. (1994) *Ann. Int. Med.* 8:603-611; Haynes, B., F., et al. (1996) *Science;* 271: 324-328.). Neutralizing antibodies, by attaching to the incoming virions, can reduce or even prevent their infectivity for target cells and prevent the cell-to-cell spread of virus in tissue culture (Hu et al. (1992) *Science* 255:456-459; Burton, D., R. and Montefiori, D. (1997) *AIDS* 11(suppl. A): 587-598). However as described above, antibodies directed against gp120 do not generally exhibit broad antibody responses against different HIV strains.

Currently, the focus of vaccine development, from the perspective of humoral immunity, is on the neutralization of primary isolates that utilize the CCR5 chemokine co-receptor believed to be important in virus entry (Zhu, T., et al. (1993) *Science* 261:1179-1181; Fiore, J., et al. (1994) Virology; 204: 297-303). These viruses are generally much more resistant to antibody neutralization than T-cell line adapted strains that use the CXCR4 co-receptor, although both can be neutralized in vitro by certain broadly and potent acting monoclonal antibodies, such as IgG1b12, 2G12 and 2F5 (Trkola, A., et al. (1995) *J. Virol.* 69:6609-6617; D'Sousa PM., et al (1997) *J. Infect. Dis.* 175:1062-1075). These monoclonal antibodies are directed to the CD4 binding site, a glycosylation site and to the gp41 fusion domain, respectively. The problem that remains, however, is that it is not known how to induce antibodies of the appropriate specificity by vaccination. Antibodies (Abs) elicited by gp120 glycoprotein from a given isolate are usually only able to neutralize closely related viruses generally from similar, usually from the same, HIV-1 subtype.

Despite the above approaches, there remains a need for Env antigens that can elicit an immunological response (e.g., neutralizing and/or protective antibodies) in a subject against multiple HIV strains and subtypes, for example when administered as a vaccine. The present invention solves these and other problems by providing modified Env polypeptides (e.g., gp120) to expose epitopes in or near the CD4 binding site.

SUMMARY OF THE INVENTION

In accordance with the present invention, modified HIV Env polypeptides are provided. In particular, deletions and/or mutations are made in one or more of the 4-β antiparallel-bridging sheet in the HIV Env polypeptide. In this way, enough structure is left to allow correct folding of the polypeptide, for example of gp120, yet enough of the bridging sheet is removed to expose the CD4 groove, allowing an immune response to be generated against epitopes in or near the CD4 binding site of the Env polypeptide (e.g., gp120).

In one aspect, the invention includes a polynucleotide encoding a modified HIV Env polypeptide wherein the polypeptide has at least one modified (e.g., deleted or replaced) amino acid residue deleted in the region corresponding to residues 421 to 436 relative to HXB-2, for example the constructs depicted in FIGS. 6-29 (SEQ ID NOs:3 to 26). In certain embodiments, the polynucleotide also has the region corresponding to residues 124-198 of the polypeptide HXB-2 (e.g., V1/V2) deleted and at least one amino acid deleted or replaced in the regions corresponding to the residues 119 to 123 and 199 to 210, relative to HXB-2. In other embodiments, these polynucleotides encode Env polypeptides having at least one amino acid of the small loop of the bridging sheet (e.g., amino acid residues 427 to 429 relative to HXB-2) deleted or replaced. The amino acid sequences of the modified polypeptides encoded by the polynucleotides of the present invention can be based on any HIV variant, for example SF162.

In another aspect, the invention includes immunogenic modified HIV Env polypeptides having at least one modified (e.g., deleted or replaced) amino acid residue deleted in the region corresponding to residues 421 to 436 relative to HXB-2, for example a deletion or replacement of one amino acids in the small loop region (e.g., amino acid residues 427 to 429 relative to HXB-2). These polypeptides may have modifications (e.g., a deletion or a replacement) of at least one amino acid between about amino acid residue 420 and amino acid residue 436, relative to HXB-2 and, optionally, may have deletions or truncations of the V1 and/or V2 regions. The immunogenic, modified polypeptides of the present invention can be based on any HIV variant, for example SF162.

In another aspect, the invention includes a vaccine composition comprising any of the polynucleotides encoding modified Env polypeptides described above. Vaccine compositions comprising the modified Env polypeptides and, optionally, an adjuvant are also included in the invention.

In yet another aspect, the invention includes a method of inducing an immune response in subject comprising, administering one or more of the polynucleotides or constructs described above in an amount sufficient to induce an immune response in the subject. In certain embodiments, the method further comprises administering an adjuvant to the subject.

In another aspect, the invention includes a method of inducing an immune response in a subject comprising administering a composition comprising any of the modified Env polypeptides described above and an adjuvant. The composition is administered in an amount sufficient to induce an immune response in the subject.

In another aspect, the invention includes a method of inducing an immune response in a subject comprising (a) administering a first composition comprising any of the polynucleotides described above in a priming step and (b) administering a second composition comprising any of the modified Env polypeptides described above, as a booster, in an amount sufficient to induce an immune response in the subject. In certain embodiments, the first composition, the second composition or both the first and second compositions further comprise an adjuvant.

These and other embodiments of the subject invention will readily occur to those of skill in the art in light of the disclosure herein.

BRIEF DESCRIPTION OF THE DRAWINGS

FIGS. 2A-C depict alignment of the amino acid sequence of wild-type HIV-1$_{HXB-2}$ Env gp160 polypeptide (SEQ ID NO:1) with amino acid sequence of HIV variants SF162 (shown as "162") (SEQ ID NO:2), SF2, CM236 and US4. Arrows indicate the regions that are deleted or replaced in the modified polypeptides. Black dots indicate conserved cysteine residues. The star indicates the position of the last amino acid in gp120.

FIGS. 3A-J depict alignment of nucleotide sequences of polynucleotides encoding modified Env polypeptides having V1/V2 deletions. The unmodified amino acid residues encoded by these sequences correspond to wildtype SF162 residues but are numbered relative to HXB-2.

FIGS. 4A-M depict alignment of nucleotide sequences of polynucleotides encoding modified Env polypeptides having deletions or replacements in the small loop. The unmodified amino acid residues encoded by these sequences correspond to wildtype SF162 residues but are numbered relative to HXB-2.

FIGS. 5A-N depict alignment of nucleotide sequences of polynucleotides encoding modified Env polypeptides having both V1/V2 deletions and, in addition, deletions or replacements in the small loop. The unmodified amino acid residues encoded by these sequences correspond to wildtype SF162 residues but are numbered relative to HXB-2.

FIG. 6 depicts the nucleotide sequence of the construct designated Val120-Ala204 (SEQ ID NO:3).

FIG. 7 depicts the nucleotide sequence of the construct designated Val120-Ile201 (SEQ ID NO:4).

FIG. 8 depicts the nucleotide sequence of the construct designated Val120-Ile201B (SEQ ID NO:5).

FIG. 9 depicts the nucleotide sequence of the construct designated Lys121-Val200 (SEQ ID NO:6).

FIG. 10 depicts the nucleotide sequence of the construct designated Leu122-Ser199 (SEQ ID NO:7).

FIG. 11 depicts the nucleotide sequence of the construct designated Val 20-Thr202 (SEQ ID NO:8).

FIG. 12 depicts the nucleotide sequence of the construct designated Trp427-Gly431 (SEQ ID NO:9).

FIG. 13 depicts the nucleotide sequence of the construct designated Arg426-Gly431 (SEQ ID NO:10).

FIG. 14 depicts the nucleotide sequence of the construct designated Arg426-Gly431B (SEQ ID NO:11).

FIG. 15 depicts the nucleotide sequence of the construct designated Arg426-Lys432 (SEQ ID NO:12).

FIG. 16 depicts the nucleotide sequence of the construct designated Asn425-Lys432 (SEQ ID NO:13).

FIG. 17 depicts the nucleotide sequence of the construct designated Ile424-Ala433 (SEQ ID NO:14).

FIG. 18 depicts the nucleotide sequence of the construct designated Ile423-Met434 (SEQ ID NO:15).

FIG. 19 depicts the nucleotide sequence of the construct designated Gln422-Tyr435 (SEQ ID NO:16).

FIG. 20 depicts the nucleotide sequence of the construct designated Gln422-Tyr435B (SEQ ID NO:17).

FIG. 21 depicts the nucleotide sequence of the construct designated Leu122-Ser199; Arg426-Gly431 (SEQ ID NO:18).

FIG. 22 depicts the nucleotide sequence of the construct designated Leu122-Ser199; Arg426-Lys432 (SEQ ID NO:19).

FIG. 23 depicts the nucleotide sequence of the construct designated Leu122-Ser199; Trp427-Gly431 (SEQ ID NO:20).

FIG. 24 depicts the nucleotide sequence of the construct designated Lys121-Val200; Asn425-Lys432 (SEQ ID NO:21).

FIG. 25 depicts the nucleotide sequence of the construct designated Val120-Ile201; Ile424-Ala433 (SEQ ID NO:22).

FIG. 26 depicts the nucleotide sequence of the construct designated Val 20-Ile201B; Ile424-Ala433 (SEQ ID NO:23).

FIG. 27 depicts the nucleotide sequence of the construct designated Val120-Thr202; Ile424-Ala433 (SEQ ID NO:24).

FIG. 28 depicts the nucleotide sequence of the construct designated Val127-Asn195 (SEQ ID NO:25).

FIG. 29 depicts the nucleotide sequence of the construct designated Val127-Asn195; Arg426-Gly431 (SEQ ID NO:26).

DETAILED DESCRIPTION OF THE INVENTION

Figure 1:
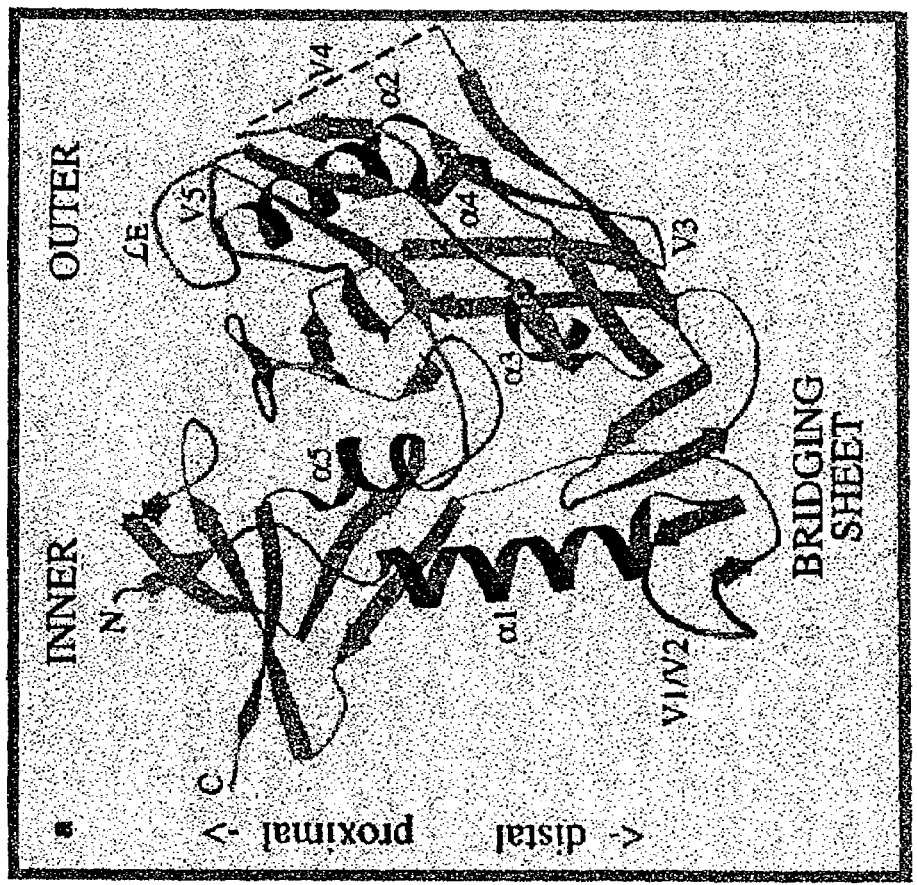
FIG. 1 is a schematic depiction of the tertiary structure of the HIV-1$_{HXB-2}$ Env gp120 polypeptide, as determined by crystallography studies.

The practice of the present invention will employ, unless otherwise indicated, conventional methods of protein chemistry, viral immunobiology, molecular biology and recombinant DNA techniques within the skill of the art. Such techniques are explained fully in the literature. See, e.g., T. E. Creighton, *Proteins: Structures and Molecular Properties* (W. H. Freeman and Company, 1993); Nelson L. M. and Jerome H. K. *HIV Protocols* in Methods in Molecular Medicine, vol. 17, 1999; Sambrook, et al., *Molecular Cloning: A Laboratory Manual* (Cold Spring Harbor Laboratory, 1989); F. M. Ausubel et al. *Current Protocols in Molecular Biology*, Greene Publishing Associates & Wiley Interscience New York; and Lipkowitz and Boyd, *Reviews in Computational Chemistry*, volumes 1-present (Wiley-VCH, New York, N.Y., 1999).

It must be noted that, as used in this specification and the appended claims, the singular forms "a", "an" and "the" include plural referents unless the content clearly dictates otherwise. Thus, for example, reference to "a polypeptide" includes a mixture of two or more polypeptides, and the like.

All publications, patents and patent applications cited herein, whether supra or infra, are hereby incorporated by reference in their entirety.

DEFINITIONS

In describing the present invention, the following terms will be employed, and are intended to be defined as indicated below.

The terms "polypeptide," and "protein" are used interchangeably herein to denote any polymer of amino acid residues. The terms encompass peptides, oligopeptides, dimers, multimers, and the like. Such polypeptides can be derived from natural sources or can be synthesized or recombinantly produced. The terms also include postexpression modifications of the polypeptide, for example, glycosylation, acetylation, phosphorylation, etc.

A polypeptide as defined herein is generally made up of the 20 natural amino acids Ala (A), Arg (R), Asn (N), Asp (D), Cys (C), Gln (O), Glu (E), Gly (G), H is (H), Ile (I), Leu (L), Lys (K), Met (M), Phe (F), Pro (P), Ser (S), Thr (T), Trp (W), Tyr (Y) and Val (V) and may also include any of the several known amino acid analogs, both naturally occurring and synthesized analogs, such as but not limited to homoisoleucine, asaleucine, 2-(methylenecyclopropyl)glycine, S-methylcysteine, S-(prop-1-enyl)cysteine, homoserine, ornithine, norleucine, norvaline, homoarginine, 3-(3-carboxyphenyl)alanine, cyclohexylalanine, mimosine, pipecolic acid, 4-methylglutamic acid, canavanine, 2,3-diaminopropionic acid, and the like. Further examples of polypeptide agents which will find use in the present invention are set forth below.

By "geometry" or "tertiary structure" of a polypeptide or protein is meant the overall 3-D configuration of the protein. As described herein, the geometry can be determined, for example, by crystallography studies or by using various programs or algorithms which predict the geometry based on interactions between the amino acids making up the primary and secondary structures.

By "wild type" polypeptide, polypeptide agent or polypeptide drug, is meant a naturally occurring polypeptide sequence, and its corresponding secondary structure. An "isolated" or "purified" protein or polypeptide is a protein which is separate and discrete from a whole organism with which the protein is normally associated in nature. It is apparent that the term denotes proteins of various levels of purity. Typically, a composition containing a purified protein will be one in which at least about 35%, preferably at least about 40-50%, more preferably, at least about 75-85%, and most preferably at least about 90% or more, of the total protein in the composition will be the protein in question.

By "Env polypeptide" is meant a molecule derived from an envelope protein, preferably from HIV Env. The envelope protein of HIV-1 is a glycoprotein of about 160 kd (gp160). During virus infection of the host cell, gp160 is cleaved by host cell proteases to form gp120 and the integral membrane protein, gp41. The gp41 portion is anchored in (and spans) the membrane bilayer of virion, while the gp120 segment protrudes into the surrounding environment. As there is no covalent attachment between gp120 and gp41, free gp120 is released from the surface of virions and infected cells. Env polypeptides may also include gp140 polypeptides. Env polypeptides can exist as monomers, dimers or multimers.

By a "gp120 polypeptide" is meant a molecule derived from a gp120 region of the Env polypeptide. Preferably, the gp120 polypeptide is derived from HIV Env. The primary amino acid sequence of gp120 is approximately 511 amino acids, with a polypeptide core of about 60,000 daltons. The polypeptide is extensively modified by N-linked glycosylation to increase the apparent molecular weight of the molecule to 120,000 daltons. The amino acid sequence of gp120 contains five relatively conserved domains interspersed with five hypervariable domains. The positions of the 18 cysteine residues in the gp120 primary sequence of the HIV-1$_{HXB-2}$ (hereinafter "HXB-2") strain, and the positions of 13 of the approximately 24 N-linked glycosylation sites in the gp120 sequence are common to most, if not all, gp120 sequences. The hypervariable domains contain extensive amino acid substitutions, insertions and deletions. Despite this variation, most, if not all, gp120 sequences preserve the virus's ability to bind to the viral receptor CD4. A "gp120 polypeptide" includes both single subunits or multimers.

Env polypeptides (e.g., gp120, gp140 and gp160) include a "bridging sheet" comprised of 4 anti-parallel β-strands (β-2, β-3, β-20 and β-21) that form a β-sheet. Extruding from one pair of the β-strands (β-2 and β-3) are two loops, V1 and V2. The β-2 sheet occurs at approximately amino acid residue 119 (Cys) to amino acid residue 123 (Thr) while β-3 occurs at approximately amino acid residue 199 (Ser) to amino acid residue 201 (Ile), relative to HXB-2. The "V1/V2 region" occurs at approximately amino acid positions 126 (Cys) to residue 196 (Cys), relative to HXB-2. (see, e.g., Wyatt et al. (1995) J. Virol. 69:5723-5733; Stamatatos et al. (1998) J. Virol. 72:7840-7845). Extruding from the second pair of β-strands (β-20 and β-21) is a "small-loop" structure, also referred to herein as "the bridging sheet small loop." In HXB-2, β-20 extends from about amino acid residue 422 (Gln) to amino acid residue 426 (Met) while β-21 extends from about amino acid residue 430 (Val) to amino acid residue 435 (Tyr). In variant SF162, the Met-426 is an Arg (R) residue. The "small loop" extends from about amino acid residue 427 (Trp) through 429 (Lys), relative to HXB-2. A representative diagram of gp120 showing the bridging sheet, the small loop, and V1/V2 is shown in FIG. 1. In addition, alignment of the amino acid sequences of Env polypeptide gp160 of selected variants is shown, relative to HXB-2, in FIGS. 2A-C.

Furthermore, an "Env polypeptide" or "gp120 polypeptide" as defined herein is not limited to a polypeptide having the exact sequence described herein. Indeed, the HIV genome is in a state of constant flux and contains several variable domains which exhibit relatively high degrees of variability between isolates. It is readily apparent that the terms encompass Env (e.g., gp120) polypeptides from any of the identified HIV isolates, as well as newly identified isolates, and subtypes of these isolates. Descriptions of structural features are given herein with reference to HXB-2. One of ordinary skill in the art in view of the teachings of the present disclosure and the art can determine corresponding regions in other HIV variants (e.g., isolates HIV$_{IIIb}$, HIV$_{SF2}$, HIV-1$_{SF162}$, HIV-1$_{SF170}$, HIV$_{LAV}$, HIV$_{LAI}$, HIV$_{MN}$, HIV-1$_{CM235}$, HIV-1$_{US4}$, other HIV-1 strains from diverse subtypes (e.g., subtypes, A through G, and O), HIV-2 strains and diverse subtypes (e.g., HIV-2$_{UC1}$ and HIV-2$_{UC2}$), and simian immunodeficiency virus (SIV). (See, e.g., Virology, 3rd Edition (W. K. Joklik ed. 1988); Fundamental Virology, 2nd Edition (B. N. Fields and D. M. Knipe, eds. 1991); Virology, 3rd Edition (Fields, B N, D M Knipe, P M Howley, Editors, 1996, Lippincott-Raven, Philadelphia, Pa.; for a description of these and other related viruses), using for example, sequence comparison programs (e.g., BLAST and others described herein) or identification and alignment of structural features (e.g., a program such as the "ALB" program described herein that can identify β-sheet regions). The actual amino acid sequences of the modified Env polypeptides can be based on any HIV variant.

Additionally, the term "Env polypeptide" (e.g., "gp120 polypeptide") encompasses proteins which include additional modifications to the native sequence, such as additional internal deletions, additions and substitutions. These modifications may be deliberate, as through site-directed mutagenesis, or may be accidental, such as through naturally occurring mutational events. Thus, for example, if the Env polypeptide is to be used in vaccine compositions, the modifications must be such that immunological activity (i.e., the ability to elicit an antibody response to the polypeptide) is not lost. Similarly, if the polypeptides are to be used for diagnostic purposes, such capability must be retained.

Thus, a "modified Env polypeptide" is an Env polypeptide (e.g., gp120 as defined above), which has been manipulated to delete or replace all or a part of the bridging sheet portion and, optionally, the variable regions V1 and V2. Generally, modified Env (e.g., gp120) polypeptides have enough of the bridging sheet removed to expose the CD4 binding site, but leave enough of the structure to allow correct folding (e.g., correct geometry). Thus, modifications to the β-20 and β-21 regions (between about amino acid residues 420 and 435 relative to HXB-2) are preferred. Additionally, modifications to the β-2 and β-3 regions (between about amino acid residues 119 (Cys) and 201 (Ile)) and modifications (e.g., truncations) to the V1 and V2 loop regions may also be made. Although not all possible i-sheet and V1/V2 modifications have been exemplified herein, it is to be understood that other disrupting modifications are also encompassed by the present invention.

Normally, such a modified polypeptide is capable of secretion into growth medium in which an organism expressing the protein is cultured. However, for purposes of the present invention, such polypeptides may also be recovered intracellularly. Secretion into growth media is readily determined using a number of detection techniques, including, e.g., polyacrylamide gel electrophoresis and the like, and immunological techniques such as Western blotting and immunoprecipitation assays as described in, e.g., International Publication No. WO 96/04301, published Feb. 15, 1996.

A gp120 or other Env polypeptide is produced "intracellularly" when it is found within the cell, either associated with components of the cell, such as in association with the endoplasmic reticulum (ER) or the Golgi Apparatus, or when it is present in the soluble cellular fraction. The gp120 and other Env polypeptides of the present invention may also be secreted into growth medium so long as sufficient amounts of the polypeptides remain present within the cell such that they can be purified from cell lysates using techniques described herein.

An "immunogenic" gp120 or other Env protein is a molecule that includes at least one epitope such that the molecule is capable of either eliciting an immunological reaction in an individual to which the protein is administered or, in the diagnostic context, is capable of reacting with antibodies directed against the HIV in question.

By "epitope" is meant a site on an antigen to which specific B cells and/or T cells respond, rendering the molecule including such an epitope capable of eliciting an immunological reaction or capable of reacting with HIV antibodies present in a biological sample. The term is also used interchangeably with "antigenic determinant" or "antigenic determinant site." An epitope can comprise 3 or more amino acids in a spatial conformation unique to the epitope. Generally, an epitope consists of at least 5 such amino acids and, more usually, consists of at least 8-10 such amino acids. Methods of determining spatial conformation of amino acids are known in the art and include, for example, x-ray crystallography and 2-dimensional nuclear magnetic resonance. Furthermore, the identification of epitopes in a given protein is readily accomplished using techniques well known in the art, such as by the use of hydrophobicity studies and by site-directed serology. See, also, Geysen et al., *Proc. Natl. Acad. Sci. USA* (1984) 81:3998-4002 (general method of rapidly synthesizing peptides to determine the location of immunogenic epitopes in a given antigen); U.S. Pat. No. 4,708,871 (procedures for identifying and chemically synthesizing epitopes of antigens); and Geysen et al., *Molecular Immunology* (1986) 23:709-715 (technique for identifying peptides with high affinity for a given antibody). Antibodies that recognize the same epitope can be identified in a simple immunoassay showing the ability of one antibody to block the binding of another antibody to a target antigen.

An "immunological response" or "immune response" as used herein is the development in the subject of a humoral and/or a cellular immune response to the Env (e.g., gp120) polypeptide when the polypeptide is present in a vaccine composition. These antibodies may also neutralize infectivity, and/or mediate antibody-complement or antibody dependent cell cytotoxicity to provide protection to an immunized host. Immunological reactivity may be determined in standard immunoassays, such as a competition assays, well known in the art.

Techniques for determining amino acid sequence "similarity" are well known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively.

Two or more polynucleotide sequences can be compared by determining their "percent identity." Two or more amino acid sequences likewise can be compared by determining their "percent identity." The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be extended to use with peptide sequences using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An implementation of this algorithm for nucleic acid and peptide sequences is provided by the Genetics Computer Group (Madison, Wis.) in their BestFit utility application. The default parameters for this method are described in the Wisconsin Sequence Analysis Package Program Manual, Version 8 (1995) (available from Genetics Computer Group, Madison, Wis.). Other equally suitable programs for calculating the percent identity or similarity between sequences are generally known in the art.

For example, percent identity of a particular nucleotide sequence to a reference sequence can be determined using the homology algorithm of Smith and Waterman with a default scoring table and a gap penalty of six nucleotide positions. Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated, the "Match" value reflects "sequence identity." Other suitable programs for calculating the percent identity or similarity between sequences are generally known in the art, such as the alignment program BLAST, which can also be used with default parameters. For example, BLASTN and BLASTP can be used with the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST.

One of skill in the art can readily determine the proper search parameters to use for a given sequence in the above programs. For example, the search parameters may vary based on the size of the sequence in question. Thus, for example, a representative embodiment of the present invention would include an isolated polynucleotide having X contiguous nucleotides, wherein (i) the X contiguous nucleotides have at least about 50% identity to Y contiguous nucleotides derived from any of the sequences described herein, (ii) X equals Y, and (iii) X is greater than or equal to 6 nucleotides and up to 5000 nucleotides, preferably greater than or equal to 8 nucleotides and up to 5000 nucleotides, more preferably 10-12 nucleotides and up to 5000 nucleotides, and even more preferably 15-20 nucleotides, up to the number of nucleotides present in the full-length sequences described herein (e.g., see the Sequence Listing and claims), including all integer values falling within the above-described ranges.

The synthetic expression cassettes (and purified polynucleotides) of the present invention include related polynucleotide sequences having about 80% to 100%, greater than 80-85%, preferably greater than 90-92%, more preferably greater than 95%, and most preferably greater than 98% sequence (including all integer values falling within these described ranges) identity to the synthetic expression cassette sequences disclosed herein (for example, to the claimed sequences or other sequences of the present invention) when the sequences of the present invention are used as the query sequence.

Computer programs are also available to determine the likelihood of certain polypeptides to form structures such as β-sheets. One such program, described herein, is the "ALB" program for protein and polypeptide secondary structure calculation and predication. In addition, secondary protein structure can be predicted from the primary amino acid sequence, for example using protein crystal structure and aligning the protein sequence related to the crystal structure (e.g., using Molecular Operating Environment (MOE) programs available from the Chemical Computing Group Inc., Montreal, P.Q., Canada). Other methods of predicting secondary structures are described, for example, in Garnier et al. (1996) *Methods Enzymol.* 266:540-553; Geourjon et al. (1995) *Comput. Applic. Biosci.* 11:681-684; Levin (1997) *Protein Eng.* 10:771-776; and Rost et al. (1993) *J. Molec. Biol.* 232:584-599.

Homology can also be determined by hybridization of polynucleotides under conditions which form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80%-85%, preferably at least about 90%, and most preferably at least about 95%-98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

A "coding sequence" or a sequence which "encodes" a selected protein, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to cDNA from viral nucleotide sequences as well as synthetic and semisynthetic DNA sequences and sequences including base analogs. A transcription termination sequence may be located 3' to the coding sequence.

"Control elements" refers collectively to promoter sequences, ribosome binding sites, polyadenylation signals, transcription termination sequences, upstream regulatory domains, enhancers, and the like, which collectively provide for the transcription and translation of a coding sequence in a host cell. Not all of these control elements need always be present so long as the desired gene is capable of being transcribed and translated.

A control element "directs the transcription" of a coding sequence in a cell when RNA polymerase will bind the promoter sequence and transcribe the coding sequence into mRNA, which is then translated into the polypeptide encoded by the coding sequence.

"Operably linked" refers to an arrangement of elements wherein the components so described are configured so as to perform their usual function. Thus, control elements operably linked to a coding sequence are capable of effecting the expression of the coding sequence when RNA polymerase is present. The control elements need not be contiguous with the coding sequence, so long as they function to direct the expression thereof. Thus, for example, intervening untranslated yet transcribed sequences can be present between, e.g., a promoter sequence and the coding sequence and the promoter sequence can still be considered "operably linked" to the coding sequence.

"Recombinant" as used herein to describe a nucleic acid molecule means a polynucleotide of genomic, cDNA, semi-synthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

By "vertebrate subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

As used herein, a "biological sample" refers to a sample of tissue or fluid isolated from an individual, including but not limited to, for example, blood, plasma, serum, fecal matter, urine, bone marrow, bile, spinal fluid, lymph fluid, samples of the skin, external secretions of the skin, respiratory, intestinal, and genitourinary tracts, samples derived from the gastric epithelium and gastric mucosa, tears, saliva, milk, blood cells, organs, biopsies and also samples of in vitro cell culture constituents including but not limited to conditioned media resulting from the growth of cells and tissues in culture medium, e.g., recombinant cells, and cell components.

The terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof which is capable of exhibiting fluorescence in the detectable range: Particular examples of labels which may be used with the invention include, but are not limited to fluorescein, rhodamine, dansyl, umbelliferone, Texas red, luminol, acradimum esters, NADPH, $\alpha$-$\beta$-galactosidase, horseradish peroxidase, glucose oxidase, alkaline phosphatase and urease.

Overview

The present invention concerns modified Env polypeptide molecules (e.g., glycoprotein ("gp") 120). Without being bound by a particular theory, it appears that it has been difficult to generate immunological responses against Env because the CD4 binding site is buried between the outer domain, the inner domain and the V1/V2 domains. Thus, although deletion of the V1/V2 domain may render the virus more susceptible to neutralization by monoclonal antibody directed to the CD4 site, the bridging sheet covering most of the CD4 binding domain may prevent an antibody response. Thus, the present invention provides Env polypeptides that maintain their general overall structure yet expose the CD4 binding domain. This allows the generation of an immune response (e.g., an antibody response) to epitopes in or near the CD4 binding site.

Various forms of the different embodiments of the invention, described herein, may be combined.

β-Sheet Conformations

In the present invention, location of the β-sheet structures were identified relative to 3-D (crystal) structure of an HXB-2 crystallized Env protein (see, Example 1A). Based on this structure, constructs encoding polypeptides having replacements and or excisions which maintain overall geometry while exposing the CD4 binding site were designed. In particular, the crystal structure of HXB-2 was downloaded from the Brookhaven Database. Using the default parameters of the Loop Search feature of the Biopolymer module of the Sybyl molecular modeling package, homology and fit of amino acids which could replace the native loops between β-strands yet maintain overall tertiary structure were determined. Constructs encoding the modified Env polypeptides were then designed (Example 1.B.).

Thus, the modified Env polypeptides typically have enough of the bridging sheet removed to expose the CD4 groove, but have enough of the structure to allow correct folding of the Env glycoprotein. Exemplary constructs are described below.

Polypeptide Production

The polypeptides of the present invention can be produced in any number of ways which are well known in the art.

In one embodiment, the polypeptides are generated using recombinant techniques, well known in the art. In this regard, oligonucleotide probes can be devised based on the known sequences of the Env (e.g., gp120) polypeptide genome and used to probe genomic or cDNA libraries for Env genes. The gene can then be further isolated using standard techniques and, e.g., restriction enzymes employed to truncate the gene at desired portions of the full-length sequence. Similarly, the Env gene(s) can be isolated directly from cells and tissues containing the same, using known techniques, such as phenol extraction and the sequence further manipulated to produce the desired truncations. See, e.g., Sambrook et al., supra, for a description of techniques used to obtain and isolate DNA.

The genes encoding the modified (e.g., truncated and/or substituted) polypeptides can be produced synthetically, based on the known sequences. The nucleotide sequence can be designed with the appropriate codons for the particular amino acid sequence desired. The complete sequence is generally assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311; Stemmer et al. (1995) *Gene* 164:49-53.

Recombinant techniques are readily used to clone a gene encoding an Env polypeptide gene which can then be mutagenized in vitro by the replacement of the appropriate base pair(s) to result in the codon for the desired amino acid. Such a change can include as little as one base pair, effecting a change in a single amino acid, or can encompass several base pair changes. Alternatively, the mutations can be effected using a mismatched primer which hybridizes to the parent nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. See, e.g., Innis et al, (1990) PCR Applications: Protocols for Functional Genomics; Zoller and Smith, Methods Enzymol. (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. Proc. Natl. Acad. Sci. USA (1982) 79:6409.

Once coding sequences for the desired proteins have been isolated or synthesized, they can be cloned into any suitable vector or replicon for expression. As will be apparent from the teachings herein, a wide variety of vectors encoding modified polypeptides can be generated by creating expression constructs which operably link, in various combinations, polynucleotides encoding Env polypeptides having deletions or mutation therein. Thus, polynucleotides encoding a particular deleted V1/V2 region can be operably linked with polynucleotides encoding polypeptides having deletions or replacements in the small loop region and the construct introduced into a host cell for polypeptide expression. Non-limiting examples of such combinations are discussed in the Examples.

Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Strepto-*

*myces*), pUC6 (*Streptomyces*), YIp5 (*Saccharomyces*), YCp19 (*Saccharomyces*) and bovine papilloma virus (mammalian cells). See, generally, *DNA Cloning*: Vols. I & II, supra; Sambrook et al., supra; B. Perbal, supra.

Insect cell expression systems, such as baculovirus systems, can also be used and are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego Calif. ("MaxBac" kit).

Plant expression systems can also be used to produce the modified Env proteins. Generally, such systems use virus-based vectors to transfect plant cells with heterologous genes. For a description of such systems see, e.g., Porta et al., *Mol. Biotech.* (1996) 5:209-221; and Hackland et al., *Arch. Virol.* (1994) 139:1-22.

Viral systems, such as a vaccinia based infection/transfection system, as described in Tomei et al., *J. Virol.* (1993) 67:4017-4026 and Selby et al., *J. Gen. Virol.* (1993) 74:1103-1113, will also find use with the present invention. In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation product(s).

The gene can be placed under the control of a promoter, ribosome binding site (for bacterial expression) and, optionally, an operator (collectively referred to herein as "control" elements), so that the DNA sequence encoding the desired Env polypeptide is transcribed into RNA in the host cell transformed by a vector containing this expression construction. The coding sequence may or may not contain a signal peptide or leader sequence. With the present invention, both the naturally occurring signal peptides or heterologous sequences can be used. Leader sequences can be removed by the host in post-translational processing. See, e.g., U.S. Pat. Nos. 4,431,739; 4,425,437; 4,338,397. Such sequences include, but are not limited to, the TPA leader, as well as the honey bee mellitin signal sequence.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; *DNA Cloning*, Vols. I and II, supra; *Nucleic Acid Hybridization*, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Vero293 cells, as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californiccz, Bombyx mori, Drosophila melanogaster, Spodoptera frugiperda*, and *Trichoplusia ni*.

Depending on the expression system and host selected, the proteins of the present invention are produced by growing host cells transformed by an expression vector described above under conditions whereby the protein of interest is expressed. The selection of the appropriate growth conditions is within the skill of the art.

In one embodiment, the transformed cells secrete the polypeptide product into the surrounding media. Certain regulatory sequences can be included in the vector to enhance secretion of the protein product, for example using a tissue plasminogen activator (TPA) leader sequence, a γ-interferon signal sequence or other signal peptide sequences from known secretory proteins. The secreted polypeptide product can then be isolated by various techniques described herein, for example, using standard purification techniques such as but not limited to, hydroxyapatite resins, column chromatography, ion-exchange chromatography, size-exclusion chromatography, electrophoresis, HPLC, immunoadsorbent techniques, affinity chromatography, immunoprecipitation, and the like.

Alternatively, the transformed cells are disrupted, using chemical, physical or mechanical means, which lyse the cells yet keep the Env polypeptides substantially intact. Intracellular proteins can also be obtained by removing components from the cell wall or membrane, e.g., by the use of detergents or organic solvents, such that leakage of the Env polypeptides occurs. Such methods are known to those of skill in the art and are described in, e.g., *Protein Purification Applications: A Practical Approach*, (E. L. V. Harris and S. Angal, Eds., 1990)

For example, methods of disrupting cells for use with the present invention include but are not limited to: sonication or ultrasonication; agitation; liquid or solid extrusion; heat treatment; freeze-thaw; desiccation; explosive decompression; osmotic shock; treatment with lytic enzymes including proteases such as trypsin, neuraminidase and lysozyme; alkali treatment; and the use of detergents and solvents such as bile salts, sodium dodecylsulphate, Triton, NP40 and CHAPS. The particular technique used to disrupt the cells is largely a matter of choice and will depend on the cell type in which the polypeptide is expressed, culture conditions and any pretreatment used.

Following disruption of the cells, cellular debris is removed, generally by centrifugation, and the intracellularly produced Env polypeptides are further purified, using standard purification techniques such as but not limited to, column chromatography, ion-exchange chromatography, size-exclusion chromatography, electrophoresis, HPLC, immunoadsorbent techniques, affinity chromatography, immunoprecipitation, and the like.

For example, one method for obtaining the intracellular Env polypeptides of the present invention involves affinity purification, such as by immunoaffinity chromatography using anti-Env specific antibodies, or by lectin affinity chromatography. Particularly preferred lectin resins are those that recognize mannose moieties such as but not limited to resins derived from *Galanthus nivalis* agglutinin (GNA), *Lens culinaris* agglutinin (LCA or lentil lectin), *Pisum sativum* agglutinin (PSA or pea lectin), *Narcissus pseudonarcissus* agglutinin (NPA) and *Allium ursinum* agglutinin (AUA). The choice of a suitable affinity resin is within the skill in the art. After affinity purification, the Env polypeptides can be further purified using conventional techniques well known in the art, such as by any of the techniques described above.

It may be desirable to produce Env (e.g., gp120) complexes, either with itself or other proteins. Such complexes are readily produced by e.g., co-transfecting host cells with constructs encoding for the Env (e.g., gp120) and/or other polypeptides of the desired complex. Co-transfection can be accomplished either in trans or cis, i.e., by using separate vectors or by using a single vector which bears both of the Env and other gene. If done using a single vector, both genes can be driven by a single set of control elements or, alternatively, the genes can be present on the vector in individual expression cassettes, driven by individual control elements. Following expression, the proteins will spontaneously associate. Alternatively, the complexes can be formed by mixing the individual proteins together which have been produced separately, either in purified or semi-purified form, or even by mixing culture media in which host cells expressing the proteins, have been cultured. See, International Publication No. WO 96/04301, published Feb. 15, 1996, for a description of such complexes.

Relatively small polypeptides, i.e., up to about 50 amino acids in length, can be conveniently synthesized chemically, for example by any of several techniques that are known to those skilled in the peptide art. In general, these methods employ the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, *Solid Phase Peptide Synthesis* (Pierce Chemical Co., Rockford, Ill. 1984) and G. Barany and R. B. Merrifield, *The Peptides: Analysis, Synthesis, Biology*, editors E. Gross and J. Meienhofer, Vol. 2, (Academic Press, New York, 1980), pp. 3-254, for solid phase peptide synthesis techniques; and M. Bodansky, *Principles of Peptide Synthesis*, (Springer-Verlag, Berlin 1984) and E. Gross and J. Meienhofer, Eds., *The Peptides: Analysis, Synthesis, Biology*, Vol. 1, for classical solution synthesis.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like.

Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

The polypeptide analogs of the present invention can also be chemically prepared by other methods such as by the method of simultaneous multiple peptide synthesis. See, e.g., Houghten *Proc. Natl. Acad. Sci. USA* (1985) 82:5131-5135; U.S. Pat. No. 4,631,211.

Diagnostic and Vaccine Applications

The intracellularly produced Env polypeptides of the present invention, complexes thereof, or the polynucleotides coding therefor, can be used for a number of diagnostic and therapeutic purposes. For example, the proteins and polynucleotides or antibodies generated against the same, can be used in a variety of assays, to determine the presence of reactive antibodies/and or Env proteins in a biological sample to aid in the diagnosis of HIV infection or disease status or as measure of response to immunization.

The presence of antibodies reactive with the Env (e.g., gp120) polypeptides and, conversely, antigens reactive with antibodies generated thereto, can be detected using standard electrophoretic and immunodiagnostic techniques, including immunoassays such as competition, direct reaction, or sandwich type assays. Such assays include, but are not limited to, western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, or enzymatic labels or dye molecules, or other methods for detecting the formation of a complex between the antigen and the antibody or antibodies reacted therewith.

Solid supports can be used in the assays such as nitrocellulose, in membrane or microtiter well form; polyvinylchloride, in sheets or microtiter wells; polystyrene latex, in beads or microtiter plates; polyvinylidine fluoride; diazotized paper; nylon membranes; activated beads, and the like.

Typically, the solid support is first reacted with the biological sample (or the gp120 proteins), washed and then the antibodies, (or a sample suspected of containing antibodies), applied. After washing to remove any non-bound ligand, a secondary binder moiety is added under suitable binding conditions, such that the secondary binder is capable of associating selectively with the bound ligand. The presence of the secondary binder can then be detected using techniques well known in the art. Typically, the secondary binder will comprise an antibody directed against the antibody ligands. A number of anti-human immunoglobulin (Ig) molecules are known in the art (e.g., commercially available goat anti-human Ig or rabbit anti-human Ig). Ig molecules for use herein will preferably be of the IgG or IgA type, however, IgM may also be appropriate in some instances. The Ig molecules can be readily conjugated to a detectable enzyme-label, such as horseradish peroxidase, glucose oxidase, Beta-galactosidase, alkaline phosphatase and urease, among others, using methods known to those of skill in the art. An appropriate enzyme substrate is then used to generate a detectable signal.

Alternatively, a "two antibody sandwich" assay can be used to detect the proteins of the present invention. In this technique, the solid support is reacted first with one or more of the antibodies directed against Env (e.g., gp120), washed and then exposed to the test sample. Antibodies are again added and the reaction visualized using either a direct color reaction or using a labeled second antibody, such as an anti-immunoglobulin labeled with horseradish peroxidase, alkaline phosphatase or urease.

Assays can also be conducted in solution, such that the viral proteins and antibodies thereto form complexes under precipitating conditions. The precipitated complexes can then be separated from the test sample, for example, by centrifugation. The reaction mixture can be analyzed to determine the presence or absence of antibody-antigen complexes using any of a number of standard methods, such as those immunodiagnostic methods described above.

The modified Env proteins, produced as described above, or antibodies to the proteins, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

The Env polypeptides and polynucleotides encoding the polypeptides can also be used in vaccine compositions, individually or in combination, in e.g., prophylactic (i.e., to prevent infection) or therapeutic (to treat HIV following infection) vaccines. The vaccines can comprise mixtures of one or more of the modified Env proteins (or nucleotide sequences encoding the proteins), such as Env (e.g., gp120) proteins derived from more than one viral isolate. The vaccine may also be administered in conjunction with other antigens and immunoregulatory agents, for example, immunoglobulins, cytokines, lymphokines, and chemokines, including but not limited to IL-2, modified IL-2 (cys125→ser125), GM-CSF, IL-12, γ-interferon, IP-10, MIP1β and RANTES. The vaccines may be administered as polypeptides or, alternatively, as naked nucleic acid vaccines (e.g., DNA), using viral vectors (e.g., retroviral vectors, adenoviral vectors, adeno-associated viral vectors) or non-viral vectors (e.g., liposomes, particles coated with nucleic acid or protein). The vaccines may also comprise a mixture of protein and nucleic acid, which in turn may be delivered using the same or different vehicles. The vaccine may be given more than once (e.g., a "prime" administration followed by one or more "boosts") to achieve the desired effects. The same composition can be administered as the prime and as the one or more boosts. Alternatively, different compositions can be used for priming and boosting.

The vaccines will generally include one or more "pharmaceutically acceptable excipients or vehicles" such as water, saline, glycerol, ethanol, etc. Additionally, auxiliary substances, such as wetting or emulsifying agents, pH buffering substances, and the like, may be present in such vehicles.

A carrier is optionally present which is a molecule that does not itself induce the production of antibodies harmful to the individual receiving the composition. Suitable carriers are typically large, slowly metabolized macromolecules such as proteins, polysaccharides, polylactic acids, polyglycollic acids, polymeric amino acids, amino acid copolymers, lipid aggregates (such as oil droplets or liposomes), and inactive virus particles. Such carriers are well known to those of ordinary skill in the art. Furthermore, the Env polypeptide may be conjugated to a bacterial toxoid, such as toxoid from diphtheria, tetanus, cholera, etc.

Adjuvants may also be used to enhance the effectiveness of the vaccines. Such adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc.; (6) detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. WO93/13202 and WO92/19265); and (7) other substances that act as immunostimulating agents to enhance the effectiveness of the composition.

Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetylmuramyl-L-alanyl-D-isogluatminyl-L-alanine-2-(1'-2'-dipalmitoyl-sn-glycero-3-huydroxyphosphoryloxy)-ethylamine (MTP-PE), etc.

Typically, the vaccine compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above.

The vaccines will comprise a therapeutically effective amount of the modified Env proteins, or complexes of the proteins, or nucleotide sequences encoding the same, and any other of the above-mentioned components, as needed. By "therapeutically effective amount" is meant an amount of a modified Env (e.g., gp120) protein which will induce a protective immunological response in the uninfected, infected or unexposed individual to which it is administered. Such a response will generally result in the development in the subject of a secretory, cellular and/or antibody-mediated immune response to the vaccine. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell.

Preferably, the effective amount is sufficient to bring about treatment or prevention of disease symptoms. The exact amount necessary will vary depending on the subject being treated; the age and general condition of the individual to be treated; the capacity of the individual's immune system to synthesize antibodies; the degree of protection desired; the severity of the condition being treated; the particular Env polypeptide selected and its mode of administration, among other factors. An appropriate effective amount can be readily determined by one of skill in the art. A "therapeutically effective amount" will fall in a relatively broad range that can be determined through routine trials.

Once formulated, the nucleic acid vaccines may be accomplished with or without viral vectors, as described above, by injection using either a conventional syringe or a gene gun, such as the Accell® gene delivery system (PowderJect Technologies, Inc., Oxford, England). Delivery of DNA into cells of the epidermis is particularly preferred as this mode of administration provides access to skin-associated lymphoid cells and provides for a transient presence of DNA in the recipient. Both nucleic acids and/or peptides can be injected either subcutaneously, epidermally, intradermally, intramucosally such as nasally, rectally and vaginally, intraperitoneally, intravenously, orally or intramuscularly. Other modes of administration include oral and pulmonary administration, suppositories, needle-less injection, transcutaneous and transdermal applications. Dosage treatment may be a single dose schedule or a multiple dose schedule. Administration of nucleic acids may also be combined with administration of peptides or other substances.

While the invention has been described in conjunction with the preferred specific embodiments thereof, it is to be understood that the foregoing description as well as the examples which follow are intended to illustrate and not limit the scope of the invention. Other aspects, advantages and modifications within the scope of the invention will be apparent to those skilled in the art to which the invention pertains.

EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

A.1. Best-Fit and Homology Searches

The crystal structure of HXB-2 gp120 was downloaded from the Brookhaven database (COMPLEX (HIV ENVELOPE PROTEIN/CD4/FAB) 15-JUN-98 1GCI TITLE: HIV-1 GP120 CORE COMPLEXED WITH CD4 AND A NEUTRALIZING HUMAN ANTIBODY). Beta strands 3, 2, 21, and 20 of gp120 form a sheet near the CD4 binding site. Strands $\beta$-3 and $\beta$-2 are connected by the V1/V2 loop. Strands $\beta$-21 and $\beta$-20 are connected by another small loop. The H-bonds at the interface between strands $\beta$-2 and $\beta$-21 are the only connection between domains of the "lower" half of the protein (joining helix alpha 1 to the CD4 binding site). This beta sheet and these loops mask some antigens (e.g., antigens which may generate neutralizing antibodies) that are only exposed during the CD4 binding.

Constructs that remove enough of the beta sheet to expose the antigens in the CD4 binding site, but leave enough of the protein to allow correct folding were designed. Specifically targeted were modifications to the small loop and, optional deletion of the V1/V2 loops. Three different types of constructs were designed: (1) constructs encoding polypeptides that leave the number of residues making up the entire 4-strand beta sheet intact, but replace one or more residues; (2) constructs that encode polypeptide having at least one residue of at least one beta strand excised or (3) constructs encoding polypeptides having at least two residues of at least one beta strand excised. Thus, a total of 6 different turns were needed to rejoin the ends of the strands.

Initially, residues in the small loop (residues 427-430, relative to HXB-2) and connected beta strands ($\beta$-20 and $\beta$-21) were modified to contain Gly and Pro (common in beta turns). These sequences were then used as the target to match in each search. The geometry of the target was matched to known proteins in the Brookhaven Protein Data Bank. In particular, 5-residue turns (including an overlapping single residue at the N-terminal, the 2 residue target turn and 2 overlapping residues at the C-terminal) were searched in the databases. In other words, these modified loops add a 2 residue turn that should be able to support a geometry that will maintain the beta-sheet structure of the wild type protein. The calculations were performed using the default parameters in the Loop Search feature of the Biopolymer module of the Sybyl molecular modeling package. In each case, the 25 best fits based on geometry alone were reviewed and, of those, several selected for homology and fit.

In addition, it was also determined what modifications could be made to remove most of the V1/V2 loop (residues 124-198, relative to HXB-2) yet leave the geometry of the protein intact. As with the small loop, constructs were also designed which excised one or more residues from the $\beta$-2 strand (residues 119-123 of HXB-2), the $\beta$-3 strand (residues 199-201 of HXB-2) or both $\beta$-2 and $\beta$-3. For these constructs, known loops were searched to match the geometry of a pentamer (including two remaining residues from the N-terminal side, a 2 residue turn and 1 C-terminal residue). For these searches, Gly-Gly was preferred as the insert along with at least one C-terminal substitution.

A.2. Small Loop Replacements

In one aspect, the native sequence was replaced with residues that expose the CD4 binding site, but leave the overall geometry of the protein relatively unchanged. For the small loop replacements, the target to match was: ASN425-MET426-GLY427-GLY428-GLY43 1. Results of the search are summarized in Table 1.

TABLE 1

Search of Small Loop (Asn425 through Gly431)

| Rank | Sequence | RMSD | % Homology | Seq Id No. |
|---|---|---|---|---|
| Best fit | LYS-ASP-SER-ASN-ASN | 0.16689 | 62.5 | 27 |
| 3 | TYR-GLY-LEU-GLY-LEU | 0.220308 | 62.5 | 28 |
| 4 | GLU-ARG-GLU-ASP-GLY | 0.241754 | 62.5 | 29 |
| 7 | ARG-LYS-GLY-GLY-ASN | 0.24881 | 100 | 30 |
| 12 | TRP-THR-GLY-SER-TYR | 0.26417 | 83.33 | 31 |

Based on these results, constructs encoding Gly-Gly (#7), Gly-Ser (#12) or Gly-Gly-Asn (#7) were recommended.

As V1/V2 and one or more residues of β-2 and β-3 are also optionally deleted in the modified polypeptides of the invention, known loops to match the geometry of the V1/V2 loop were also searched. The V1/V2 loop the target to match was: Lys121-Leu-122-Gly123-Gly124-Ser199. Some notable matches are shown in Table 2:

TABLE 2

Search of V1/V2 loop (Lys121 through Ser199)

| Rank | Sequence | RMSD | % Homology | Seq Id. No. |
|---|---|---|---|---|
| Best fit | GLN-VAL-HIS-ASP-GLU | 0.154764 | 68.75 | 32 |
| 2 | LYS-GLU-GLY-ASP-LYS | 0.15718 | 81.25 | 33 |
| 9 | ARG-SER-GLY-ARG-SER | 0.173731 | 68.75 | 34 |
| 11 | THR-LEU-GLY-ASN-SER | 0.175554 | 81.25 | 35 |
| 16 | HIS-PHE-GLY-ALA-GLY | 0.178772 | 93.75 | 36 |

Based on these searches, constructs encoding Gly-Asn in place of V1/V2 were recommended.

A.3. One Additional Residue Excisions

For a slightly truncated small loop, one more residue was trimmed from each beta strand to slightly shorten the beta sheet. The target to match was: ILE424-ASN425-GLY426-GLY427-LYS432. Results are shown in Table 3:

TABLE 3

Search of Beta sheet shortened by One residue (Ile424 through Lys432)

| Rank | Sequence | RMSD | % Homology | Seq Id No. |
|---|---|---|---|---|
| Best fit: | ARG-MET-ALA-PRO-VAL | 0.316805 | 58.33 | 37 |
| Best hom: | ASP-SER-ASP-GLY-PRO | 0.440896 | 83.33 | 38 |

Although these searches showed more variation and worse fits than the previous truncation, the Pro-Val or Pro-Leu encoding constructs were very similar. Accordingly, Ala-Pro encoding constructs were recommended.

Sequences encoding gp120 polypeptides having V1/V2 deleted and an additional residue from β-2 or β-3 excised were also searched. The V1/V2 loop the target to match was: VAL120-LYS121-GLY122-GLY123-VAL200. Some notable matches are shown in Table 4.

TABLE 4

Search of V1/V2 loop (Val120 through Val200)

| Rank | Sequence | RMSD | % Homology | Seq Id No |
|---|---|---|---|---|
| Best fit: | THR-VAL-ASP-PRO-TYR | 0.400892 | 58.33333 | 39 |
| 2 | SER-THR-ASN-PRO-LEU | 0.402575 | 54.16667 | 40 |
| 3 | THR-ARG-SER-PRO-LEU | 0.403965 | 58.33333 | 41 |
| 7 | ARG-MET-ALA-PRO-VAL | 0.440118 | 58.33333 | 42 |

The construct encoding Ala-Pro (e.g., #7) was recommended.

A.4. Further Excisions

In yet another truncation, an additional residue was trimmed from the β-20 and β-21 strands to further shorten the beta sheet. The target to match was ILE423-ILE424-GLY425-GLY426-ALA433. Notable matches are shown in Table 5.

TABLE 5

Search of Beta sheet shortened by Two Residues (Ile423 through Ala433)

| Rank | Sequence | RMSD | % Homology | Seq Id No |
|---|---|---|---|---|
| Best fit: | THR-TYR-GLU-GLY-VAL | 0.130107 | 79.16666 | 43 |
| 2 | GLN-VAL-GLY-ASN-THR | 0.138245 | 79.16666 | 44 |
| 3: | THR-VAL-GLY-GLY-ILE | 0.153362 | 100 | 45 |

A construct encoding Gly-Gly (e.g., #3), which has 100% homology, was recommended.

Also searched were sequences encoding a deleted V1/V2 region and at least two residues excised from β-2, β-3 or at least one residue excised from β-2 and β-3. The target to match was: CYS119-VAL120-GLY121-GLY122-ILE201. Notable matches are shown in Table 6.

TABLE 6

Search of V1/V2 loop (Cys119 through Ile201)

| Rank | Sequence | RMSD | % Homology | Seq Id No |
|---|---|---|---|---|
| Best fit: | ASP-LEU-PRO-GLY-CYS | 0.250501 | 75 | 46 |
| 4 | ASP-VAL-GLY-GLY-LEU | 0.290383 | 100 | 47 |

It was determined that both constructs would be used.

B.1. Constructs Encoding Modified Env Polypeptides

As described above, the native loops extruding from the 4-β, antiparallel-stands were excised and replaced with 1 to 3 residue turns. The loops were replaced so as to leave the entire β-strands or excised by trimming one or more amino acid from each side of the connected strands. The ends of the strands were rejoined with turns that preserve the same backbone geometry (e.g., tertiary structure of β-20 and β-21), as determined by searching the Brookhaven Protein Data Bank.

Table 7A is a summary of the truncations of the variable regions 1 and 2 recommended for this study, as determined in Example 1.A. above.

TABLE 7A

| V1/V2 Modifications | SEQ ID NO | Figure |
|---|---|---|
| -LEU122-GLY-ASN-SER199 | 7 | 10 |
| -LYS121-ALA-PRO-VAL200- | 6 | 9 |
| -VAL120-GLY-GLY-ILE201- | 4 | 7 |
| -VAL120-PRO-GLY-ILE201B- | 5 | 8 |
| -VAL120-GLY-ALA-GLY-ALA204- | 3 | 6 |
| -VAL120-GLY-GLY-ALA-THR202- | 8 | 11 |
| -VAL127-GLY-ALA-GLY-ASN195- | 25 | 28 |

As previously noted, the polypeptides encoded by the constructs of the present invention are numbered relative to HXB-2, but the particular amino acid residue of the polypeptides encoded by these exemplary constructs is based on SF-162. Thus, for example, although amino acid residue 195 in HXB-2 is a serine (S), constructs encoding polypeptides having then wild type SF162 sequence will have an asparagine (N) at this position. Table 7B shows just three of the variations in amino acid sequence between strains HXB-2 and SF162. The entire sequences, including differences in residue and amino acid number, of HXB-2 and SF162 are shown in the alignment of FIG. 2 (SEQ ID NOs:1 and 2).

TABLE 7B

| HXB-2 amino acid number | HXB-2 Residue | SF162 Residue/amino acid number |
|---|---|---|
| 128 | Serine (S) | Thr (T)/114 |
| 195 | Serine (S) | Asn (N)/188 |
| 426 | Met (M) | Arg (R)/411 |

Constructs containing deletions in the β-20 strand, β-21 stand and small loop were also constructed. Shown in Table 8 are constructs encoding truncations in these regions. The constructs in Table 8 are numbered relative to HXB-2 but the unmodified amino acid sequence is based on SF162. Thus, the construct encodes an arginine (Arg) as is found in SF162 in the amino acid position numbered 426 relative to HXB-2 (See, also, Table 7B). Changes from wildtype (SF162) are shown in bold in Table 8B.

TABLE 8

| Small Loop/β-20 and β-21 (Modified) | SEQ ID NO | Figure |
|---|---|---|
| -TRP427-GLY-GLY431- | 9 | 12 |
| -ARG426-GLY-GLY-GLY431- | 10 | 13 |
| -ARG426-GLY-SER-GLY431B- | 11 | 14 |
| -ARG426-GLY-GLY-ASN-LYS432- | 12 | 15 |
| -ASN425-ALA-PRO-LYS432- | 13 | 16 |
| -ILE424-GLY-GLY-ALA433- | 14 | 17 |
| -ILE423-GLY-GLY-MET434- | 15 | 18 |
| GLN422-GLY-GLY-TYR435- | 16 | 19 |
| -GLN422-ALA-PRO-TYR435B- | 17 | 20 |

The deletion constructs shown in Tables 7 and 8 for each one of the P-strands and combinations of them are constructed. These deletions will be tested in the Env forms gp120, gp140 and gp160 from different HIV strains like subtype B strains (e.g., SF162, US4, SF2), subtype E strains (e.g., CM235) and subtype C strains (e.g., AF110968 or AF110975). Exemplary constructs for SF162 are shown in the Figures and are summarized in Table 9. As noted above in FIG. 2 and Table 7B, in the bridging sheet region, the amino acid sequence of SF162 differs from HXB-2 in that the Met426 of HXB-2 is an Arg in SF162. In Table 9, V1/V2 refers to deletions in the V1/V2 region; # bsm refers to a modification in the bridging sheet small loop.

TABLE 9

| Construct | Seq. Id. | Fig. | Modification/Amino acid sequence |
|---|---|---|---|
| Val120-Ala204 | 3 | 6 | V1/V2: Val120-Gly-Ala-Gly-Ala204 |
| Val120-Ile201 | 4 | 7 | V1/V2: Val120-Gly-Gly-Ile201 |
| Val120-Ile201B | 5 | 8 | V1/V2: Val120-Pro-Gly-Ile201 |
| Lys121-Val200 | 6 | 9 | V1/V2: Lys121-Ala-Pro-Val200 |
| Leu122-Ser199 | 7 | 10 | V1/V2: Leu122-Gly-Asn-Ser199 |
| Val120-Thr202 | 8 | 11 | V1/V2: Val120-Gly-Gly-Ala-Thr202 |
| Trp427-Gly431 | 9 | 12 | bsm: Trp427-Gly-Gly431 |
| Arg426-Gly431 | 10 | 13 | bsm: Arg426-Gly-Gly-Gly431 |
| Arg426-Gly431B | 11 | 14 | bsm: Arg426-Gly-Ser-Gly431 |
| Arg426-Lys432 | 12 | 15 | bsm: Arg426-Gly-Gly-Asn-Lys432 |
| Asn425-Lys432 | 13 | 16 | bsm: Asn425-Ala-Pro-Lys432 |
| Ile424-Ala433 | 14 | 17 | bsm: Ile424-Gly-Gly-Ala433 |
| Ile423-Met434 | 15 | 18 | bsm: Ile423-Gly-Gly-Met434 |
| Gln422-Tyr435 | 16 | 19 | bsm: Gln422-Gly-Gly-Tyr435 |
| Va1127-Asnl95 | 25 | 28 | bsm: Val127-Gly-Ala-Gly-Asn195 |
| Gln422-Tyr435B | 17 | 20 | bsm: Gln422-Ala-Pro-Tyr435 |
| Leu122-Ser199; Arg426-Gly431 | 18 | 21 | V1/V2/bsm: Leu122-Gly-Asn-Ser199 - Arg426-Gly-Gly-Gly431 |
| Leu122-Ser199; Arg426-Lys432 | 19 | 22 | V1/V2/bsm: Leu122-Gly-Asn-Ser199 - Arg426-Gly-Gly-Asn-Lys432 |
| Leu122-Ser199-Trp427-Gly431 | 20 | 23 | V1/V2/bsm: Leu122-Gly-Asn-Ser199 -Trp427-Gly-Gly431 |
| Lys121-Val200-Asn425-Lys432 | 21 | 24 | V1/V2/bsm: Lys121-Ala-Pro-Val200 - Asn425-Ala-Pro-Lys432 |
| Val120-Ile201-Ile424-Ala433 | 22 | 25 | V1/V2/bsm: Val120-Gly-Gly-Ile201 - Ile424-Gly-Gly-Ala433 |
| Val120-Ile201B-Ile424-Ala433 | 23 | 26 | V1/V2/bsm: Val120-Pro-Gly-Ile201 - Ile424-Gly-Gly-Ala43 |
| Val120-Thr202; Ile424-Ala433 | 24 | 27 | V1/V2/bsm: Val120-Gly-Gly-Ala-Thr202 - Ile424-Gly-Gly-Ala433 |
| Val127-Asn195; Arg426-Gly431 | 25 | 29 | V1/V2/bsm: Val127-Gly-Ala-Gly-Asn195 - Arg426-Gly-Gly-Gly431 |

Combinations of V1/V2 deletions and bridging sheet small loop modifications in addition to those specifically shown in Table 9 are also within the scope of the present invention. Various forms of the different embodiments of the invention, described herein, may be combined.

The first screening will be done after transient expression in COS-7, RD and/or 293 cells. The proteins that are expressed will be analyzed by immunoblot, ELISA, and for binding to mAbs directed to the CD4 binding site and other important epitopes on gp120 to determine integrity of structure. They will also be tested in a CD4 binding assay and, in addition, the binding of neutralizing antibodies, for example using patient sera or mAb 448D (directed to Glu370 and Tyr384, a region of the CD4 binding groove that is not altered by the deletions).

The immunogenicity of these novel Env glycoproteins will be tested in rodents and primates. The structures will be administered as DNA vaccines or adjuvanted protein vaccines or in combined modalities. The goal of these vaccinations will be to archive broadly reactive neutralizing antibody responses.

What is claimed is:

1. An immunogenic modified HIV Env polypeptide of a selected variant of HIV, the modified HIV Env polypeptide having at least one amino acid deleted relative to the wild-type Env polypeptide of the selected variant, in the region corresponding to residues 420 through 436 numbered relative to HXB-2 (SEQ ID NO:1) such that epitopes that are not exposed in the wild-type Env polypeptide of the selected variant are exposed in the modified Env polypeptide.

2. The polypeptide of claim 1, wherein one amino acid is deleted.

3. The polypeptide of claim 1, wherein more than one amino acid is deleted.

4. The polypeptide of claim 1, wherein at least one of amino acid residues 427, 428, and 429 is deleted.

5. The polypeptide of claim 1, wherein the V1 and V2 regions of the polypeptide are truncated.

6. The polypeptide of claim 4, wherein the V1 and V2 regions of the polypeptide are truncated.

7. The polypeptide of claim 1, wherein the selected variant is HIV strain SF162 (SEQ ID NO:2).

8. An immunogenic composition comprising a modified Env polypeptide according to claim 1 and an adjuvant.

9. An immunogenic composition comprising a modified Env polypeptide according to claim 4 and an adjuvant.

10. A method of inducing an immune response in a subject, comprising administering a composition comprising a modified Env polypeptide according to claim 1 and an adjuvant, wherein the composition is administered in an amount sufficient to induce an immune response in the subject.

11. An immunogenic modified HIV Env polypeptide of a selected variant of HIV, the modified HIV Env polypeptide, wherein:
   (a) amino acid 425 is lysine, amino acid 426 is aspartic acid, amino acid 427 is serine, amino acid 428 is asparagine, and amino acid 431 is asparagine;
   (b) amino acid 425 is tyrosine, amino acid 426 is glycine, amino acid 427 is leucine, amino acid 428 is glycine, and amino acid 431 is leucine;
   (c) amino acid 425 is glutamate, amino acid 426 is arginine, amino acid 427 is glutamate, amino acid 428 is aspartic acid, and amino acid 431 is glycine;
   (d) amino acid 425 is arginine, amino acid 426 is lysine, amino acid 427 is glycine, amino acid 428 is glycine, and amino acid 431 is asparagine; or
   (e) amino acid 425 is tryptophan, amino acid 426 is threonine, amino acid 427 is glycine, amino acid 428 is serine, and amino acid 431 is tyrosine, wherein the amino acids are numbered relative to HXB-2 (SEQ ID NO:1).

* * * * *